United States Patent
Gray et al.

(10) Patent No.: US 12,275,731 B2
(45) Date of Patent: Apr. 15, 2025

(54) AZAINDOLE INHIBITORS OF WILD-TYPE AND MUTANT FORMS OF LRRK2

(71) Applicants: DANA-FARBER CANCER INSTITUTE, INC., Boston, MA (US); VORONOI INC., Incheon (KR)

(72) Inventors: Nathanael S. Gray, Boston, MA (US); John Hatcher, Boston, MA (US); Jieun Choi, Seoul (KR); Hwangeun Choi, Seoul (KR); Eunhwa Ko, Incheon (KR); Namdoo Kim, Incheon (KR)

(73) Assignees: DANA-FARBER CANCER INSTITUTE, INC., Boston, MA (US); VORONOI INC., Incheon (KR)

( * ) Notice: Subject to any disclaimer, the term of this patent is extended or adjusted under 35 U.S.C. 154(b) by 918 days.

(21) Appl. No.: 17/283,441

(22) PCT Filed: Oct. 16, 2019

(86) PCT No.: PCT/US2019/056545
§ 371 (c)(1),
(2) Date: Apr. 7, 2021

(87) PCT Pub. No.: WO2020/081689
PCT Pub. Date: Apr. 23, 2020

(65) Prior Publication Data
US 2021/0347772 A1    Nov. 11, 2021

Related U.S. Application Data

(60) Provisional application No. 62/913,578, filed on Oct. 10, 2019, provisional application No. 62/746,273, filed on Oct. 16, 2018.

(51) Int. Cl.
*C07D 471/04* (2006.01)
(52) U.S. Cl.
CPC ................. *C07D 471/04* (2013.01)

(58) Field of Classification Search
None
See application file for complete search history.

(56) References Cited

U.S. PATENT DOCUMENTS

| | | | |
|---|---|---|---|
| 2011/0039822 | A1 | 2/2011 | Inoue et al. |
| 2017/0027956 | A1 | 2/2017 | Hopkins et al. |
| 2017/0137424 | A1 | 5/2017 | Wu et al. |
| 2018/0244676 | A1 | 8/2018 | Gray et al. |

FOREIGN PATENT DOCUMENTS

| | | |
|---|---|---|
| CN | 106543143 A | 3/2017 |
| JP | 2008545660 A5 | 12/2008 |
| JP | 2013511541 A | 4/2013 |
| JP | 2013537218 A | 9/2013 |
| JP | 2015521600 A5 | 7/2015 |
| JP | 2016540794 B2 | 12/2016 |
| WO | 2006127587 A1 | 11/2006 |
| WO | 2011063159 A1 | 5/2011 |
| WO | 2012038743 A1 | 3/2012 |
| WO | 2014007951 A1 | 1/2014 |
| WO | 2015/092592 A1 | 6/2015 |
| WO | 2017049462 A1 | 3/2017 |
| WO | 2018/136202 A2 | 7/2018 |

OTHER PUBLICATIONS

Database Registry Chemical Abstracts Service, Columbus, Ohio, Accession No. RN 1638760-48-1, Entered STN: Dec. 15, 2014.*
PubChem-CID-20784594, 2007.
Henderson et al., "Palladium-Catalyzed Amination of Unprotected Halo-7-azaindoles", Org. Lett., 2010, vol. 12, No. 20, pp. 4438-4441.

* cited by examiner

*Primary Examiner* — Samantha L Shterengarts
(74) *Attorney, Agent, or Firm* — ArentFox Schiff LLP; Daniel W. J. Clarke D.; Shawn P. Foley

(57) ABSTRACT

Disclosed are compounds that possess inhibitory activity against LRRK2. Also disclosed are pharmaceutical compositions containing the compounds and methods of using the compounds to treat diseases and disorders including neurodegenerative diseases and disorders such as Parkinson's disease, and brain cancer (e.g., gliomas and glioblastomas).

20 Claims, No Drawings

AZAINDOLE INHIBITORS OF WILD-TYPE AND MUTANT FORMS OF LRRK2

RELATED APPLICATIONS

This application is a national stage application, filed under 35 U.S.C. § 371, of International Application No. PCT/US2019/056545, filed Oct. 16, 2019, which claims the benefit of priority under 35 U.S.C. § 119 (e) to U.S. Provisional Application No. 62/746,273, filed on Oct. 16, 2018 and to U.S. Provisional Application No. 62/913,578, filed on Oct. 10, 2019, each of which is incorporated herein by reference in its entirety.

BACKGROUND OF THE INVENTION

Parkinson's disease (PD) is a movement disorder resulting from progressive loss of dopamine producing neurons. It is the second most common neurodegenerative disease in the world, and affects over 1 million Americans. More than 60 000 patients are newly diagnosed each year (Gandhi et al., J. Neurosci. Res. 87:1283-1295 (2009); Daniëls et al., Neurosignals 19:1-15 (2011)). Symptoms associated with Parkinson's disease include motor impairment, tremor, bradykinesia, instability, and other movement related disorders. There are also non-motor symptoms such as cognitive dysfunction, autonomic dysfunction, and sleep disruption. These symptoms greatly reduce the quality of life of those suffering from Parkinson's disease.

Insofar as the genes associated with PD are concerned, leucine-rich repeat kinase 2 (LRRK2) having a missense mutation, G2019S, is frequently found in both familial and sporadic PD cases. (Healy et al., Lancet Neurol. 7:583-590 (2008), Dächsel et al., Neurol. 67:542-547 (2010), Lee et al., Trends Pharmacol. Sci. 33(7):365-373 (2012), Liu et al., Hum. Mol. Genet. 20:3933-3942 (2011)). The G2019S mutation increases kinase activity, which may result in activation of the neuronal death signal pathway (Greggio et al., ASN Neuro 1(1):e00002 (2009), Kumar et al., Expert Rev. Mol. Med. 13:e20 (2011)). Transgenic G2019S LRRK2 mice aged to 12-16 months displayed progressive degeneration of the substantia nigra pars *compacta* (SNpc) dopaminergic neurons and Parkinson's phenotypes of motor dysfunction (Chen et al., Cell Death Differ. 19(10):1623-33 (2012)).

SUMMARY OF THE INVENTION

A first aspect of the present invention is directed to a compound having a structure represented by formula (I):

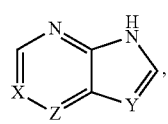

(I)

wherein:

X and Y each independently represents $CR_1$ or $CR_2$, wherein $R_1$ represents

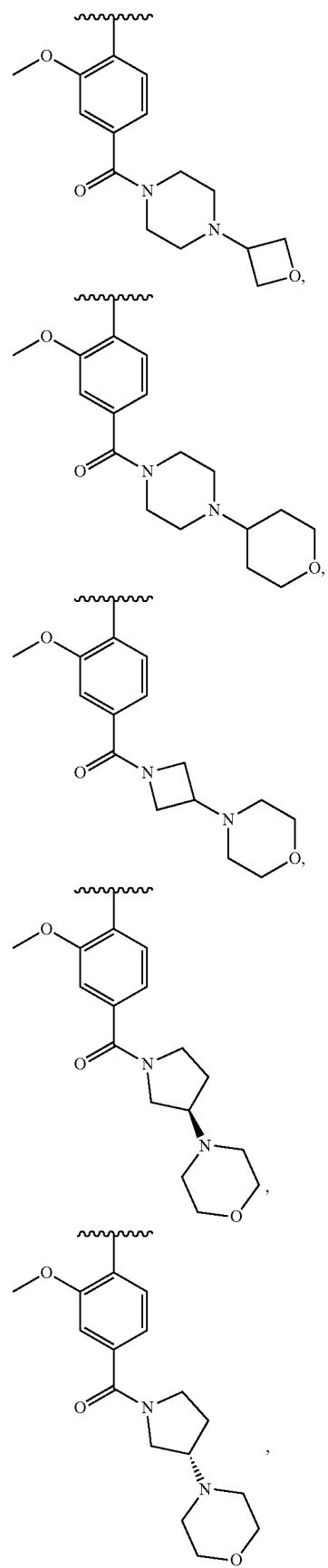

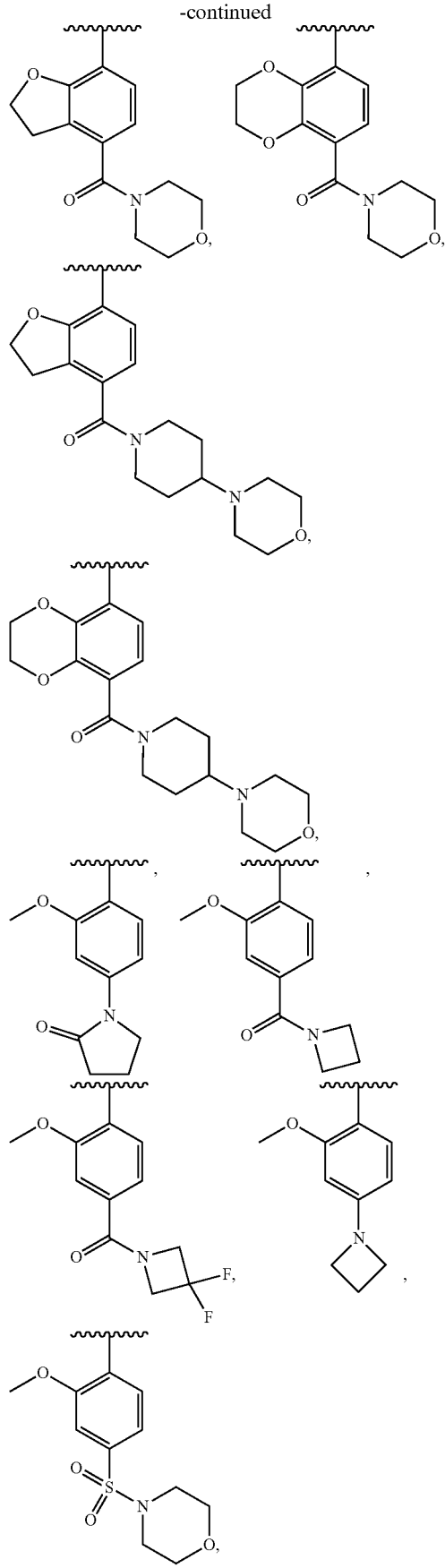
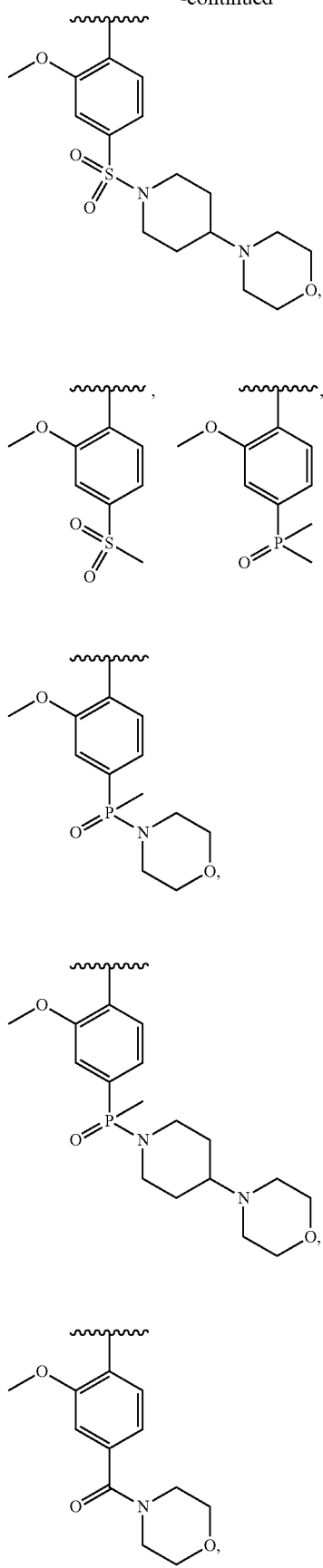

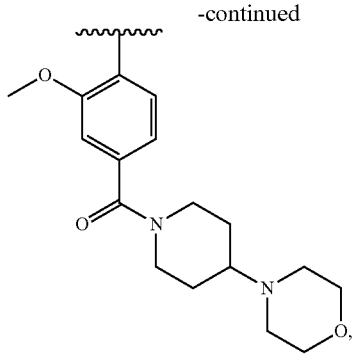
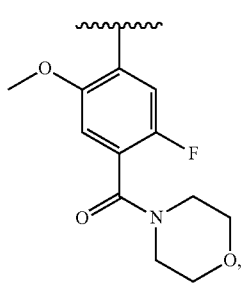
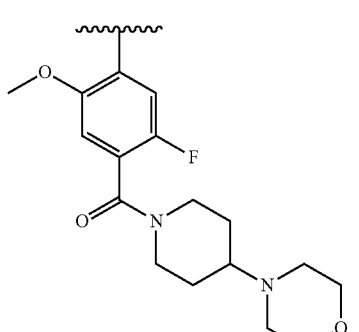
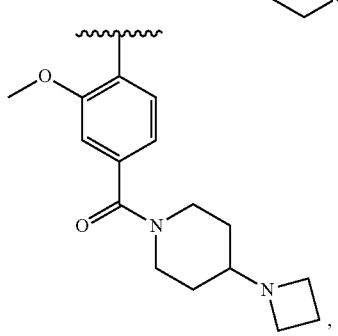
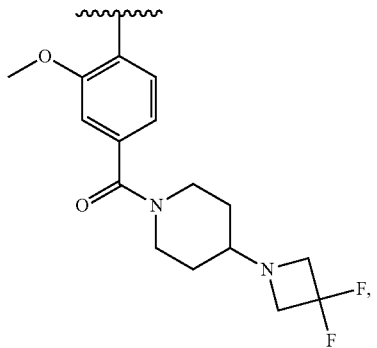
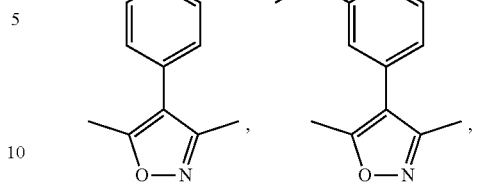
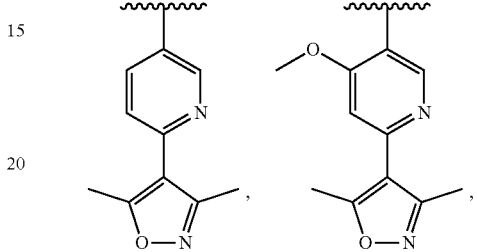
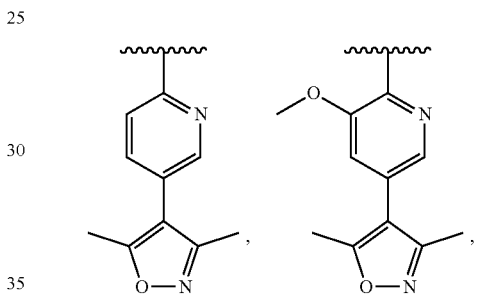
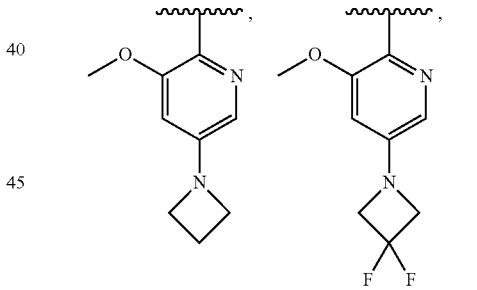

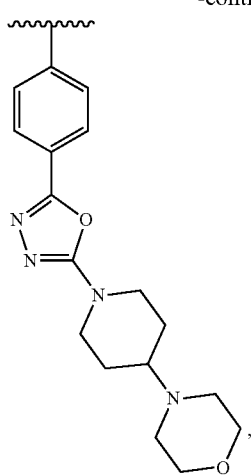
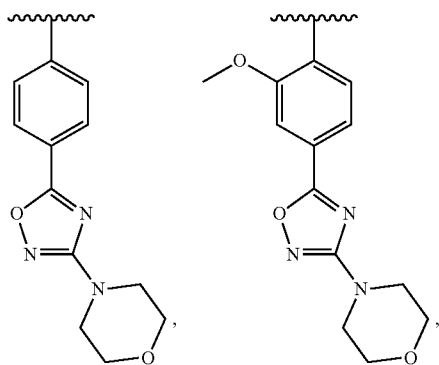
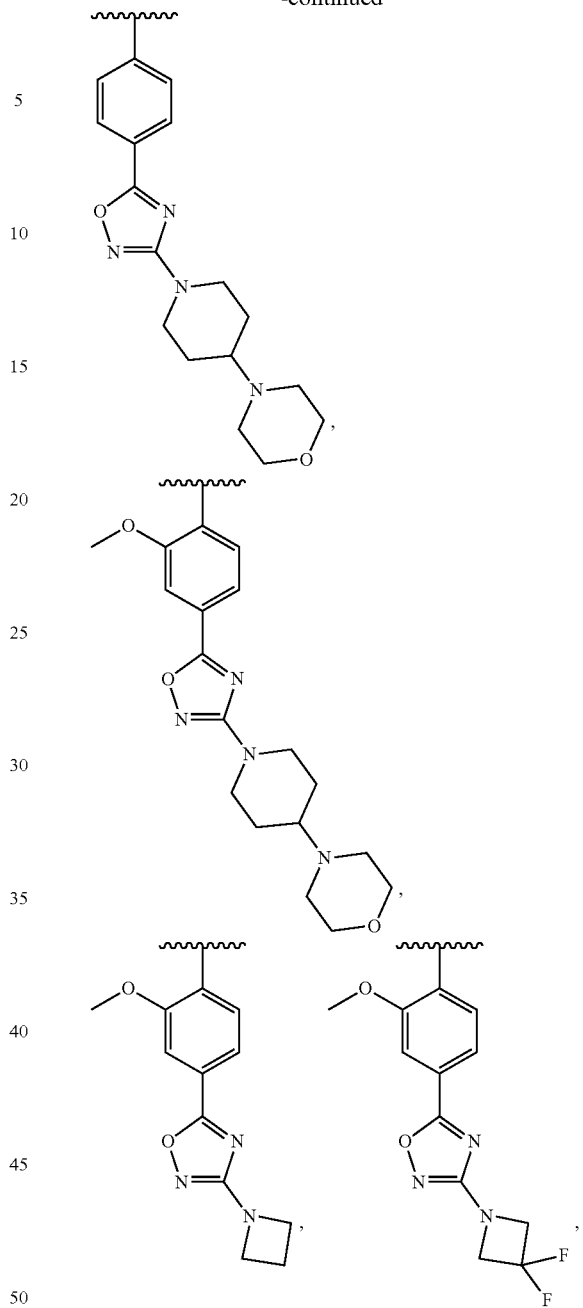

-continued
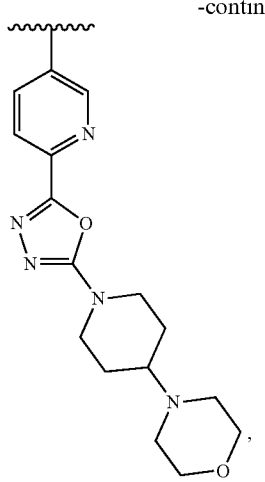
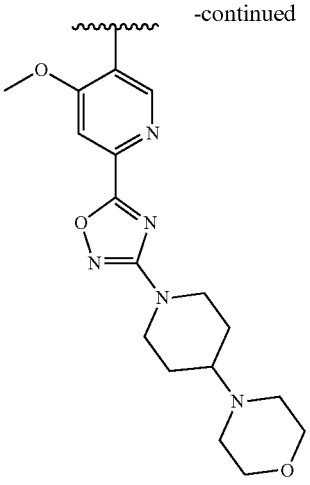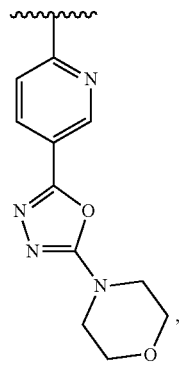
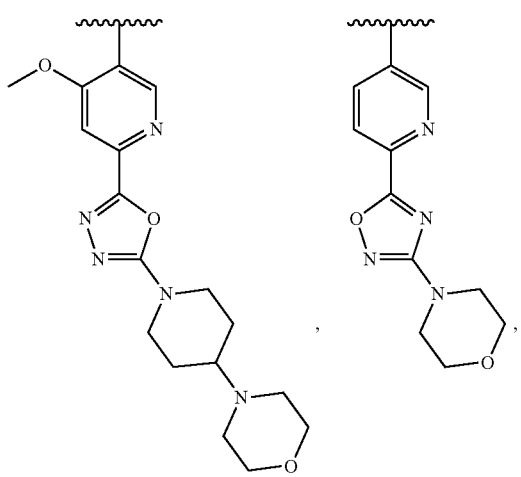
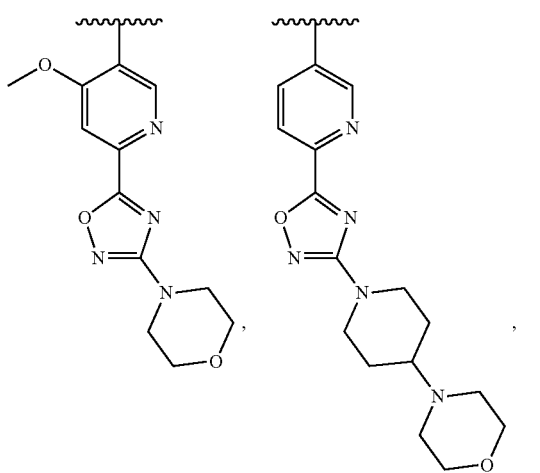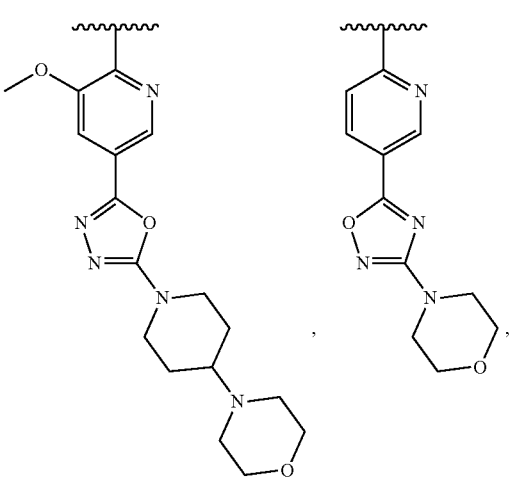

-continued
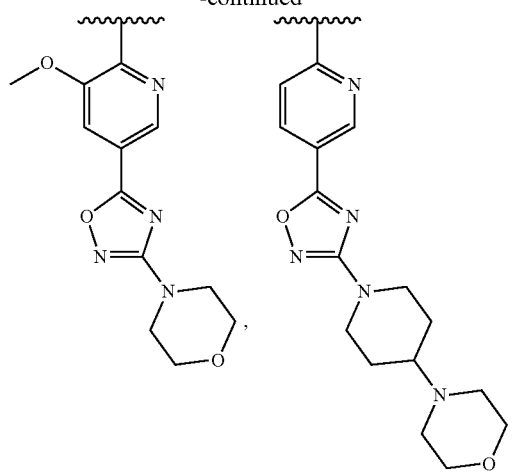
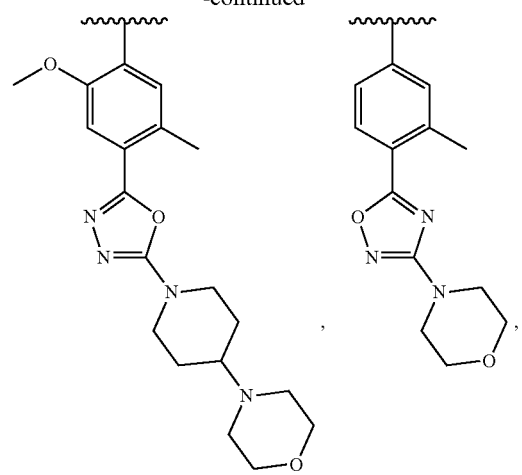
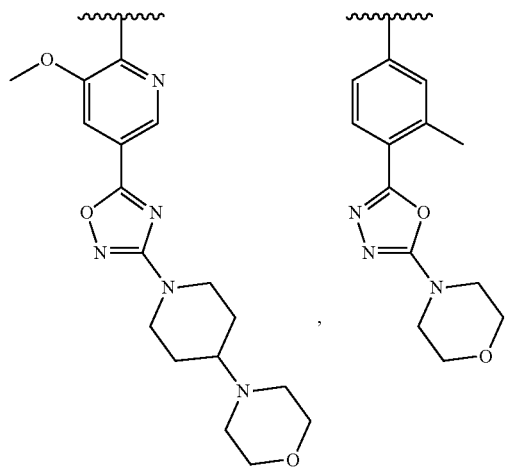
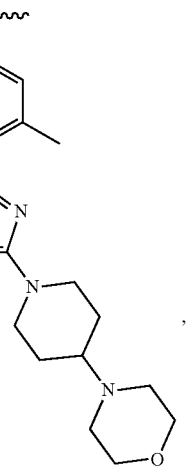
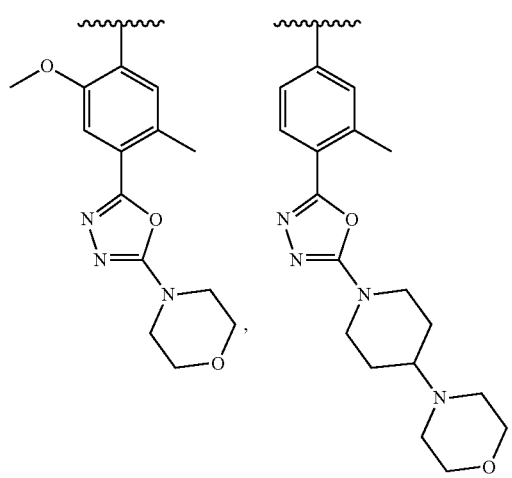
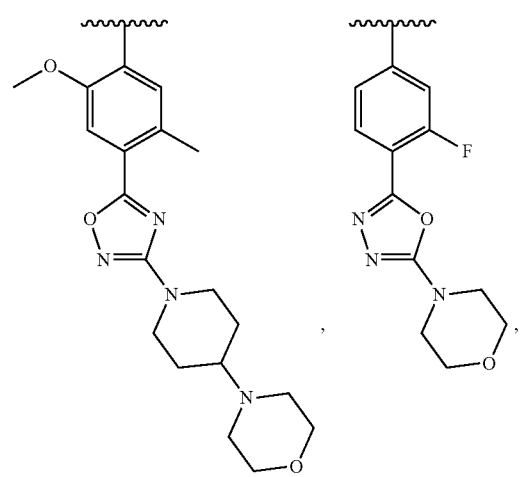

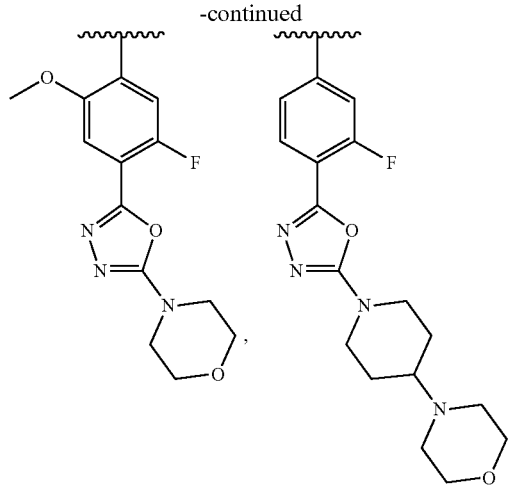
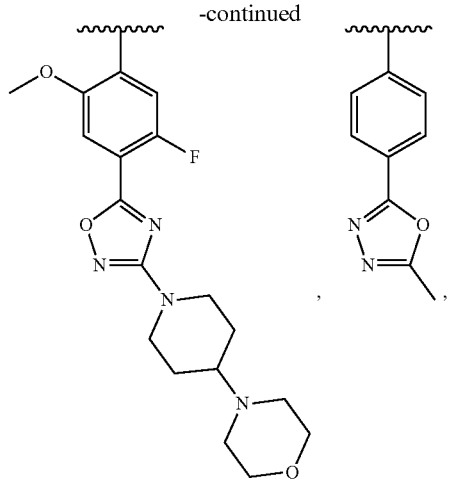
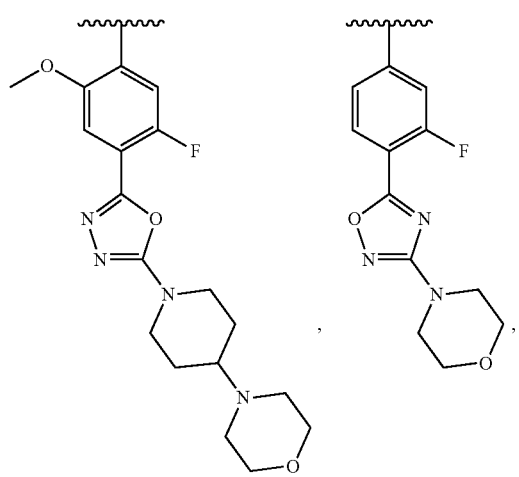
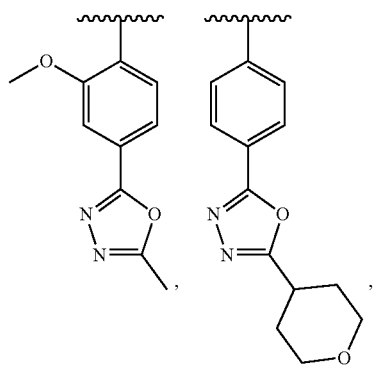
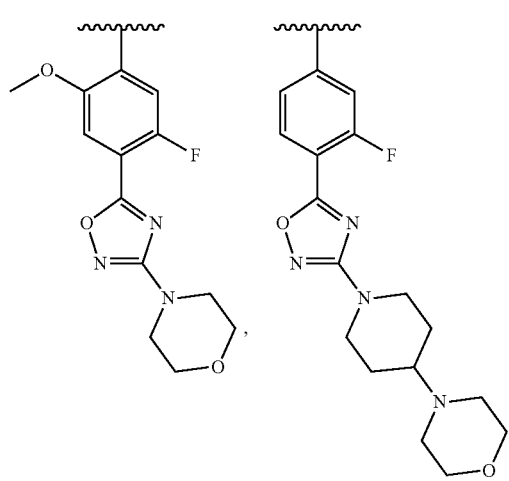
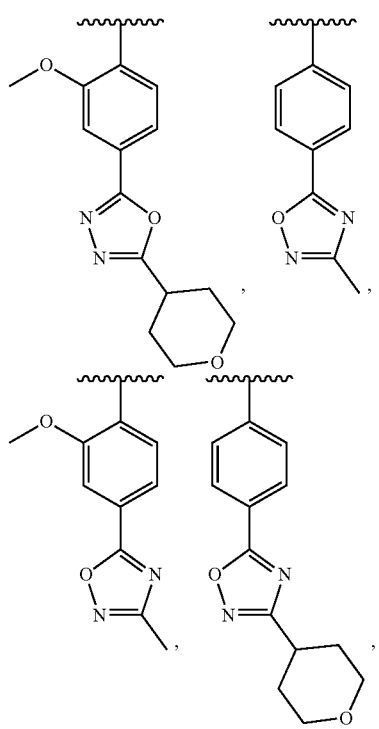

-continued
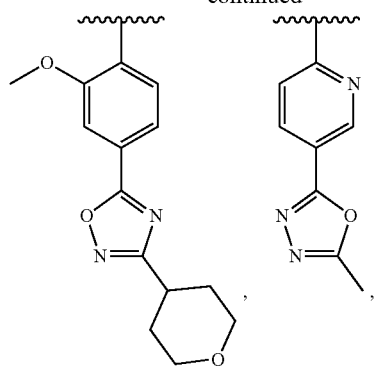 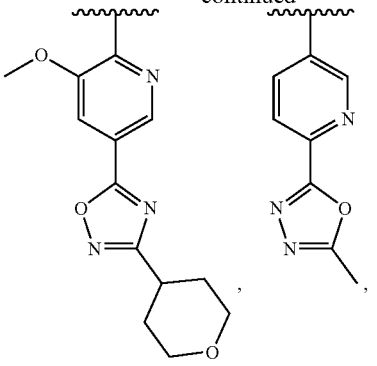
 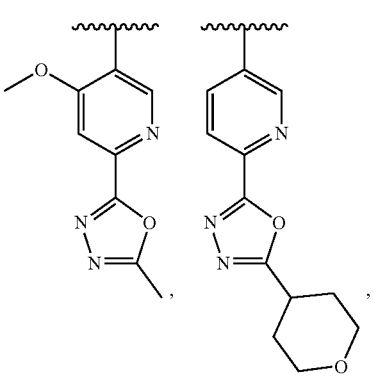
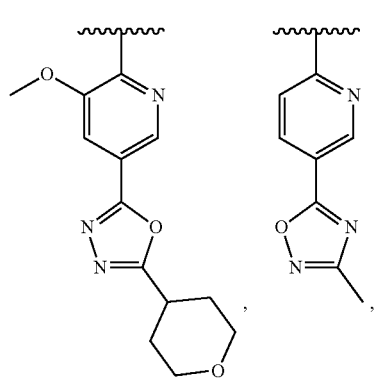 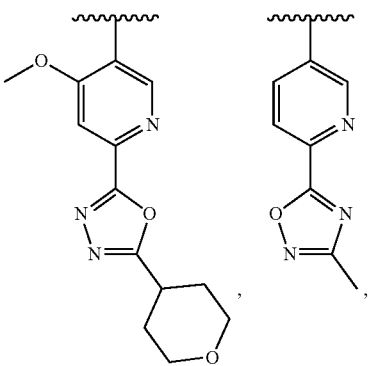
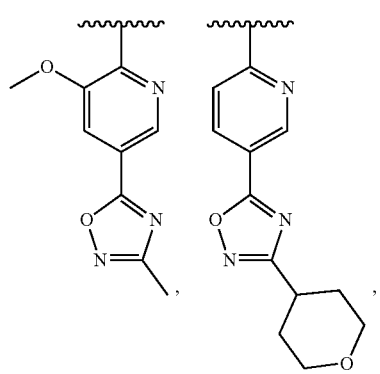 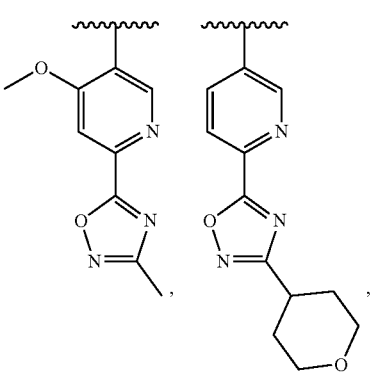

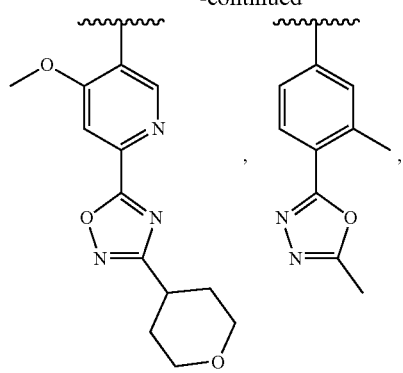 , 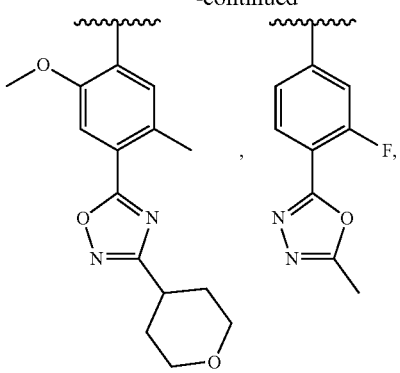 ,
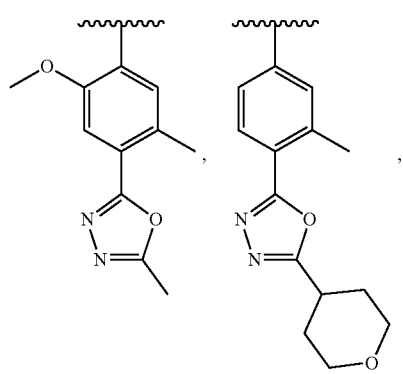 , 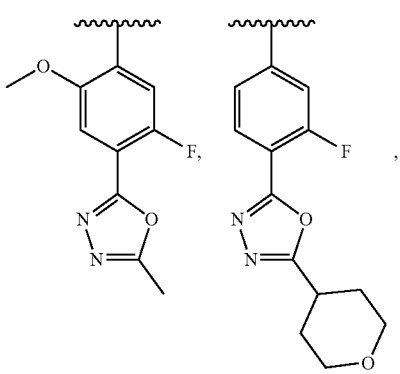 ,
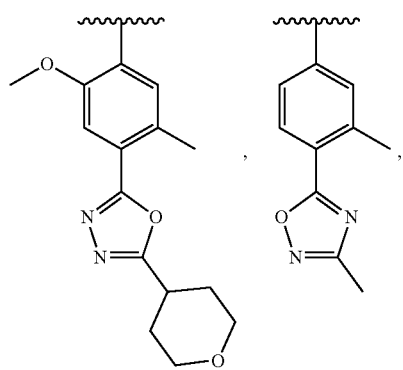 , 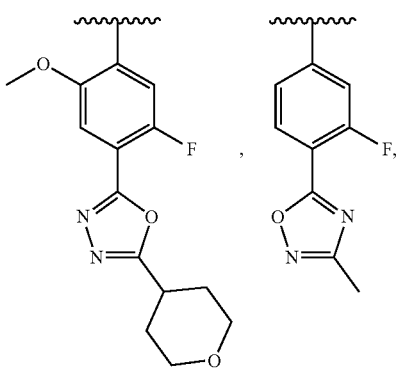 ,
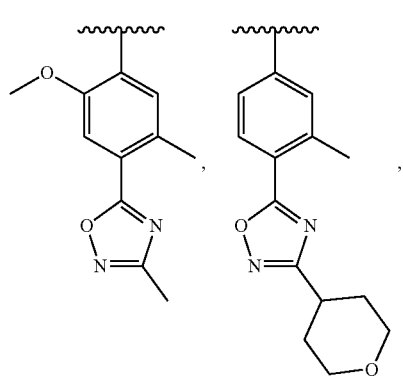 , 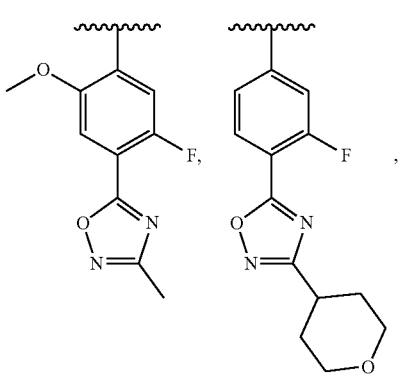 ,

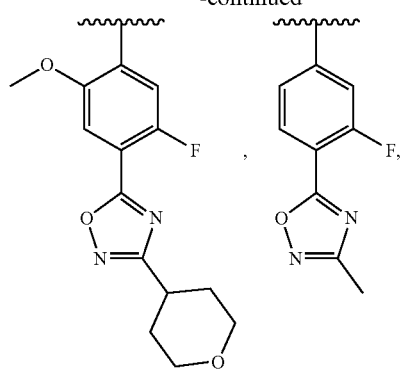
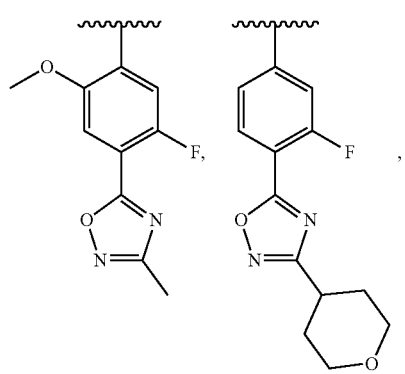
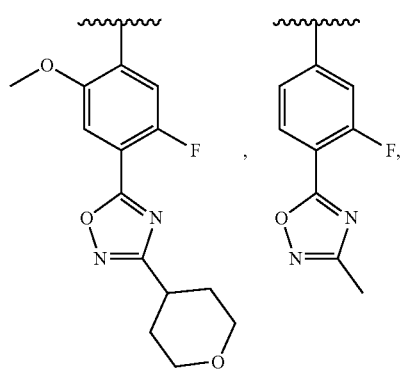
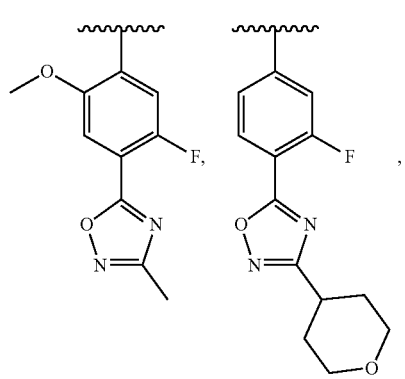
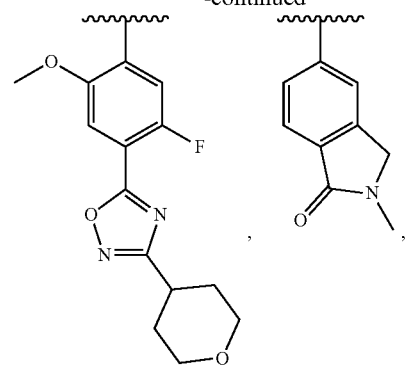

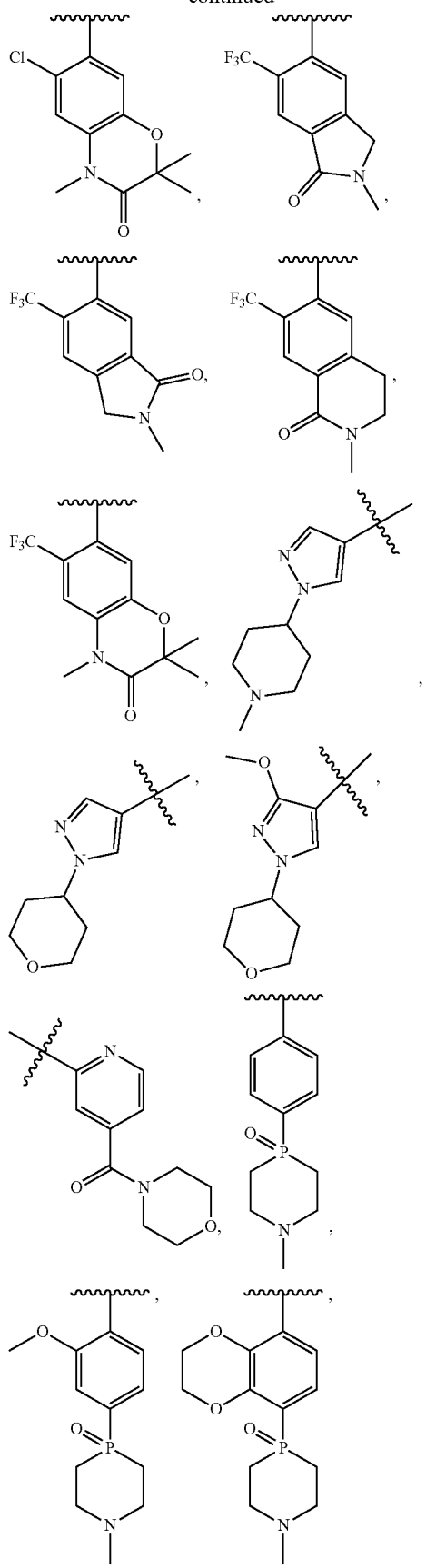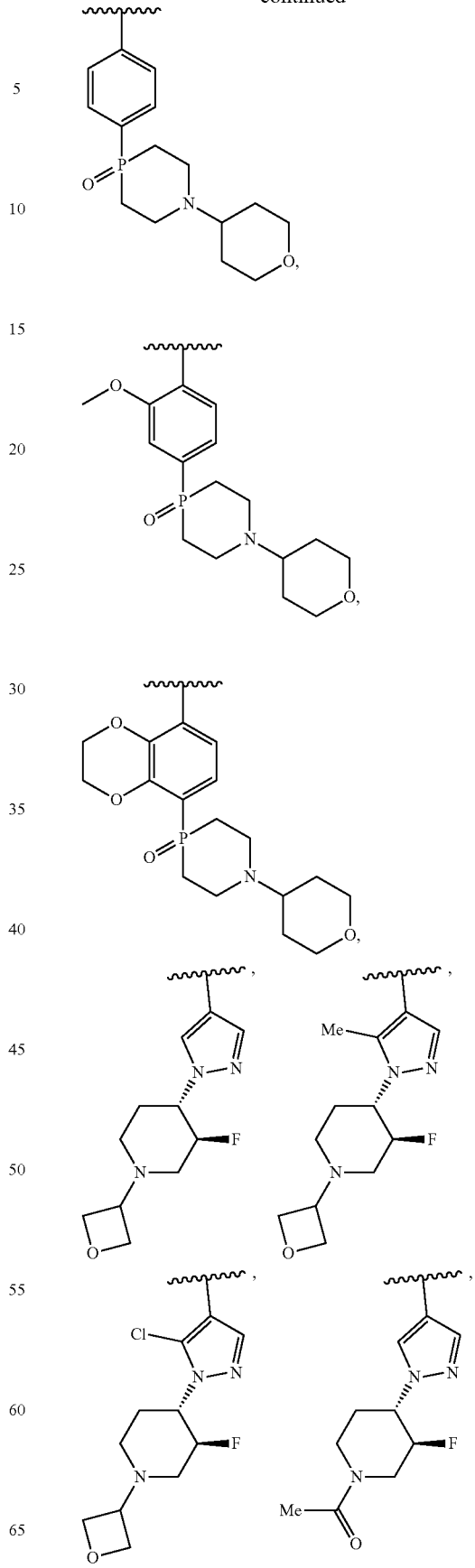

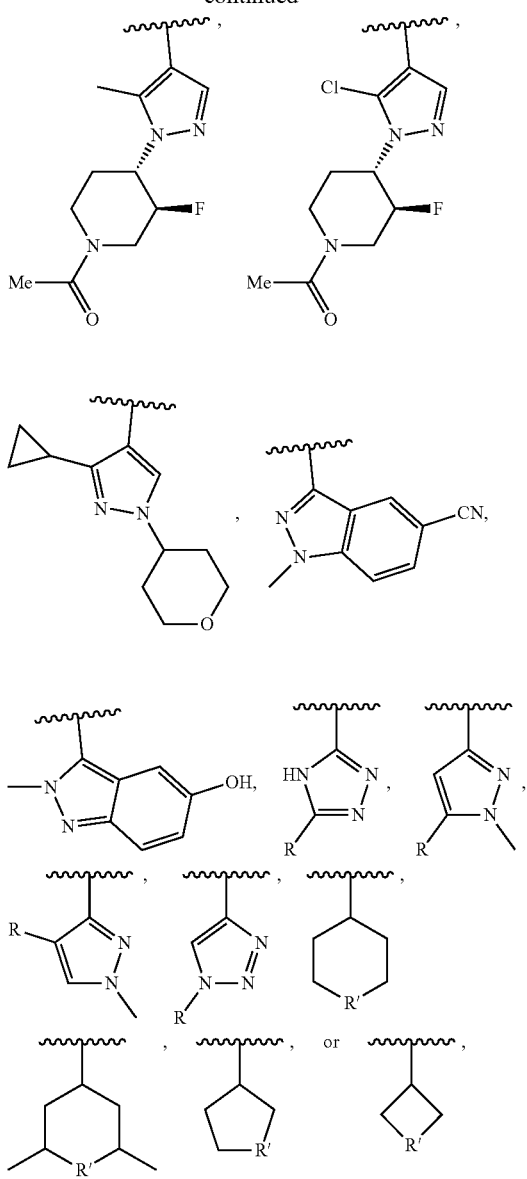

wherein R represents methyl, ethyl, isopropyl, cyclopropyl, or CF₃, and R' is O, NH or NMe;

R₂ represents H, halogen (e.g., F, Cl), or CF₃;

and Z represents CR₃, wherein R₃ represents

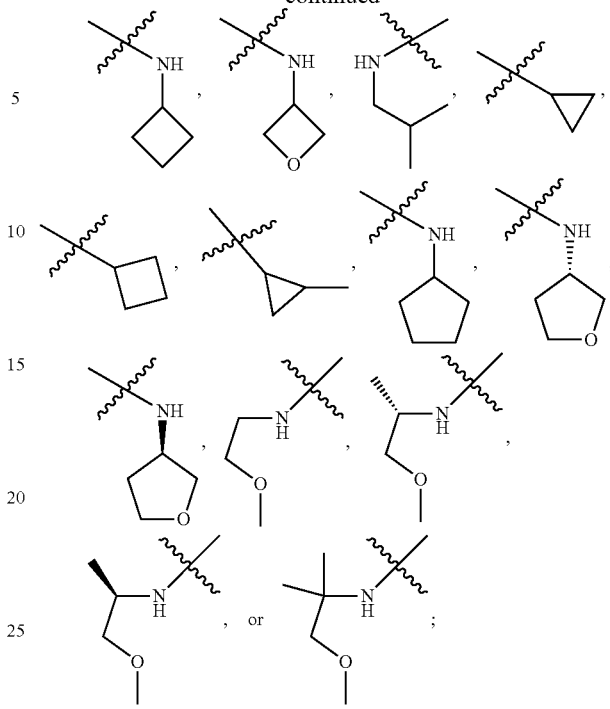

or a pharmaceutically acceptable salt or stereoisomer thereof.

A second aspect of the present invention is directed to a pharmaceutical composition containing a therapeutically effective amount of a compound of formula (I) or a pharmaceutically acceptable salt or stereoisomer thereof, and pharmaceutically acceptable carrier.

A further aspect of the invention is directed to a method of treating a disease or disorder mediated by aberrant (e.g., dysregulated or dysfunctional) LRRK2 activity, that includes administrating a therapeutically effective amount of a compound of formula (I) or a pharmaceutically acceptable salt or stereoisomer thereof, to a subject in need thereof.

In some embodiments, the disease or disorder is a neurodegenerative disease or brain cancer.

Further aspects of the present invention are directed to methods of making the compounds.

Compounds of the present invention may thus provide a therapeutic entree for neurodegenerative diseases such as Parkinson's disease by inhibiting LRRK2.

As demonstrated in one or more working examples, compounds of formula (I) and their pharmaceutically acceptable salts and stereoisomers thereof may inhibit a plurality of aberrant kinases, including at least one of adaptor-associated protein kinase 1 (AAK1), receptor tyrosine kinase (ABL1(T315I)-phosphorylated), apoptosis signal-regulating kinase 1 (ASK1), ASK2, aurora kinase A (AURKA), AURKB, AURKC, AXL receptor tyrosine kinase (AXL), BMP-2-inducible protein kinase (BIKE), BMX (BMX non-receptor tyrosine kinase), cell division cycle 2-like protein kinase 5 (CDCl₂L5), cyclin-dependent kinase 11 (CDK11), checkpoint kinase 2 (CHEK2), citron rho-interacting serine/threonine kinase (CIT), CDC-like kinase 1 (CLK1), CLK2, CLK4, colony stimulating factor 1 receptor (CSF1R), CSF1R-autoinhibited, C-terminal Src kinase (CSK), casein kinase I isoform epsilon (CSNK1E), casein kinase I isoform gamma 1 (CSNK1G1), CSNK1G3, dual leucine zipper kinase (DLK), death-associated protein kinase-related 2 (DRAK2), dual-specificity tyrosine phosphorylation-regulated kinase 1A (DYRK1A), DYRK2, ephrin type-A receptor 2 (EPHA2), fins-related tyrosine kinase 1 (FLT1), FLT3, FLT3(D835H), FLT3(D835V), FLT3 (D835Y), FLT3(ITD), FLT3(ITD,D835V), FLT3(ITD, F691L), FLT3(K663Q), FLT3(N841I), G protein-coupled receptor kinase 4 (GRK4), serine/threonine-protein kinase haspin (HASPIN), homeodomain-interacting protein kinase 1 (HPK1), intestinal cell kinase (ICK), I kappa B kinase alpha (IKK-alpha), IKK-beta, interleukin 1 receptor associated kinase 1 (IRAK1), IRAK4, Janus kinase 2 (JAK2) (JH1domain-catalytic), JAK3(JH1domain-catalytic), c-Jun N-terminal kinase 1 (JNK1), JNK2, JNK3, tyrosine-protein kinase kit (KIT), KIT(L576P), KIT(V559D), KIT(V559D, T670I), KIT-autoinhibited, LRRK2, LRRK2(G2019S), mitogen-activated protein kinase kinase 2 (MAP3K2), MAP3K15, mitogen-activated protein kinase kinase kinase kinase 2 (MAP4K2), MAP4K4, microtubule associated serine/threonine kinase 1 (MAST1), mitogen-acitvated protein kinase kinase 1 (MEK1), MEK2, MEK3, MEK4, MEK5, MEK6, maternal embryonic leucine zipper kinase (MELK), met proto-oncogene (MET), MET(M1250T), MET (Y1235D), Misshapen-like kinase 1 (MINK), mitogen-activated protein kinase-interacting serine/threonine kinase-2 (MKNK2), myosin light chain kinase (MLCK), nuclear Dbf2-related kinase 2 (NDR2), F-kappa-B-inducing kinase (NIK), p21-activated kinase 4 (PAK4), platelet-derived growth factor receptor alpha (PDGFRA), PDGFR beta (PDGFRB), phosphorylase b kinase gamma catalytic chain, skeletal muscle isoform 2 (PHKG2), phosphatidylinositol-4,5-bisphosphate 3-kinase catalytic subunit alpha (PIK3CA) (E545K), phosphatidylinositol 4-Phosphate-5 kinase 1A (PIP5K1A), PIP5K2B, polo-like kinase 4 (PLK4), serine/threonine-protein kinase D1 (PRKD1), PRKD2, PRKD3, ret proto-oncogene (RET), (RET)(M918T), RIO kinase 1 (RIOK1), RIOK2, RIOK3, receptor-interacting serine/threonine-protein kinase 1 (RIPK1), RIPK4, dual serine/threonine and tyrosine protein kinase (RIPK5), rho-associated protein kinase 1 (ROCK1), ROCK2, ribosomal S6 Kinase 4 (RSK4)(Kin.Dom.1-N-terminal), serum and glucocorticoid-regulated kinase (SGK), SGK2, serine-arginine protein kinase 1 (SRPK1), SRPK2, SRPK3, serine/threonine kinase 16 (STK16), STK39, TGF-beta activated kinase 1 (TAK1), TRAF2 and NCK-interacting kinase (TNIK), tropomyosin receptor kinase A (TRKA), TRKB, monopolar spindle 1 (Mps1) kinase (TTK), tyrosine kinase 2 (TYK2) (JH1domain-catalytic), unc-51 like autophagy activating kinase 1 (ULK1), ULK2, ULK3, vascular endothelial growth factor receptor 2 (VEGFR2), and YSK4, also known as MAP3K19. Thus, yet further aspects of the present invention entail use of inventive compounds to treat diseases and disorders that are mediated by aberrant activity of any one or more of these kinases.

DETAILED DESCRIPTION OF THE INVENTION

Unless defined otherwise, all technical and scientific terms used herein have the same meaning as is commonly understood by one of skill in the art to which the subject matter herein belongs. As used in the specification and the appended claims, unless specified to the contrary, the following terms have the meaning indicated in order to facilitate the understanding of the present invention.

As used in the description and the appended claims, the singular forms "a", "an", and "the" include plural referents unless the context clearly dictates otherwise. Thus, for example, reference to "a composition" includes mixtures of two or more such compositions, reference to "an inhibitor" includes mixtures of two or more such inhibitors, and the like.

Unless stated otherwise, the term "about" means within 10% (e.g., within 5%, 2% or 1%) of the particular value modified by the term "about."

The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

With respect to compounds of the present invention, and to the extent the following terms are used herein to further describe them, the following definitions apply.

As used herein, the term "alkyl" refers to a saturated linear or branched-chain monovalent hydrocarbon radical. In one embodiment, the alkyl radical is a $C_1$-$C_{18}$ group. In other embodiments, the alkyl radical is a $C_0$-$C_6$, $C_0$-$C_5$, $C_0$-$C_3$, $C_1$-$C_{12}$, $C_1$-$C_8$, $C_1$-$C_6$, $C_1$-$C_5$, $C_1$-$C_4$ or $C_1$-$C_3$ group (wherein $C_0$ alkyl refers to a bond). Examples of alkyl groups include methyl, ethyl, 1-propyl, 2-propyl, i-propyl, 1-butyl, 2-methyl-1-propyl, 2-butyl, 2-methyl-2-propyl, 1-pentyl, n-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, heptyl, octyl, nonyl, decyl, undecyl and dodecyl. In some embodiments, an alkyl group is a $C_1$-$C_3$ alkyl group. In some embodiments, an alkyl group is a $C_1$-$C_2$ alkyl group.

As used herein, the term "halogen" (or "halo" or "halide") refers to fluorine, chlorine, bromine, or iodine.

Broadly, the compounds of the invention have a structure represented by formula (I):

wherein:
X and Y each independently represents $CR_1$ or $CR_2$, wherein $R_1$ represents

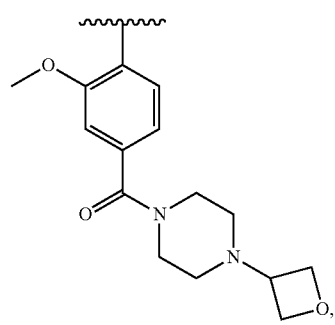

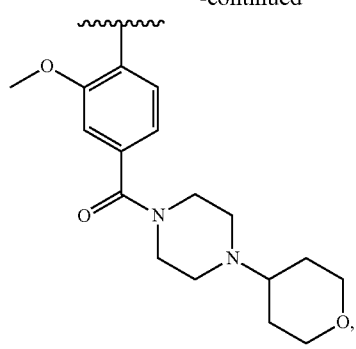
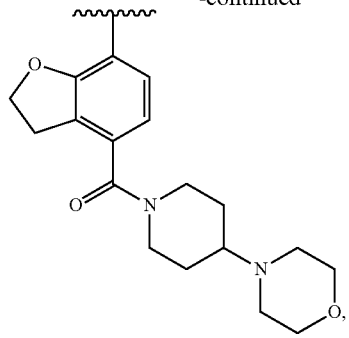
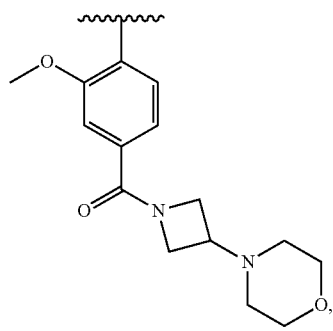
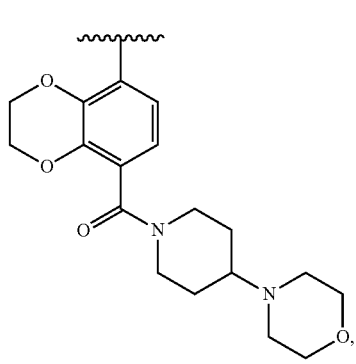
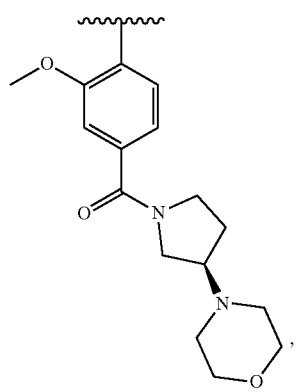
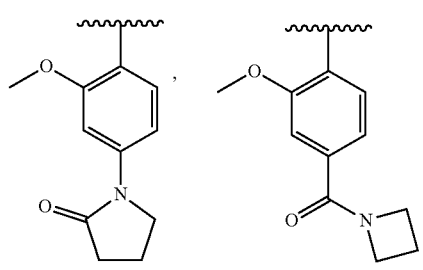
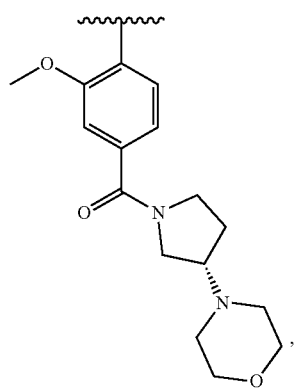
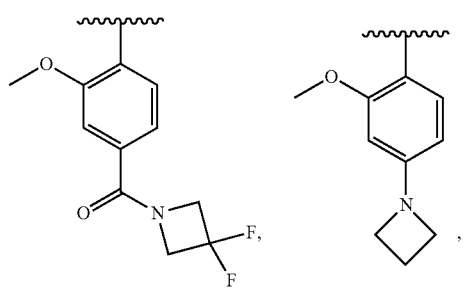
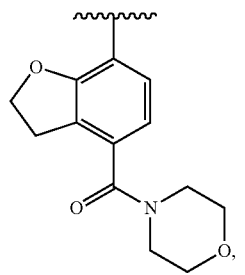 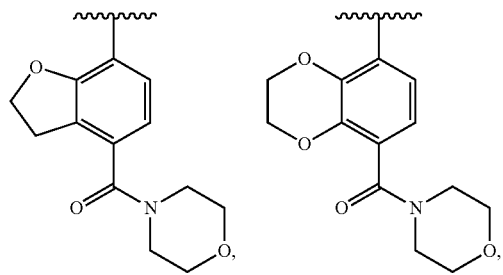
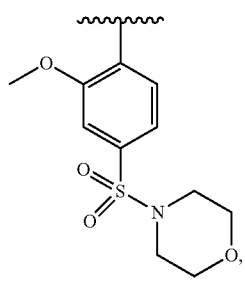

-continued
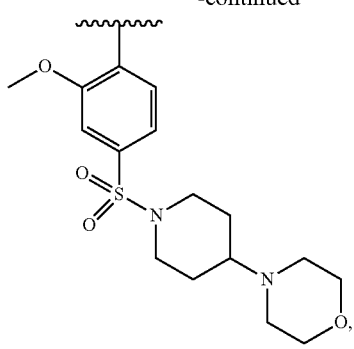
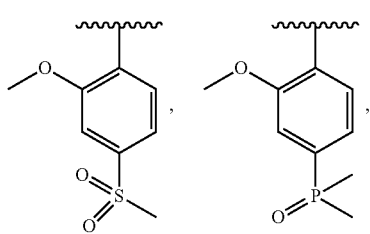
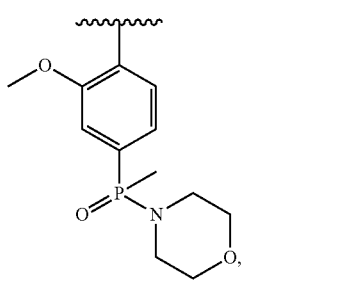
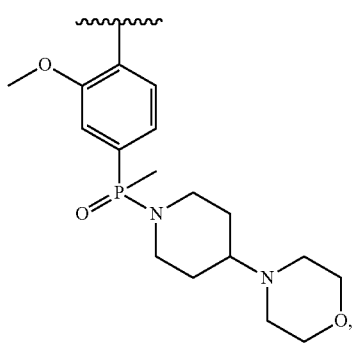
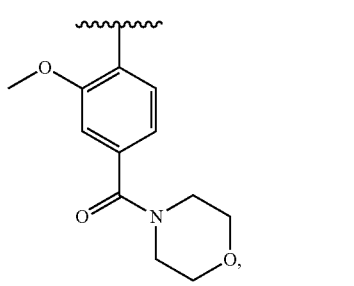
-continued
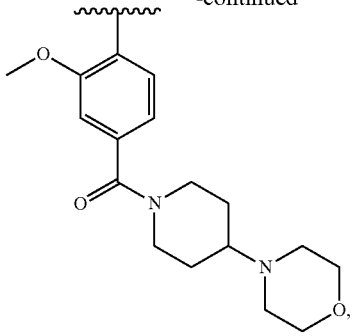
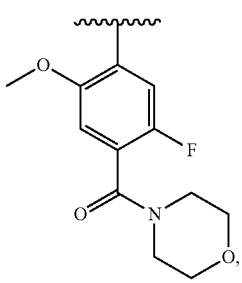
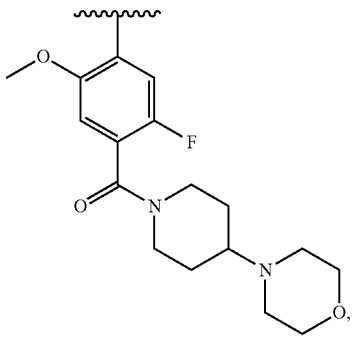
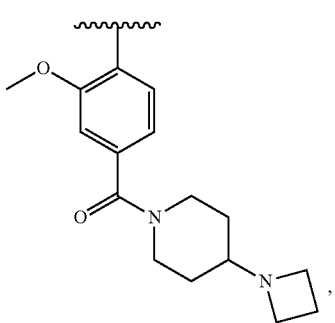
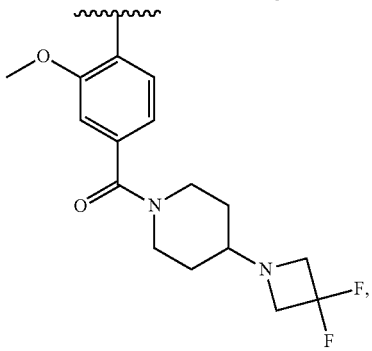

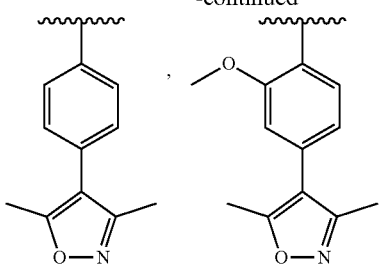
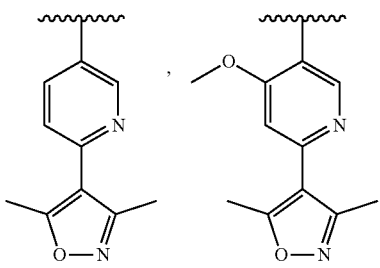
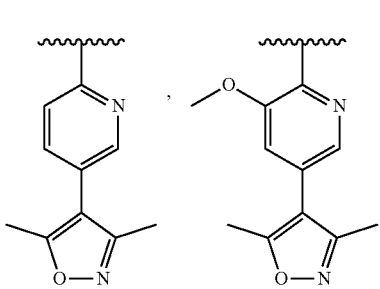
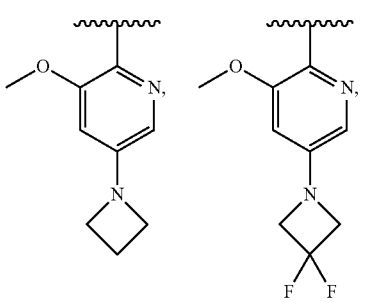
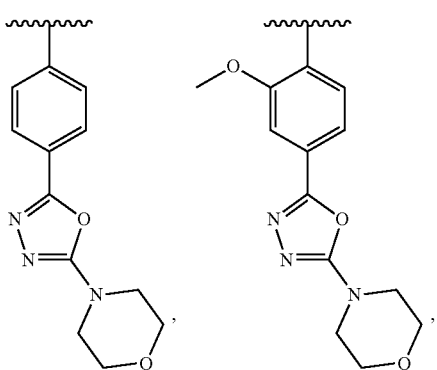
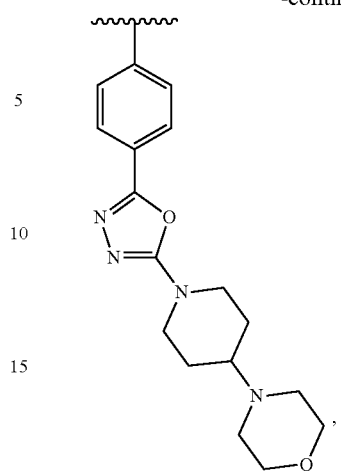
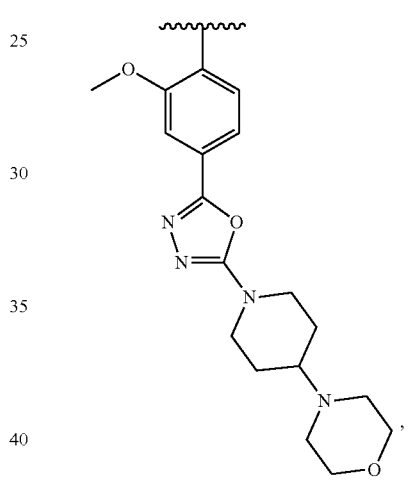
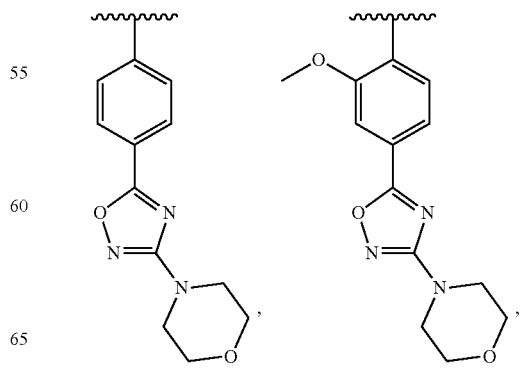

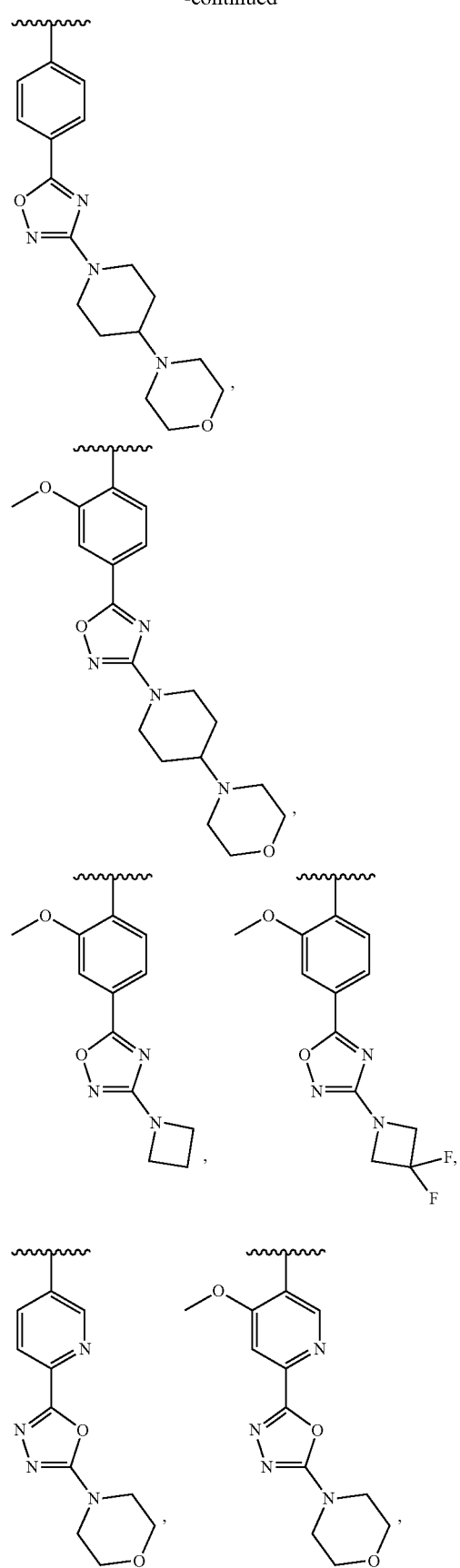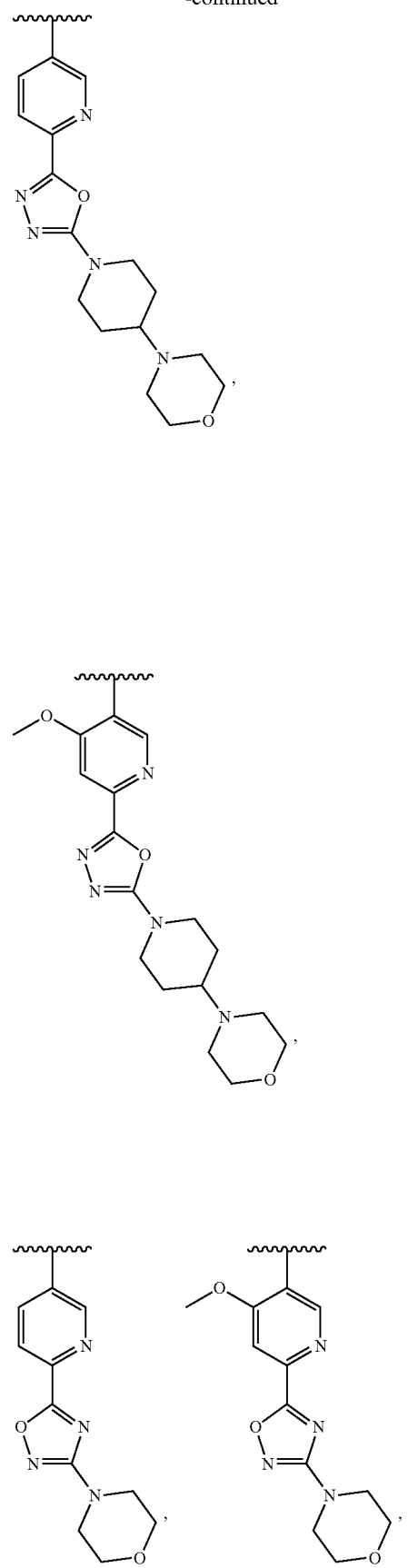

-continued
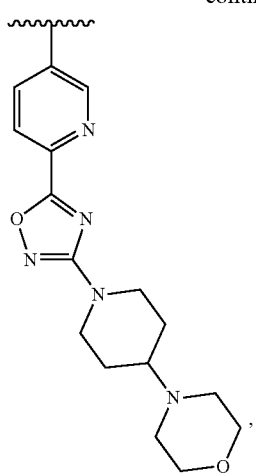
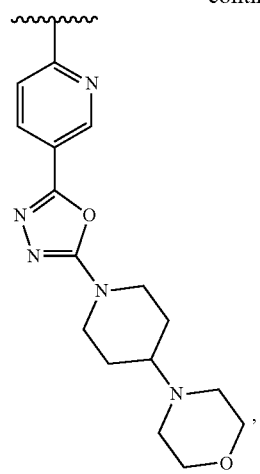
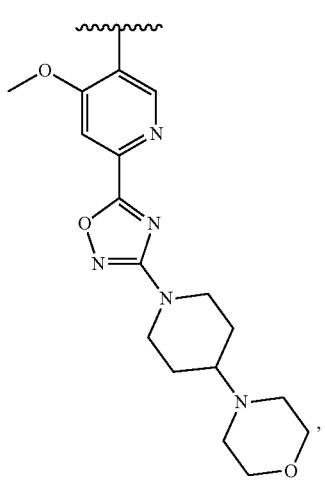
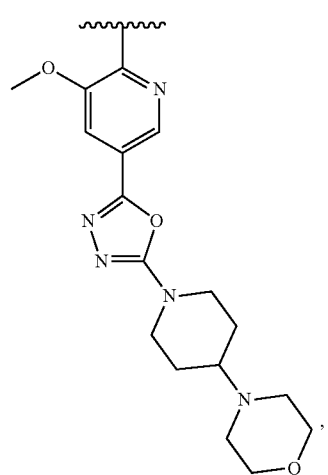
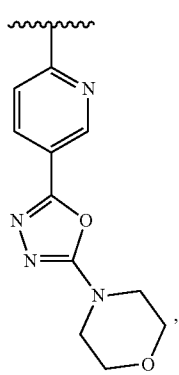 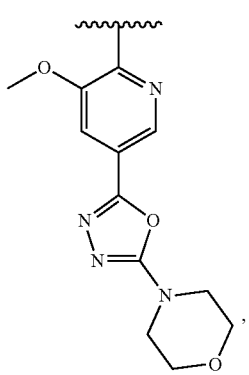
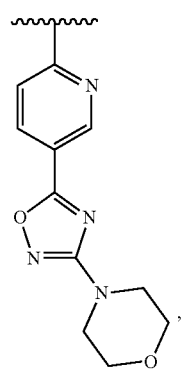 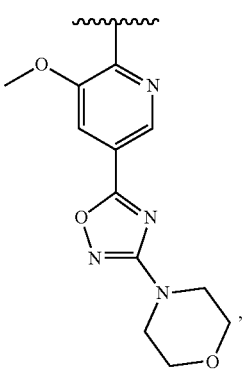

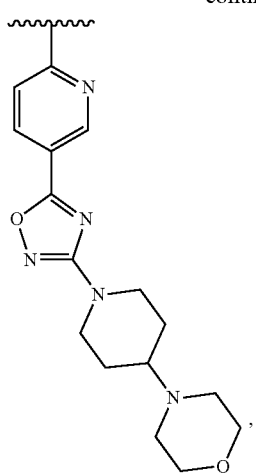
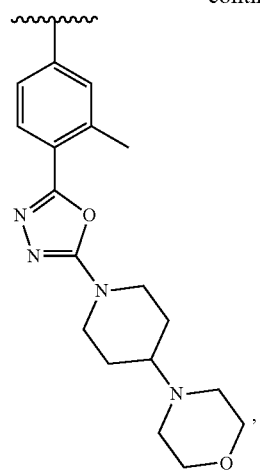
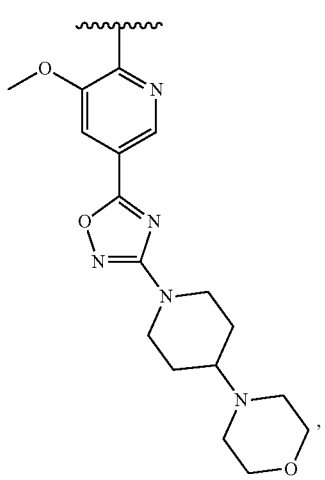
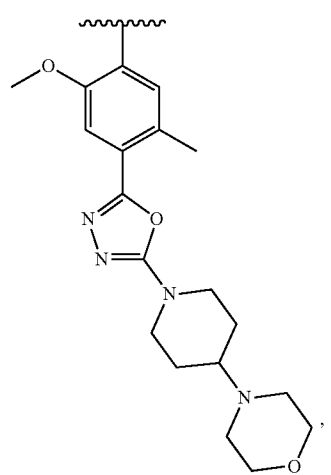
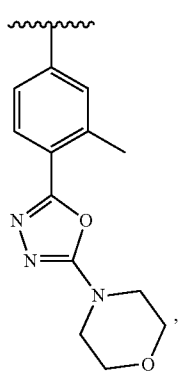
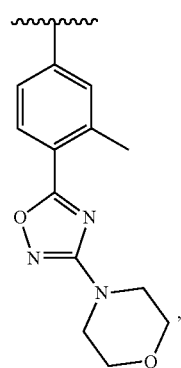

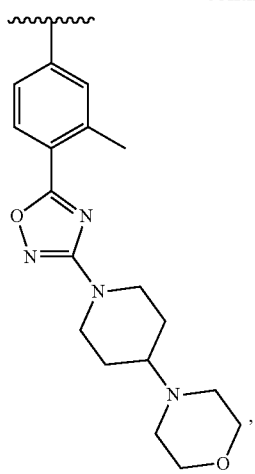
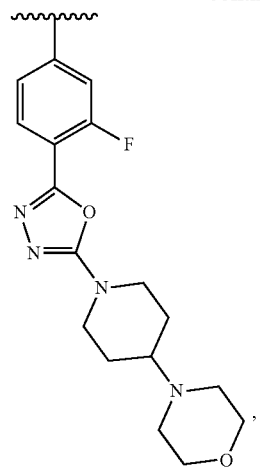
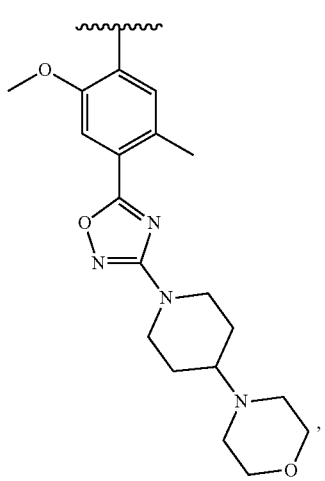
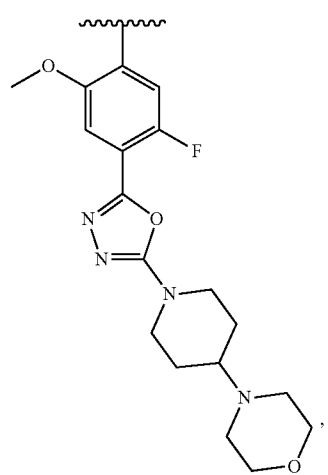
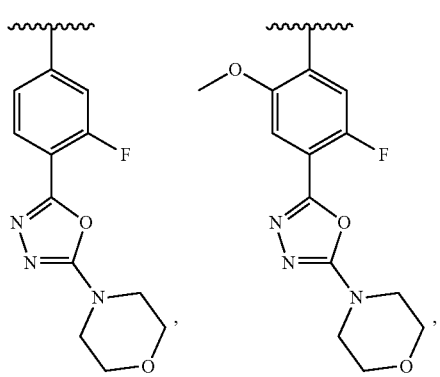
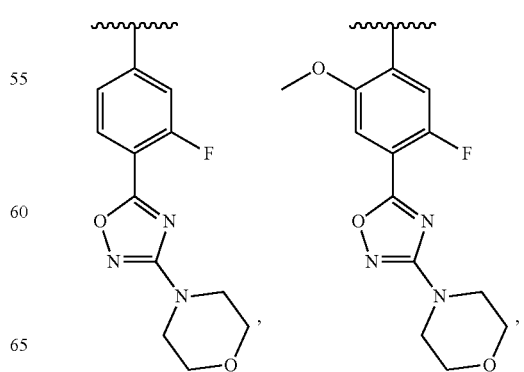

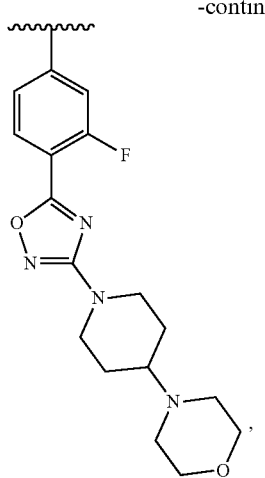
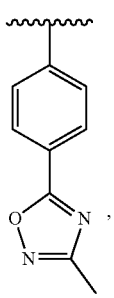 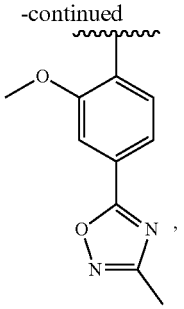
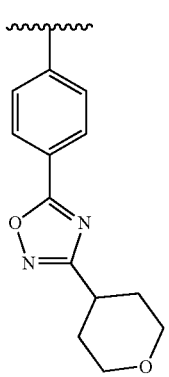 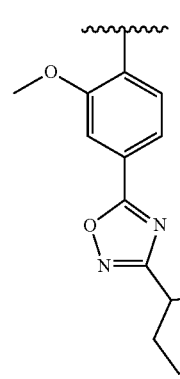
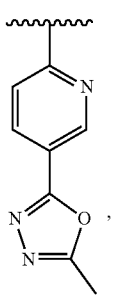 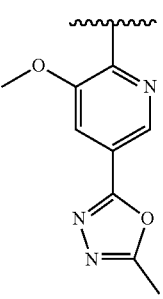
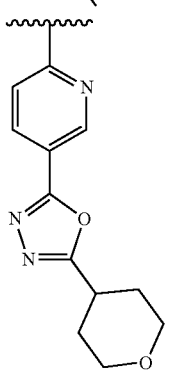 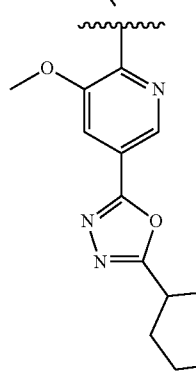
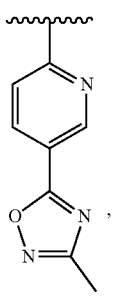 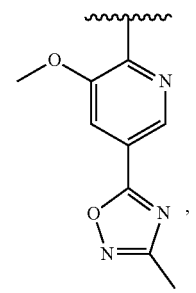

-continued
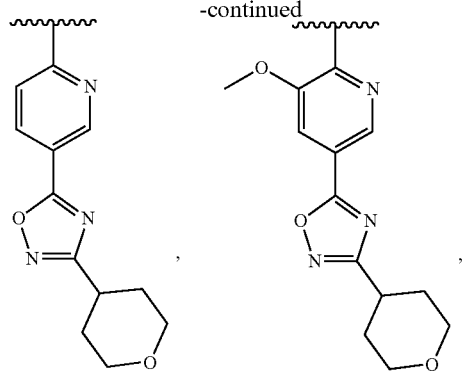
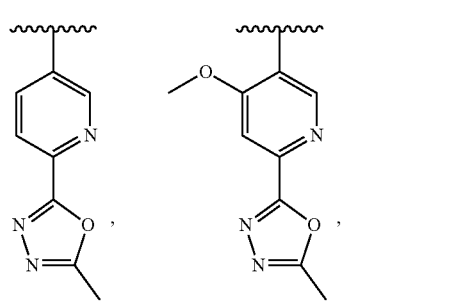
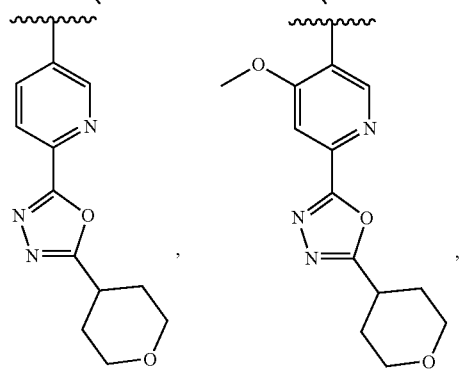
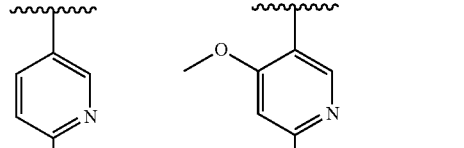
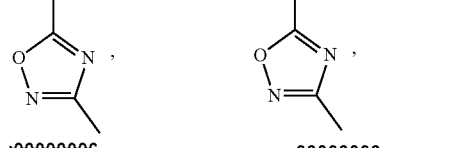
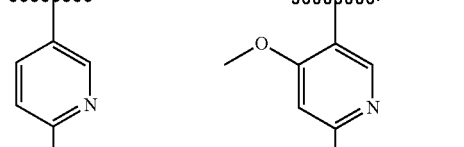
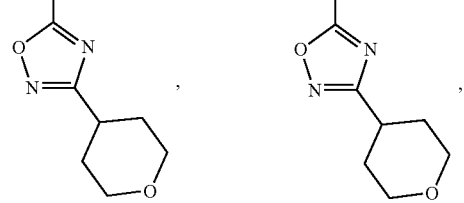
-continued
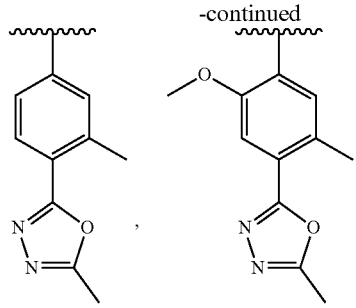
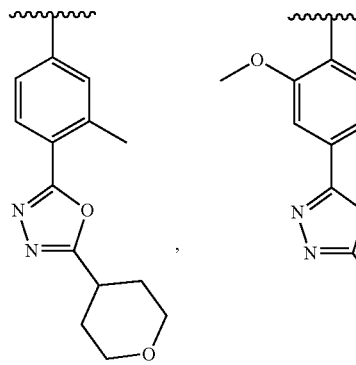
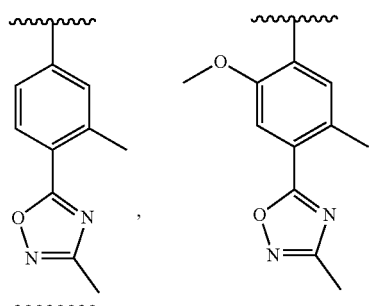
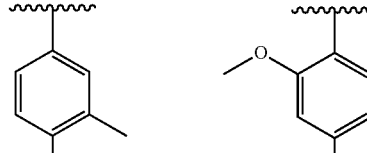
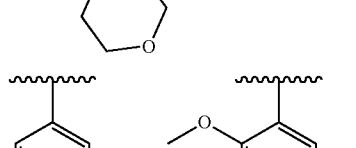
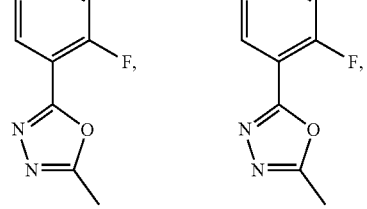

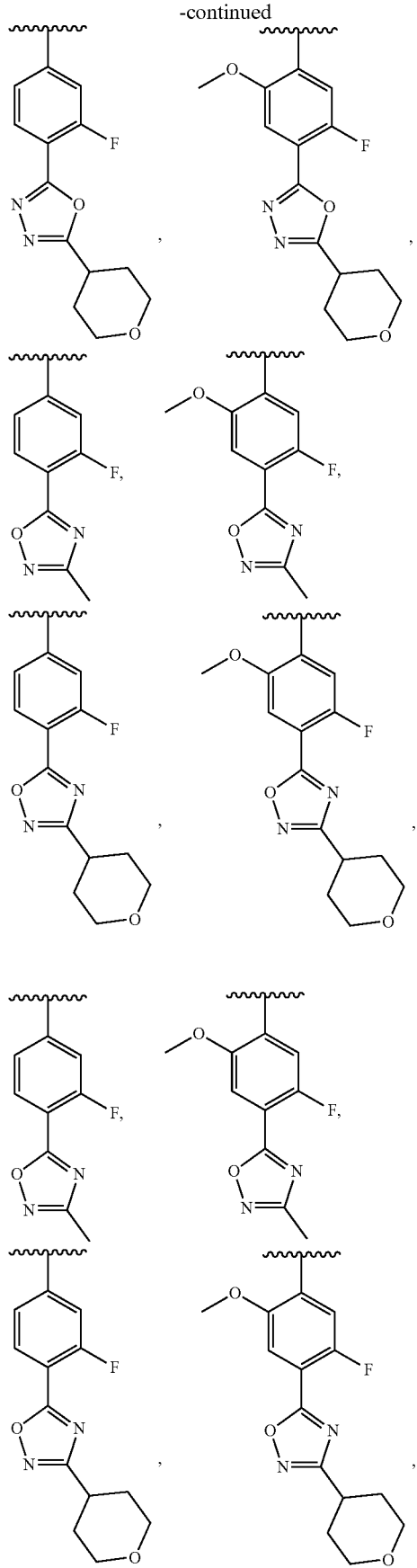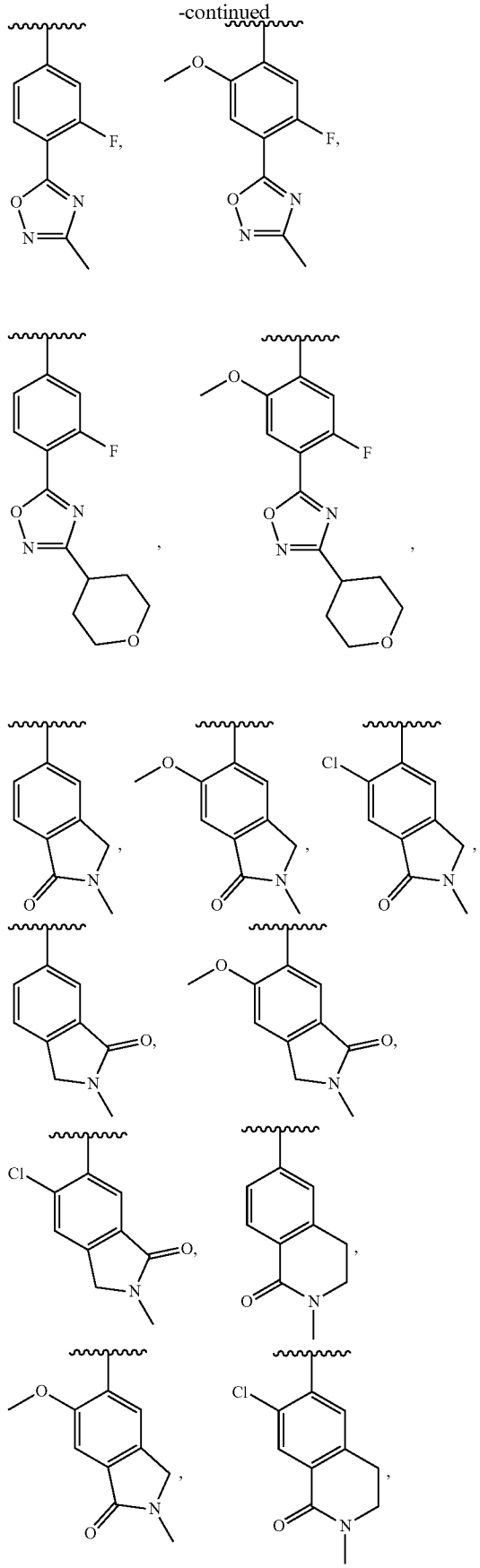

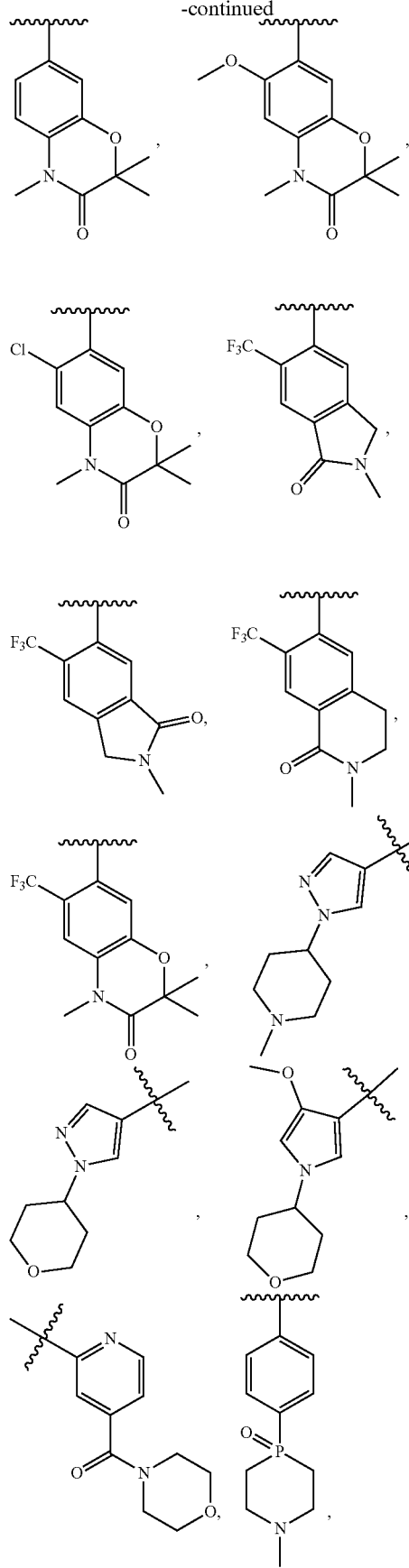
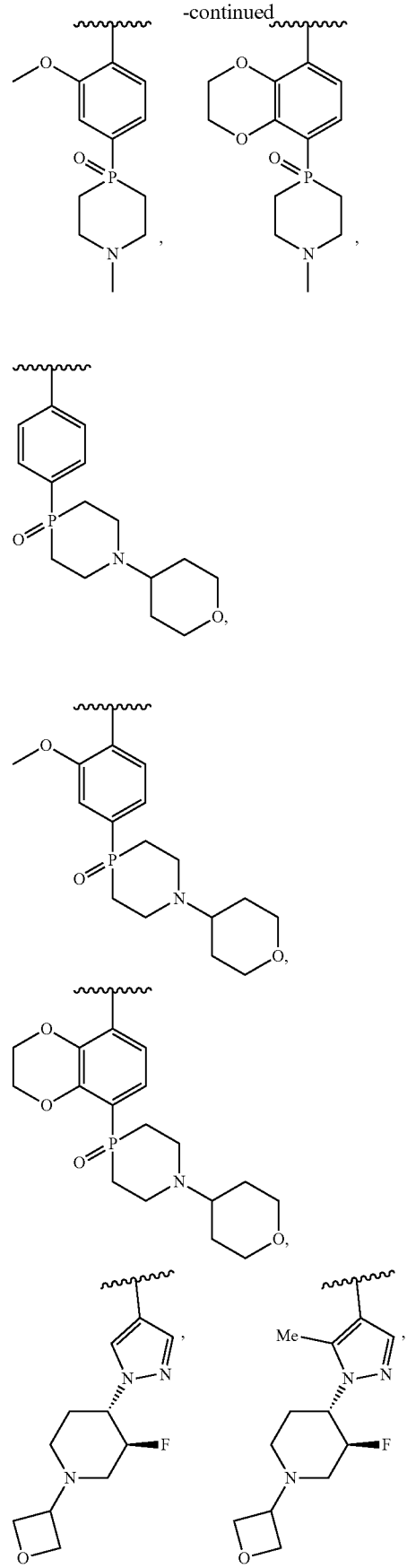

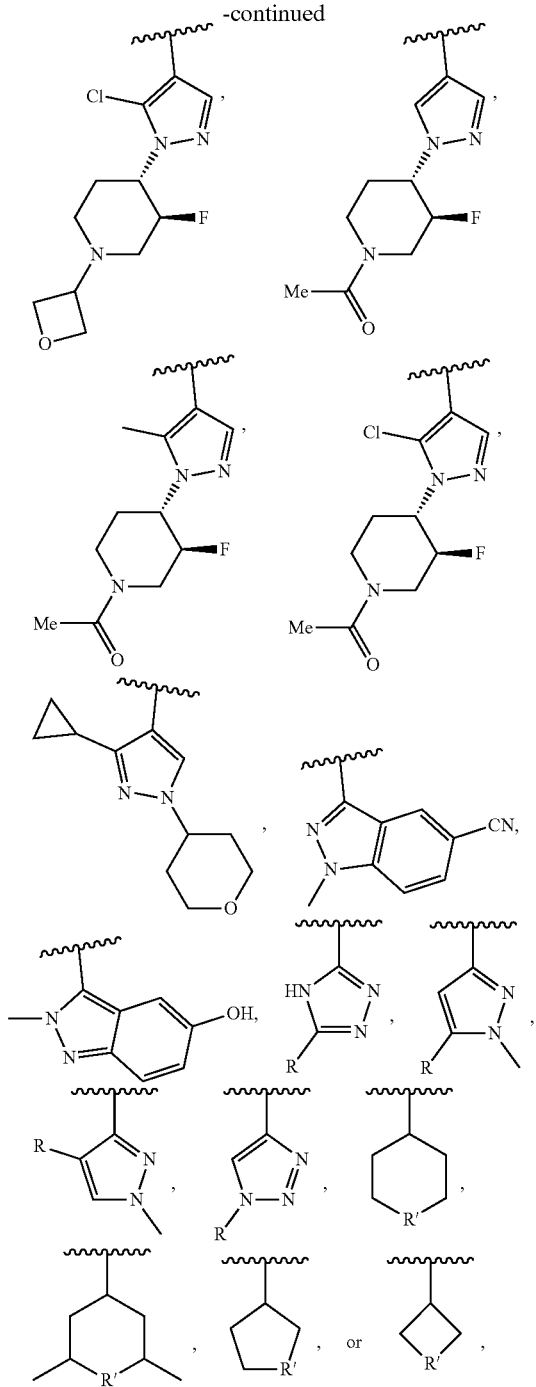

wherein R represents methyl, ethyl, isopropyl, cyclopropyl, or CF$_3$, and R' represents O, NH or NMe, R$_2$ represents H, halogen (e.g., F, Cl), or CF$_3$;

and Z represents CR$_3$, wherein R$_3$ represents

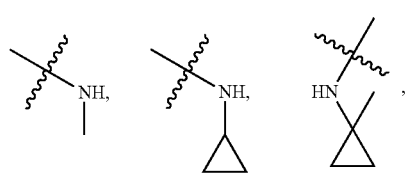

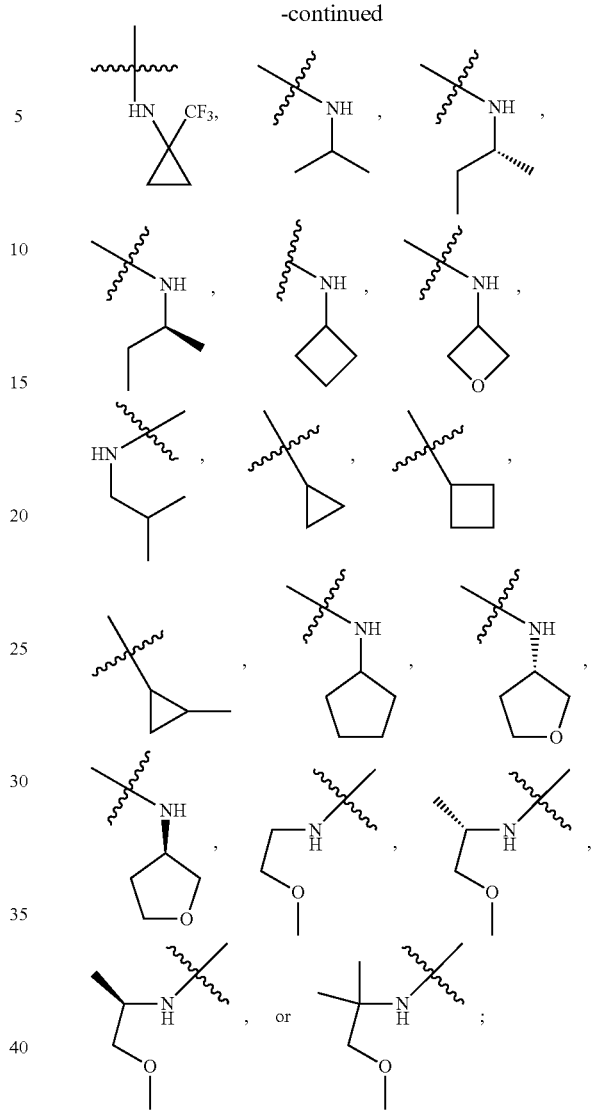

or a pharmaceutically acceptable salt or stereoisomer thereof.

In some embodiments, wherein X represents CR$_1$, Y represents CR$_2$, and Z represents CR$_3$, and wherein R$_1$, R$_2$, and R$_3$ are as described above, the inventive compounds have a structure represented by formula (Ia):

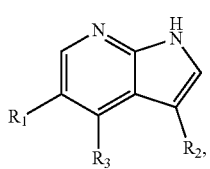

(Ia)

or a pharmaceutically acceptable salt or stereoisomer thereof.

In some embodiments, wherein X represents CR$_2$, Y represents CR$_1$, and Z represents CR$_3$, and wherein R$_1$, R$_2$, and R$_3$ are as described above, the inventive compounds have a structure represented by the following formula (Ib):

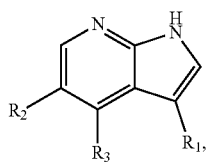
(Ib)
or a pharmaceutically acceptable salt or stereoisomer thereof.
In some embodiments, the compounds of the present invention are represented by any of the following structures:
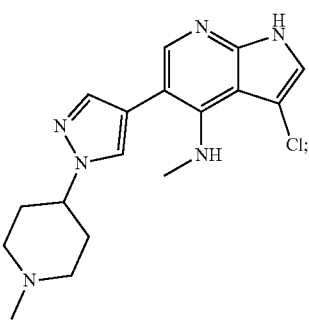
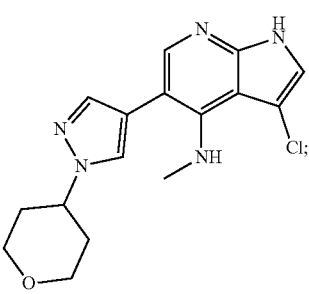
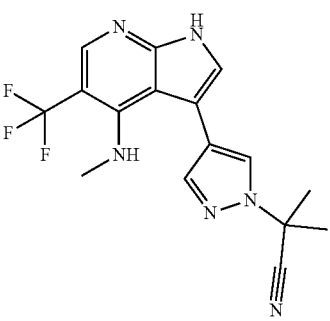
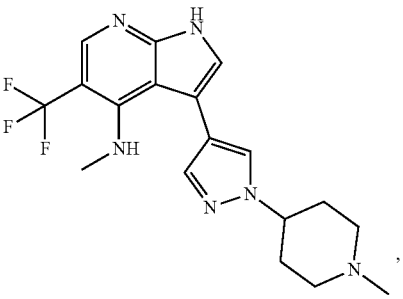
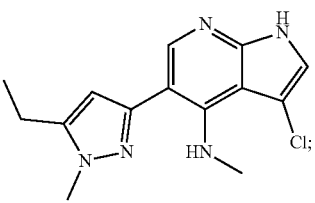

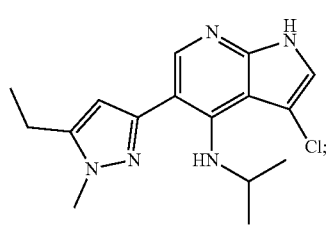
(10)
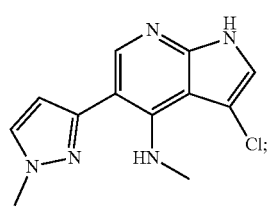
(11)
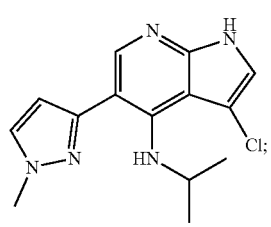
(12)
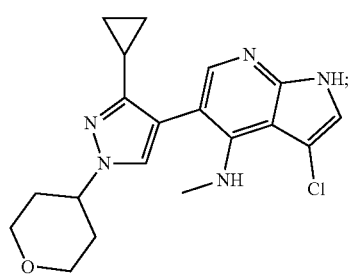
(13)
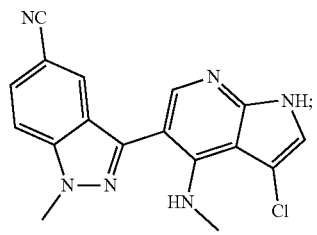
(14)
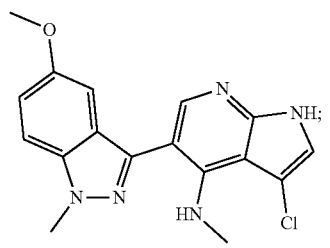
(15)
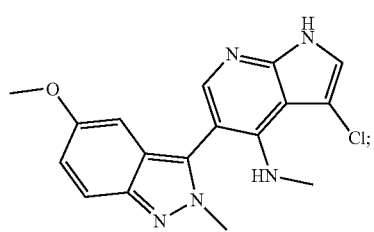
(16)
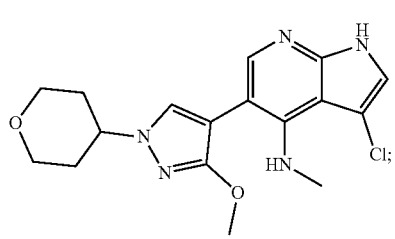
(17)
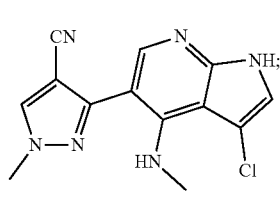
(18)
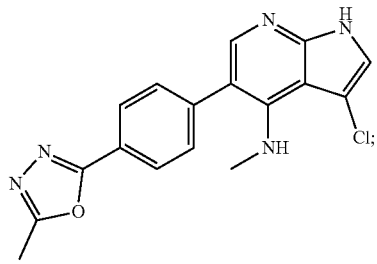
(19)
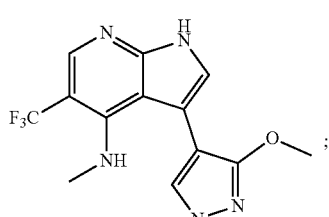
(20)
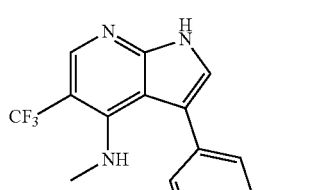
(21)
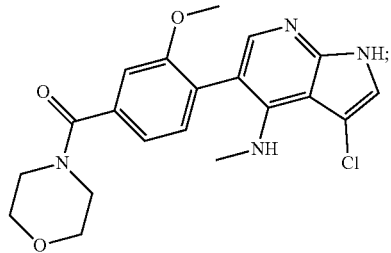
(22)

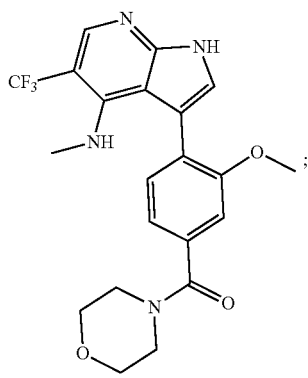
(23)
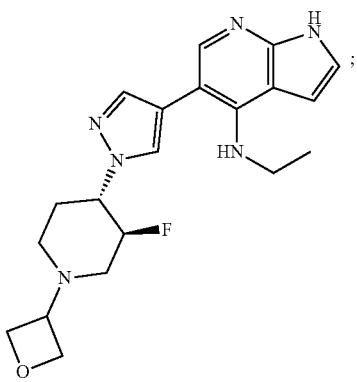
(27)
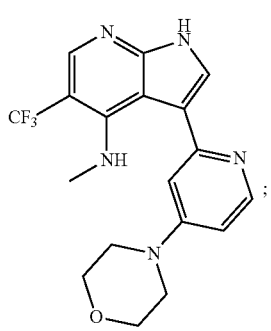
(24)
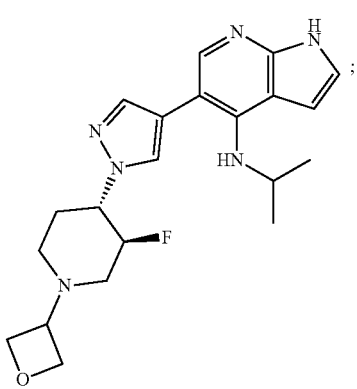
(28)
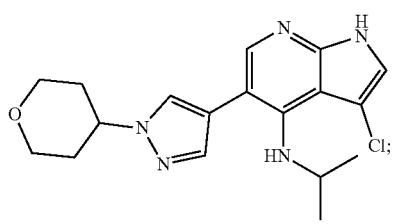
(25)
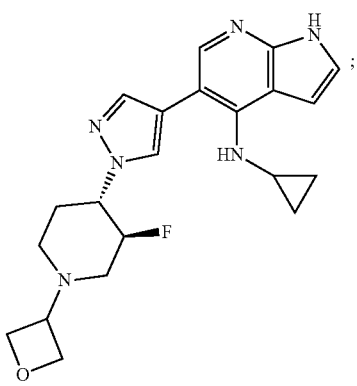
(29)
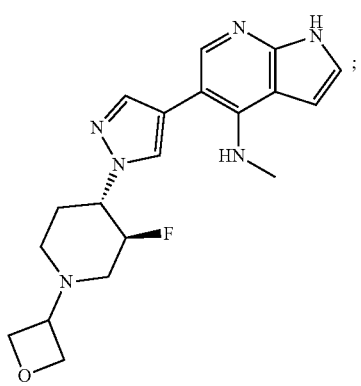
(26)
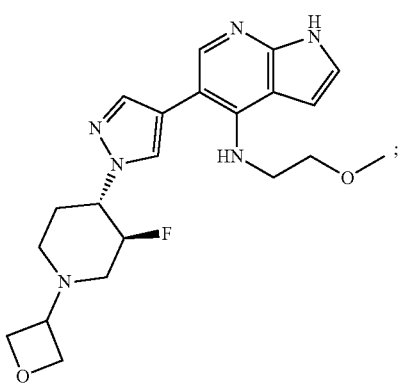
(30)

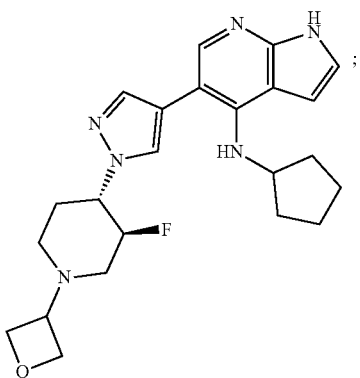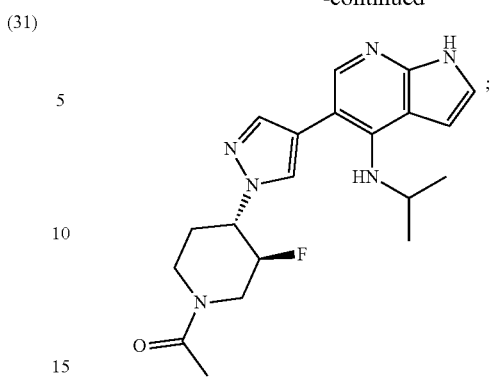

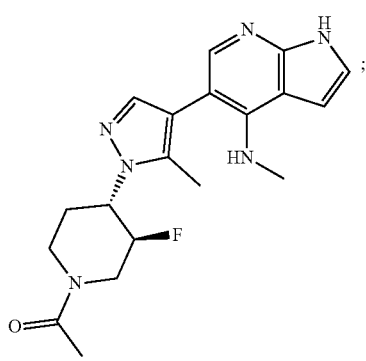
(39)
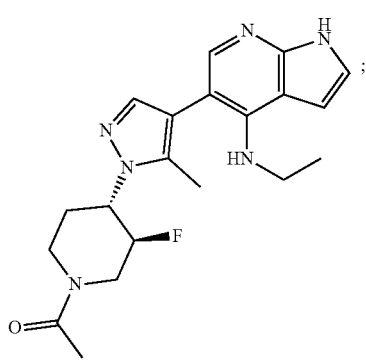
(40)
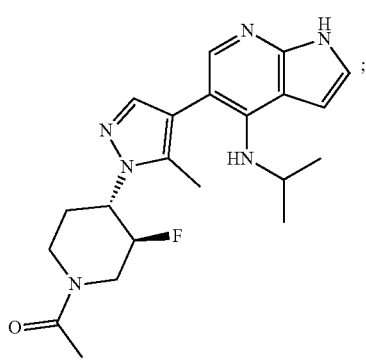
(41)
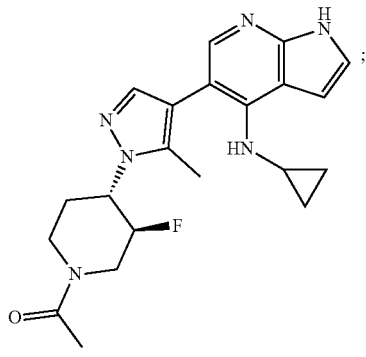
(42)
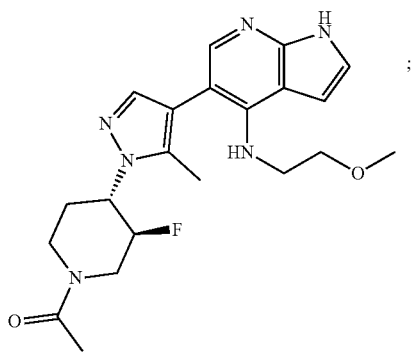
(43)
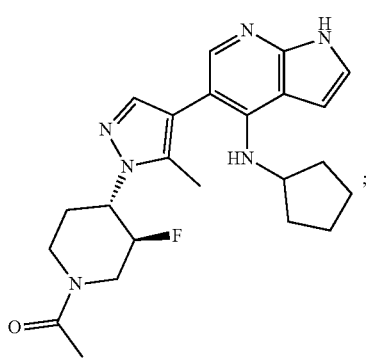
(44)
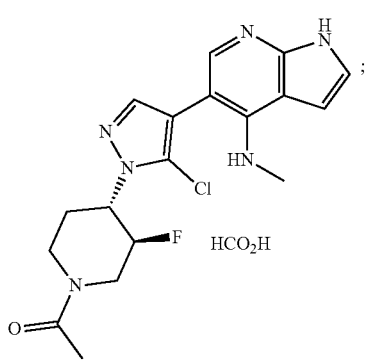
(45)
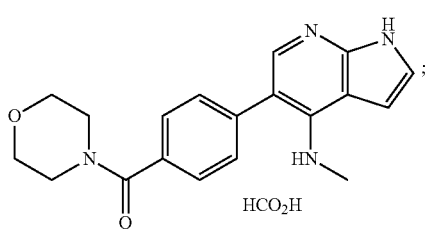
(46)
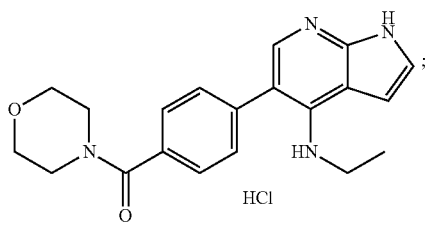
(47)

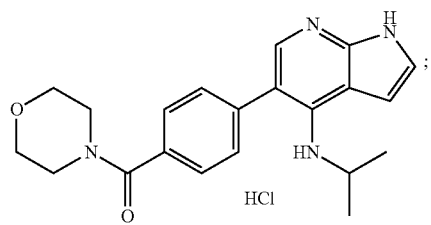
(48)
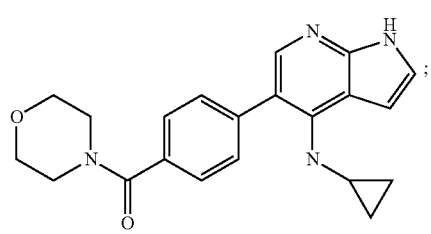
(49)
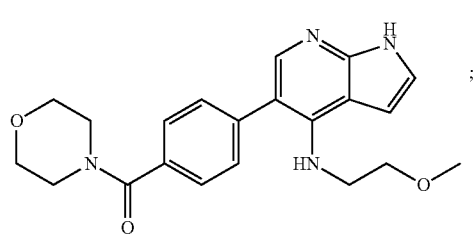
(50)
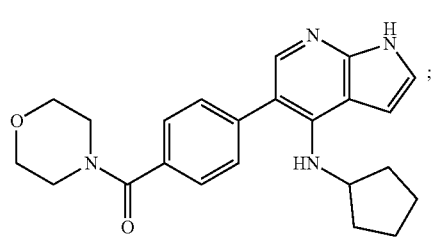
(51)
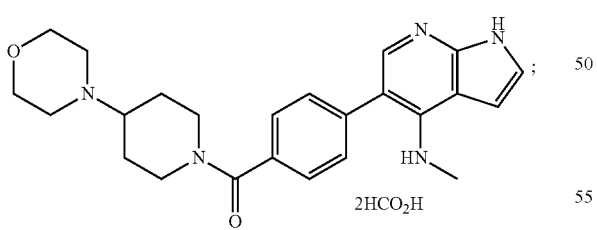
(52)
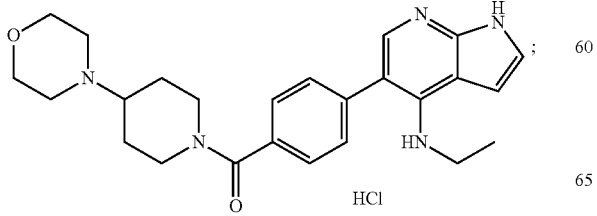
(53)
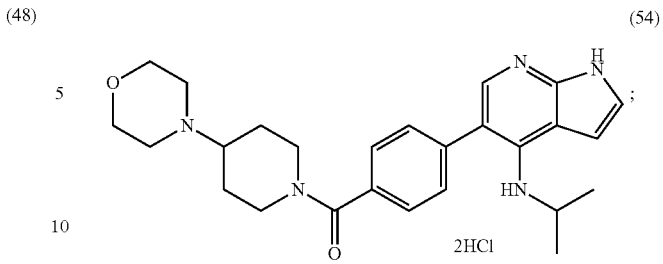
(54)
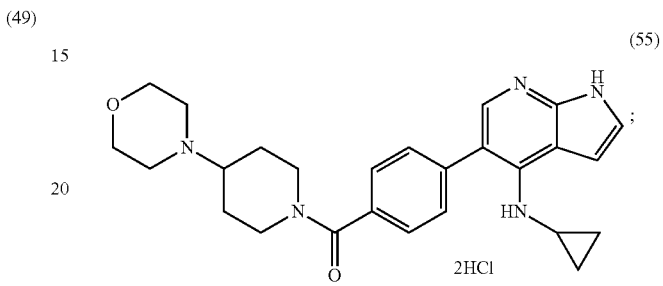
(55)
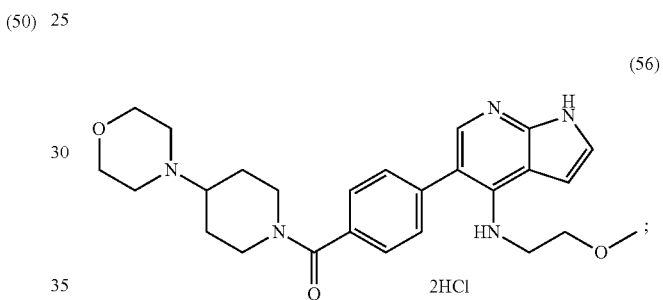
(56)
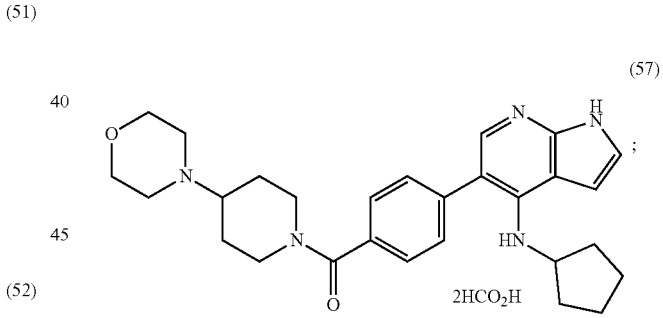
(57)
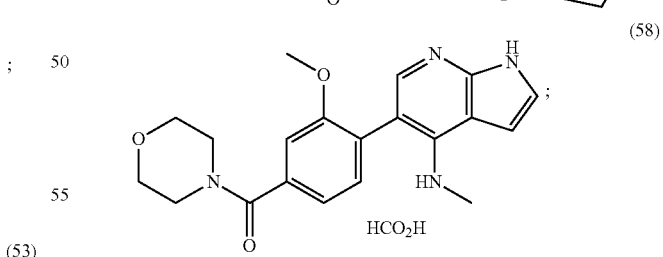
(58)
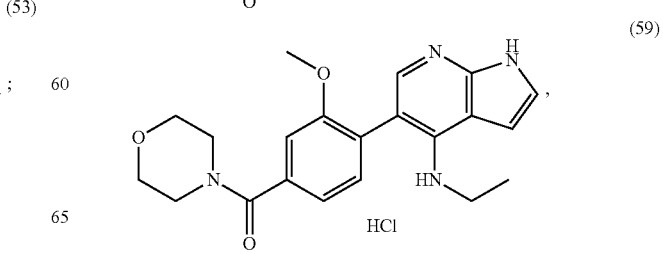
(59)

(60)
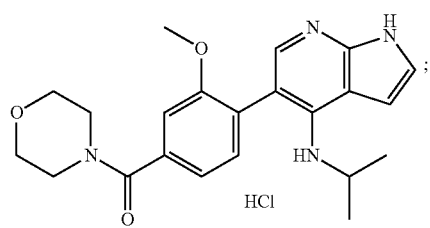
HCl
(66)
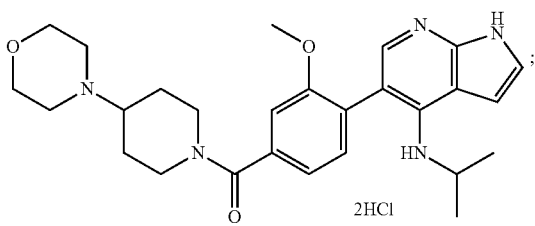
2HCl
(61)
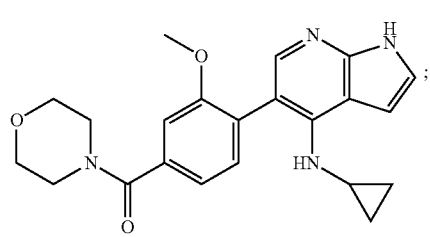
(67)
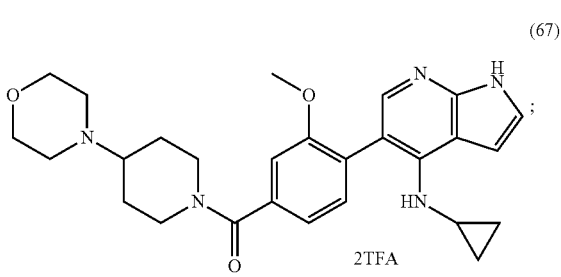
2TFA
(62)
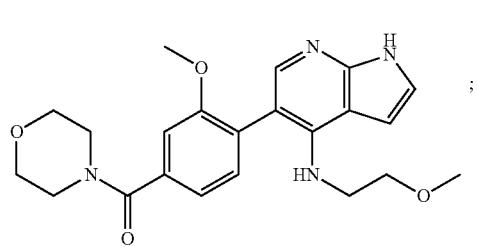
(68)
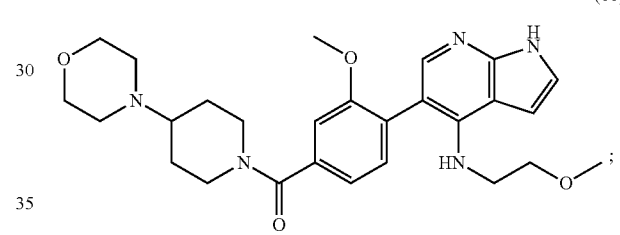
(63)
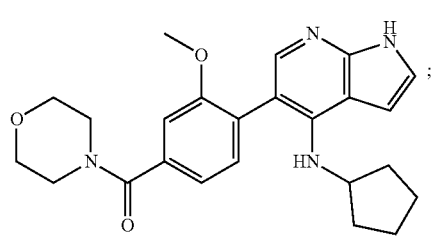
(69)
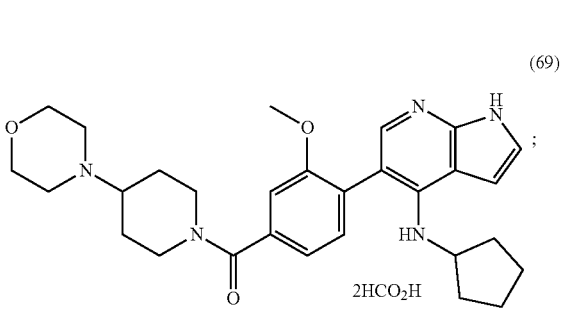
2HCO₂H
(64)
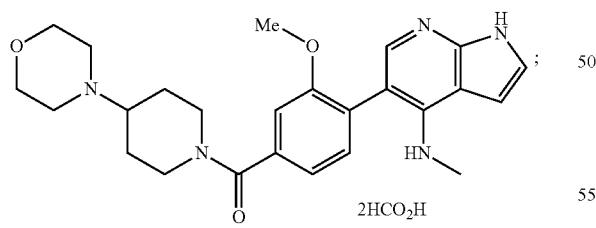
2HCO₂H
(70)
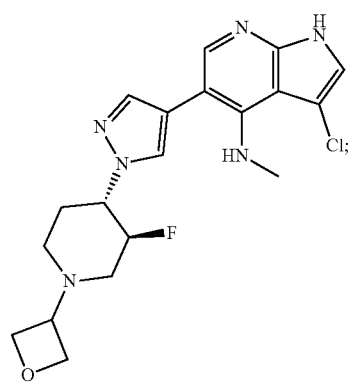
(65)
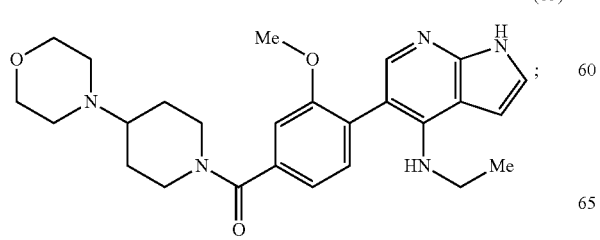

-continued
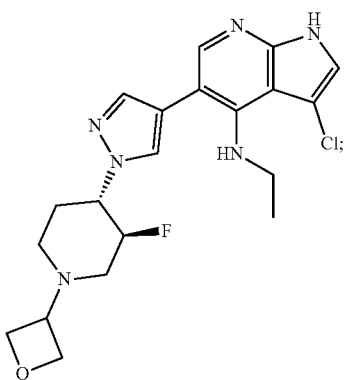
(71)
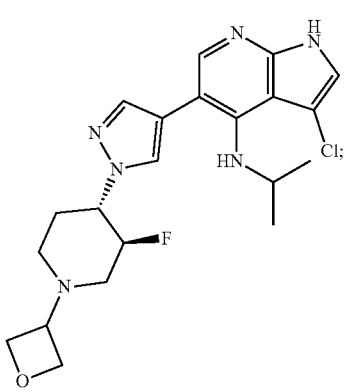
(72)
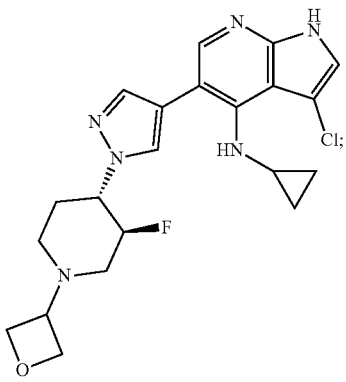
(73)
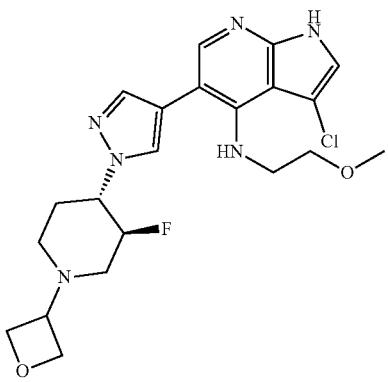
(74)
-continued
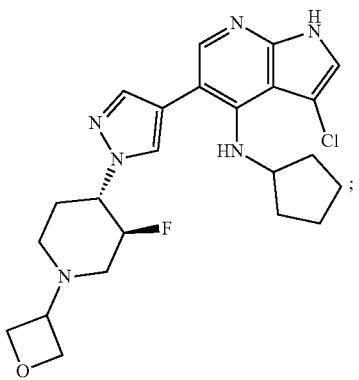
(75)
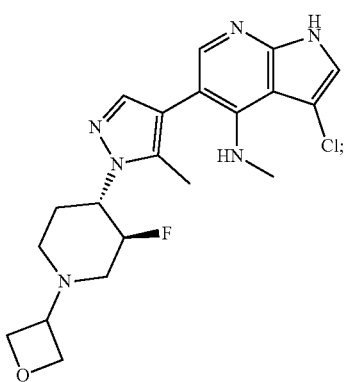
(76)
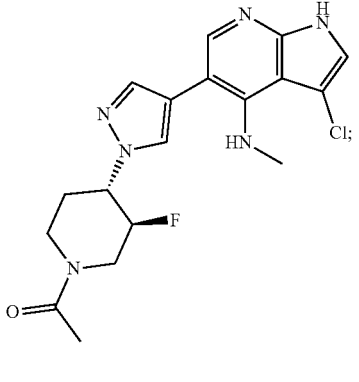
(77)
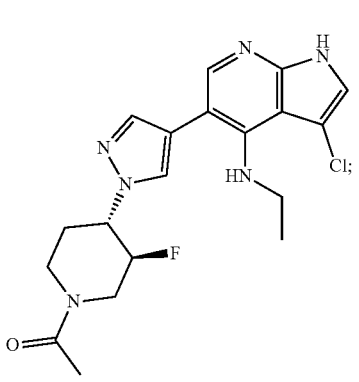
(78)

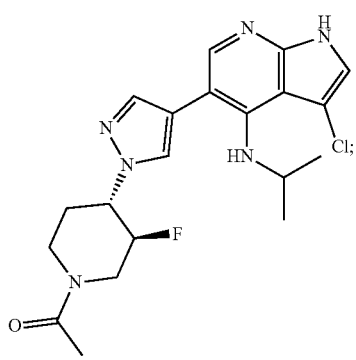
(79)
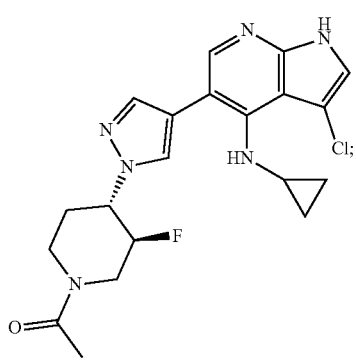
(80)
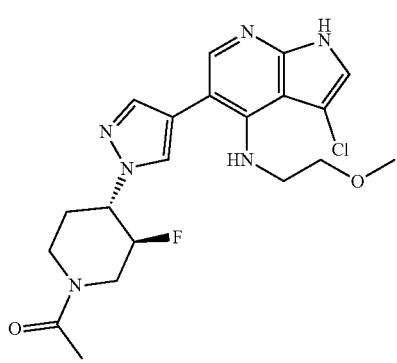
(81)
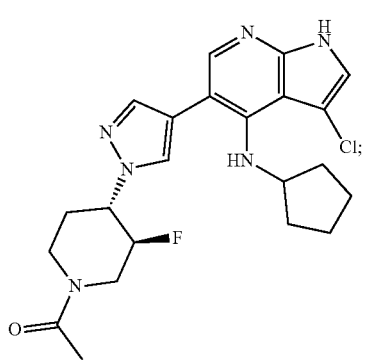
(82)
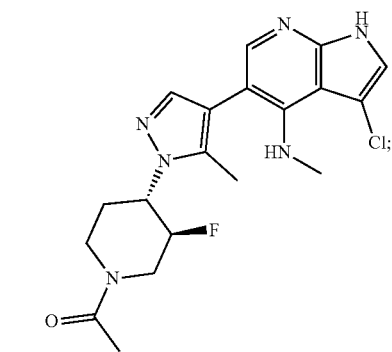
(83)
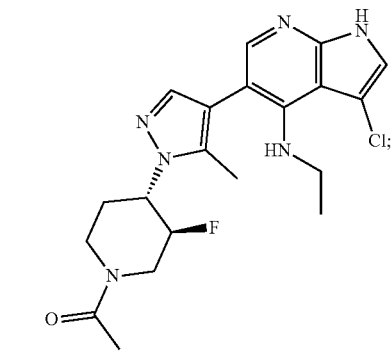
(84)
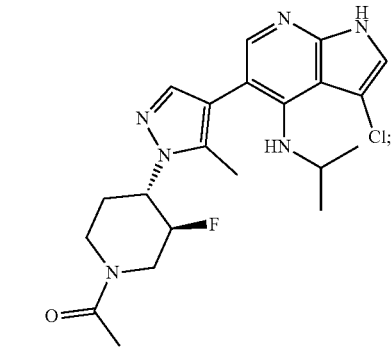
(85)
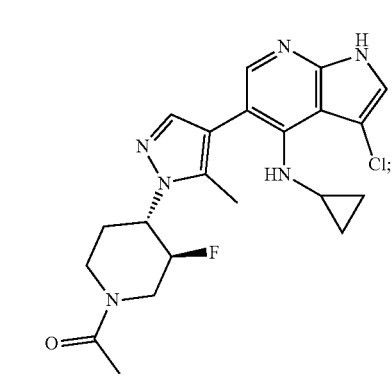
(86)

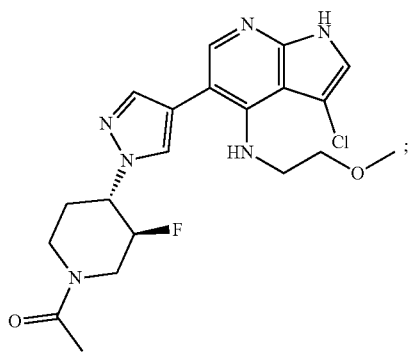 (87)
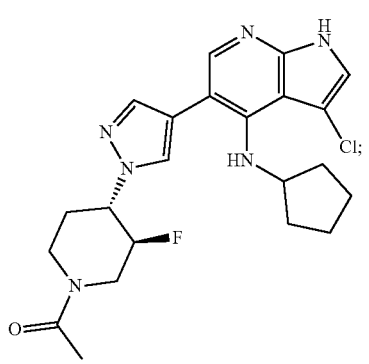 (88)
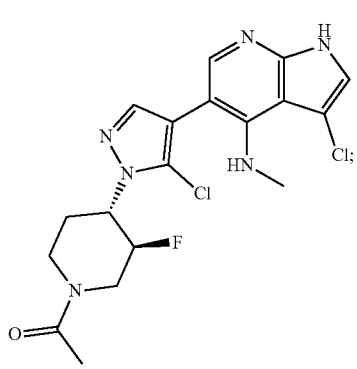 (89)
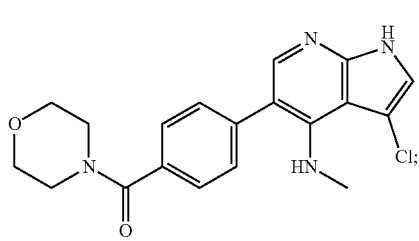 (90)
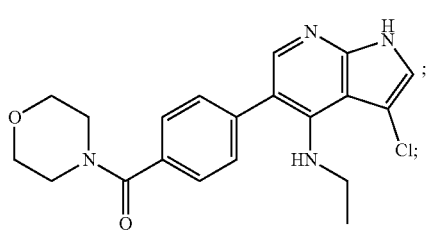 (91)
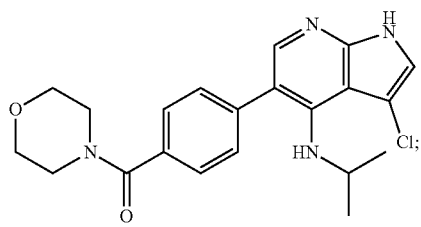 (92)
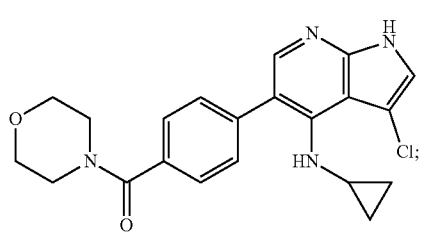 (93)
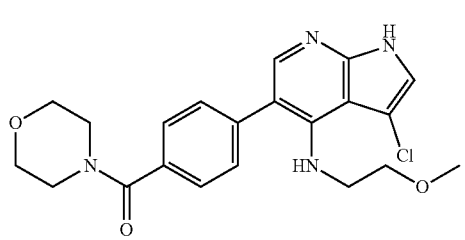 (94)
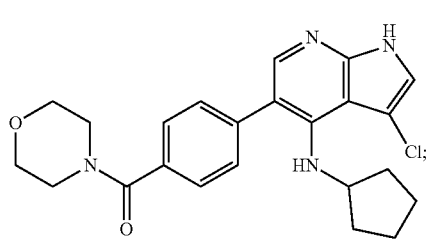 (95)
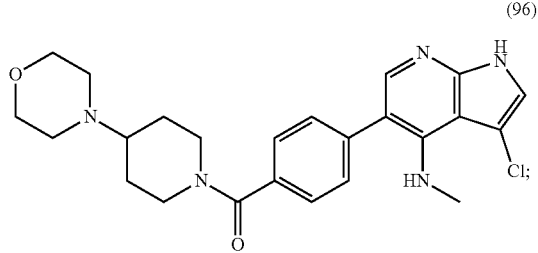 (96)
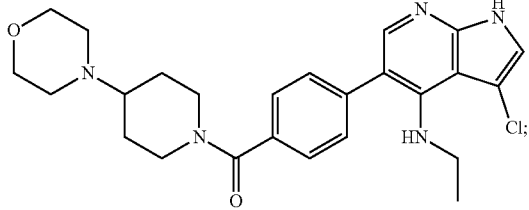 (97)

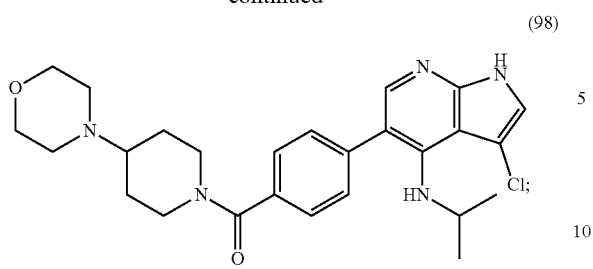
(98)
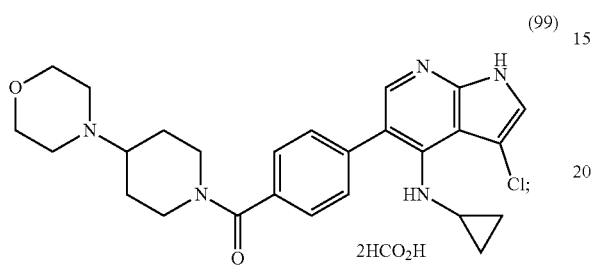
(99)
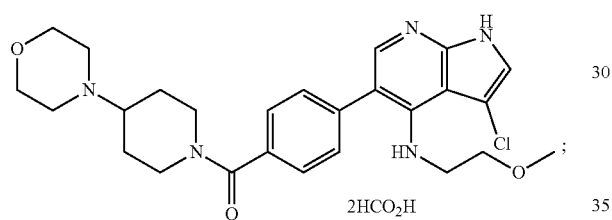
(100)
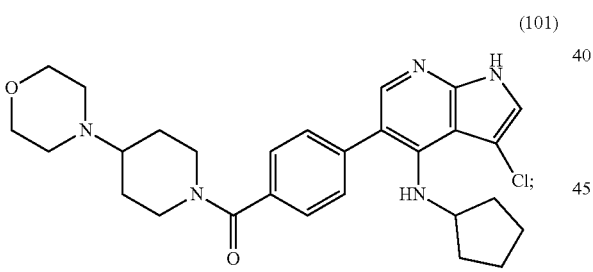
(101)
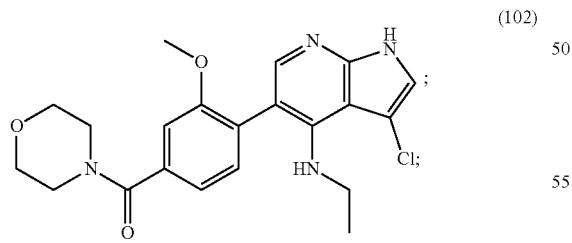
(102)
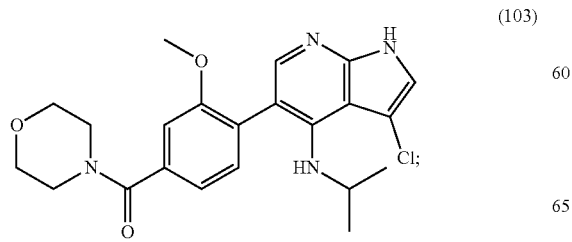
(103)
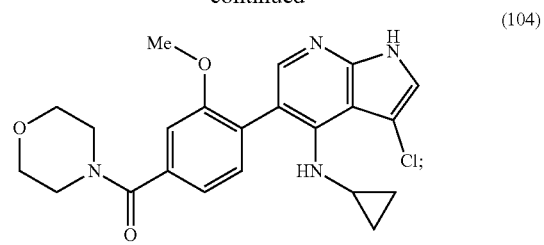
(104)
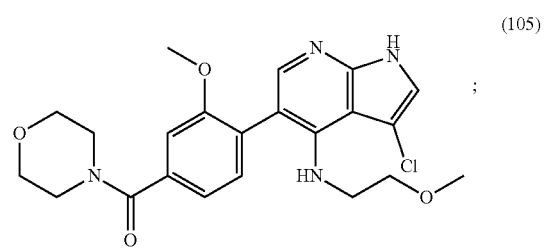
(105)
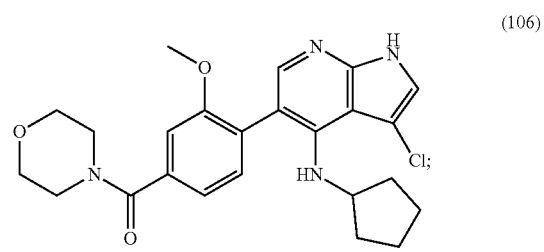
(106)
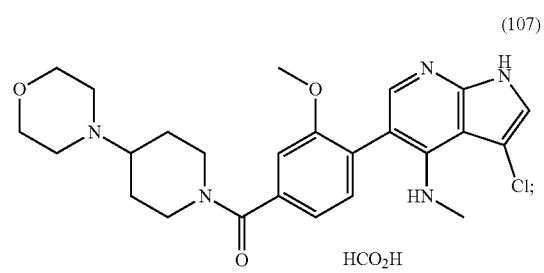
(107)
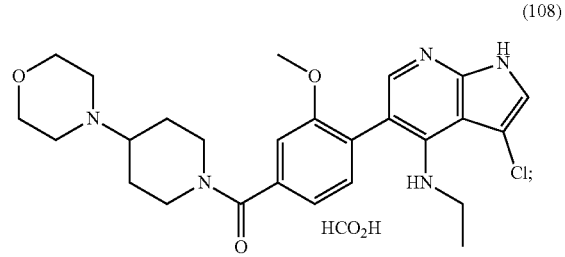
(108)
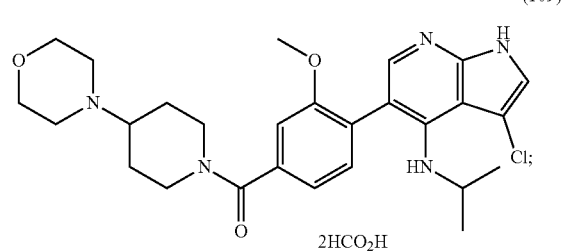
(109)

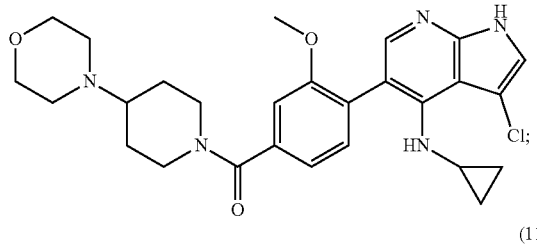

(110)

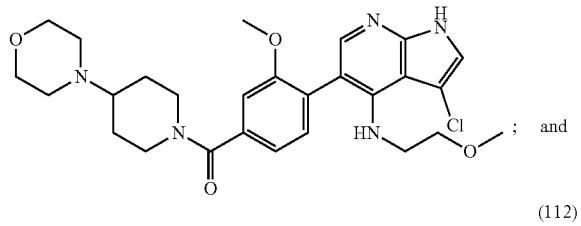

(111)

and

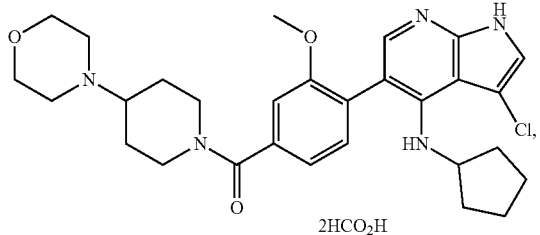

(112)

2HCO$_2$H or pharmaceutically acceptable salts and stereoisomers thereof.

Compounds of formula (I) may be in the form of a free acid or free base, or a pharmaceutically acceptable salt. As used herein, the term "pharmaceutically acceptable" in the context of a salt refers to a salt of the compound that does not abrogate the biological activity or properties of the compound, and is relatively non-toxic, i.e., the compound in salt form may be administered to a subject without causing undesirable biological effects (such as dizziness or gastric upset) or interacting in a deleterious manner with any of the other components of the composition in which it is contained. The term "pharmaceutically acceptable salt" refers to a product obtained by reaction of the compound of the present invention with a suitable acid or a base. Examples of pharmaceutically acceptable salts of the compounds of this invention include those derived from suitable inorganic bases such as Li, Na, K, Ca, Mg, Fe, Cu, Al, Zn and Mn salts. Examples of pharmaceutically acceptable, nontoxic acid addition salts are salts of an amino group formed with inorganic acids such as hydrochloride, hydrobromide, hydroiodide, nitrate, sulfate, bisulfate, phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, 4-methylbenzenesulfonate or p-toluenesulfonate salts and the like. Certain compounds of the invention can form pharmaceutically acceptable salts with various organic bases such as lysine, arginine, guanidine, diethanolamine or metformin.

Compounds of formula (I) may have at least one chiral center and thus may be in the form of a stereoisomer, which as used herein, embraces all isomers of individual compounds that differ only in the orientation of their atoms in space. The term stereoisomer includes mirror image isomers (enantiomers which include the (R-) or (S-) configurations of the compounds), mixtures of mirror image isomers (physical mixtures of the enantiomers, and racemates or racemic mixtures) of compounds, geometric (cis/trans or E/Z, R/S) isomers of compounds and isomers of compounds with more than one chiral center that are not mirror images of one another (diastereoisomers). The chiral centers of the compounds may undergo epimerization in vivo; thus, for these compounds, administration of the compound in its (R-) form is considered equivalent to administration of the compound in its (S-) form. Accordingly, the compounds of the present invention may be made and used in the form of individual isomers and substantially free of other isomers, or in the form of a mixture of various isomers, e.g., racemic mixtures of stereoisomers.

In some embodiments, the compound formula (I) is an isotopic derivative in that it has at least one desired isotopic substitution of an atom, at an amount above the natural abundance of the isotope, i.e., enriched. In one embodiment, the compound includes deuterium or multiple deuterium atoms. Substitution with heavier isotopes such as deuterium, i.e. $^2$H, may afford certain therapeutic advantages resulting from greater metabolic stability, for example, increased in vivo half-life or reduced dosage requirements, and thus may be advantageous in some circumstances.

In addition, compounds of formula (I) embrace the use of N-oxides, crystalline forms (also known as polymorphs), active metabolites of the compounds having the same type of activity, tautomers, and unsolvated as well as solvated forms with pharmaceutically acceptable solvents such as water, ethanol, and the like, of the compounds. The solvated forms of the conjugates presented herein are also considered to be disclosed herein.

Methods of Synthesis

In some aspects, the present invention is directed to a method for making a compound of formula (I) or a pharmaceutically acceptable salt or stereoisomer thereof, of the invention. Broadly, compounds of formula (I) and pharmaceutically-acceptable salts or stereoisomers thereof may be prepared by any process known to be applicable to the preparation of chemically related compounds. The compounds of the present invention will be better understood in connection with the synthetic schemes that described in various working examples and which illustrate non-limiting methods by which the compounds of the invention may be prepared.

Pharmaceutical Compositions

In another aspect, the present invention is directed to a pharmaceutical composition that includes a therapeutically effective amount of a compound of formula (I) or a pharmaceutically acceptable salt or stereoisomer thereof, and a pharmaceutically acceptable carrier. The compounds of the present invention may be formulated into several different types of pharmaceutical compositions, appropriate for any desired mode of administration, and that contain a therapeutically effective amount of the compound, and a pharmaceutically acceptable carrier.

Broadly, compounds of formula (I) may be formulated into a given type of composition in accordance with conventional pharmaceutical practice such as conventional mixing, dissolving, granulating, dragee-making, levigating, emulsifying, encapsulating, entrapping and compression processes (see, e.g., Remington: *The Science and Practice of Pharmacy* (20th ed.), ed. A. R. Gennaro, Lippincott Williams & Wilkins, 2000 and *Encyclopedia of Pharmaceutical Technology*, eds. J. Swarbrick and J. C. Boylan, 1988-1999, Marcel Dekker, New York). The type of formulation depends on the mode of administration which may include enteral (e.g., oral, buccal, sublingual and rectal), parenteral (e.g., subcutaneous (s.c.), intravenous (i.v.), intramuscular (i.m.), and intrasternal injection, or infusion techniques, intra-ocular, intra-arterial, intramedullary, intrathecal, intraventricular, transdermal, interdermal, intravaginal, intraperitoneal, mucosal, nasal, intratracheal instillation, bronchial instillation, and inhalation) and topical (e.g., transdermal). In general, the most appropriate route of administration will depend upon a variety of factors including, for example, the nature of the agent (e.g., its stability in the environment of the gastrointestinal tract), and/or the condition of the subject (e.g., whether the subject is able to tolerate oral administration). For example, parenteral (e.g., intravenous) administration may also be advantageous in that the compound may be administered relatively quickly such as in the case of a single-dose treatment and/or an acute condition.

In some embodiments, the compounds are formulated for oral or intravenous administration (e.g., systemic intravenous injection).

The term "pharmaceutically acceptable carrier," as known in the art, refers to a pharmaceutically acceptable material, composition or vehicle, suitable for administering compounds of the present invention to mammals. Suitable carriers may include, for example, liquids (both aqueous and non-aqueous alike, and combinations thereof), solids, encapsulating materials, gases, and combinations thereof (e.g., semi-solids), that function to carry or transport the compound from one organ, or portion of the body, to another organ, or portion of the body. A carrier is "acceptable" in the sense of being physiologically inert to and compatible with the other ingredients of the formulation, and which are non-toxic to the subject or patient. Depending on the type of formulation, the composition may include one or more pharmaceutically acceptable excipients.

Accordingly, compounds of formula (I) may be formulated into solid compositions (e.g., powders, tablets, dispersible granules, capsules, cachets, and suppositories), liquid compositions (e.g., solutions in which the compound is dissolved, suspensions in which solid particles of the compound are dispersed, emulsions, and solutions containing liposomes, micelles, or nanoparticles, syrups and elixirs); semi-solid compositions (e.g., gels, suspensions and creams); and gases (e.g., propellants for aerosol compositions). Compounds may also be formulated for rapid, intermediate or extended release.

Solid dosage forms for oral administration include capsules, tablets, pills, powders, and granules. In such solid dosage forms, the active compound is mixed with a carrier such as sodium citrate or dicalcium phosphate and an additional carrier or excipient such as: a) fillers or extenders such as starches, lactose, sucrose, glucose, mannitol, and silicic acid, b) binders such as, for example, methylcellulose, microcrystalline cellulose, hydroxypropylmethylcellulose, carboxymethylcellulose, sodium carboxymethylcellulose, alginates, gelatin, polyvinylpyrrolidinone, sucrose, and acacia, c) humectants such as glycerol, d) disintegrating agents such as crosslinked polymers (e.g., crosslinked polyvinylpyrrolidone (crospovidone), crosslinked sodium carboxymethyl cellulose (croscarmellose sodium), sodium starch glycolate, agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also include buffering agents. Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings. They may further contain an opacifying agent.

In some embodiments, compounds of formula (I) may be formulated in a hard or soft gelatin capsule. Representative excipients that may be used include pregelatinized starch, magnesium stearate, mannitol, sodium stearyl fumarate, lactose anhydrous, microcrystalline cellulose and croscarmellose sodium. Gelatin shells may include gelatin, titanium dioxide, iron oxides and colorants.

In some embodiments, compounds of formula (I) may be formulated into tablets that may include excipients such as lactose monohydrate, microcrystalline cellulose, sodium starch glycolate, magnesium tartrate, and hydrophobic colloidal silica.

They may be formulated as solutions for parenteral and oral delivery forms, particularly to the extent that they are water-soluble. Parenteral administration may also be advantageous in that the compound may be administered relatively quickly such as in the case of a single-dose treatment and/or an acute condition.

Injectable preparations for parenteral administration may include sterile aqueous solutions or oleaginous suspensions. They may be formulated according to standard techniques using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables. The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use. The effect of the compound may be prolonged by slowing its absorption, which may be accomplished by the use of a liquid suspension or crystalline or amorphous material with poor water solubility. Prolonged absorption of the compound from a parenterally administered formulation may also be accomplished by suspending the compound in an oily vehicle.

In certain embodiments, compounds of formula (I) may be administered in a local rather than systemic manner, for example, via injection of the conjugate directly into an organ, often in a depot preparation or sustained release formulation. In specific embodiments, long acting formulations are administered by implantation (for example subcutaneously or intramuscularly) or by intramuscular injection. Injectable depot forms are made by forming microencapsule matrices of the compound in a biodegradable polymer, e.g., polylactide-polyglycolides, poly(orthoesters) and poly(anhydrides). The rate of release of the compound may be controlled by varying the ratio of compound to polymer and the nature of the particular polymer employed. Depot injectable formulations are also prepared by entrapping the compound in liposomes or microemulsions that are compatible with body tissues. Furthermore, in other embodiments, the compound is delivered in a targeted drug delivery system, for example, in a liposome coated with organ-specific antibody. In such embodiments, the liposomes are targeted to and taken up selectively by the organ.

Liquid dosage forms for oral administration include solutions, dispersions, suspensions, emulsions, micro-emulsions, syrups and elixirs. In addition to the compound, the liquid dosage forms may contain an aqueous or non-aqueous carrier (depending upon the solubility of the compounds) commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Oral compositions may also include excipients such as wetting agents, suspending agents, coloring, sweetening, flavoring, and perfuming agents.

The compounds may be formulated for buccal or sublingual administration, examples of which include tablets, lozenges and gels.

Compounds of formula (I) may be formulated for administration by inhalation. Various forms suitable for administration by inhalation include aerosols, mists and powders. Pharmaceutical compositions may be delivered in the form of an aerosol spray presentation from pressurized packs or a nebulizer, with the use of a suitable gaseous propellant (e.g., dichlorodifluoromethane, trichlorofluoromethane, dichlorotetrafluoroethane, carbon dioxide or other suitable gas). In some embodiments, the dosage unit of a pressurized aerosol may be determined by providing a valve to deliver a metered amount. In some embodiments, capsules and cartridges including gelatin, for example, for use in an inhaler or insufflator, may be formulated containing a powder mix of the compound and a suitable powder base such as lactose or starch.

Compounds of formula (I) may be formulated for topical administration which as used herein, refers to administration intradermally by application of the formulation to the epidermis. These types of compositions are typically in the form of ointments, pastes, creams, lotions, gels, solutions and sprays.

Representative examples of carriers useful in formulating compositions for topical application include solvents (e.g., alcohols, poly alcohols, water), creams, lotions, ointments, oils, plasters, liposomes, powders, emulsions, microemulsions, and buffered solutions (e.g., hypotonic or buffered saline). Creams, for example, may be formulated using saturated or unsaturated fatty acids such as stearic acid, palmitic acid, oleic acid, palmito-oleic acid, cetyl, or oleyl alcohols. Creams may also contain a non-ionic surfactant such as polyoxy-40-stearate.

In some embodiments, the topical formulations may also include an excipient, an example of which is a penetration enhancing agent. These agents are capable of transporting a pharmacologically active compound through the stratum corneum and into the epidermis or dermis, preferably, with little or no systemic absorption. A wide variety of compounds have been evaluated as to their effectiveness in enhancing the rate of penetration of drugs through the skin. See, for example, *Percutaneous Penetration Enhancers*, Maibach H. I. and Smith H. E. (eds.), CRC Press, Inc., Boca Raton, Fla. (1995), which surveys the use and testing of various skin penetration enhancers, and Buyuktimkin et al., *Chemical Means of Transdermal Drug Permeation Enhancement in Transdermal and Topical Drug Delivery Systems*, Gosh T. K., Pfister W. R., Yum S. I. (Eds.), Interpharm Press Inc., Buffalo Grove, Ill. (1997). Representative examples of penetration enhancing agents include triglycerides (e.g., soybean oil), aloe compositions (e.g., aloe-vera gel), ethyl alcohol, isopropyl alcohol, octolyphenylpolyethylene glycol, oleic acid, polyethylene glycol 400, propylene glycol, N-decylmethylsulfoxide, fatty acid esters (e.g., isopropyl myristate, methyl laurate, glycerol monooleate, and propylene glycol monooleate), and N-methylpyrrolidone.

Representative examples of yet other excipients that may be included in topical as well as in other types of formulations (to the extent they are compatible), include preservatives, antioxidants, moisturizers, emollients, buffering agents, solubilizing agents, skin protectants, and surfactants. Suitable preservatives include alcohols, quaternary amines, organic acids, parabens, and phenols. Suitable antioxidants include ascorbic acid and its esters, sodium bisulfite, butylated hydroxytoluene, butylated hydroxyanisole, tocopherols, and chelating agents like EDTA and citric acid. Suitable moisturizers include glycerin, sorbitol, polyethylene glycols, urea, and propylene glycol. Suitable buffering agents include citric, hydrochloric, and lactic acid buffers. Suitable solubilizing agents include quaternary ammonium chlorides, cyclodextrins, benzyl benzoate, lecithin, and polysorbates. Suitable skin protectants include vitamin E oil, allatoin, dimethicone, glycerin, petrolatum, and zinc oxide.

Transdermal formulations typically employ transdermal delivery devices and transdermal delivery patches wherein a compound of formula (I) is formulated in lipophilic emulsions or buffered, aqueous solutions, dissolved and/or dispersed in a polymer or an adhesive. Patches may be constructed for continuous, pulsatile, or on demand delivery of pharmaceutical agents. Transdermal delivery of the compound may be accomplished by means of an iontophoretic patch. Transdermal patches may provide controlled delivery of the compounds wherein the rate of absorption is slowed by using rate-controlling membranes or by trapping the compound within a polymer matrix or gel. Absorption enhancers may be used to increase absorption, examples of which include absorbable pharmaceutically acceptable solvents that assist passage through the skin.

Ophthalmic Formulations Include Eye Drops.

Formulations for rectal administration include enemas, rectal gels, rectal foams, rectal aerosols, and retention enemas, which may contain conventional suppository bases such as cocoa butter or other glycerides, as well as synthetic polymers such as polyvinylpyrrolidone, PEG, and the like. Compositions for rectal or vaginal administration may also be formulated as suppositories which can be prepared by mixing the compound with suitable non-irritating carriers and excipients such as cocoa butter, mixtures of fatty acid glycerides, polyethylene glycol, suppository waxes, and combinations thereof, all of which are solid at ambient temperature but liquid at body temperature and therefore melt in the rectum or vaginal cavity and release the compound.

Dosage Amounts

As used herein, the term, "therapeutically effective amount" refers to an amount of a compound of formula (I) or a pharmaceutically acceptable salt or a stereoisomer thereof effective in producing the desired therapeutic response in a particular patient suffering from a disease or disorder. The term "therapeutically effective amount" includes the amount of the compound or a pharmaceutically acceptable salt or a stereoisomer thereof, that when administered, may induce a positive modification in the disease or disorder to be treated (e.g., to inhibit and/or reduce LRRK2 GTP binding activity and/or LRRK2 protein kinase activity and microglial activation, and to inhibit mutant LRRK2-induced neuronal degeneration), or is sufficient to inhibit or arrest development or progression of the disease or disorder, or otherwise alleviates to some extent, one or more symptoms of the disease or disorder being treated in a subject, or which simply kills or inhibits the growth of diseased cells, or reduces the amount of LRRK2 in diseased cells (e.g. basal ganglia and the substantia nigra nerve cells). The therapeutically effective amount of the compound is low enough to avoid causing undue or severe side effects, as determined in accordance with established or otherwise sound medical criteria.

The total daily dosage of a compound of formula (I) and usage thereof may be decided in accordance with standard medical practice, e.g., by the attending physician using sound medical judgment. The specific therapeutically effective dose for any particular subject will depend upon any one of more of a variety of factors including the disease or disorder being treated and the severity thereof (e.g., its present status); the activity of the specific compound employed; the specific composition employed; the age, body weight, general health, sex and diet of the subject; the time of administration, route of administration, and rate of excretion of the specific compound employed; the duration of the treatment; drugs used in combination or coincidental with the specific compound employed; and like factors well known in the medical arts (see, for example, *Goodman and Gilman's The Pharmacological Basis of Therapeutics*, 10th Edition, A. Gilman, J. Hardman and L. Limbird, eds., McGraw-Hill Press, 155-173, 2001).

Compounds of formula (I) and their pharmaceutically acceptable salts and stereoisomers may be effective over a wide dosage range. In some embodiments, the total daily dosage (e.g., for adult humans) may range from about 0.001 to about 1600 mg, from 0.01 to about 1000 mg, from 0.01 to about 500 mg, from about 0.01 to about 100 mg, from about 0.5 to about 100 mg, from 1 to about 100-400 mg per day, from about 1 to about 50 mg per day, from about 5 to about 40 mg per day, and in yet other embodiments from about 10 to about 30 mg per day. Individual dosages may be formulated to contain the desired dosage amount depending upon the number of times the compound is administered per day. By way of example, capsules may be formulated with from about 1 to about 200 mg of compound (e.g., 1, 2, 2.5, 3, 4, 5, 10, 15, 20, 25, 50, 100, 150, and 200 mg). In some embodiments, the compound may be administered at a dose in range from about 0.01 mg to about 200 mg/kg of body weight per day. In some embodiments, a dose of from 0.1 to 100, e.g. from 1 to 30 mg/kg per day in one or more dosages per day may be effective By way of example, a suitable dose for oral administration may be in the range of 1-30 mg/kg of body weight per day, and a suitable dose for intravenous administration may be in the range of 1-10 mg/kg of body weight per day.

In some embodiments, the daily dosage of the compound is from about 37.5 mg to about 50 mg. To facilitate such dosing, the compounds may be formulated in capsules in dosages of 12.5 mg, 25 mg, and 50 mg.

Methods of Use

In some aspects, compounds of formula (I) and their pharmaceutically acceptable salts and stereoisomers may be used in the treatment of diseases and disorders characterized or mediated by aberrant (e.g., dysfunctional or dysregulated (e.g., upregulated)) LRRK2 activity. The dysfunctional protein activity may be due to elevated levels of protein relative to a non-pathological state or a mutant version of the protein (e.g., a G2019S mutation). A "disease" is generally regarded as a state of health of a subject wherein the subject cannot maintain homeostasis, and wherein if the disease is not ameliorated then the subject's health continues to deteriorate. In contrast, a "disorder" in a subject is a state of health in which the subject is able to maintain homeostasis, but in which the subject's state of health is less favorable than it would be in the absence of the disorder. Left untreated, a disorder does not necessarily cause a further decrease in the animal's state of health.

The present methods thus include administering a therapeutically effective amount of a compound of formula (I) or a pharmaceutically acceptable salt or stereoisomer thereof, to a subject in need thereof. The term "subject" (or "patient") as used herein includes all members of the animal kingdom prone to or suffering from the indicated disease or disorder. In some embodiments, the subject is a mammal, e.g., a human or a non-human mammal. The methods are also applicable to companion animals such as dogs and cats as well as livestock such as cows, horses, sheep, goats, pigs, and other domesticated and wild animals. A subject "suffering from or suspected of suffering from" a specific disease or disorder may have a sufficient number of risk factors or presents with a sufficient number or combination of signs or symptoms such that a medical professional could diagnose or suspect that the subject was suffering from the disease or disorder. Thus, subjects suffering from, and suspected of suffering from, a specific disease or disorder are not necessarily two distinct groups.

In some embodiments, the inventive compounds and their pharmaceutically acceptable salts and stereoisomers may be useful in the treatment of neurodegenerative diseases and disorders. As used herein, the term "neurodegenerative diseases and disorders" refers to the conditions characterized by progressive degeneration or death of nerve cells, or both, including problems with movement (ataxias), or mental functioning (dementias). Representative examples of such diseases and disorders include Alzheimer's disease (AD) and AD-related dementias, Parkinson's disease (PD) and PD-related dementias, prion disease, motor neuron diseases (MND), Huntington's disease (HD), spinocerebellar ataxia (SCA), spinal muscular atrophy (SMA), primary progressive aphasia (PPA), amyotrophic lateral sclerosis (ALS), traumatic brain injury (TBI), multiple sclerosis (MS), dementias (e.g., vascular dementia (VaD), Lewy body dementia (LBD), semantic dementia, and frontotemporal lobar dementia (FTD)).

In other embodiments, the inventive compounds and their pharmaceutically acceptable salts and stereoisomers may be useful in treating brain cancer. Representative examples of brain cancers include, capillary hemangioblastomas, meningiomas, cerebral metastases, gliomas, neuroblastomas, medulloblastomas and ependymomas.

Representative examples of gliomas that may be treatable with the modalities of the present invention include recurrent high-grade gliomas, including glioblastoma, anaplastic astrocytoma and anaplastic oligodendroglioma, and high-grade pediatric gliomas such as diffuse intrinsic pontine glioma (DIPG).

Representative examples of glioblastomas that may be treatable with the modalities of the present invention include grade II (low-grade astrocytoma), grade III (anaplastic astrocytoma), and grade IV (glioblastoma) and glioblastoma multiforme (GBM).

Compounds of formula (I) and their pharmaceutically acceptable salts and stereoisomers may inhibit a plurality of aberrant kinases, including at least one of adaptor-associated protein kinase 1 (AAK1), receptor tyrosine kinase (ABL1 (T315I)-phosphorylated), apoptosis signal-regulating kinase 1 (ASK1), ASK2, aurora kinase A (AURKA), AURKB, AURKC, AXL receptor tyrosine kinase (AXL), BMP-2-inducible protein kinase (BIKE), BMX (BMX non-receptor tyrosine kinase), cell division cycle 2-like protein kinase 5 (CDCl2L5), cyclin-dependent kinase 11 (CDK11), checkpoint kinase 2 (CHEK2), citron rho-interacting serine/threonine kinase (CIT), CDC-like kinase 1 (CLK1), CLK2, CLK4, colony stimulating factor 1 receptor (CSF1R), CSF1R-autoinhibited, C-terminal Src kinase (CSK), casein kinase I isoform epsilon (CSNK1E), casein kinase I isoform gamma 1 (CSNK1G1), CSNK1G3, dual leucine zipper kinase (DLK), death-associated protein kinase-related 2 (DRAK2), dual-specificity tyrosine phosphorylation-regulated kinase 1A (DYRK1A), DYRK2, ephrin type-A receptor 2 (EPHA2), fms-related tyrosine kinase 1 (FLT1), FLT3, FLT3(D835H), FLT3(D835V), FLT3(D835Y), FLT3(ITD), FLT3(ITD,D835V), FLT3(ITD,F691L), FLT3(K663Q), FLT3(N841I), G protein-coupled receptor kinase 4 (GRK4), serine/threonine-protein kinase haspin (HASPIN), homeodomain-interacting protein kinase 1 (HPK1), intestinal cell kinase (ICK), I kappa B kinase alpha (IKK-alpha), IKK-beta, interleukin 1 receptor associated kinase 1 (IRAK1), IRAK4, Janus kinase 2 (JAK2)(JH1domain-catalytic), JAK3(JH1domain-catalytic), c-Jun N-terminal kinase 1 (JNK1), JNK2, JNK3, tyrosine-protein kinase kit (KIT), KIT(L576P), KIT(V559D), KIT(V559D,T670I), KIT-autoinhibited, LRRK2, LRRK2(G2019S), mitogen-activated protein kinase kinase 2 (MAP3K2), MAP3K15, mitogen-activated protein kinase kinase kinase kinase 2 (MAP4K2), MAP4K4, microtubule associated serine/threonine kinase 1 (MAST1), mitogen-acitvated protein kinase kinase 1 (MEK1), MEK2, MEK3, MEK4, MEK5, MEK6, maternal embryonic leucine zipper kinase (MELK), met proto-oncogene (MET), MET(M1250T), MET(Y1235D), Misshapen-like kinase 1 (MINK), mitogen-activated protein kinase-interacting serine/threonine kinase-2 (MKNK2), myosin light chain kinase (MLCK), nuclear Dbf2-related kinase 2 (NDR2), F-kappa-B-inducing kinase (NIK), p21-activated kinase 4 (PAK4), platelet-derived growth factor receptor alpha (PDGFRA), PDGFR beta (PDGFRB), phosphorylase b kinase gamma catalytic chain, skeletal muscle isoform 2 (PHKG2), phosphatidylinositol-4,5-bisphosphate 3-kinase catalytic subunit alpha (PIK3CA)(E545K), phosphatidylinositol 4-Phosphate-5 kinase 1A (PIP5K1A), PIP5K2B, polo-like kinase 4 (PLK4), serine/threonine-protein kinase D1 (PRKD1), PRKD2, PRKD3, ret proto-oncogene (RET), (RET)(M918T), RIO kinase 1 (RIOK1), RIOK2, RIOK3, receptor-interacting serine/threonine-protein kinase 1 (RIPK1), RIPK4, dual serine/threonine and tyrosine protein kinase (RIPK5), rho-associated protein kinase 1 (ROCK1), ROCK2, ribosomal S6 Kinase 4 (RSK4)(Kin.Dom.1-N-terminal), serum and glucocorticoid-regulated kinase (SGK), SGK2, serine-arginine protein kinase 1 (SRPK1), SRPK2, SRPK3, serine/threonine kinase 16 (STK16), STK39, TGF-beta activated kinase 1 (TAK1), TRAF2 and NCK-interacting kinase (TNIK), tropomyosin receptor kinase A (TRKA), TRKB, monopolar spindle 1 (Mps1) kinase (TTK), tyrosine kinase 2 (TYK2)(JH1domain-catalytic), unc-51 like autophagy activating kinase 1 (ULK1), ULK2, ULK3, vascular endothelial growth factor receptor 2 (VEGFR2), and YSK4, also known as MAP3K19. Thus, the compounds and their pharmaceutically acceptable salts and stereoisomers of the present invention may be useful in treating diseases and disorders mediated by aberrant activity of any one of more of these kinases. Such diseases and disorders are known in the art.

The methods of the present invention may entail administration of a compound of formula (I) or pharmaceutical compositions thereof to the patient in a single dose or in multiple doses (e.g., 1, 2, 3, 4, 5, 6, 7, 8, 10, 15, 20, or more doses). For example, the frequency of administration may range from once a day up to about once every eight weeks. In some embodiments, the frequency of administration ranges from about once a day for 1, 2, 3, 4, 5, or 6 weeks, and in other embodiments entails a 28-day cycle which includes daily administration for 3 weeks (21 days). In other embodiments, the compound may be dosed twice a day (BID) over the course of two and a half days (for a total of 5 doses) or once a day (QD) over the course of two days (for a total of 2 doses). In other embodiments, the compound may be dosed once a day (QD) over the course of five days.

The compounds of the present invention may be administered to a patient, e.g., a patient suffering from a neurodegenerative disease or disorder, or brain cancer (e.g., gliomas and glioblastomas), as a monotherapy. In other embodiments, the subject is treated by way of combination therapy whereby an inventive compound is administered concurrently with another active agent. Representative examples of active agents known to treat neurodegenerative diseases and disorders include dopaminergic treatments (e.g., Carbidopa-levodopa, pramipexole (Mirapex), ropinirole (Requip) and rotigotine (Neupro, given as a patch)). Apomorphine and monoamine oxidase B (MAO-B) inhibitors (e.g., selegiline (Eldepryl, Zelapar), rasagiline (Azilect) and safinamide (Xadago)) for PD and movement disorders, cholinesterase inhibitors for cognitive disorders (e.g., benztropine (Cogentin) or trihexyphenidyl), antipsychotic drugs for behavioral and psychological symptoms of dementia, as well as agents aimed to slow the development of diseases, such as Riluzole for ALS, cerebellar ataxia and Huntington's disease, non-steroidal anti-inflammatory drugs for Alzheimer's disease, and caffeine A2A receptor antagonists and CERE-120 (adeno-associated virus serotype 2-neurturin) for the neuroprotection of Parkinson's disease. Representative examples of active agents known to treat brain cancer include temozolomide (Temodar), bevacizumab (Avastin), lomustine (CCNU, Ceenu), carmustine wafer (BCNU, Gliadel), and Toca 5 (Tocagen). The term "concurrently" is not limited to the administration of the anti-neurodegenerative or anti-cancer therapeutics at exactly the same time. Rather, it is meant that they are administered to a subject as part of the same course of treatment such as in a sequence and within a time interval such that they can act together (e.g., synergistically) to provide an increased benefit than if they were administered otherwise.

Pharmaceutical Kits

The present compositions may be assembled into kits or pharmaceutical systems. Kits or pharmaceutical systems according to this aspect of the invention include a carrier or package such as a box, carton, tube or the like, having in close confinement therein one or more containers, such as vials, tubes, ampoules, or bottles, which contain a compound of the present invention or a pharmaceutical composition.

The kits or pharmaceutical systems of the invention may also include printed instructions for using the compounds and compositions.

EXAMPLES

Example 1: Synthesis of 2-methyl-2-(4-(4-(methylamino)-1H-pyrrolo[2,3-b]pyridin-5-yl)-1H-pyrazol-1-yl)propanenitrile (1)

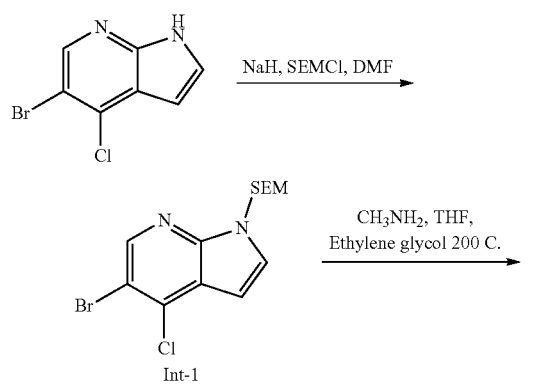

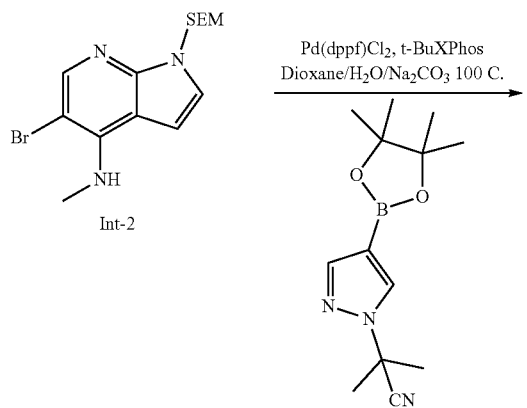

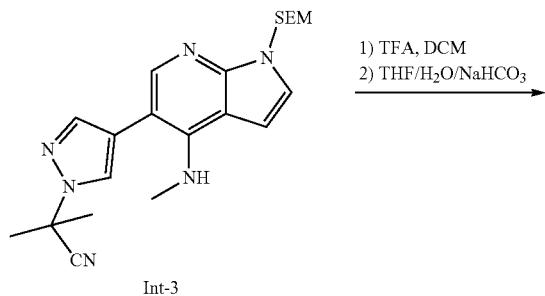

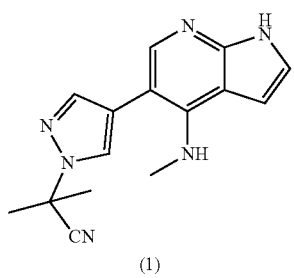

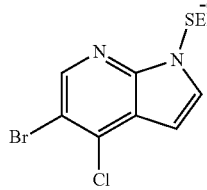

5-bromo-4-chloro-1-((2-(trimethylsilyl)ethoxy)methyl)-1H-pyrrolo[2,3-b]pyridine (Int-1)

Intermediate 1 (Int-1) was prepared according to the procedure described in International Publication WO 2018/8150914.

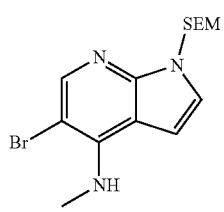 [SMILES: CNc1c(Br)cnc2c1ccn2COCC[Si](C)(C)C]

5-bromo-N-methyl-1-((2-(trimethylsilyl)ethoxy)methyl)-1H-pyrrolo[2,3-b]pyridin-4-amine (Int-2)

5-bromo-4-chloro-1-((2-(trimethylsilyl)ethoxy)methyl)-1H-pyrrolo[2,3-b]pyridine (200 mg, 0.56 mmol) was dissolved in ethylene glycol (5 mL). $CH_3NH_2$ (2M) in THF (2.72 mL, 5.6 mmol) was added and the mixture was heated to 200° C. under microwave irradiation for 1 hour. The mixture was quenched with $H_2O$ and extracted with EtOAc. The combined organic layer was washed with $H_2O$, brine, dried over $MgSO_4$ and condensed to give a yellow oil. The crude product was purified by flash chromatography using a gradient of 5-15% EtOAc in Hexanes to give the desired product as a yellow oil (187 mg, 94% yield).

MS (ESI) m/z 357.43 $(M+H)^+$.

5-bromo-N-methyl-1-((2-(trimethylsilyl)ethoxy)methyl)-1H-pyrrolo[2,3-b]pyridin-4-amine (31 mg, 0.087 mmol) and 2-methyl-2-(4-(4,4,5,5-tetramethyl-1,3,2-dioxaborolan-2-yl)-1H-pyrazol-1-yl)propanenitrile (25 mg, 0.096 mmol) were dissolved in 1,4-dioxane (2 mL) and 2M aqueous $Na_2CO_3$ (0.22 mL, 0.44 mmol). The mixture was degassed using a sonicator before adding $Pd(dppf)Cl_2$ (8 mg, 0.01 mmol) and t-BuXPhos (7 mg, 0.016 mmol) to the reaction vial. The vial was flushed with $N_2$, and the mixture was stirred at 100° C. for 1 hour. The reaction was quenched with $H_2O$ and extracted with EtOAc. The combined organic layer was washed with H₂O, brine, dried over MgSO₄ and condensed to give a brown oil. The obtained oil was dissolved in DCM (10 mL) before adding trifluoroacetic acid (TFA) (1 mL). The mixture was stirred for 1 hour before removing the solvent under reduced pressure. To the dissolved residue in THF (5 mL) was added saturated aqueous NaHCO₃ (2 mL), and the mixture was stirred for 6 hours at room temperature (rt). The reaction was quenched with H₂O and extracted with EtOAc. The combined organic layer was washed with H₂O, brine, dried over MgSO₄, and condensed under reduced pressure to give a brown oil. The crude product was purified by reverse phase HPLC using a gradient of 1-60% MeCN in H₂O to give the desired product as a white solid (8 mg, 33% yield).

¹H NMR (500 MHz, DMSO) δ 12.3 (s, 1H), 8.23 (s, 1H), 7.81 (d, J=20 Hz, 2H), 7.35 (s, 2H), 7.0 (s, 1H), 3.28 (d, J=5 Hz, 3H), 2.02 (s, 6H).

MS (ESI) m/z: 281.62 (M+H)⁺.

Example 2: Synthesis of N-methyl-5-(1-(1-methylpiperidin-4-yl)-1H-pyrazol-4-yl)-1H-pyrrolo[2,3-b]pyridin-4-amine (2)

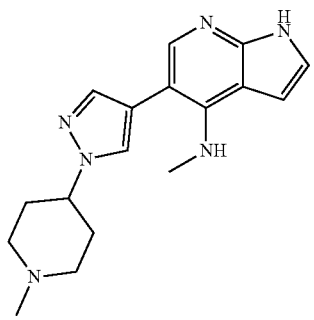

(2)

Compound 2 was prepared in an analogous manner to compound 1 in Example 1 (9 mg, 34% yield).

¹H NMR (500 MHz, DMSO) δ 12.3 (s, 1H), 8.05 (s, 1H), 7.78 (s, 1H), 7.68 (s, 1H), 7.35 (s, 1H), 7.27 (s, 1H), 6.99 (s, 1H), 4.49 (m, 1H), 3.60 (m, 2H), 3.28 (d, J=5 Hz, 3H), 3.19 (m, 2H), 2.84 (s, 3H), 3.38-2.15 (m, 4H).

MS (ESI) m/z: 311.41 (M+H)⁺.

Example 3: Synthesis of N-methyl-5-(1-(tetrahydro-2H-pyran-4-yl)-1H-pyrazol-4-yl)-1H-pyrrolo[2,3-b]pyridin-4-amine (3)

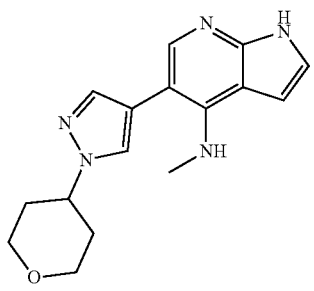

(3)

Compound 3 was prepared in an analogous manner to compound 1 in Example 1 (9 mg, 35% yield).

¹H NMR (500 MHz, DMSO) δ 12.32 (s, 1H), 8.04 (s, 1H), 7.79 (s, 1H), 7.64 (s, 1H), 7.34 (s, 1H), 7.3 (s, 1H), 6.99 (s, 1H), 4.46 (m, 1H), 3.99 (m, 2H), 3.50 (m, 2H), 3.28 (d, J=5 Hz, 3H), 2.02-1.91 (m, 4H).

MS (ESI) m/z: 298.83 (M+H)⁺.

Example 4: Synthesis of 2-(4-(3-chloro-4-(methylamino)-1H-pyrrolo[2,3-b]pyridin-5-yl)-1H-pyrazol-1-yl)-2-methylpropanenitrile (4)

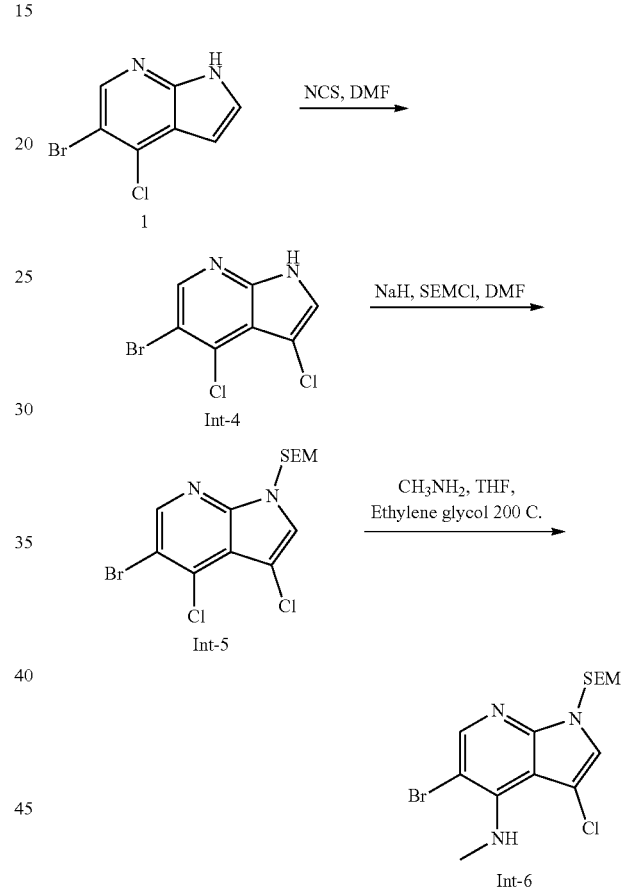

5-bromo-3,4-dichloro-1H-pyrrolo[2,3-b]pyridine (Int-4)

To a solution of 5-bromo-4-chloro-1H-pyrrolo[2,3-b]pyridine (1 g, 4.32 mmol) in DMF (15 mL) was added N-chlorosuccinimide (NCS) (634 mg, 4.75 mmol). The mixture was stirred for 16 hours before quenching the reaction with water (150 mL). The resulting precipitate was filtered, washed with water and dried under N₂ to give the desired product as a beige solid (1.14 g, 97% yield).

MS (ESI) m/z: 266.53 (M+H)⁺.

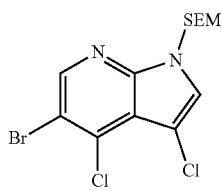 [SMILES: C[Si](C)(C)CCOCn1cc(Cl)c2c(Cl)c(Br)cnc21]

5-bromo-3,4-dichloro-1-((2-(trimethylsilyl)ethoxy)methyl)-1H-pyrrolo[2,3-b]pyridine (Int-5)

Intermediate 5 (Int-5) was prepared in an analogous manner to compound Int-1 in Example 1.

MS (ESI) m/z: 397.34 (M+H)⁺.

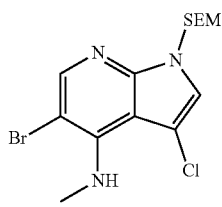 [SMILES: CNc1c(Br)cnc2c1c(Cl)cn2COCC[Si](C)(C)C]

5-bromo-3-chloro-N-methyl-1-((2-(trimethylsilyl)ethoxy)methyl)-1H-pyrrolo[2,3-b]pyridin-4-amine (Int-6)

Intermediate 6 (Int-6) was prepared in an analogous manner to compound Int-2 in Example 1.

MS (ESI) m/z: 391.59 (M+H)⁺.

(4)

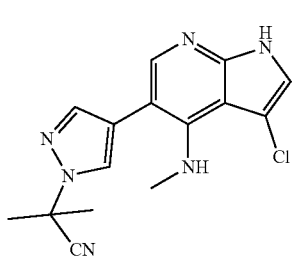

Compound 4 was prepared in an analogous manner to compound 1 in Example 1. The desired product was isolated as a yellow solid (4 mg, 15% yield).

¹H NMR (500 MHz, DMSO) δ 12.41 (br, 1H), 8.21 (s, 1H), 7.90 (s, 1H), 7.78 (s, 1H), 7.52 (s, 1H), 6.85 (br, 1H), 2.84 (s, 3H), 2.02 (s, 6H).

MS (ESI) m/z: 315.27 (M+H)⁺.

Example 5: Synthesis of 3-chloro-N-methyl-5-(1-(1-methylpiperidin-4-yl)-1H-pyrazol-4-yl)-1H-pyrrolo[2,3-b]pyridin-4-amine (5)

(5)

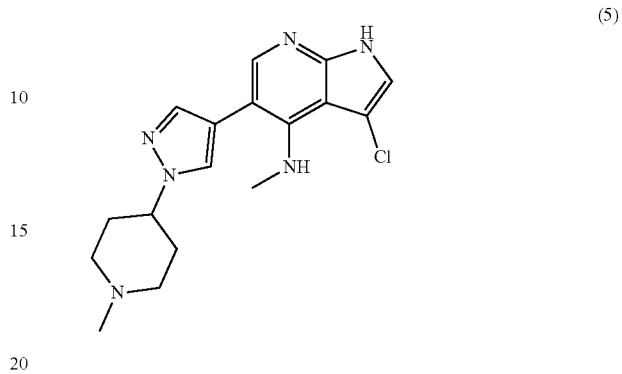

Compound 5 was prepared in an analogous manner to compound 4 in Example 4. The desired product was isolated as a yellow solid (4 mg, 16% yield).

¹H NMR (500 MHz, DMSO) δ 12.38 (br, 1H), 8.07 (d, J=5 Hz, 1H), 7.97 (s, 1H), 7.86 (s, 1H), 7.64 (s, 1H), 7.50 (s, 1H), 6.65 (br, 1H), 4.49 (m, 1H), 3.17 (m, 2H), 3.03 (d, J=5 Hz, 3H), 2.84 (s, 3H), 2.33-2.15 (m, 4H).

MS (ESI) m/z: 345.68 (M+H)⁺.

Example 6: Synthesis of 3-chloro-N-methyl-5-(1-(tetrahydro-2H-pyran-4-yl)-1H-pyrazol-4-yl)-1H-pyrrolo[2,3-b]pyridin-4-amine (6)

(6)

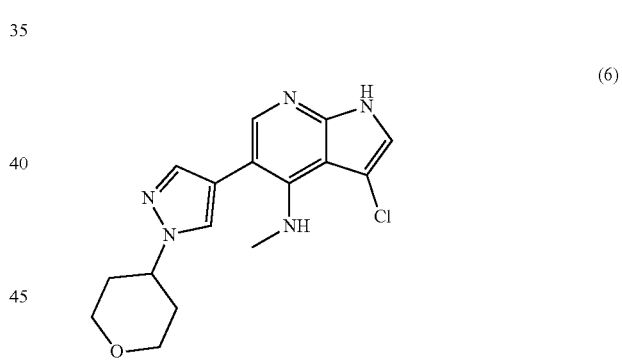

Compound 6 was prepared in an analogous manner to compound 4 in Example 4. The desired product was isolated as a yellow solid (5 mg, 18% yield).

MS (ESI) m/z: 332.53 (M+H)⁺.

Example 7: Synthesis of 2-methyl-2-(4-(4-(methylamino)-5-(trifluoromethyl)-1H-pyrrolo[2,3-b]pyridin-3-yl)-1H-pyrazol-1-yl)propanenitrile (7)

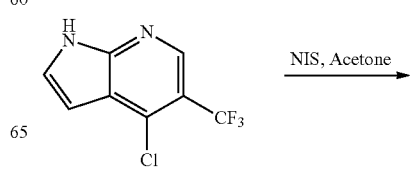

-continued

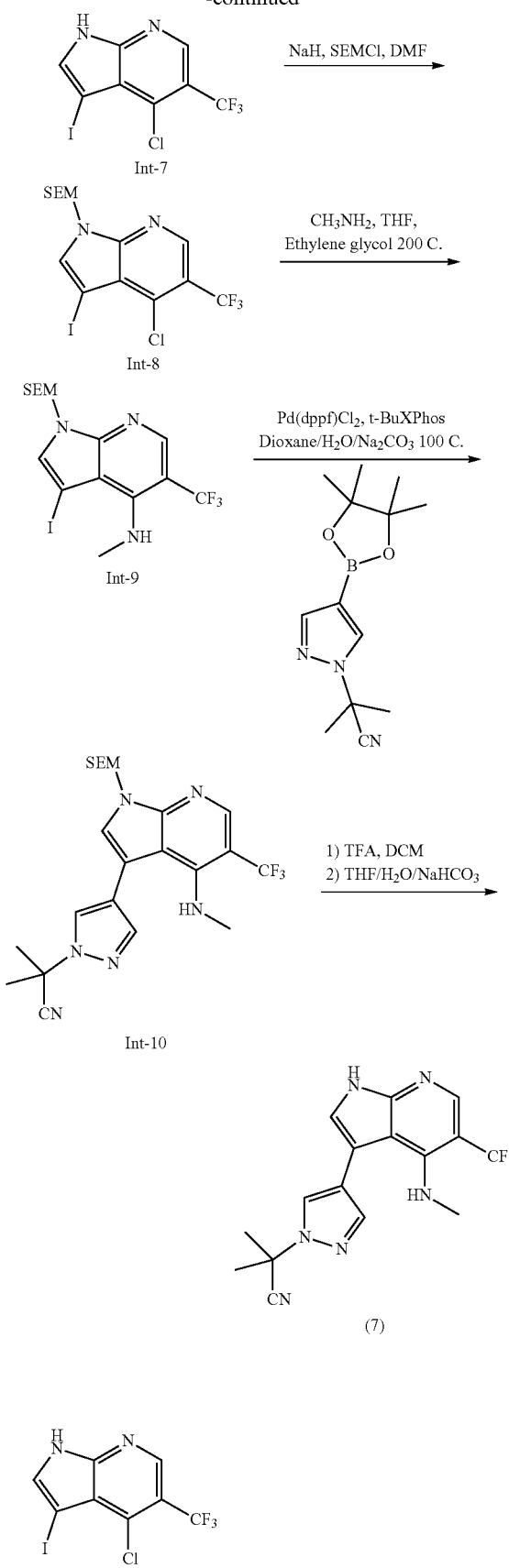

4-chloro-3-iodo-5-(trifluoromethyl)-1H-pyrrolo[2,3-b]pyridine (Int-7)

4-chloro-5-(trifluoromethyl)-1H-pyrrolo[2,3-b]pyridine (1 g, 4.53 mmol) and N-iodosuccinimide (NIS) (1.12 g, 4.99 mmol) were stirred together in acetone (20 mL) for 2 hours at rt. $H_2O$ (100 mL) and saturated aqueous sodium thiosulfate solution (20 mL) were added to quench the reaction. The resulting precipitate was filtered, washed with $H_2O$, and dried under $N_2$ to give the desired product as a white solid that was used without further purification (1.5 g, 96% yield). MS (ESI) m/z: 347.87 $(M+H)^+$.

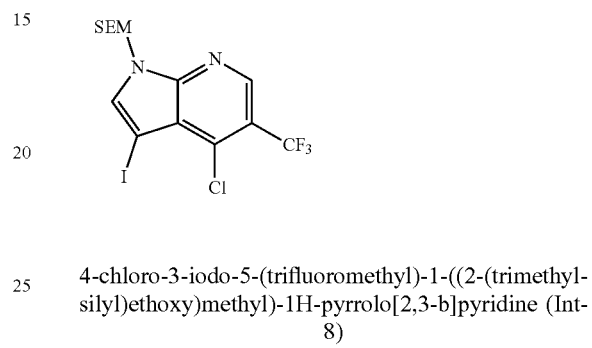

4-chloro-3-iodo-5-(trifluoromethyl)-1-((2-(trimethylsilyl)ethoxy)methyl)-1H-pyrrolo[2,3-b]pyridine (Int-8)

Intermediate 8 (Int-8) was prepared in an analogous manner to compound Int-1 in Example 1.
MS (ESI) m/z: 477.56 $(M+H)^+$.

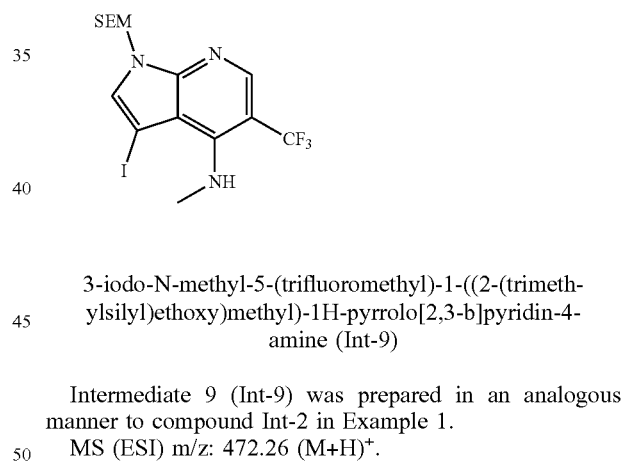

3-iodo-N-methyl-5-(trifluoromethyl)-1-((2-(trimethylsilyl)ethoxy)methyl)-1H-pyrrolo[2,3-b]pyridin-4-amine (Int-9)

Intermediate 9 (Int-9) was prepared in an analogous manner to compound Int-2 in Example 1.
MS (ESI) m/z: 472.26 $(M+H)^+$.

(7)

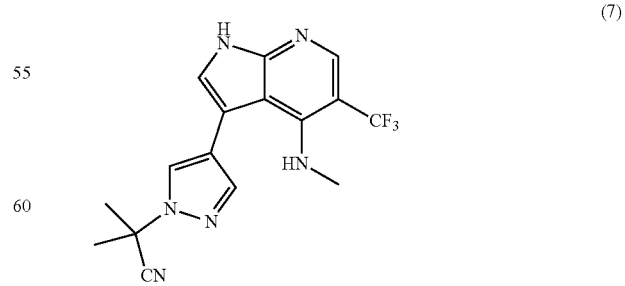

Compound 7 was prepared in an analogous manner to compound 1 in Example 1. The desired product was isolated as a yellow solid (10 mg, 28% yield).

¹H NMR (500 MHz, DMSO) δ 12.21 (br, 1H), 8.30 (s, 1H), 8.17 (s, 1H), 7.78 (s, 1H), 7.43 (s, 1H), 5.90 (br, 1H), 2.71 (s, 3H), 2.01 (s, 6H).
MS (ESI) m/z: 349.62 (M+H)⁺.

Example 8: Synthesis of N-methyl-3-(1-(1-methylpiperidin-4-yl)-1H-pyrazol-4-yl)-5-(trifluoromethyl)-1H-pyrrolo[2,3-b]pyridin-4-amine (8)

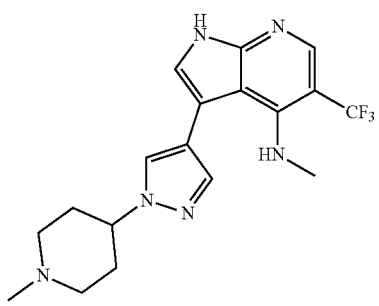
(8)

Compound 8 was prepared in an analogous manner to compound 1 in Example 1. The desired product was isolated as a yellow solid (8 mg, 20% yield).
MS (ESI) m/z: 379.32 (M+H)⁺.

Example 9: Synthesis of 3-chloro-5-(3-methoxy-1-(tetrahydro-2H-pyran-4-yl)-1H-pyrazol-4-yl)-N-methyl-1H-pyrrolo[2,3-b]pyridin-4-amine (17)

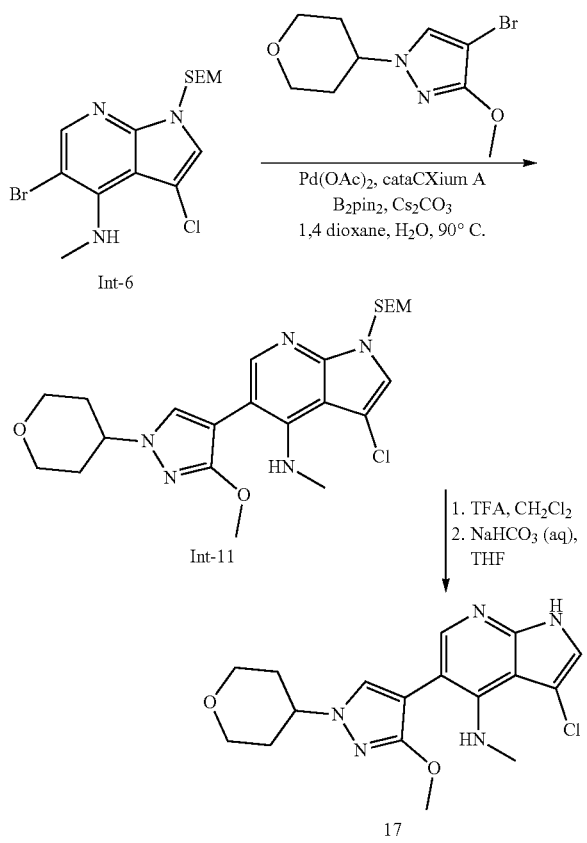

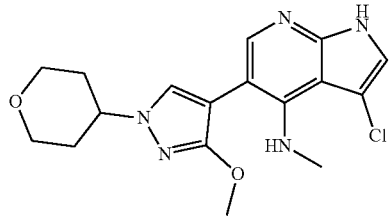
(17)

To a degassed solution of 5-bromo-3-chloro-N-methyl-1-((2-(trimethylsilyl)ethoxy)methyl)-1H-pyrrolo[2,3-b]pyridin-4-amine (Int-6) (50 mg, 0.127 mmol), 4-bromo-3-methoxy-1-(tetrahydro-2H-pyran-4-yl)-1H-pyrazole (43.4 mg, 0.166 mmol), bis(pinacolato)diboron (48.7 mg, 0.192 mmol) and Cs₂CO₃ (208 mg, 0.639 mmol) in 1,4-dioxane (0.8 mL) and H₂O (0.2 mL) was added Pd(OAc)₂ (4.3 mg, 0.019 mmol) and CataCXium® A (13.76 mg, 0.038 mmol). The mixture was backfilled with N₂ and was stirred rt at 90° C. for until completion of the reaction (about 1 hour). The mixture was then cooled to rt, quenched with water, extracted with EtOAc. The pooled organic layers were washed with brine, dried over Na₂SO₄ and concentrated under reduced pressure. To a solution of the crude product (Int-11) in DCM (10 mL) was added TFA (1 mL). The reaction was stirred at rt for 1 hour (until consumption of starting material). The solvent was removed under reduced pressure and the residue was dissolved in THF (5 mL). Saturated aqueous NaHCO₃ (2 mL) was added and the mixture stirred for 6 hours at rt. The mixture was quenched with H₂O and extracted with EtOAc. The pooled organic layers were washed with H₂O, brine, dried over MgSO₄ and condensed under reduced pressure. The crude was dissolved in DMSO-d6, filtered and then purified by reverse phase HPLC using a gradient of 1 to 60% acetonitrile (CAN) in H₂O to give 9 mg of the desired product (17) in 19.4% yield.
¹H NMR (500 MHz, DMSO-d₆) δ 12.43 (br, 1H), 7.80 (s, 1H), 7.78 (s, 1H), 7.51 (s, 1H), 6.95 (br, 1H), 4.29-4.23 (m, 1H), 3.98-3.95 (m, 2H), 3.82 (s, 3H), 3.49-3.44 (m, 2H), 2.89 (s, 3H), 2.01-1.89 (m, 4H).
MS (ESI) m/z: 362.12 (M+H)⁺.

Example 10: Synthesis of 3-chloro-5-(5-ethyl-1-methyl-1H-pyrazol-3-yl)-N-methyl-1H-pyrrolo[2,3-b]pyridin-4-amine (9)

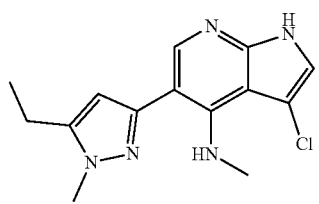
(9)

Compound 9 was prepared in an analogous manner to compound 17 in Example 9 (16.3 mg, 23% yield).
¹H NMR (500 MHz, DMSO-d₆) δ 12.43 (br, 1H), 9.18 (br, 1H), 8.28 (s, 1H), 7.54 (s, 1H), 6.58 (s, 1H), 3.82 (s, 3H), 3.25 (s, 3H), 2.68 (q, J=10 Hz, 2H), 1.25 (t, J=10 Hz, 3H).
MS (ESI) m/z: 290.1 (M+H)⁺.

Example 11: Synthesis of 3-chloro-5-(5-ethyl-1-methyl-1H-pyrazol-3-yl)-N-isopropyl-1H-pyrrolo[2,3-b]pyridin-4-amine (10)

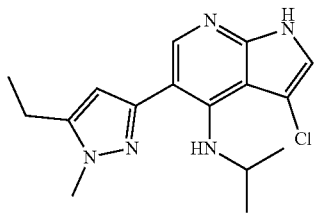

(10)

Compound 10 was prepared in an analogous manner to compound 17 in Example 9 (17.7 mg, 16% yield).

$^1$H NMR (500 MHz, DMSO-d$_6$) δ 12.34 (br, 1H), 8.88 (br, 1H), 8.36 (s, 1H), 7.54 (s, 1H), 6.62 (s, 1H), 4.42-4.38 (m, 1H), 3.82 (s, 3H), 2.68 (q, J=10 Hz, 2H), 1.26 (t, J=10 Hz, 3H), 1.22 (d, J=5 Hz, 6H).

MS (ESI) m/z: 318.01 (M+H)$^+$.

Example 12: Synthesis of 3-chloro-N-methyl-5-(1-methyl-1H-pyrazol-3-yl)-1H-pyrrolo[2,3-b]pyridin-4-amine (11)

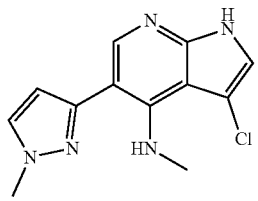

(11)

Compound 11 was prepared in an analogous manner to compound 17 in Example 9 (6.1 mg, 18% yield).

$^1$H NMR (500 MHz, DMSO-d$_6$) δ 12.43 (br, 1H), 8.26 (s, 1H), 7.85 (d, J=5 Hz, 1H), 7.54 (s, 1H), 6.72 (d, J=5 Hz, 1H), 3.93 (s, 3H), 3.19 (s, 3H).

MS (ESI) m/z: 262.01 (M+H)$^+$.

Example 13: Synthesis of 3-chloro-N-isopropyl-5-(1-methyl-1H-pyrazol-3-yl)-1H-pyrrolo[2,3-b]pyridin-4-amine (12)

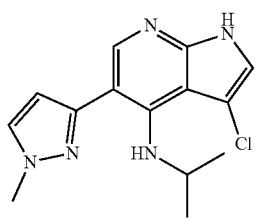

(12)

Compound 12 was prepared in an analogous manner to compound 17 in Example 9 (10.7 mg, 34% yield).

$^1$H NMR (500 MHz, DMSO-d$_6$) δ 12.34 (br, 1H), 8.35 (s, 1H), 7.86 (d, J=5 Hz, 1H), 7.55 (s, 1H), 6.76 (d, J=5 Hz, 1H), 4.38-4.28 (m, 1H), 3.94 (s, 3H), 1.20 (d, J=10 Hz, 6H).

MS (ESI) m/z: 290.04 (M+H)$^+$.

Example 14: Synthesis of 3-chloro-5-(3-cyclopropyl-1-(tetrahydro-2H-pyran-4-yl)-1H-pyrazol-4-yl)-N-methyl-1H-pyrrolo[2,3-b]pyridin-4-amine (13)

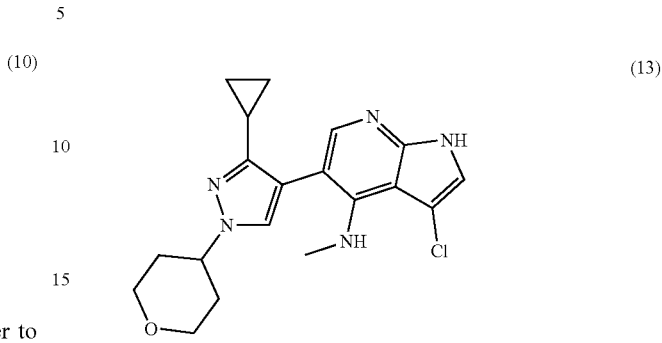

(13)

Compound 13 was prepared in an analogous manner to compound 17 in Example 9 (8.4 mg, 6% yield).

$^1$H NMR (500 MHz, DMSO-d$_6$) δ 12.41 (br, 1H), 7.86 (s, 1H), 7.81 (s, 1H), 7.53 (s, 1H), 7.05 (br, 1H), 4.35-4.28 (m, 1H), 3.96-3.93 (m, 2H), 2.81 (s, 3H), 1.98-1.92 (m, 4H), 1.91-1.87 (m, 2H), 1.64-1.59 (m, 1H), 0.78-0.73 (m, 4H).

MS (ESI) m/z: 372.16 (M+H)$^+$.

Example 15: Synthesis of 3-(3-chloro-4-(methylamino)-1H-pyrrolo[2,3-b]pyridin-5-yl)-1-methyl-1H-indazole-5-carbonitrile (14)

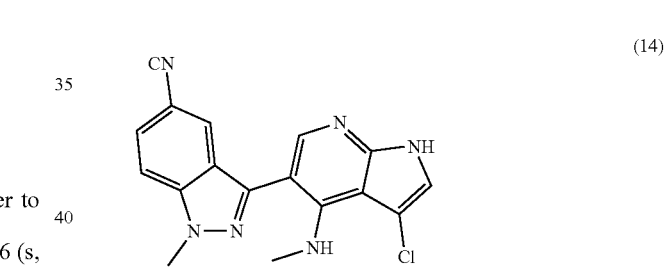

(14)

Compound 14 was prepared in an analogous manner to compound 17 in Example 9 (14 mg, 8% yield).

$^1$H NMR (500 MHz, DMSO-d$_6$) δ 12.42 (br, 1H), 8.33 (s, 1H), 8.11 (s, 1H), 7.95 (d, J=10 Hz, 1H), 7.81 (d, J=10 Hz, 1H), 7.55 (s, 1H), 7.22 (br, 1H), 4.19 (s, 3H), 2.58 (s, 3H).

MS (ESI) m/z: 336.96 (M+H)$^+$.

Example 16: Synthesis of 3-(3-chloro-4-(methylamino)-1H-pyrrolo[2,3-b]pyridin-5-yl)-5-methoxy-1-methyl-1H-indazole (15)

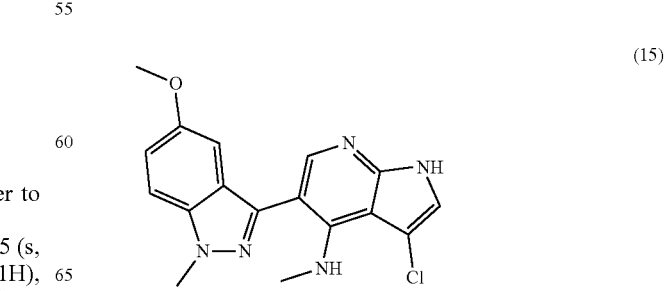

(15)

Compound 15 was prepared in an analogous manner to compound 17 in Example 9 (4.7 mg, 9% yield).

¹H NMR (500 MHz, DMSO-d₆) δ 12.41 (br, 1H), 8.07 (s, 1H), 7.65 (d, J=10 Hz, 1H), 7.54 (s, 1H), 7.13 (d, J=10 Hz, 1H), 7.02 (s, 1H), 4.09 (s, 3H), 3.76 (s, 3H), 2.62 (s, 3H).

MS (ESI) m/z: 341.98 (M+H)⁺.

Example 17: Synthesis of 3-chloro-5-(5-methoxy-2-methyl-2H-indazol-3-yl)-N-methyl-1H-pyrrolo[2,3-b]pyridin-4-amine (16)

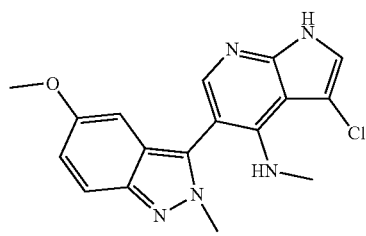

(16)

Compound 16 was prepared in an analogous manner to compound 17 in Example 9 (6.3 mg, 12% yield).

¹H NMR (500 MHz, DMSO-d₆) δ 12.21 (br, 1H), 7.92 (s, 1H), 7.55 (d, J=10 Hz, 1H), 7.54 (s, 1H), 6.95 (d, J=10 Hz, 1H), 3.91 (s, 3H), 3.71 (s, 3H), 2.54 (s, 3H).

MS (ESI) m/z: 342.04 (M+H)⁺.

Example 18: Synthesis of 3-(3-chloro-4-(methylamino)-1H-pyrrolo[2,3-b]pyridin-5-yl)-1-methyl-1H-pyrazole-4-carbonitrile (18)

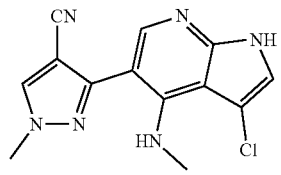

(18)

Compound 18 was prepared in an analogous manner to compound 17 in Example 9 (16.7 mg, 14% yield).

¹H NMR (500 MHz, DMSO-d₆) δ 12.32 (br, 1H), 8.64 (s, 1H), 8.00 (s, 1H), 7.51 (s, 1H), 7.06 (br, 1H), 3.97 (s, 3H), 2.70 (s, 3H).

MS (ESI) m/z: 286.94 (M+H)⁺.

Example 19: Synthesis of 3-chloro-N-methyl-5-(4-(5-methyl-1,3,4-oxadiazol-2-yl)phenyl)-1H-pyrrolo[2,3-b]pyridin-4-amine (19)

(19)

Compound 19 was prepared in an analogous manner to compound 17 in Example 9 (16 mg, 28% yield).

¹H NMR (500 MHz, DMSO-d₆) δ 12.34 (br, 1H), 8.05 (d, J=10 Hz, 2H), 7.94 (s, 1H), 7.65 (d, J=10 Hz, 2H), 7.52 (s, 1H), 6.76 (br, 1H), 2.61 (s, 3H), 2.58 (s, 3H).

MS (ESI) m/z: 340.15 (M+H)⁺.

Example 20: Synthesis of 3-(3-methoxy-1-(tetrahydro-2H-pyran-4-yl)-1H-pyrazol-4-yl)-N-methyl-5-(trifluoromethyl)-1H-pyrrolo[2,3-b]pyridin-4-amine (20)

(20)

Compound 20 was prepared in an analogous manner to compound 17 in Example 9 (2 mg, 5% yield).

¹H NMR (500 MHz, DMSO-d₆) δ 12.13 (br, 1H), 8.28 (s, 1H), 7.74 (s, 1H), 7.24 (s, 1H), 6.16 (br, 1H), 4.26-4.23 (m, 1H), 3.97-3.95 (m, 2H), 3.83 (s, 3H), 3.48-3.43 (m, 2H), 2.80 (s, 3H), 2.00-1.88 (m, 4H).

MS (ESI) m/z: 396.27 (M+H)⁺.

Example 21: Synthesis of N-methyl-3-(4-(5-methyl-1,3,4-oxadiazol-2-yl)phenyl)-5-(trifluoromethyl)-1H-pyrrolo[2,3-b]pyridin-4-amine (21)

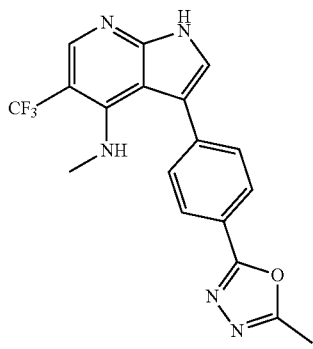

(21)

Compound 21 was prepared in an analogous manner to compound 17 in Example 9 (11 mg, 28% yield).

$^1$H NMR (500 MHz, DMSO-d$_6$) δ 12.36 (br, 1H), 8.30 (s, 1H), 8.02 (d, J=5 Hz, 2H), 7.68 (d, J=5 Hz, 2H), 7.61 (s, 1H), 2.60 (s, 3H), 1.93 (br, 1H).

MS (ESI) m/z: 374.12 (M+H)$^+$.

Example 22: Synthesis of (4-(3-chloro-4-(methylamino)-1H-pyrrolo[2,3-b]pyridin-5-yl-3-methoxyphenyl)(morpholino)methanone (22)

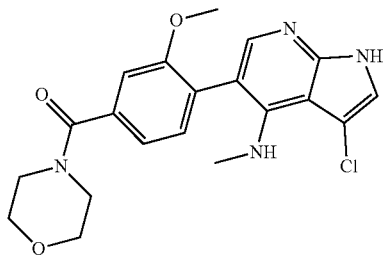

(22)

Compound 22 was prepared in an analogous manner to compound 17 in Example 9 (21 mg, 18% yield).

$^1$H NMR (500 MHz, DMSO-d$_6$) δ 12.46 (br, 1H), 7.80 (s, 1H), 7.53 (s, 1H), 7.39 (d, J=5 Hz, 1H), 7.11 (s, 1H), 7.06 (d, J=5 Hz, 1H), 3.80 (s, 3H), 3.63 (br), 2.60 (s, 3H).

MS (ESI) m/z: 401.24 (M+H)$^+$.

Example 23: Synthesis of (3-methoxy-4-(4-(methylamino)-5-(trifluoromethyl)-1H-pyrrolo[2,3-b]pyridin-3-yl)phenyl)(morpholino)methanone (23)

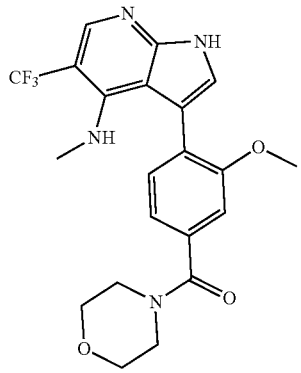

(23)

Compound 23 was prepared in an analogous manner to compound 17 in Example 9 (7.8 mg, 49% yield).

$^1$H NMR (500 MHz, DMSO-d$_6$) δ 12.22 (br, 1H), 8.26 (s, 1H), 7.35 (d, J=10 Hz, 1H), 7.33 (s, 1H), 7.09 (s, 1H), 7.05 (d, J=10 Hz, 1H), 6.19 (br, 1H), 3.75 (br), 3.64 (br, 6H).

MS (ESI) m/z: 435.31 (M+H)$^+$.

Example 24: Synthesis of N-methyl-3-(4-morpholinopyridin-2-yl)-5-(trifluoromethyl)-1H-pyrrolo[2,3-b]pyridin-4-amine (24)

(24)

Compound 24 was prepared in an analogous manner to compound 17 in Example 9 (8 mg, 15% yield).

$^1$H NMR (500 MHz, DMSO-d$_6$) δ 12.63 (br, 1H), 8.32 (s, 1H), 8.24 (d, J=5 Hz, 1H), 8.03 (s, 1H), 7.35 (d, J=5 Hz, 1H), 7.13 (s, 1H).

MS (ESI) m/z: 378.13 (M+H)$^+$.

Example 25: Synthesis of 3-chloro-N-isopropyl-5-(1-(tetrahydro-2H-pyran-4-yl)-1H-pyrazol-4-yl)-1H-pyrrolo[2,3-b]pyridin-4-amine (25)

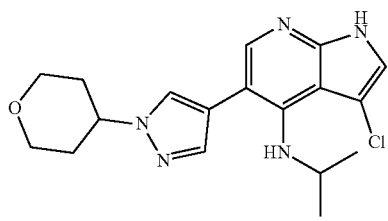
(25)

Compound 25 was prepared in an analogous manner to compound 17 in Example 9 (9 mg, 21% yield).

$^1$H NMR (500 MHz, DMSO-$d_6$) δ 12.33 (br, 1H), 8.04 (s, 1H), 7.92 (s, 1H), 7.64 (s, 1H), 7.53 (s, 1H), 5.87 (br, 1H), 4.49-4.43 (m, 1H), 3.98-3.94 (m, 2H), 3.69-3.64 (m, 2H), 2.01-1.98 (m, 4H), 1.96-1.92 (m, 1H), 1.04 (d, J=10 Hz, 6H).

MS (ESI) m/z: 360.23 (M+H)$^+$.

Example 26: Synthesis of Azaindole Intermediates Int-12 to Int-16

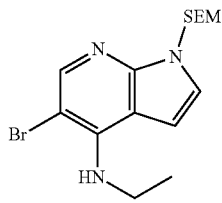 [SMILES: CCNc1c(Br)cnc2c1ccn2COCC[Si](C)(C)C]

5-Bromo-N-ethyl-1-((2-(trimethylsilyl)ethoxy)methyl)-1H-pyrrolo[2,3-b]pyri-din-4-amine (int-12)

Intermediate 12 (int-12) was synthesized in an analogous manner to intermediate int-2 in example 1. The crude product was purified by column chromatography (SiO$_2$, Petroleum ether/Ethyl acetate=50/1 to 10/1) to obtain int-12 as a yellow oil (4 g, 97% yield).

$^1$H NMR (400 MHz, CDCl$_3$) δ 8.16 (s, 1H), 7.16 (d, J=3.8 Hz, 1H), 6.69 (d, J=3.8 Hz, 1H), 5.63 (s, 2H), 3.86-3.79 (m, 2H), 3.62-3.54 (m, 2H), 1.45 (t, J=7.2 Hz, 3H), 0.99-0.93 (m, 2H), 0.02-0.03 (m, 9H).

LCMS: m/z 371.9 [M+1]$^+$.

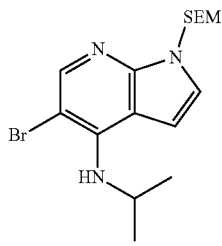 [SMILES: CC(C)Nc1c(Br)cnc2c1ccn2COCC[Si](C)(C)C]

5-bromo-N-isopropyl-1-((2-(trimethylsilyl)ethoxy)methyl)-1H-pyrrolo[2,3-b]pyridin-4-amine (int-13)

Intermediate 13 (int-13) was synthesized in an analogous manner to intermediate int-2 in example 1. The crude product was purified by column chromatography (SiO$_2$, Petroleum ether/Ethyl acetate=100/1 to 50/1) to obtain int-13 as yellow solid (3.8 g, 30% yield).

$^1$H NMR (400 MHz, CDCl$_3$) δ 8.18 (s, 1H), 7.18 (d, J=3.7 Hz, 1H), 6.62 (d, J=3.8 Hz, 1H), 5.63 (s, 2H), 4.20-4.05 (m, 1H), 3.55-3.45 (m, 2H), 1.55 (d, J=6.0 Hz, 6H), 0.98-0.94 (m, 2H), −0.06 (s, 9H).

LCMS: m/z 384.2 [M+1]$^+$.

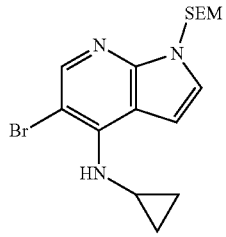 [SMILES: C[Si](C)(C)CCOCn1ccc2c(NC3CC3)c(Br)cnc21]

5-Bromo-N-isopropyl-1-((2-(trimethylsilyl)ethoxy)methyl)-1H-pyrrolo[2,3-b]pyridin-4-amine (int-14)

Intermediate 14 (int-14) was synthesized in an analogous manner to intermediate int-2 in example 1. The crude product was purified by column chromatography (SiO$_2$, Petroleum ether/Ethyl acetate=1/0 to 10/1) to obtain int-14 as a yellow oil (2.85 g, 32% yield).

$^1$H NMR (400 MHz, CDCl$_3$) δ 8.15 (s, 1H), 7.17 (d, J=3.7 Hz, 1H), 7.04 (d, J=3.7 Hz, 1H), 5.64 (s, 2H), 5.34 (brs, 1H), 3.64-3.54 (m, 2H), 3.16-3.06 (m, 1H), 1.05-0.91 (m, 4H), 0.89-0.80 (m, 2H), 0.05-0.04 (m, 9H).

LCMS: m/z 382.2 [M+1]$^+$.

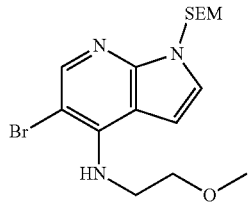 [SMILES: COCCNc1c(Br)cnc2c1ccn2COCC[Si](C)(C)C]

5-Bromo-N-(2-methoxyethyl)-1-((2-(trimethylsilyl)ethoxy)methyl)-1H-pyrrolo[2,3-b]pyridin-4-amine (int-15)

Intermediate 15 (int-15) was synthesized in an analogous manner to intermediate int-2 in example 1. The crude product was purified by column chromatography (SiO$_2$, Petroleum ether/Ethyl acetate=100/1 to 10/1) to obtain int-15 as a yellow oil (4 g, 72% yield).

$^1$H NMR (400 MHz, CDCl$_3$) δ 8.12 (s, 1H), 7.12 (d, J=3.8 Hz, 1H), 6.60 (d, J=3.8 Hz, 1H), 5.58 (s, 2H), 5.33 (brs, 1H), 3.95-3.85 (m, 2H), 3.72-3.67 (m, 2H), 3.58-3.49 (m, 2H), 3.44 (s, 3H), 0.99-0.83 (m, 2H), −0.06 (s, 9H).

LCMS: m/z 400.0 [M+1]$^+$.

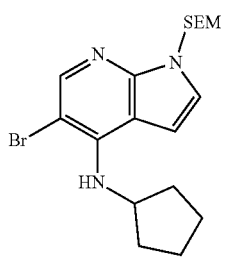 [SMILES: C[Si](C)(C)CCOCn1ccc2c(NC3CCCC3)c(Br)cnc21]

5-Bromo-N-cyclopentyl-1-((2-(trimethylsilyl)ethoxy)methyl)-1H-pyrrolo[2,3-b]pyridin-4-amine (int-16)

Intermediate 16 (int-16) was synthesized in an analogous manner to intermediate int-2 in example 1. The crude product was purified by column chromatography (SiO$_2$, Petroleum ether/Ethyl acetate=50/1 to 10/1) to obtain int-16 as a yellow oil (3.9 g, 73% yield).

$^1$H NMR (400 MHz, CDCl$_3$) δ 8.11 (s, 1H), 7.12 (d, J=3.8 Hz, 1H), 6.62 (d, J=3.8 Hz, 1H), 5.58 (s, 2H), 4.97 (brs, 1H), 4.56-4.45 (m, 1H), 3.57-3.52 (m, 2H), 2.15-2.05 (m, 2H), 1.87-1.78 (m, 2H), 1.77-1.64 (m, 4H), 0.94-0.88 (m, 2H), −0.05 (s, 9H).

LCMS: m/z 410.1 [M+1]$^+$.

Example 27: Synthesis of Intermediates Bis(Pinacolato)Diboron (Bpin) Intermediates (Int-21 to Int-41)

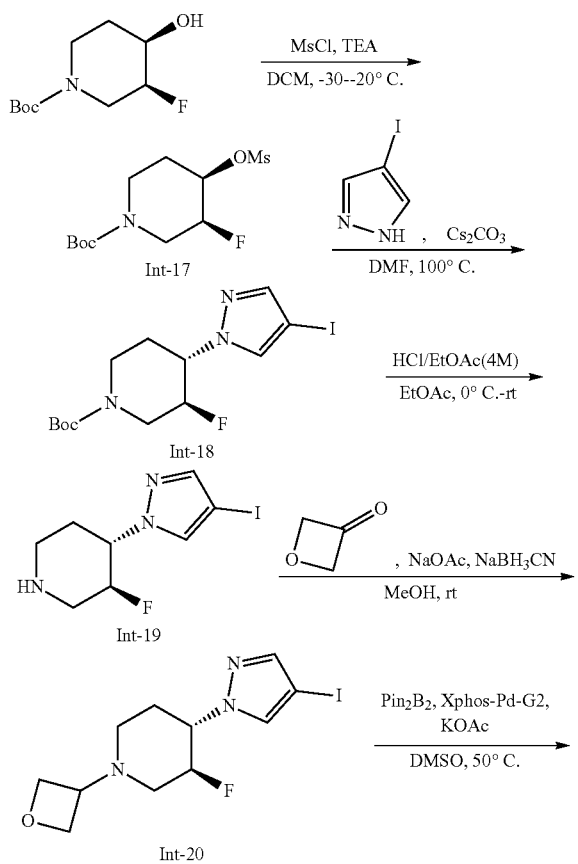

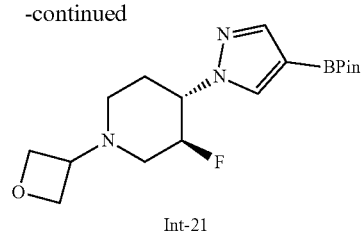

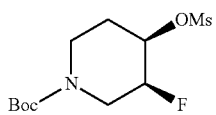 [SMILES: CC(C)(C)OC(=O)N1CC[C@@H](OS(C)(=O)=O)[C@@H](F)C1]

(3S,4R)-tert-Butyl 3-fluoro-4-((methylsulfonyl)oxy)piperidine-1-carboxylate (int-17)

To a mixture of tert-butyl (3S,4R)-tert-butyl 3-fluoro-4-hydroxypiperidine-1-carboxylate (40 g, 182.44 mmol), triethylamine (TEA) (36.92 g, 364.88 mmol, 50.79 mL) in DCM (500 mL) was added MsCl (25.08 g, 218.93 mmol, 16.94 mL) at −30° C. under N$_2$. Then the mixture was stirred at −30° C. for 2 hours. TLC (Petroleum ether/Ethyl acetate=1/1) showed the reactant was consumed completely and a new spot was observed. The mixture was poured into ice-water (800 mL) and extracted with DCM (300 mL×2). The combined organic phase was dried with anhydrous Na$_2$SO$_4$, filtered and concentrated in vacuo to give int-17 (54 g, 181.61 mmol, 99% yield) as a white solid.

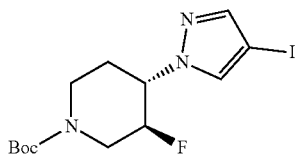 [SMILES: CC(C)(C)OC(=O)N1CC[C@H](n2cc(I)cn2)[C@@H](F)C1]

(3S,4S)-Tert-Butyl 3-Fluoro-4-(4-Iodo-1H-Pyrazol-1-Yl) Piperidine-1-Carboxylate (Int-18)

To a mixture of int-17 (54 g, 181.61 mmol), 4-iodo-1H-pyrazole (35.23 g, 181.61 mmol) in DMF (600 mL) was added Cs$_2$CO$_3$ (88.76 g, 272.41 mmol). Then the mixture was stirred at 100° C. for 5 hours. LCMS showed the reactant was consumed completely, 55% of desired mass was detected. The mixture was poured into ice-water (1000 mL) and extracted with ethyl acetate (500 mL×2). The combined organic phase was washed with brine (1000 mL), dried with anhydrous Na$_2$SO$_4$, filtered and concentrated in vacuo. The residue was purified by column chromatography (SiO$_2$, Petroleum ether/Ethyl acetate=100/1 to 10/1) to give int-18 (49 g, 121.50 mmol, 67% yield) as a colorless oil.

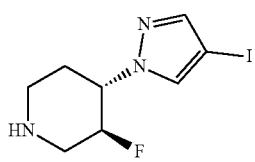 [SMILES: F[C@H]1CNCC[C@@H]1n1cc(I)cn1]

(3S,4S)-3-fluoro-4-(4-iodo-1H-pyrazol-1-yl)piperidine (int-19)

To a solution of int-18 (12.4 g, 31.38 mmol) in EtOAc (50 mL) was added HCl/EtOAc (4 M, 100 mL) at 0° C. Then the mixture was stirred at 15° C. for 2 h. LCMS showed the reactant was consumed completely, 86% of desired mass was detected. The residue was concentrated in vacuum to give int-19 (9.6 g, 28.95 mmol, 92% yield, HCl) as a white solid.

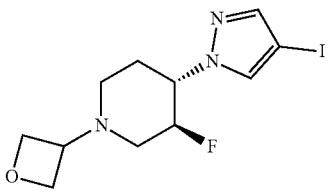 [SMILES: F[C@H]1CN(C2COC2)CC[C@@H]1n1cc(I)cn1]

(3S,4S)-3-fluoro-4-(4-iodo-1H-pyrazol-1-yl)-1-(oxetan-3-yl)piperidine (int-20)

A mixture of int-19 (4.8 g, 14.48 mmol, HCl), oxetan-3-one (3.13 g, 43.43 mmol), NaOAc (1.43 g, 17.37 mmol) in MeOH (50 mL) was degassed, purged 3 times with $N_2$ and then stirred at 15° C. for 1 hour. $NaBH_3CN$ (2.73 g, 43.43 mmol) was then added to the mixture and the reaction was stirred at 15° C. for 16 hours. LCMS showed the reactant was consumed completely and 75% of desired mass was detected. The mixture was poured into ice-$H_2O$ (300 mL) and extracted with ethyl acetate (100 mL). The combined organic phase was washed with brine (300 mL), dried with anhydrous $Na_2SO_4$, filtered and concentrated in vacuo. The residue was purified by column chromatography ($SiO_2$, Petroleum ether/Ethyl acetate=100/1 to 0/1) to give int-20 (3.6 g, 10.05 mmol, 69% yield) as a white solid.

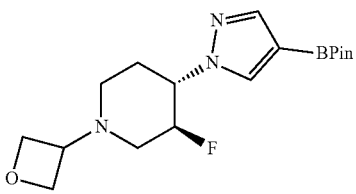

(3S,4S)-3-fluoro-1-(oxetan-3-yl)-4-(4-(4,4,5,5-tetramethyl-1,3,2-dioxaborolan-2-yl)-1H-pyrazol-1-yl)piperidine (int-21)

To a mixture of int-20 (3.6 g, 10.25 mmol), 4,4,4',4',5,5,5',5'-octamethyl-2,2'-bi(1,3,2-dioxaborolane) (3.90 g, 15.38 mmol), KOAc (3.02 g, 30.76 mmol) in DMSO (40 mL) was added XPHOS-PD-G2 (806.61 mg, 1.03 mmol) under $N_2$. The mixture was stirred at 50° C. for 2 hours. LCMS showed the reactant was consumed completely and 62% of desired mass was detected. The mixture was poured into $H_2O$ (100 mL) and extracted with ethyl acetate (50 mL×2). The combined organic phase was washed with brine (100 mL), dried with anhydrous $Na_2SO_4$, filtered and concentrated in vacuo. The residue was purified by column chromatography ($SiO_2$, Petroleum ether/Ethyl acetate=100/1 to 0/1) to give int-21 (3.2 g, 8.29 mmol, 81% yield) as a yellow solid.

$^1$H NMR (400 MHz, $CDCl_3$) δ 7.84 (s, 1H), 7.79 (s, 1H), 5.02-4.81 (m, 1H), 4.70-4.66 (m, 2H), 4.64-4.59 (m, 2H), 4.23-4.08 (m, 1H), 3.71-3.59 (m, 1H), 3.24-3.12 (m, 1H), 2.87-2.74 (m, 1H), 2.37-2.25 (m, 1H), 2.18-1.97 (m, 3H), 1.32 (s, 12H).

LCMS: m/z 352.0 [M+1]$^+$.

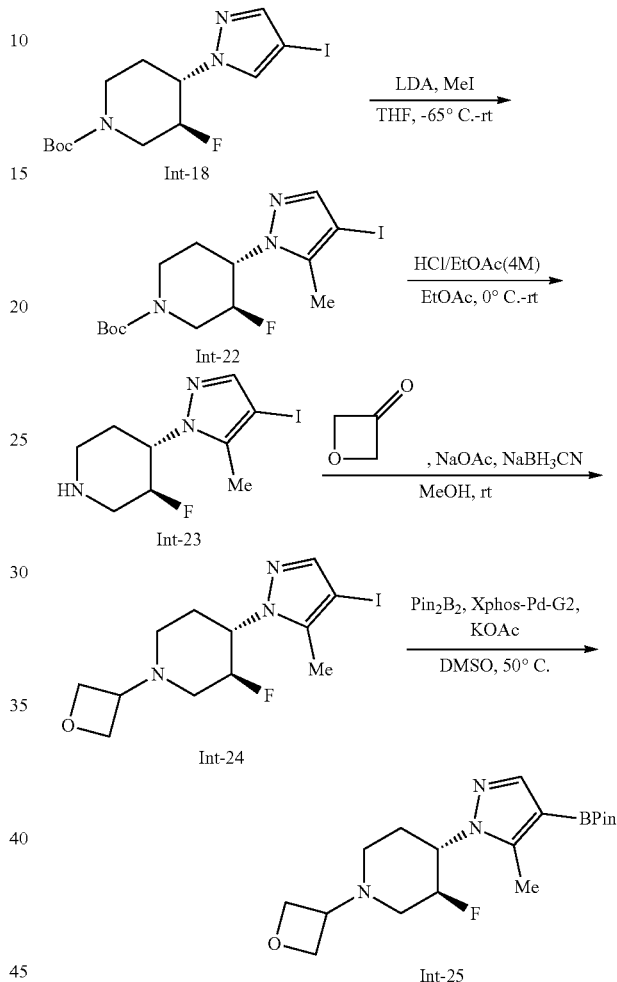

(3S,4S)-tert-butyl 3-fluoro-4-(4-iodo-5-methyl-1H-pyrazol-1-yl)piperidine-1-carboxylate (int-22)

To a solution of int-18 (10 g, 25.30 mmol) in THF (120 mL) was added lithium diisopropylamide (LDA) (2 M, 31.63 mL) at −65° C. under $N_2$. The mixture was stirred at −65° C. for 1 hour. MeI (24.24 g, 170.80 mmol, 10.63 mL) was added to the mixture at −65° C. under $N_2$. The reaction was stirred at 15° C. for 1 hour. LCMS showed the reactant was consumed completely and 81% of desired mass was detected. The reaction mixture was poured into ice-water (400 mL) and then extracted with ethyl acetate (200 mL×2). The combined organic layers were washed with brine (400 mL×2), dried over Na₂SO₄, filtered and concentrated under reduced pressure to give a residue. The residue was purified by column chromatography (SiO₂, Petroleum ether/Ethyl acetate=100/1 to 5/1) to give int-22 (10 g, 23.70 mmol, 94% yield) as a white solid.

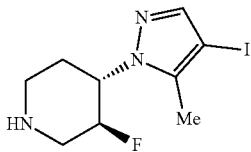 [SMILES: Cc1c(I)cnn1[C@H]1CCNC[C@@H]1F]

(3S,4S)-3-fluoro-4-(4-iodo-5-methyl-1H-pyrazol-1-yl)piperidine (int-23)

To a solution of int-22 (14.4 g, 35.19 mmol) in EtOAc (50 mL) was added HCl/EtOAc (4 M, 100 mL) at 0° C., and then the mixture was stirred at 15° C. for 2 hours. LCMS showed the reactant was consumed completely and 98% of the desired mass was detected. The mixture was concentrated in vacuo to give int-23 (12.16 g, 35.19 mmol, 100% yield, HCl) as a white solid.

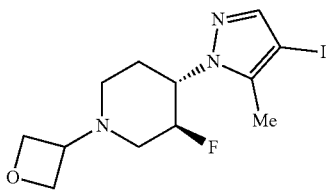 [SMILES: Cc1c(I)cnn1[C@H]1CCN(C2COC2)C[C@@H]1F]

(3S,4S)-3-fluoro-4-(4-iodo-5-methyl-1H-pyrazol-1-yl)-1-(oxetan-3-yl)piperidine (int-24)

A mixture of int-23 (12.16 g, 35.19 mmol, HCl), oxetan-3-one (7.61 g, 105.56 mmol), NaOAc (3.46 g, 42.22 mmol) in MeOH (130 mL) was degassed and 3 times purged with N₂ and then stirred at 15° C. for 1 hour. NaBH₃CN (6.63 g, 105.56 mmol) was then added and the reaction was stirred at 15° C. for 16 hours. LCMS showed the reactant was consumed completely, 81% of desired mass was detected. The mixture was poured into ice-water (800 mL). The aqueous phase was extracted with ethyl acetate (400 mL×2). The combined organic phase was washed with brine (800 mL), dried with anhydrous Na₂SO₄, filtered and concentrated in vacuo. The residue was triturated by EtOAc (15 mL) to give int-24 (10 g, 27.38 mmol, 78% yield) as a white solid.

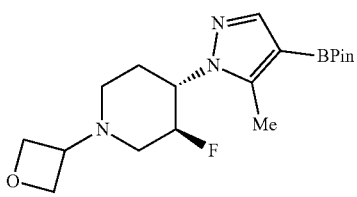

(3S,4S)-3-fluoro-4-(5-methyl-4-(4,4,5,5-tetramethyl-1,3,2-dioxaborolan-2-yl)-1H-pyrazol-1-yl)-1-(oxetan-3-yl)piperidine (int-25)

To a mixture of int-24 (5 g, 13.69 mmol), 4,4,4',4',5,5,5',5'-octamethyl-2,2'-bi(1,3,2-dioxaborolane) (5.22 g, 20.54 mmol), KOAc (4.03 g, 41.08 mmol) in DMSO (50 mL) was added XPHOS-PD-G2 (1.08 g, 1.37 mmol) under N₂, and then the mixture was stirred at 50° C. for 4 hours. LCMS showed the reactant was consumed completely and 55% of desired mass was detected. The mixture was poured into H₂O (100 mL). The aqueous phase was extracted with ethyl acetate (50 mL×2). The combined organic phase was washed with brine (100 mL), dried with anhydrous Na₂SO₄, filtered and concentrated in vacuo. The residue was purified by column chromatography (SiO₂, Petroleum ether/Ethyl acetate=100/1 to 0/1) to give int-25 (4.1 g, 11.23 mmol, 82% yield) as a yellow solid.

¹H NMR (400 MHz, CDCl₃) δ 7.77 (s, 1H), 5.14-4.89 (m, 1H), 4.70-4.60 (m, 4H), 4.17-4.00 (m, 1H), 3.72-3.59 (m, 1H), 3.27-3.12 (m, 1H), 2.89-2.75 (m, 1H), 2.47-2.46 (m, 3H), 2.20-1.84 (m, 4H), 1.31 (s, 12H).

LCMS: m/z 366.2 [M+1]⁺.

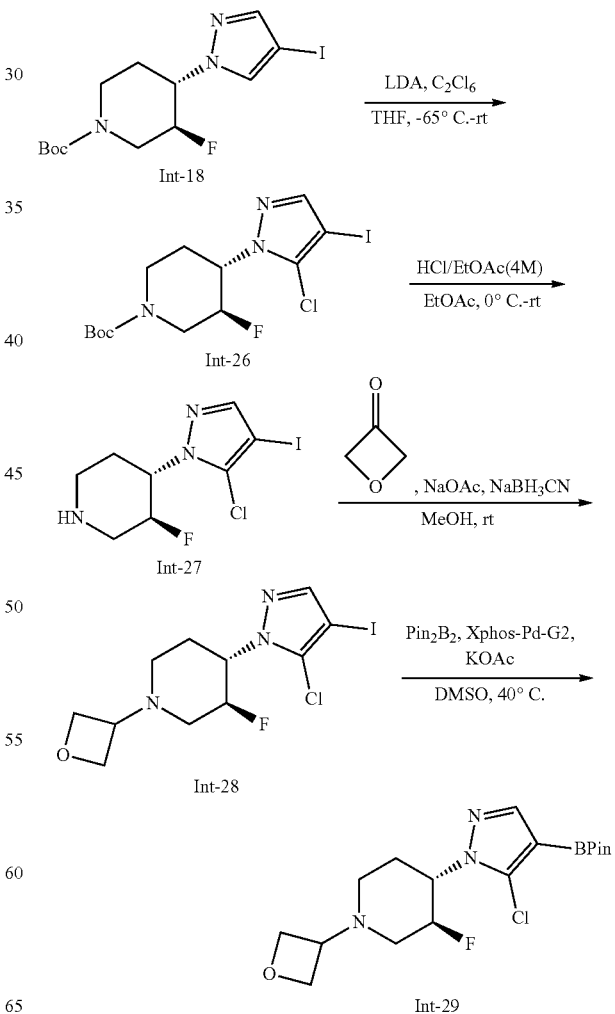

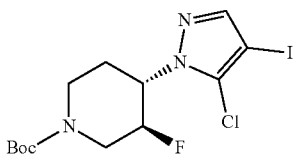 [SMILES: CC(C)(C)OC(=O)N1CC[C@H](n2ncc(I)c2Cl)[C@@H](F)C1]

(3S,4S)-Tert-Butyl 4-(5-Chloro-4-Iodo-1H-Pyrazol-1-Yl)-3-Fluoro Piperidine-1-Carboxylate (int-26)

To a solution of int-18 (29 g, 73.38 mmol) in THF (300 mL) was added LDA (2 M, 91.72 mL) at −65° C. under $N_2$, then the mixture was stirred at −65° C. for 1 hour. 1,1,1,2,2,2-hexachloroethane (52.11 g, 220.14 mmol, 24.94 mL) was added to the mixture at −65° C. and the resulting mixture was stirred at 15° C. for 1 hour under $N_2$ atmosphere. TLC (Petroleum ether/Ethyl acetate=5/1) showed the reactant was consumed completely and a new spot was observed. The mixture was poured into ice-HCl (1 M, 600 mL). The aqueous phase was extracted with ethyl acetate (300 mL×2). The combined organic phase was washed with brine (600 mL), dried with anhydrous $Na_2SO_4$, filtered and concentrated in vacuo. The residue was purified by column chromatography (SiO$_2$, Petroleum ether/Ethyl acetate=100/1 to 10/1) to give int-26 (25 g, 58.19 mmol, 79% yield) as a yellow solid.

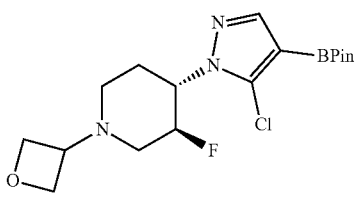

(3S,4S)-4-(5-chloro-4-(4,4,5,5-tetramethyl-1,3,2-dioxaborolan-2-yl)-1H-pyrazol-1-yl)-3-fluoro-1-(oxetan-3-yl)piperidine (int-29)

Int-29 was prepared in an analogous manner to int-26 as described above. The crude product was purified by column chromatography (SiO$_2$, Petroleum ether/Ethyl acetate=100/1 to 0/1) to give int-29 (367 mg, 523.38 µmol, 40% yield) as a yellow solid.

$^1$H NMR (400 MHz, CDCl$_3$) δ 7.83 (s, 1H), 5.20-4.96 (m, 1H), 4.74-4.57 (m, 4H), 4.49-4.33 (m, 1H), 3.71-3.58 (m, 1H), 3.28-3.15 (m, 1H), 2.89-2.76 (m, 1H), 2.40-2.23 (m, 1H), 2.18-1.92 (m, 3H), 1.42-1.29 (s, 12H).

LCMS: m/z 386.3 [M+1]$^+$.

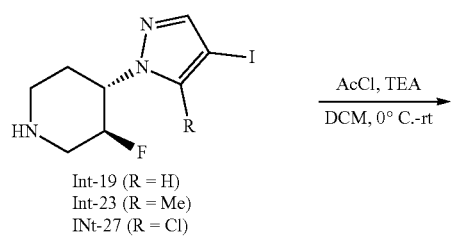

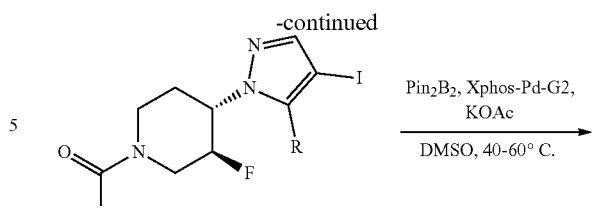

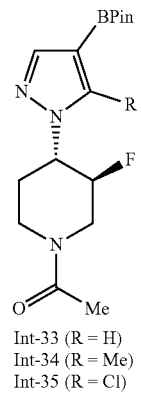

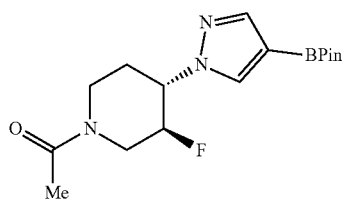

1-((3S,4S)-3-fluoro-4-(4-(4,4,5,5-tetramethyl-1,3,2-dioxaborolan-2-yl)-1H-pyrazol-1-yl)piperidin-1-yl)ethanone (int-33)

To a solution of intermediate int-19 (1 eq) in DCM was added TEA (3 eq) and acetyl chloride (1.1 eq) at 0° C. under $N_2$. The mixture was stirred at rt for 16 h. LCMS showed the reactant was consumed completely. The mixture was poured into ice-water. The aqueous phase was extracted with DCM. The combined organic phase was dried with anhydrous $Na_2SO_4$, filtered and concentrated in vacuo. The residue was purified by column chromatography to give int-30.

To a solution of int-30 (1 eq) in DMSO was added 4,4',4',5,5,5',5'-octamethyl-2,2'-bi(1,3,2-dioxaborolane) (1.5 eq), KOAc (3 eq), XPHOS-PD-G2 (0.1 eq) under $N_2$, and then the mixture was stirred at 40-60° C. for 2-16 hours. LCMS showed the reactant was consumed completely. The mixture was poured into water. The aqueous phase was extracted with ethyl acetate. The combined organic phase was washed with brine, dried with anhydrous $Na_2SO_4$, filtered and concentrated in vacuo. The residue was purified by column chromatography (SiO$_2$, Petroleum ether/Ethyl acetate=10/1 to 0/1) to give int-33 as a white solid (3.0 g, 62% yield over 2 steps).

$^1$H NMR (400 MHz, CDCl$_3$) δ 7.84 (s, 1H), 7.79-7.78 (d, J=2.8 Hz, 1H), 5.04-4.46 (m, 2H), 4.39-4.26 (m, 1H), 4.22-3.87 (m, 1H), 3.40-3.16 (m, 1H), 3.03-2.76 (m, 1H), 2.33-2.14 (m, 5H), 1.32 (s, 12H).

LCMS (Method 1): m/z 338.0 [M+1]$^+$.

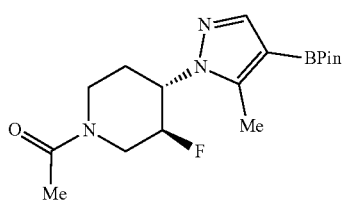

1-((3S,4S)-3-fluoro-4-(5-methyl-4-(4,4,5,5-tetramethyl-1,3,2-dioxaborolan-2-yl)-1H-pyrazol-1-yl)piperidin-1-yl)ethanone (int-34)

Int-34 was prepared in an analogous manner to int-33 as described above. The crude product was purified by column chromatography (SiO$_2$, Petroleum ether/Ethyl acetate=10/1 to 0/1) to give int-34 (2.3 g, 76% yield over 2 steps) as a white solid.

$^1$H NMR (400 MHz, CDCl$_3$) δ 7.75 (s, 1H), 5.09-4.56 (m, 2H), 4.34-3.91 (m, 2H), 3.36-3.16 (m, 1H), 2.92-2.73 (m, 1H), 2.49-2.23 (m, 4H), 2.15 (d, J=5.0 Hz, 3H), 2.09-1.94 (m, 1H), 1.31 (s, 12H).

LCMS (Method 1): m/z 352.1 [M+1]$^+$.

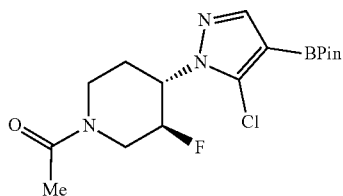

1-((3S,4S)-4-(5-chloro-4-(4,4,5,5-tetramethyl-1,3,2-dioxaborolan-2-yl)-1H-pyrazol-1-yl)-3-fluoropiperidin-1-yl)ethanone (int-35)

Int-35 was prepared in an analogous manner to int-33 as described above. The crude product was purified by column chromatography (SiO$_2$, Petroleum ether/Ethyl acetate=100/1 to 0/1) to give int-35 (1.0 g, 39% yield over 2 steps) as a yellow solid.

LCMS (Method 1): m/z 372.1 [M+1]$^+$.

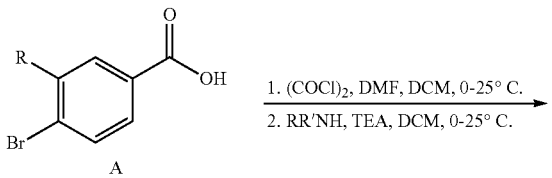

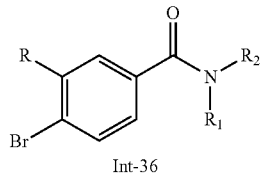

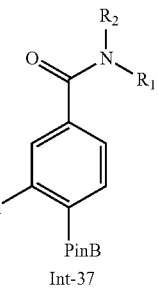

Int-37

(int-37)

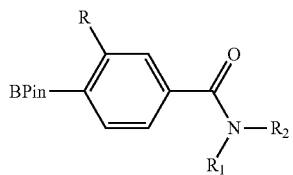

To a solution of compound A (1 eq) in DCM was added (COCl)$_2$ (1.5 eq) and DMF (0.1 eq) at 0° C. The mixture was stirred at 25° C. for 1 hour and was concentrated under reduced pressure. The resulting residue was added dropwise to a mixture of morpholine (1 eq) and TEA (3 eq) in DCM at 0° C. The mixture was stirred at 25° C. for 16 hours. TLC indicated the reaction reached completion. The mixture was then diluted with water and extracted with dichloromethane. The combined organic layers were washed with brine, dried with anhydrous Na$_2$SO$_4$, filtered and concentrated under reduced pressure. The residue was purified by column chromatography to give intermediate int-36.

To a solution of intermediate int-36 (1 eq) and 4,4,5,5-tetramethyl-2-(4,4,5,5-tetramethyl-1,3,2-dioxaborolan-2-yl)-1,3,2-dioxaborolane (1.5 eq) in dioxane was added Pd(dppf)Cl$_2$ (0.1 eq) and KOAc (3 eq). The mixture was stirred at 100° C. for 16 hour. LCMS indicated the reaction was completed. The mixture concentrated under reduced pressure and purified by column chromatography to give int-37.

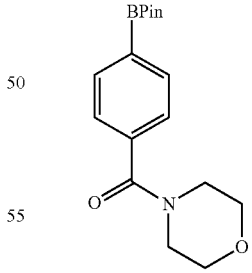

Morpholino(4-(4,4,5,5-tetramethyl-1,3,2-dioxaborolan-2-yl)phenyl)methanone (int-38)

Int-38 was prepared in an analogous manner to int-37 as described above. The crude product was purified by column chromatography (SiO$_2$, Petroleum ether/Ethyl acetate=1/0 to 2/1) to give int-38 (4.5 g, 94% yield over 3 steps) as a yellow solid.

¹H NMR (400 MHz, CDCl₃) δ 7.78 (d, J=7.3 Hz, 2H), 7.31 (d, J=7.3 Hz, 2H), 3.79-3.27 (m, 8H), 1.26 (s, 12H).

LCMS: m/z 318.0 [M+1]⁺.

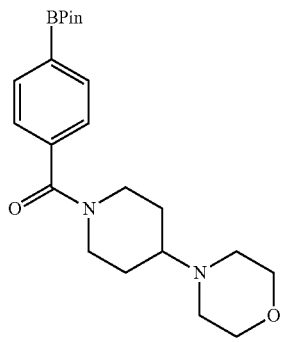

(4-Morpholinopiperidin-1-yl)(4-(4,4,5,5-tetramethyl-1,3,2-dioxaborolan-2yl)phenyl)methanone (int-39)

Int-39 was prepared in an analogous manner to int-37 as described above. The crude product was purified by column chromatography (SiO2, Dichloromethane/Methanol=100/1 to 50/1) to give int-39 (7.43 g, 77% yield over 3 steps) as a dark brown solid.

¹H NMR (400 MHz, CDCl₃) δ 7.89-7.78 (m, 2H), 7.39-7.33 (m, 2H), 4.84-4.61 (m, 1H), 3.80-3.65 (m, 5H), 3.13-2.62 (m, 2H), 2.62-2.27 (m, 5H), 2.09-1.43 (m, 4H), 1.26 (s, 12H).

LCMS: m/z 401.1 [M+1]⁺.

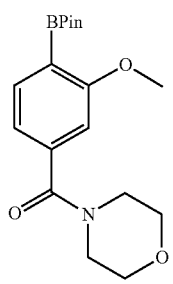

(3-Methoxy-4-(4,4,5,5-tetramethyl-1,3,2-dioxaborolan-2-yl)phenyl)(morpholino)methanone (int-40)

Int-40 was prepared in an analogous manner to int-37 as described above. The crude product was purified by column chromatography (SiO₂, Petroleum ether/Ethyl acetate=50/1 to 10/1) to give int-40 (6.78 g, 45% yield over 3 steps) as a yellow gum.

¹H NMR (400 MHz, CDCl₃) δ 7.68 (d, J=7.3 Hz, 1H), 6.96-6.89 (m, 2H), 3.84 (s, 3H), 3.83-3.71 (m, 4H), 3.66-3.39 (m, 4H), 1.34 (s, 12H).

LCMS (Method 1): m/z 348.0 [M+1]⁺.

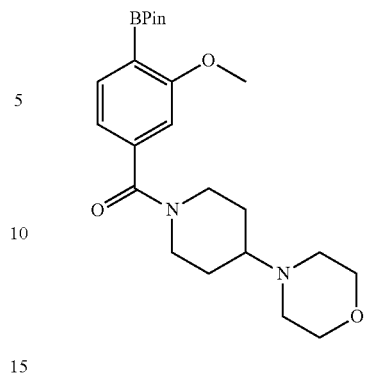

(3-Methoxy-4-(4,4,5,5-tetramethyl-1,3,2-dioxaborolan-2-yl)phenyl)(4-morpholinopiperidin-1-yl)methanone (int-41)

Int-41 was prepared in an analogous manner to int-37 as described above. The crude product was purified by column chromatography (SiO₂, Dichloromethane/Methanol=100/1 to 50/1) to give int-41 (5.70 g, 46% yield over 3 steps) as a dark brown solid.

¹H NMR (400 MHz, CDCl₃) δ 7.68 (d, J=7.3 Hz, 1H), 6.94-6.87 (m, 2H), 4.83-4.65 (m, 1H), 3.87-3.84 (m, 3H), 3.74 (br t, J=4.5 Hz, 4H), 3.08-2.94 (m, 1H), 2.86-2.74 (m, 1H), 2.57 (br s, 4H), 2.48-2.41 (m, 1H), 2.07 (s, 1H), 2.02-1.95 (m, 1H), 1.79 (br d, J=9.5 Hz, 1H), 1.59-1.51 (m, 1H), 1.36 (s, 12H).

LCMS (Method 1): m/z 431.2 [M+1]⁺.

Example 28: General Methods for the Synthesis of Compounds 26-69 from Appropriate Azaindole Intermediates in Example 26 and Bis(Pinacolato)Diboron (Bpin)-Intermediates in Example 27

General Procedure for Coupling Reactions

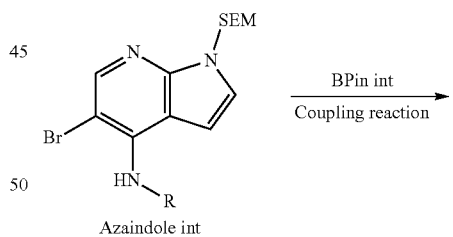

Azaindole int

Int-42

Procedure 1: To a solution of azaindole intermediate (1 eq) in a mixture of n-BuOH and H₂O (10:1, 0.1 M-0.2 M) was added BPin intermediate (1 eq), SPhos Pd G3 (0.1 eq) and K₃PO₄ (3 eq). The reaction mixture was stirred at 60° C. or 50° C. for 16 hours under N₂ atmosphere. The mixture was filtered and concentrated in vacuo. The residue was purified by column chromatography to give intermediate int-42.

Procedure 2: To a solution of azaindole intermediate (1 eq) in THF (0.1 M-0.2 M) was added BPin intermediate (1 eq), $K_3PO_4$ (3 eq) and $Ad_2nBuP\ Pd\ G3$ (0.1 eq). The reaction mixture was stirred at 60° C. for 16 h under $N_2$ atmosphere. The mixture was filtered and concentrated in vacuo. The residue was purified by column chromatography to give intermediate int-42.

Procedure 3: To a solution of azaindole intermediate (1 eq) in a mixture of dioxane and $H_2O$ (10:1, 0.1 M-0.2 M) was added BPin intermediate (1.5 eq), $Pd(dppf)Cl_2$ (0.1 eq) and $K_2CO_3$ (2 eq). The reaction mixture was heated to 100° C. and stirred for 4-12 hours under $N_2$ atmosphere. The mixture was cooled to rt and filtered. The resulting solution was concentrated in vacuo. The residue was purified by column chromatography to give intermediate int-42.

General Procedures for 2-(Trimethylsilyl)ethoxymethyl (SEM) Deprotection

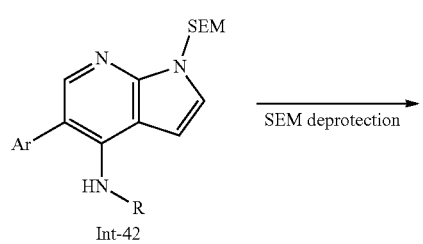

Procedure 4: To a solution of int-42 (1 eq) in DCM (0.1 M-0.2 M) was added HCl/dioxane (4 M, 2 mL, 15-20 eq). The mixture was stirred at 30° C. for 4 hours. Reaction was monitored by LCMS. The crude mixture was concentrated in vacuo. The resulting residue was dissolved in EtOH (0.1 M-0.2 M) and treated with $NH_3.H_2O$ (28% purity, 40-50 eq). The mixture was stirred at 60° C. for 2 hours, allowed to cool to rt and concentrated in vacuo. The crude product purified by reversed-phase HPLC to give the desired product.

Procedure 5: To a solution of int-42 (1 eq) in DCM (0.1 M-0.2 M) was added TFA (90-100 eq). The mixture was stirred at 40° C. for 4 h. Reaction was monitored by LCMS. The crude mixture was concentrated in vacuo. The resulting residue was dissolved in EtOH (0.1 M-0.2 M) and treated with $NH_3.H_2O$ (28% purity, 40-50 eq). The mixture was stirred at 60° C. for 2 hours, allowed to cool to rt and concentrated in vacuo. The crude product was purified by reversed-phase HPLC to give the desired product.

Example 29: Synthesis of 5-(1-((3S,4S)-3-fluoro-1-(oxetan-3-yl)piperidin-4-yl)-1H-pyrazol-4-yl)-N-methyl-1H-pyrrolo[2,3-b]pyridin-4-amine (26)

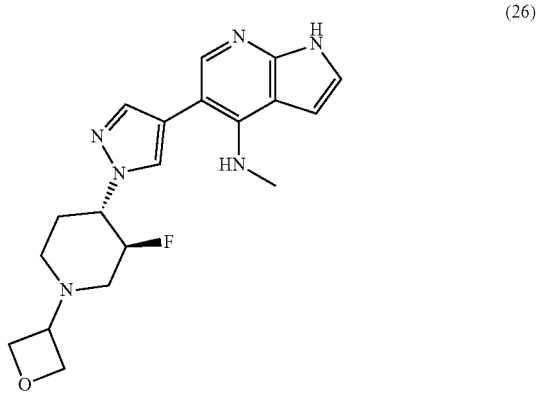 [SMILES: CNc1c(-c2cnn([C@H]3CCN(C4COC4)C[C@@H]3F)c2C)cnc2[nH]ccc12]

Compound 26 was synthesized via procedures 1 and 5 in Example 28 and obtained as a white solid (10.75 mg, 26% yield over 3 steps).

$^1$HNMR (400 MHz, DMSO-$d_6$) δ 11.15 (s, 1H), 7.97 (s, 1H), 7.69 (s, 1H), 7.63 (s, 1H), 7.10 (d, J=3.6 Hz, 1H), 6.67 (d, J=3.2 Hz, 1H), 5.53-5.49 (m, 1H), 5.10-4.90 (m, 1H), 4.60-4.25 (m, 5H), 3.60-3.50 (m, 1H), 3.25-3.10 (m, 4H), 2.85-2.75 (m, 1H), 2.15-1.90 (m, 4H).

LCMS: m/z 371.1 [M+1]$^+$.

Example 30: Synthesis of N-ethyl-5-(1-((3S,4S)-3-fluoro-1-(oxetan-3-yl)piperidin-4-yl)-1H-pyrazol-4-yl)-1H-pyrrolo[2,3-b]pyridin-4-amine (27)

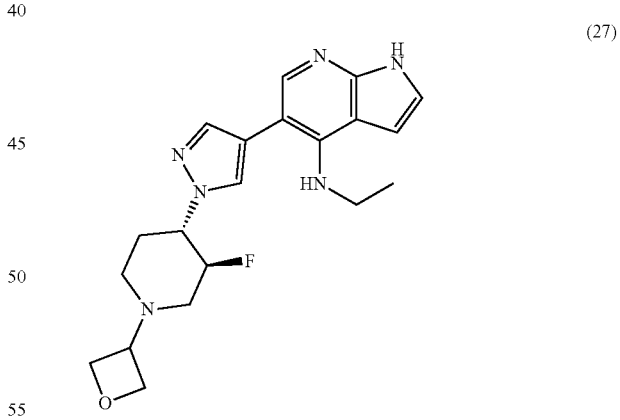

Compound 27 was synthesized via procedures 1 and 5 in Example 28 and obtained as a white solid (91.18 mg, 22% yield over 3 steps).

$^1$H NMR (400 MHz, CDCl$_3$) δ 9.91-9.34 (m, 1H), 7.89 (s, 1H), 7.70 (s, 1H), 7.60 (s, 1H), 7.11 (d, J=3.6 Hz, 1H), 6.65 (d, J=3.6 Hz, 1H), 5.07-4.86 (m, 1H), 4.73-4.62 (m, 5H), 4.34-4.12 (m, 1H), 3.76-3.64 (m, 3H), 3.28-3.20 (m, 1H), 2.93-2.85 (m, 1H), 2.47-2.35 (m, 1H), 2.27 (m, 1H), 2.18-2.05 (m, 2H), 1.29 (t, J=7.2 Hz, 3H).

LCMS: m/z 385.2 [M+1]$^+$.

Example 31: Synthesis of 5-(1-((3S,4S)-3-fluoro-1-(oxetan-3-yl)piperidin-4-yl)-1H-pyrazol-4-yl)-N-isopropyl-1H-pyrrolo[2,3-b]pyridin-4-amine (28)

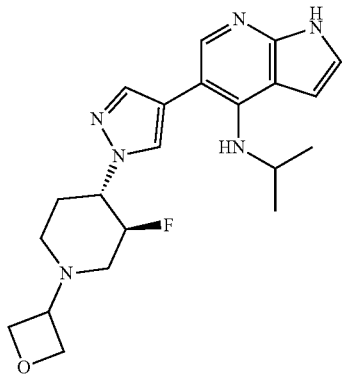

Compound 28 was synthesized via procedures 1 and 5 in Example 28 and obtained as a white solid (85.0 mg, 24% yield over 3 steps).

$^1$H NMR (400 MHz, CDCl$_3$) δ 9.70 (brs, 1H), 7.89 (s, 1H), 7.69 (s, 1H), 7.59 (s, 1H), 7.12 (d, J=3.7 Hz, 1H), 6.58 (d, J=3.7 Hz, 1H), 5.06-4.85 (m, 1H), 4.76-4.55 (m, 5H), 4.37-4.16 (m, 2H), 3.68 (m, 1H), 3.28-3.20 (m, 1H), 2.95-2.85 (m, 1H), 2.42 (m, 1H), 2.32-2.23 (m, 1H), 2.19-2.05 (m, 2H), 1.28 (m, 6H).

LCMS: m/z 399.2 [M+1]$^+$.

Example 32: Synthesis of N-cyclopropyl-5-(1-((3S,4S)-3-fluoro-1-(oxetan-3-yl)piperidin-4-yl)-1H-pyrazol-4-yl)-1H-pyrrolo[2,3-b]pyridin-4-amine (29)

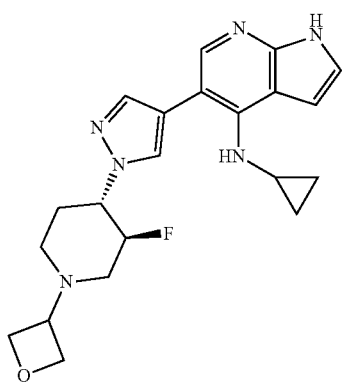

Compound 29 was synthesized via procedures 1 and 5 in Example 28 and obtained as a white solid (85.0 mg, 25% yield over 3 steps).

$^1$H NMR (400 MHz, CDCl$_3$) δ 9.77 (brs, 1H), 7.89 (s, 1H), 7.66 (s, 1H), 7.56 (s, 1H), 7.12 (d, J=3.5 Hz, 1H), 7.01 (d, J=3.7 Hz, 1H), 5.11-4.86 (m, 2H), 4.74-4.62 (m, 4H), 4.20 (m, 1H), 3.67 (m, 1H), 3.27-3.20 (m, 1H), 3.05-2.98 (m, 1H), 2.92-2.85 (m, 1H), 2.47-2.35 (m, 1H), 2.26 (m, 1H), 2.17-2.04 (m, 2H), 0.94-0.87 (m, 2H), 0.75-0.67 (m, 2H).

LCMS: m/z 397.2 [M+1]$^+$.

Example 33: Synthesis of 5-(1-((3S,4S)-3-fluoro-1-(oxetan-3-yl)piperidin-4-yl)-1H-pyrazol-4-yl)-N-(2-methoxyethyl)-1H-pyrrolo[2,3-b]pyridin-4-amine (30)

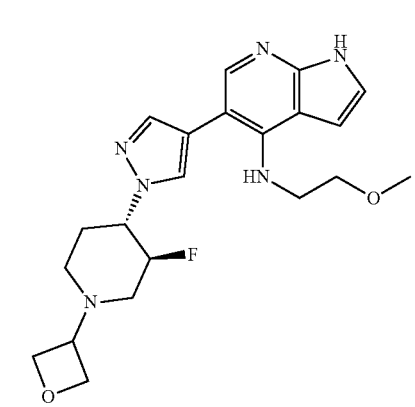

Compound 30 was synthesized via procedures 1 and 5 in Example 28 and obtained as a white solid (124.0 mg, 30% yield over 3 steps).

$^1$H NMR (400 MHz, CDCl$_3$) δ 9.20 (brs, 1H), 7.92 (s, 1H), 7.71 (s, 1H), 7.63 (s, 1H), 7.11 (d, J=3.5 Hz, 1H), 6.61 (d, J=3.7 Hz, 1H), 5.12-4.86 (m, 2H), 4.73-4.62 (m, 4H), 4.21 (m, 1H), 3.84 (m, 2H), 3.71-3.61 (m, 3H), 3.36 (s, 3H), 3.27-3.20 (m, 1H), 2.92-2.85 (m, 1H), 2.47-2.34 (m, 1H), 2.26 (m, 1H), 2.17-2.06 (m, 2H)

LCMS: m/z 415.2 [M+1]$^+$.

Example 34: Synthesis of N-cyclopentyl-5-(1-((3S,4S)-3-fluoro-1-(oxetan-3-yl)piperidin-4-yl)-1H-pyrazol-4-yl)-1H-pyrrolo[2,3-b]pyridin-4-amine (31)

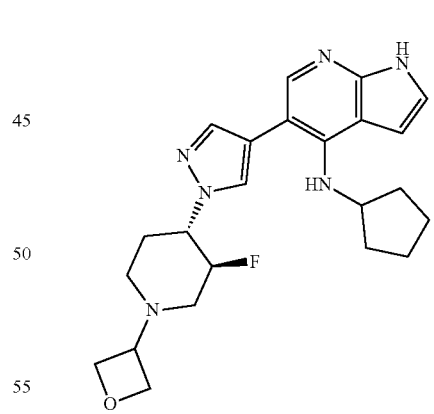

Compound 31 was synthesized via procedures 1 and 5 in Example 28 and obtained as a white solid (115.2 mg, 28% yield over 3 steps).

$^1$H NMR (400 MHz, CDCl$_3$) δ 9.38-9.14 (m, 1H), 7.88 (s, 1H), 7.68 (s, 1H), 7.58 (s, 1H), 7.11 (d, J=3.7 Hz, 1H), 6.63 (d, J=3.7 Hz, 1H), 5.05-4.83 (m, 1H), 4.75-4.61 (m, 5H), 4.54-4.43 (m, 1H), 4.28-4.13 (m, 1H), 3.67 (m, 1H), 3.30-3.16 (m, 1H), 2.95-2.82 (m, 1H), 2.49-2.35 (m, 1H), 2.33-2.23 (m, 1H), 2.18-1.98 (m, 4H), 1.71-1.48 (m, 6H).

LCMS: m/z 425.2 [M+1]$^+$.

Example 35: Synthesis of 5-(1-((3S,4S)-3-fluoro-1-(oxetan-3-yl)piperidin-4-yl)-5-methyl-1H-pyrazol-4-yl)-N-methyl-1H-pyrrolo[2,3-b]pyridin-4-amin (32)

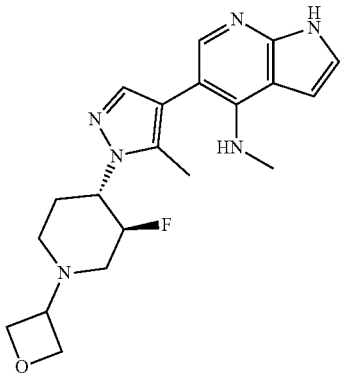
(32)

Compound 32 was synthesized via procedures 1 and 5 in Example 28 and obtained as a white solid (81.0 mg, 56% yield over 3 steps).

$^1$H NMR (400 MHz, CDCl$_3$) δ 9.25 (brs, 1H), 7.77 (s, 1H), 7.57 (s, 1H), 7.10 (d, J=3.6 Hz, 1H), 6.75 (d, J=3.6 Hz, 1H), 5.17-4.96 (m, 1H), 4.73-4.64 (m, 4H), 4.54 (m, 1H), 4.19-4.08 (m, 1H), 3.69 (m, 1H), 3.32-3.21 (m, 4H), 2.90 (m, 1H), 2.61-2.48 (m, 1H), 2.22-2.05 (m, 6H).

LCMS: m/z 385.2 [M+1]$^+$.

Example 36: Synthesis of 1-((3S,4S)-3-fluoro-4-(4-(4-(methylamino)-1H-pyrrolo[2,3-b]pyridin-5-yl)-1H-pyrazol-1-yl)piperidin-1-yl)ethan-1-one (33)

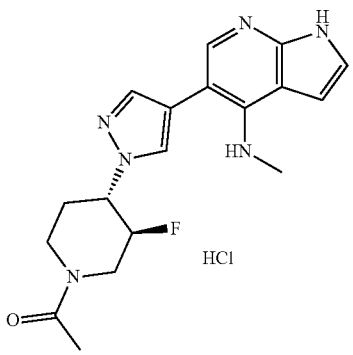
(33)

Compound 33 was synthesized via procedures 1 and 5 in Example 28 and obtained as a yellow solid (90.0 mg, 23% yield over 3 steps).

$^1$H NMR (400 MHz, DMSO-d$_6$) δ 13.86 (brs, 1H), 12.17 (s, 1H), 8.08 (s, 1H), 7.74 (s, 1H), 7.69 (s, 1H), 7.29 (d, J=4 Hz, 1H), 7.11 (s, 1H), 6.98 (d, J=1.6 Hz, 1H), 4.83-4.69 (m, 1H), 4.68-4.63 (m, 1H), 4.6-4.26 (m, 2H), 3.40-3.31 (m, 5H), 2.16-2.04 (m, 5H).

LCMS: m/z 357.1 [M+1]$^+$.

Example 37: Synthesis of 1-((3S,4S)-4-(4-(4-(ethylamino)-1H-pyrrolo[2,3-b]pyridin-5-yl)-1H-pyrazol-1-yl)-3-fluoropiperidin-1-yl)ethan-1-one (34)

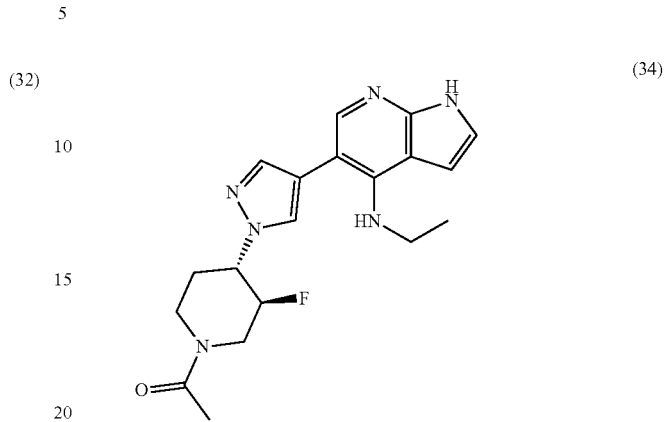
(34)

Compound 34 was synthesized via procedures 1 and 5 in Example 28 and obtained as a white solid (154.0 mg, 38% yield over 3 steps).

$^1$H NMR (400 MHz, CDCl$_3$) δ 9.64 (brs, 1H), 7.87 (s, 1H), 7.70 (s, 1H), 7.59 (d, J=5.1 Hz, 1H), 7.11 (d, J=3.7 Hz, 1H), 6.65 (d, J=3.7 Hz, 1H), 5.10-4.62 (m, 3H), 4.46-4.32 (m, 1H), 4.29-3.96 (m, 1H), 3.76-3.69 (m, 2H), 3.40-3.22 (m, 1H), 2.99-2.77 (m, 1H), 2.43-2.26 (m, 2H), 2.19 (d, J=3.3 Hz, 3H), 1.29 (t, J=7.2 Hz, 3H).

LCMS: m/z 371.2 [M+1]$^+$.

Example 38: Synthesis of 1-((3S,4S)-3-fluoro-4-(4-(4-(isopropylamino)-1H-pyrrolo[2,3-b]pyridin-5-yl)-1H-pyrazol-1-yl)piperidin-1-yl)ethan-1-one (35)

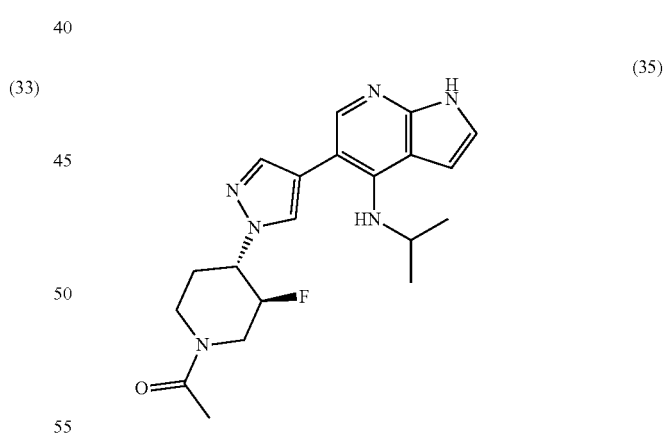
(35)

Compound 35 was synthesized via procedures 1 and 5 in Example 28 and obtained as a white solid (180.0 mg, 52% yield over 3 steps).

$^1$H NMR (400 MHz, CDCl$_3$) δ 9.36 (brs, 1H), 7.88 (s, 1H), 7.68 (s, 1H), 7.59 (d, J=5.4 Hz, 1H), 7.12 (d, J=3.6 Hz, 1H), 6.58 (d, J=3.6 Hz, 1H), 5.11-4.80 (m, 1H), 4.76-4.51 (m, 2H), 4.45-4.20 (m, 3H), 3.99 (m, 1H), 3.41-3.22 (m, 1H), 3.00-2.78 (m, 1H), 2.48-2.25 (m, 2H), 2.19 (d, J=2.4 Hz, 3H), 1.28 (m, 6H).

LCMS: m/z 385.2 [M+1]$^+$.

Example 39: Synthesis of 1-((3S,4S)-4-(4-(4-(cyclopropylamino)-1H-pyrrolo[2,3-b]pyridin-5-yl)-1H-pyrazol-1-yl)-3-fluoropiperidin-1-yl)ethan-1-one (36)

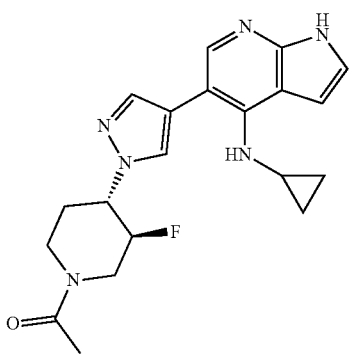

(36)

Compound 36 was synthesized via procedures 1 and 5 in Example 28 and obtained as a white solid (160.0 mg, 46% yield over 3 steps).

$^1$H NMR (400 MHz, CDCl$_3$) δ 9.46 (brs, 1H), 7.88 (s, 1H), 7.65 (s, 1H), 7.55 (d, J=4.1 Hz, 1H), 7.11 (d, J=3.6 Hz, 1H), 7.01 (d, J=3.6 Hz, 1H), 5.13-4.57 (m, 3H), 4.44-3.94 (m, 2H), 3.41-3.21 (m, 1H), 3.06-2.77 (m, 2H), 2.44-2.22 (m, 2H), 2.18 (d, J=3.4 Hz, 3H), 0.95-0.87 (m, 2H), 0.74-0.66 (m, 2H).

LCMS: m/z 383.2 [M+1]$^+$.

Example 40: Synthesis of 1-((3S,4S)-3-fluoro-4-(4-(4-((2-methoxyethyl)amino)-1H-pyrrolo[2,3-b]pyridin-5-yl)-1H-pyrazol-1-yl)piperidin-1-yl)ethan-1-one (37)

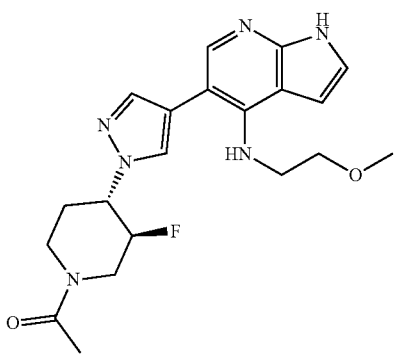

(37)

Compound 37 was synthesized via procedures 1 and 5 in Example 28 and obtained as a white solid (160.0 mg, 46% yield over 3 steps).

$^1$H NMR (400 MHz, CDCl$_3$) δ 9.26 (brs, 1H), 7.91 (s, 1H), 7.71 (s, 1H), 7.63 (d, J=5.6 Hz, 1H), 7.12 (d, J=3.7 Hz, 1H), 6.61 (d, J=3.7 Hz, 1H), 5.11-4.56 (m, 3H), 4.45-3.95 (m, 2H), 3.84 (m, 2H), 3.67-3.58 (m, 2H), 3.41-3.36 (m, 3H), 3.36-3.22 (m, 1H), 3.01-2.79 (m, 1H), 2.44-2.25 (m, 2H), 2.19 (d, J=3.3 Hz, 3H).

LCMS: m/z 401.2 [M+1]$^+$.

Example 41: Synthesis of 1-((3S,4S)-4-(4-(4-(cyclopentylamino)-1H-pyrrolo[2,3-b]pyridin-5-yl)-1H-pyrazol-1-yl)-3-fluoropiperidin-1-yl)ethan-1-one (38)

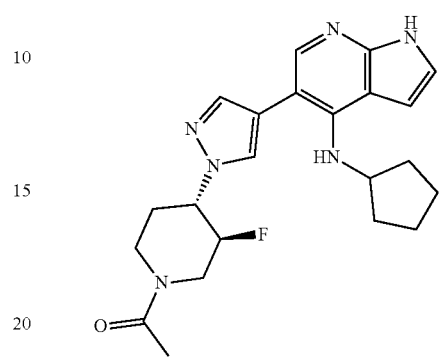

(38)

Compound 38 was synthesized via procedures 1 and 5 in Example 28 and obtained as a white solid (148.0 mg, 55% yield over 3 steps).

$^1$H NMR (400 MHz, CDCl$_3$) δ 9.33 (brs, 1H), 7.89 (s, 1H), 7.69 (s, 1H), 7.59 (d, J=5.3 Hz, 1H), 7.12 (d, J=3.5 Hz, 1H), 6.65 (d, J=3.1 Hz, 1H), 5.21-4.59 (m, 3H), 4.57-3.93 (m, 3H), 3.45-3.21 (m, 1H), 3.03-2.76 (m, 1H), 2.50-2.26 (m, 2H), 2.20 (s, 3H), 2.14-1.98 (m, 2H), 1.89-1.72 (m, 4H), 1.62-1.47 (m, 2H).

LCMS: m/z 411.2 [M+1]$^+$.

Example 42: Synthesis of 1-((3S,4S)-3-fluoro-4-(5-methyl-4-(4-(methylamino)-1H-pyrrolo[2,3-b]pyridin-5-yl)-1H-pyrazol-1-yl)piperidin-1-yl)ethan-1-one (39)

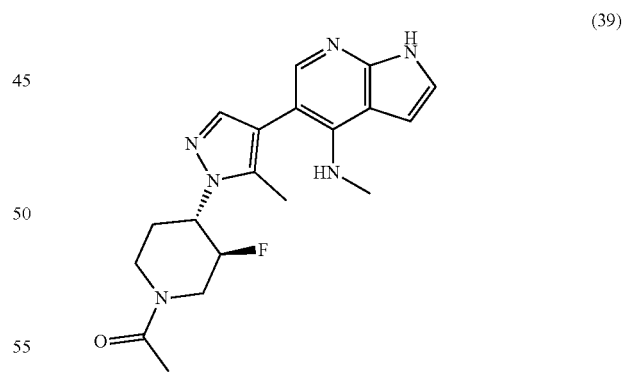

(39)

Compound 39 was synthesized via procedures 1 and 5 in Example 28 and obtained as a yellow solid (133.0 mg, 31% yield over 3 steps).

$^1$HNMR (400 MHz, DMSO-d$_6$) δ 11.22-11.10 (m, 1H), 7.53-7.51 (m, 1H), 7.46-7.44 (m, 1H), 7.12-7.08 (m, 1H), 6.68-6.63 (m, 1H), 5.31-5.20 (m, 1H), 5.08-4.36 (m, 3H), 4.29-3.81 (m, 1H), 3.33-3.25 (m, 1H), 3.13-3.07 (m, 3H), 2.97-2.79 (m, 1H), 2.15-1.91 (m, 8H).

LCMS: m/z 371.2[M+1]$^+$.

Example 43: Synthesis of 1-((3S,4S)-4-(4-(4-(ethylamino)-1H-pyrrolo[2,3-b]pyridin-5-yl)-5-methyl-1H-pyrazol-1-yl)-3-fluoropiperidin-1-yl)ethan-1-one (40)

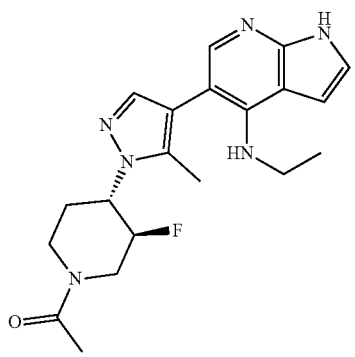

(40)

Compound 40 was synthesized via procedures 1 and 5 in Example 28 and obtained as a white solid (70.0 mg, 26% yield over 3 steps).

$^1$H NMR (400 MHz, CDCl$_3$) δ 9.45 (brs, 1H), 7.79 (s, 1H), 7.56 (s, 1H), 7.11 (d, J=3.5 Hz, 1H), 6.65 (d, J=3.7 Hz, 1H), 5.16-4.64 (m, 2H), 4.42-4.23 (m, 3H), 4.01 (d, J=12.3 Hz, 1H), 3.69 (m, 2H), 3.42-3.20 (m, 1H), 2.98-2.72 (m, 1H), 2.57-2.29 (m, 1H), 2.22 (s, 3H), 2.19 (d, J=2.1 Hz, 3H), 1.26 (t, J=7.2 Hz, 3H).

LCMS: m/z 385.2 [M+1]$^+$.

Example 44: Synthesis of 1-((3S,4S)-3-fluoro-4-(4-(4-(isopropylamino)-1H-pyrrolo[2,3-b]pyridin-5-yl)-5-methyl-1H-pyrazol-1-yl)piperidin-1-yl)ethan-1-one (41)

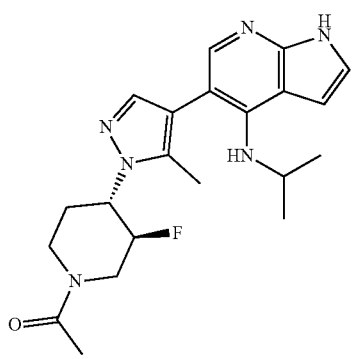

(41)

Compound 41 was synthesized via procedures 1 and 5 in Example 28 and obtained as a white solid (65.0 mg, 23% yield over 3 steps).

$^1$H NMR (400 MHz, CDCl$_3$) δ 9.38 (brs, 1H), 7.80 (s, 1H), 7.55 (s, 1H), 7.12 (d, J=3.5 Hz, 1H), 6.58 (d, J=3.7 Hz, 1H), 5.13-4.66 (m, 2H), 4.40-4.21 (m, 4H), 4.05-3.98 (m, 1H), 3.40-3.22 (m, 1H), 2.94-2.77 (m, 1H), 2.59-2.31 (m, 1H), 2.21 (s, 3H), 2.19 (s, 3H), 1.24 (m, 6H).

LCMS: m/z 399.2 [M+1]$^+$.

Example 45: Synthesis of 1-((3S,4S)-4-(4-(4-(cyclopropylamino)-1H-pyrrolo[2,3-b]pyridin-5-yl)-5-methyl-1H-pyrazol-1-yl)-3-fluoropiperidin-1-yl)ethan-1-one (42)

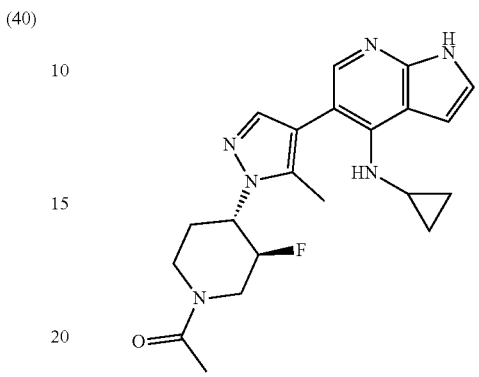

(42)

Compound 42 was synthesized via procedures 1 and 5 in Example 28 and obtained as a white solid (74.0 mg, 25% yield over 3 steps).

$^1$HNMR (400 MHz, CDCl$_3$) δ 9.49 (brs, 1H), 7.79 (s, 1H), 7.52 (s, 1H), 7.12 (d, J=3.5 Hz, 1H), 7.00 (d, J=3.7 Hz, 1H), 5.14-4.64 (m, 3H), 4.38-3.97 (m, 2H), 3.40-3.22 (m, 1H), 3.04-2.77 (m, 2H), 2.57-2.28 (m, 1H), 2.19 (m, 7H), 0.92-0.86 (m, 2H), 0.69-0.63 (m, 2H).

LCMS: m/z 397.2 [M+1]$^+$.

Example 46: Synthesis of 1-((3S,4S)-3-fluoro-4-(4-(4-((2-methoxyethyl)amino)-1H-pyrrolo[2,3-b]pyridin-5-yl)-5-methyl-1H-pyrazol-1-yl)piperidin-1-yl)ethan-1-one (43)

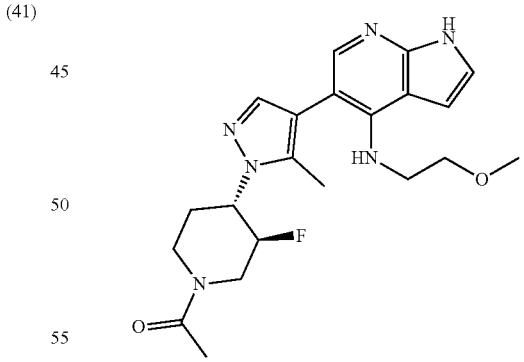

(43)

Compound 43 was synthesized via procedures 1 and 5 in Example 28 and obtained as a white solid (92.0 mg, 31% yield over 3 steps).

$^1$HNMR (400 MHz, CDCl$_3$) δ 9.45 (brs, 1H), 7.82 (s, 1H), 7.56 (s, 1H), 7.12 (d, J=3.7 Hz, 1H), 6.61 (d, J=3.5 Hz, 1H), 5.17-4.61 (m, 3H), 4.44-3.96 (m, 2H), 3.90-3.74 (m, 2H), 3.67-3.53 (m, 2H), 3.45-3.21 (m, 4H), 2.99-2.76 (m, 1H), 2.63-2.29 (m, 1H), 2.28-2.12 (m, 7H).

LCMS: m/z 415.2 [M+1]$^+$.

Example 47: Synthesis of 1-((3S,4S)-4-(4-(4-(cyclopentylamino)-1H-pyrrolo[2,3-b]pyridin-5-yl)-5-methyl-1H-pyrazol-1-yl)-3-fluoropiperidin-1-yl)ethan-1-one (44)

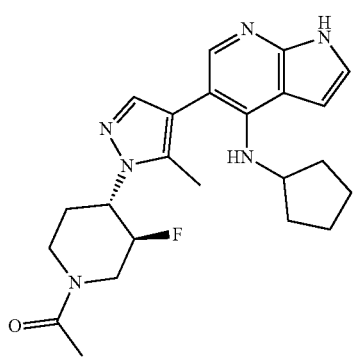

(44)

Compound 44 was synthesized via procedures 1 and 5 in Example 28 and obtained as a white solid (55.0 mg, 18% yield over 3 steps).

$^1$HNMR (400 MHz, CDCl$_3$) δ 9.39 (brs, 1H), 7.79 (s, 1H), 7.54 (s, 1H), 7.12 (d, J=3.5 Hz, 1H), 6.63 (d, J=3.7 Hz, 1H), 5.14-4.66 (m, 2H), 4.51-3.98 (m, 4H), 3.40-3.22 (m, 1H), 2.94-2.75 (m, 1H), 2.60-2.31 (m, 1H), 2.20 (d, J=6.8 Hz, 7H), 1.75-1.60 (m, 6H), 1.55-1.42 (m, 2H).

LCMS: m/z 425.2 [M+1]$^+$.

Example 48: Synthesis of 1-((3S,4S)-4-(5-chloro-4-(4-(methylamino)-1H-pyrrolo[2,3-b]pyridin-5-yl)-1H-pyrazol-1-yl)-3-fluoropiperidin-1-yl)ethan-1-one (45)

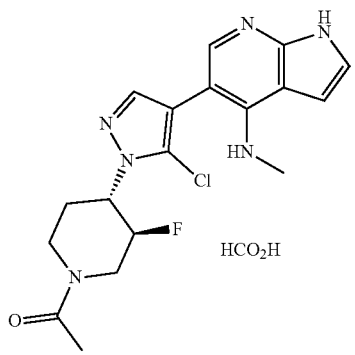

(45)

Compound 45 was synthesized via procedures 2 and 5 in Example 28 and obtained as a yellow solid (101.0 mg, 37% yield over 3 steps).

$^1$HNMR (400 MHz, CDCl$_3$) δ 13.71 (brs, 1H), 8.65-8.61 (m, 1H), 7.71-7.66 (m, 1H), 7.61-7.56 (m, 1H), 7.23-7.19 (m, 1H), 6.82-6.77 (m, 1H), 5.36-5.27 (m, 1H), 5.18-4.78 (m, 2H), 4.72-4.62 (m, 1H), 4.35-3.97 (m, 1H), 3.42 (d, J=5.3 Hz, 3H), 3.39 (s, 1H), 2.94-2.77 (m, 1H), 2.40-2.15 (m, 5H).

LCMS: m/z 391.1 [M+1]$^+$.

Example 49: Synthesis of (4-(4-(methylamino)-1H-pyrrolo[2,3-b]pyridin-5-yl)phenyl)(morpholino)methanone (46)

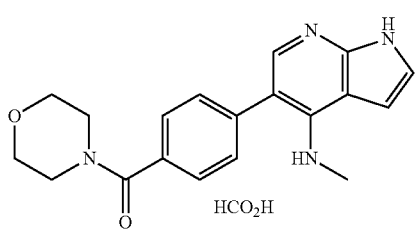

(46)

Compound 46 was synthesized via procedures 3 and 4 in Example 28 and obtained as an off-white solid (47.43 mg, 19% yield over 3 steps). Compound 46 was isolated as a formic acid salt.

$^1$HNMR (400 MHz, DMSO-d$_6$) δ 11.23 (s, 1H), 8.15 (s, 1H), 7.61 (s, 1H), 7.48-7.42 (m, 4H), 7.13-7.13 (m, 1H), 6.70-6.70 (m, 1H), 5.66-5.65 (m, 1H), 3.54-3.45 (m, 8H), 3.08-3.06 (m, 3H).

LCMS: m/z 336.9 [M+1]$^+$.

Example 50: Synthesis of (4-(4-(ethylamino)-1H-pyrrolo[2,3-b]pyridin-5-yl)phenyl)(morpholino)methanone (47)

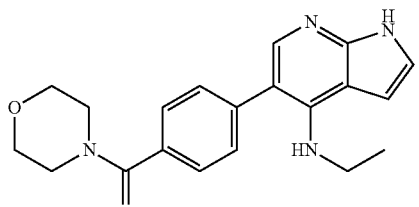

(47)

Compound 47 was synthesized via procedures 3 and 4 in Example 28 and obtained as an off-white solid (47.43 mg, 19% yield over 3 steps). Compound 47 was isolated as a hydrochloride (an HCl) salt.

$^1$HNMR (400 MHz, DMSO-d$_6$) δ 14.06 (s, 1H), 12.41 (s, 1H), 7.75 (s, 1H), 7.57-7.54 (m, 2H), 7.50-7.48 (m, 2H), 7.38-7.37 (m, 1H), 7.29 (m, 1H), 6.89-6.89 (m, 1H), 3.62 (m, 8H), 3.50-3.47 (m, 2H), 1.23-1.19 (m, 3H).

LCMS: m/z 351.2 [M+1]$^+$.

Example 51: Synthesis of (4-(4-(isopropylamino)-1H-pyrrolo[2,3-b]pyridin-5-yl)phenyl)(morpholino)methanone (48)

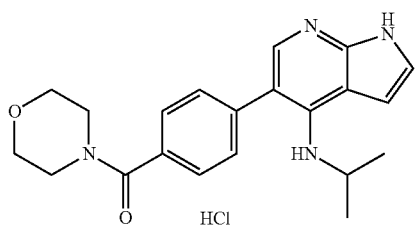
(48)

Compound 48 was synthesized via procedures 3 and 4 in Example 28 and obtained as a yellow solid (14.69 mg, 16% yield over 3 steps). Compound 48 was isolated as an HCl salt.

$^1$HNMR (400 MHz, DMSO-d$_6$) δ 14.25 (s, 1H), 12.49 (s, 1H), 7.75 (s, 1H), 7.57-7.52 (m, 4H), 7.51-7.38 (m, 1H), 6.89 (m, 1H), 6.69-6.67 (m, 1H), 4.37-4.37 (m, 1H), 3.62-3.47 (m, 8H), 1.25-1.23 (m, 6H).

LCMS: m/z 365.5 [M+1]$^+$.

Example 52: Synthesis of (4-(4-(cyclopropylamino)-1H-pyrrolo[2,3-b]pyridin-5-yl)phenyl)(morpholino)methanone (49)

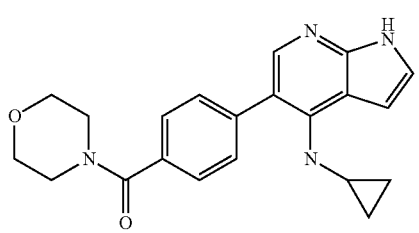
(49)

Compound 49 was synthesized via procedures 3 and 4 in Example 28 and obtained as a white solid (13.80 mg, 8% yield over 3 steps).

$^1$HNMR (400 MHz, CDCl$_3$) δ 9.1 (s, 1H), 7.84 (s, 1H), 7.52-7.50 (m, 2H), 7.48-7.44 (m, 2H), 7.13-7.12 (m, 1H), 7.04-7.03 (m, 1H), 4.889 (s, 1H), 3.75-3.65 (m, 8H), 3.01-2.99 (m, 1H), 0.91-0.88 (m, 2H), 0.69-0.65 (m, 2H).

LCMS: m/z 363.3 [M+1]$^+$.

Example 53: Synthesis of (4-(4-((2-methoxyethyl)amino)-1H-pyrrolo[2,3-b]pyridin-5-yl)phenyl)(morpholino)methanone (50)

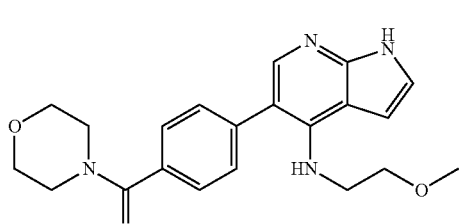
(50)

Compound 50 was synthesized via procedures 3 and 4 in Example 28 and obtained as a yellow solid (56.46 mg, 28% yield over 3 steps).

$^1$HNMR (400 MHz, DMSO-d6) δ 11.31 (s, 1H), 7.67 (s, 1H), 7.51-7.45 (m, 4H), 7.19 (m, 1H), 6.59-6.58 (m, 1H), 5.35-5.32 (m, 1H), 3.63-3.55 (m, 12H), 3.5-3.21 (m, 3H).

LCMS: m/z 381.0 [M+1]$^+$.

Example 54: Synthesis of 4-(4-(cyclopentylamino)-1H-pyrrolo[2,3-b]pyridin-5-yl)phenyl)(morpholino)methanone (51)

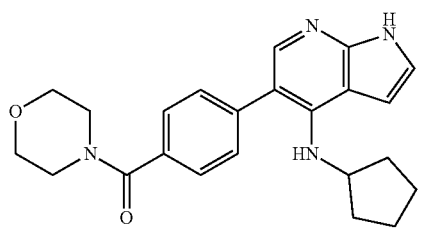
(51)

Compound 51 was synthesized via procedures 3 and 4 in Example 28 and obtained as a pink solid (26.81 mg, 14% yield over 3 steps).

$^1$H NMR (400 MHz, CDCl$_3$) δ 8.98-8.82 (m, 1H), 7.84 (s, 1H), 7.59-7.46 (m, 4H), 7.14 (m, 1H), 6.67 (m, 1H), 4.60-4.43 (m, 2H), 4.02-3.55 (m, 8H), 2.15-1.96 (m, 2H), 1.67 (s, 4H), 1.56-1.47 (m, 2H).

LCMS: m/z 391.2 [M+1]$^+$.

Example 55: Synthesis of (4-(4-(methylamino)-1H-pyrrolo[2,3-b]pyridin-5-yl)phenyl)(4-morpholinopiperidin-1-yl)methanone (52)

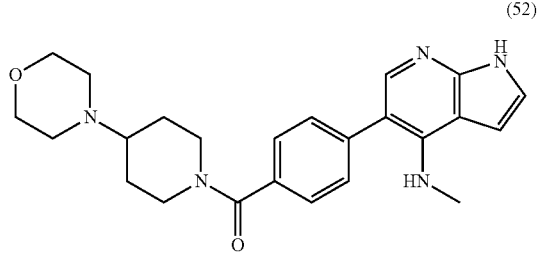
(52)

2HCO$_2$H

Compound 52 was synthesized via procedures 3 and 4 in Example 28 and obtained as a yellow solid (86.0 mg, 21% yield over 3 steps). Compound 52 was isolated as a formic acid salt.

$^1$H NMR (400 MHz, DMSO-d$_6$) δ 11.26 (s, 1H), 8.15 (s, 2H), 7.62 (s, 1H), 7.47-7.40 (m, 4H), 7.14 (d, J=3.6 Hz, 1H), 6.71 (d, J=3.6 Hz, 1H), 5.72-5.65 (m, 1H), 4.55-4.25 (m, 4H), 3.90-3.68 (m, 4H), 3.59-3.56 (m, 4H), 3.08 (d, J=5.2 Hz, 3H), 2.84 (brs, 1H), 1.94-1.71 (m, 2H), 1.47-1.30 (m, 2H).

LCMS: m/z 420.0 [M+1]$^+$.

Example 56: Synthesis of (4-(4-(ethylamino)-1H-pyrrolo[2,3-b]pyridin-5-yl)phenyl)(4-morpholinopiperidin-1-yl)methanone (53)

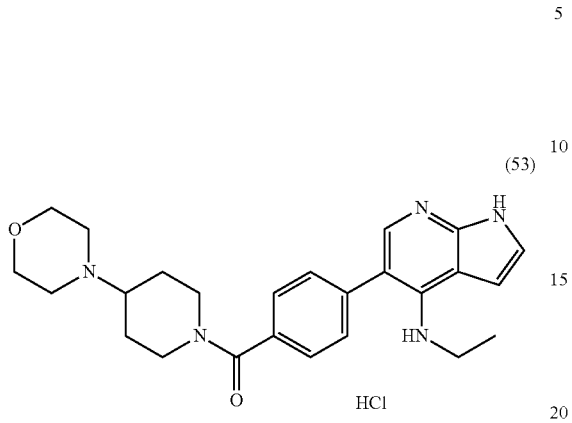

Compound 53 was synthesized via procedures 3 and 4 in Example 28 and obtained as a yellow solid (43.24 mg, 17% yield over 3 steps). Compound 53 was isolated as an HCl salt.

$^1$H NMR (400 MHz, DMSO-d$_6$) δ 14.00 (s, 1H), 12.44-12.27 (m, 1H), 7.78 (s, 1H), 7.56-7.49 (m, 4H), 7.40-7.37 (m, 1H), 7.35-7.29 (m, 1H), 6.92-6.88 (m, 1H), 4.05-3.81 (m, 8H), 3.80-3.72 (m, 2H), 3.16-2.98 (m, 4H), 2.90-2.77 (m, 1H), 2.25-2.09 (m, 2H), 1.78-1.68 (m, 2H), 1.22 (t, J=6.8 Hz, 3H).

LCMS: m/z 434.3 [M+1]$^+$.

Example 57: Synthesis of (4-(4-(isopropylamino)-1H-pyrrolo[2,3-b]pyridin-5-yl)phenyl)(4-morpholinopiperidin-1-yl)methanone (54)

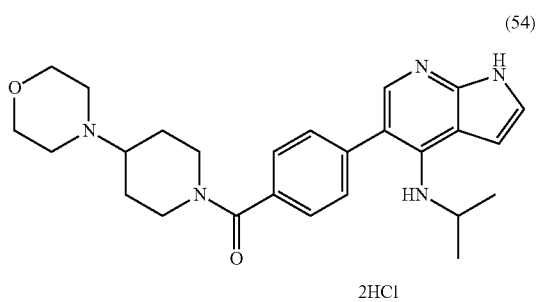 [SMILES: CC(C)Nc1c(-c2ccc(C(=O)N3CCC(N4CCOCC4)CC3)cc2)cnc2[nH]ccc12 ; "2HCl"]

Compound 54 was synthesized via procedures 3 and 4 in Example 28 and obtained as a yellow solid (135.0 mg, 36% yield over 3 steps). Compound 54 was isolated as an HCl salt.

$^1$H NMR (400 MHz, DMSO-d$_6$) δ 14.32 (s, 1H), 12.52 (s, 1H), 11.93 (s, 1H), 7.77 (s, 1H), 7.57-7.52 (m, 4H), 7.41-7.37 (m, 1H), 6.92-6.86 (m, 1H), 6.78-6.66 (m, 1H), 4.75-4.54 (m, 1H), 4.46-4.30 (m, 1H), 3.98-3.92 (m, 4H), 3.90-3.64 (m, 1H), 3.53-3.35 (m, 3H), 3.20-3.02 (m, 3H), 2.93-2.75 (m, 1H), 2.29-2.06 (m, 2H), 1.84-1.67 (m, 2H), 1.25 (d, J=6.0 Hz, 6H).

LCMS: m/z 448.4 [M+1]$^+$.

Example 58: Synthesis of (4-(4-(cyclopropylamino)-1H-pyrrolo[2,3-b]pyridin-5-yl)phenyl)(4-morpholinopiperidin-1-yl)methanone (55)

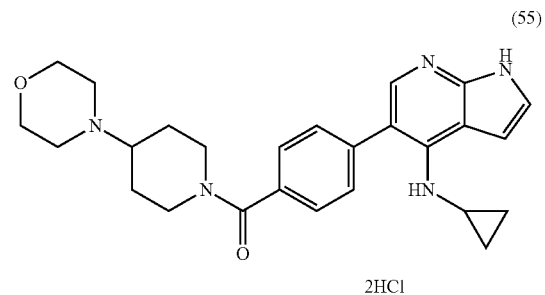 [SMILES: O=C(c1ccc(-c2cnc3[nH]ccc3c2NC2CC2)cc1)N1CCC(N2CCOCC2)CC1 ; "2HCl"]

Compound 55 was synthesized via procedures 3 and 4 in Example 28 and obtained as a yellow solid (135.0 mg, 36% yield over 3 steps). Compound 55 was isolated as an HCl salt.

$^1$H NMR (400 MHz, DMSO-d$_6$) δ 14.32 (s, 1H), 12.47 (s, 1H), 11.83 (s, 1H), 7.78 (s, 1H), 7.53-7.46 (m, 4H), 7.39-7.35 (m, 1H), 7.24-7.21 (m, 1H), 4.77-4.51 (m, 1H), 4.05-3.70 (m, 6H), 3.51-3.38 (m, 3H), 3.16-3.01 (m 4H), 2.92-2.72 (m, 1H), 2.30-2.05 (m, 2H), 1.82-1.68 (m, 2H), 0.95-0.81 (m, 2H), 0.78-0.71 (m, 2H).

LCMS: m/z 446.4 [M+1]$^+$.

Example 59: Synthesis of (4-(4-((2-methoxyethyl)amino)-1H-pyrrolo[2,3-b]pyridin-5-yl)phenyl)(4-morpholinopiperidin-1-yl)methanone (56)

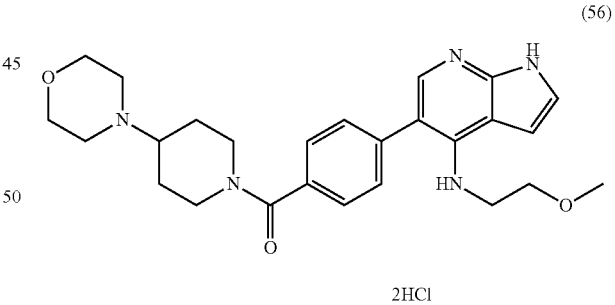

Compound 56 was synthesized via procedures 3 and 4 in Example 28 and obtained as a yellow solid (22.63 mg, 8% yield over 3 steps). Compound 56 was isolated as an HCl salt.

$^1$H NMR (400 MHz, MeOH-d$_4$) δ=7.75 (s, 1H), 7.68-7.62 (m, 2H), 7.61-7.56 (m, 2H), 7.34 (m, 1H), 6.98 (m, J=4.0 Hz, 1H), 4.14-4.06 (m, 2H), 3.95-3.85 (m, 4H), 3.65 (t, J=4.8 Hz, 2H), 3.62-3.50 (m, 3H), 3.35-3.33 (m, 3H), 3.32-3.31 (m, 2H), 3.30-3.17 (m, 3H), 3.06-2.90 (m, 1H), 2.48-2.14 (m, 2H), 1.94-1.69 (m, 2H).

LCMS: m/z 464.4 [M+1]$^+$.

Example 60: Synthesis of (4-(4-(cyclopentylamino)-1H-pyrrolo[2,3-b]pyridin-5-yl)phenyl)(4-morpholinopiperidin-1-yl)methanone (57)

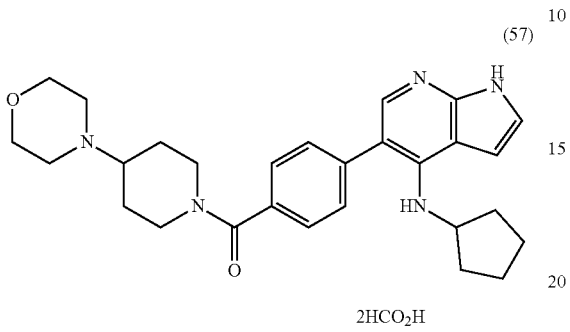

(57)

2HCO$_2$H

Compound 57 was synthesized via procedures 3 and 4 in Example 28 and obtained as a white solid (76.0 mg, 39% yield over 3 steps). Compound 57 was isolated as a formic acid salt.

$^1$H NMR (400 MHz, DMSO-d$_6$) δ11.31 (brs, 1H), 8.15 (s, 2H), 7.68 (s, 1H), 7.47 (m, 4H), 7.20 (brs, 1H), 6.63 (m, 1H), 4.87 (m, 1H), 4.60-4.36 (m, 1H), 4.35-4.19 (m, 1H), 3.81-3.50 (m, 8H), 3.15-2.99 (m, 4H), 1.98-1.71 (m, 4H), 1.65-1.32 (m, 8H).

LCMS: m/z 474.2 [M+1]$^+$.

Example 61: Synthesis of (3-methoxy-4-(4-(methylamino)-1H-pyrrolo[2,3-b]pyridin-5-yl)phenyl)(morpholino)methanone (58)

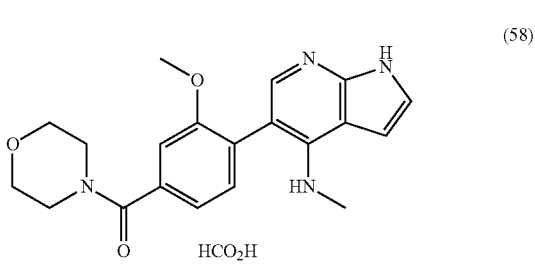 [SMILES: CNc1c(-c2ccc(C(=O)N3CCOCC3)cc2OC)cnc2[nH]ccc12 ; "HCO2H"]

(58)

HCO$_2$H

Compound 58 was synthesized via procedures 3 and 4 in Example 28 and obtained as a light brown solid (65.0 mg, 29% yield over 3 steps). Compound 58 was isolated as a formic acid salt.

$^1$H NMR (400 MHz, DMSO-d$_6$) δ 11.19 (s, 1H), 8.15 (s, 1H), 7.50 (s, 1H), 7.20 (d, J=7.6 Hz, 1H), 7.11 (d, J=3.6 Hz, 1H), 7.08 (d, J=1.2 Hz, 1H), 7.02 (m, 1H), 6.67 (d, J=3.6 Hz, 1H), 5.20-5.34 (m, 1H), 3.74 (s, 3H), 3.54-3.71 (m, 8H), 3.04 (d, J=5.2 Hz, 3H).

LCMS: m/z 367.4 [M+1]$^+$.

Example 62: Synthesis of (4-(4-(ethylamino)-1H-pyrrolo[2,3-b]pyridin-5-yl)-3-methoxyphenyl)(morpholino)methanone (59)

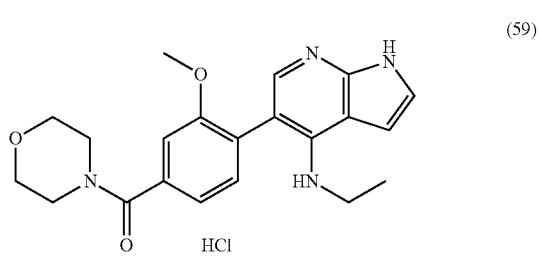 [SMILES: CCNc1c(-c2ccc(C(=O)N3CCOCC3)cc2OC)cnc2[nH]ccc12 ; Cl]

(59)

HCl

Compound 59 was synthesized via procedures 3 and 4 in Example 28 and obtained as a white solid (72.41 mg, 33% yield over 3 steps). Compound 59 was isolated as an HCl salt.

$^1$H NMR (400 MHz, CDCl$_3$) δ 14.51-14.31 (m, 1H), 11.87-11.69 (m, 1H), 7.59-7.51 (m, 1H), 7.27-7.24 (m, 1H), 7.22-7.18 (m, 1H), 7.16-7.08 (m, 2H), 6.75-6.69 (m, 1H), 5.16-5.09 (m, 1H), 3.97-3.45 (m, 13H), 1.38-1.27 (m, 3H).

LCMS: m/z 381.1 [M+1]$^+$.

Example 63: Synthesis of (4-(4-(isopropylamino)-1H-pyrrolo[2,3-b]pyridin-5-yl)-3-methoxyphenyl)(morpholino)methanone (60)

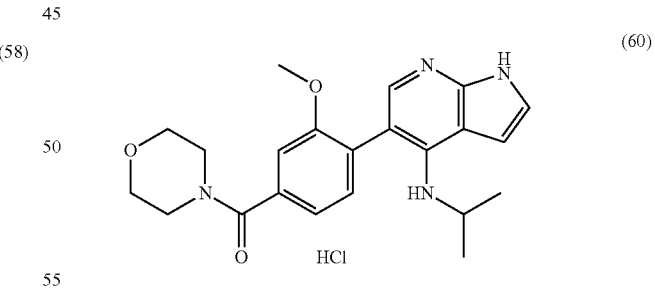

(60)

HCl

Compound 60 was synthesized via procedures 3 and 4 in Example 28 and obtained as a yellow solid (33.58 mg, 11% yield over 3 steps). Compound 60 was isolated as an HCl salt.

$^1$H NMR (400 MHz, DMSO-d$_6$) δ 14.13 (s, 1H), 12.46 (s, 1H), 7.68 (s, 1H), 7.39-7.33 (m, 2H), 7.17-7.14 (m, 1H), 7.13-7.09 (m, 1H), 6.90-6.84 (m, 1H), 6.54-6.27 (m, 1H), 4.47-4.30 (m, 1H), 3.79 (s, 3H), 3.72-3.41 (m, 8H), 1.23 (t, J=6.8 Hz, 6H).

LCMS: m/z 395.3 [M+1]$^+$.

Example 64: Synthesis of (4-(4-(cyclopropylamino)-1H-pyrrolo[2,3-b]pyridin-5-yl)-3-methoxyphenyl)(morpholino)methanone (61)

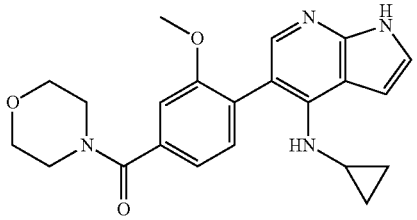
(61)

Compound 61 was synthesized via procedures 3 and 4 in Example 28 and obtained as a white solid (32.69 mg, 15% yield over 3 steps).

$^1$H NMR (400 MHz, CDCl$_3$) δ 9.13 (s, 1H), 7.80 (s, 1H), 7.29 (s, 1H), 7.13-7.10 (m, 1H), 7.09-7.08 (m, 1H), 7.06-7.03 (m, 1H), 7.02-6.99 (m, 1H), 4.53 (br s, 1H), 3.92-3.64 (m, 11H), 3.05-2.98 (m, 1H), 0.92-0.81 (m, 2H), 0.69-0.59 (m, 2H).

LCMS: m/z 393.2 [M+1]$^+$.

Example 65: Synthesis of (3-methoxy-4-(4-((2-methoxyethyl)amino)-1H-pyrrolo[2,3-b]pyridin-5-yl)phenyl)(morpholino)methanone (62)

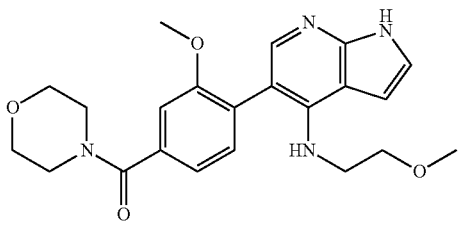
(62)

Compound 62 was synthesized via procedures 3 and 4 in Example 28 and obtained as a white solid (37.02 mg, 18% yield over 3 steps).

$^1$H NMR (400 MHz, CDCl$_3$) δ 14.41-14.25 (m, 1H), 11.94-11.81 (m, 1H), 7.61 (m, 1H), 7.27-7.24 (m, 1H), 7.21 (brs, 1H), 7.14-7.07 (m, 2H), 6.71-6.67 (m, 1H), 5.77-5.50 (m, 1H), 3.98-3.66 (m, 12H), 3.60 (m, 3H), 3.34-3.30 (m, 3H).

LCMS: m/z 411.1 [M+1]$^+$.

Example 66: Synthesis of (4-(4-(cyclopentylamino)-1H-pyrrolo[2,3-b]pyridin-5-yl)-3-methoxyphenyl)(morpholino)methanone (63)

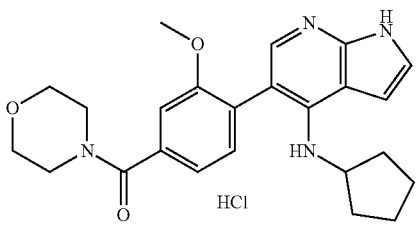
(63)

Compound 63 was synthesized via procedures 3 and 4 in Example 28 and obtained as a white solid (21.0 mg, 7% yield over 3 steps). Compound 63 was isolated as an HCl salt.

$^1$H NMR (400 MHz, CDCl$_3$) δ 14.32 (s, 1H), 11.90-11.68 (m, 1H), 7.64-7.49 (m, 1H), 7.27-7.19 (m, 2H), 7.17-7.07 (m, 2H), 6.74-6.66 (m, 1H), 5.15-5.04 (m, 1H), 4.57-4.47 (m, 1H), 3.92-3.47 (m, 11H), 2.20-1.95 (m, 2H), 1.77-1.45 (m, 6H).

LCMS: m/z 421.1 [M+1]$^+$.

Example 67: Synthesis of (3-methoxy-4-(4-(methylamino)-1H-pyrrolo[2,3-b]pyridin-5-yl)phenyl)(4-morpholinopiperidin-1-yl)methanone (64)

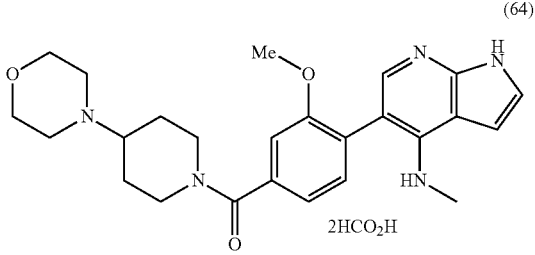 [SMILES: CNc1c(-c2ccc(C(=O)N3CCC(N4CCOCC4)CC3)cc2OC)cnc2[nH]ccc12]
(64)

Compound 64 was synthesized via procedures 3 and 4 in Example 28 and obtained as a yellow solid (190.0 mg, 34% yield over 3 steps). Compound 64 was isolated as a formic acid salt.

$^1$H NMR (400 MHz, DMSO-d$_6$) δ 11.28 (s, 1H), 8.16 (s, 2H), 7.51 (s, 1H), 7.19 (d, J=7.6 Hz, 1H), 7.12 (d, J=3.6 Hz, 1H), 7.04-7.08 (m, 1H), 7.00 (dd, J=7.6, 1.6 Hz, 1H), 6.68 (d, J=3.6 Hz, 1H), 5.48-5.38 (m, 1H), 4.89-4.26 (m, 8H), 3.74 (s, 3H), 3.66-3.61 (m, 4H), 3.05 (d, J=4.4 Hz, 3H), 2.98-2.84 (m, 1H), 2.00-1.79 (m, 2H), 1.53-1.39 (m, 2H).

LCMS: m/z 450.0 [M+1]$^+$.

Example 68: Synthesis of (4-(4-(ethylamino)-1H-pyrrolo[2,3-b]pyridin-5-yl)-3-methoxyphenyl)(4-morpholinopiperidin-1-yl)methanone (65)

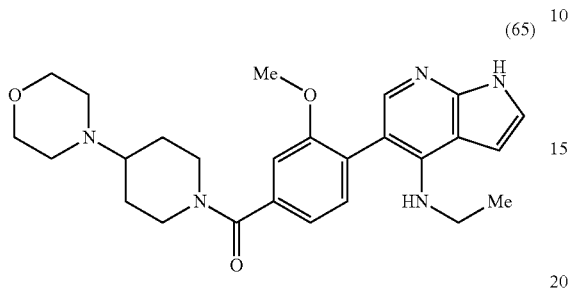

(65)

Compound 65 was synthesized via procedures 3 and 4 in Example 28 and obtained as a light yellow solid (10.83 mg, 5% yield over 3 steps).

$^1$H NMR (400 MHz, CDCl$_3$) δ 7.75 (brs, 1H), 7.32-7.29 (m, 2H), 7.15-7.04 (m, 3H), 6.68 (m, 1H), 4.91-4.60 (m, 1H), 4.32 (m, 1H), 4.09-3.90 (m, 1H), 3.82 (s, 3H), 3.79-3.73 (m, 4H), 3.70 (m, 2H), 3.25-2.82 (m, 2H), 2.65-2.56 (m, 4H), 2.50 (m, 1H), 2.08-1.91 (m, 2H), 1.63-1.49 (m, 2H), 1.31-1.21 (m, 3H).

LCMS: m/z 464.2 [M+1]$^+$.

Example 69: Synthesis of (4-(4-(isopropylamino)-1H-pyrrolo[2,3-b]pyridin-5-yl)-3-methoxyphenyl)(4-morpholinopiperidin-1-yl)methanone (66)

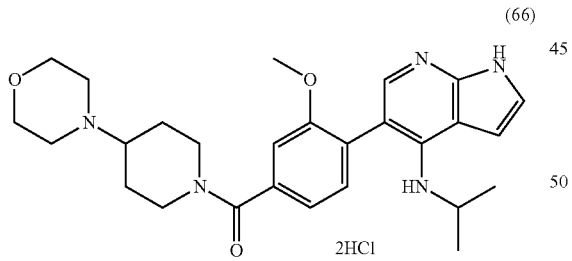

(66)

Compound 66 was synthesized via procedures 3 and 4 in Example 28 and obtained as a yellow solid 95.0 mg, 25% yield over 3 steps). Compound 66 was isolated as an HCl salt.

$^1$H NMR (400 MHz, DMSO-d$_6$) δ 14.13 (s, 1H), 12.45 (s, 1H), 11.89 (s, 1H), 7.70 (s, 1H), 7.39-7.34 (m, 2H), 7.15 (s, 1H), 7.12-7.08 (m, 1H), 6.90-6.85 (m, 1H), 6.56-6.29 (m, 1H), 4.48-4.26 (m, 2H), 4.04-3.85 (m, 5H), 3.80 (s, 3H), 3.53-3.36 (m, 3H), 3.20-3.00 (m, 3H), 2.91-2.73 (m, 1H), 2.30-2.07 (m, 2H), 1.86-1.70 (m, 2H), 1.23 (t, J=7.2 Hz, 6H).

LCMS: m/z 478.4 [M+1]$^+$.

Example 70: Synthesis of (3-methoxy-4-(4-((2-methoxyethyl)amino)-1H-pyrrolo[2,3-b]pyridin-5-yl)phenyl)(morpholino)methanone (67)

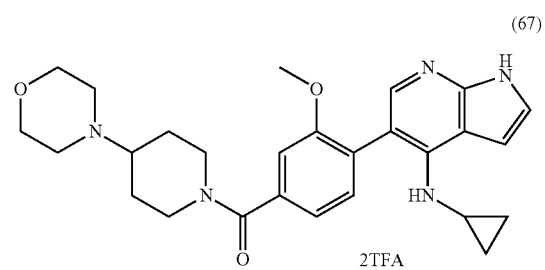 [SMILES: COc1cc(C(=O)N2CCC(N3CCOCC3)CC2)ccc1-c1cnc2[nH]ccc2c1NC1CC1]

(67)

Compound 67 was synthesized via procedures 3 and 4 in Example 28 and obtained as a yellow solid (23.06 mg, 6% yield over 3 steps). Compound 67 was isolated as a TFA salt.

$^1$H NMR (400 MHz, MeOH-d$_4$) δ 7.62 (s, 1H), 7.38-7.34 (m, 1H), 7.31-7.25 (m, 2H), 7.17-7.15 (m, 1H), 7.15-7.11 (m, 1H), 4.19-3.96 (m, 3H), 3.96-3.84 (m, 2H), 3.82 (s, 3H), 3.60-3.51 (m, 2H), 3.36-3.30 (m, 3H), 3.29-3.17 (m, 2H), 3.14-3.05 (m, 1H), 3.02-2.84 (m, 1H), 2.41-2.12 (m, 2H), 1.87-1.73 (m, 2H), 1.08-0.91 (m, 2H), 0.77-0.69 (m, 2H).

LCMS: m/z 476.3 [M+1]$^+$.

Example 71: Synthesis of (3-methoxy-4-(4-((2-methoxyethyl)amino)-1H-pyrrolo[2,3-b]pyridin-5-yl)phenyl)(4-morpholinopiperidin-1-yl)methanone (68)

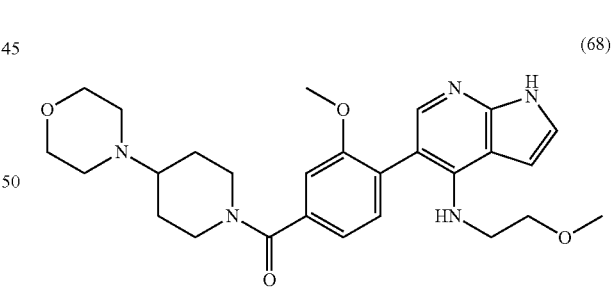

(68)

Compound 68 was synthesized via procedures 3 and 4 in Example 28 and obtained as a yellow solid (42.0 mg, 21% yield over 3 steps).

$^1$H NMR (400 MHz, CDCl$_3$) δ 8.89-8.83 (m, 1H), 7.85-7.82 (m, 1H), 7.32-7.28 (m, 1H), 7.12-7.04 (m, 3H), 6.65-6.61 (m, 1H), 4.85-4.68 (m, 1H), 4.65-4.59 (m, 1H), 4.08-3.90 (m, 1H), 3.83-3.77 (m, 5H), 3.77-3.73 (m, 4H), 3.61-3.51 (m, 2H), 3.33-3.31 (m, 3H), 3.20-2.79 (m, 2H), 2.61-2.57 (m, 4H), 2.53-2.43 (m, 1H), 2.10-1.80 (m, 2H), 1.59-1.41 (m, 2H).

LCMS: m/z 494.2 [M+1]$^+$.

Example 72: Synthesis of (4-(4-(cyclopentylamino)-1H-pyrrolo[2,3-b]pyridin-5-yl)-3-methoxyphenyl)(4-morpholinopiperidin-1-yl)methanone (69)

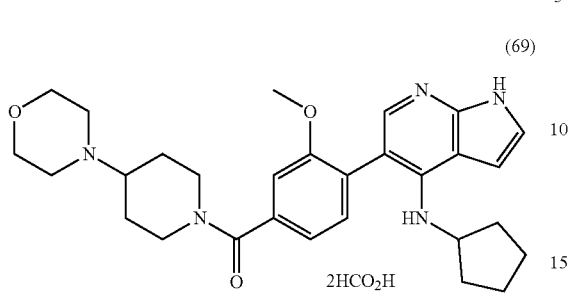

Compound 69 was synthesized via procedures 3 and 4 in Example 28 and obtained as a white solid (45.0 mg, 18% yield over 3 steps). Compound 69 was isolated as a formic acid salt.

$^1$H NMR (400 MHz, CDCl$_3$) δ 13.70 (brs, 1H), 8.46 (s, 2H), 7.56 (s, 1H), 7.25-7.19 (m, 2H), 7.14-7.03 (m, 2H), 6.66 (d, J=3.5 Hz, 1H), 5.01-4.88 (m, 1H), 4.84-4.66 (m, 1H), 4.61-4.46 (m, 1H), 4.04-3.68 (m, 8H), 3.23-2.78 (m, 2H), 2.74-2.56 (m, 5H), 2.16-1.89 (m, 4H), 1.76-1.42 (m, 8H).

LCMS: m/z 504.3 [M+1]$^+$.

Example 73: General Methods for the Synthesis of Compounds 70-113

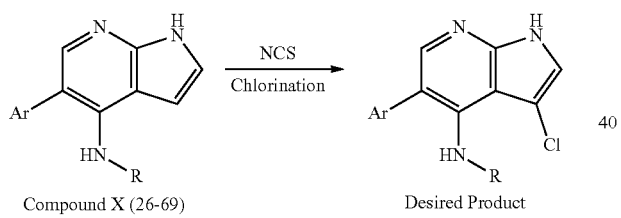

Procedure 6: To a solution of compound X (1 eq) in CH$_3$CN (0.1 M-0.2 M) was added NCS (1.2 eq). The mixture was stirred at 80° C. for 5 hours. The mixture was allowed to cool to rt, concentrated in vacuo and then purified by reversed-phase HPLC to give the desired product.

Procedure 7: To a solution of compound X (1 eq) in THF (0.1 M-0.2 M) was added NCS (1.2 eq). The mixture was stirred at rt for 2 hours. The mixture was concentrated in vacuo and then purified by reversed-phase HPLC to give the desired product.

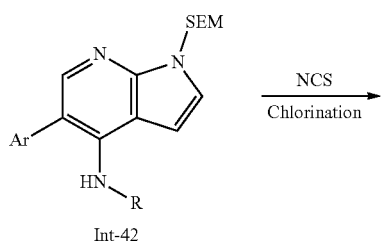

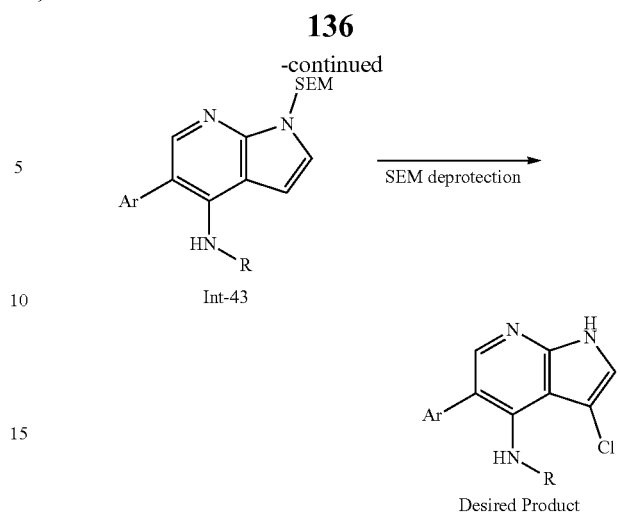

Procedure 8: To a solution of intermediate int-42 (see, Example 28) (1 eq) in CH$_3$CN (0.1 M-0.2 M) was added NCS (1.2 eq). The mixture was stirred at 80° C. for 5 hours. The mixture was allowed to cool to rt, concentrated in vacuo and then purified by reversed-phase HPLC to give intermediate int-43.

To a solution of int-43 (1 eq) in DCM (0.1 M-0.2 M) was added HCl/dioxane (4 M, 2 mL, 15-20 eq). The mixture was stirred at 30° C. for 4 hours. The reaction was monitored by LCMS. The mixture was concentrated in vacuo. The resulting residue was dissolved in EtOH (0.1 M-0.2 M) and treated with NH$_3$.H$_2$O (28% purity, 40-50 eq). The reaction was stirred at 60° C. for 2 hours. The crude mixture was concentrated in vacuo and purified by reversed-phase HPLC to give the desired product.

Example 74: Synthesis of 3-chloro-5-(1-((3S,4S)-3-fluoro-1-(oxetan-3-yl)piperidin-4-yl)-1H-pyrazol-4-yl)-N-methyl-1H-pyrrolo[2,3-b]pyridin-4-amine (70)

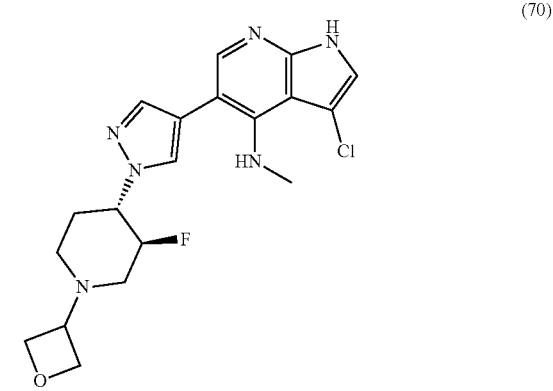 [SMILES: CNc1c(-c2cnn([C@H]3CCN(C4COC4)C[C@@H]3F)c2)cnc2[nH]cc(Cl)c12]

Compound 70 was synthesized via procedure 6 in Example 73 and obtained as a yellow solid (13.0 mg, 13% yield over 1 step).

$^1$H NMR (400 MHz, DMSO-d$_6$) δ 11.61 (brs, 1H), 7.93 (s, 1H), 7.68 (s, 1H), 7.79 (s, 1H), 7.61 (d, J=3.7 Hz, 1H), 7.32 (s, 1H), 5.49-5.45 (m, 1H), 4.58-4.44 (m, 5H), 3.60-3.59 (m, 1H), 3.31-3.28 (m, 1H), 2.64-2.63 (d, J=5.6 Hz, 1H), 2.52-2.49 (m, 3H), 2.07-2.03 (m, 4H).

LCMS: m/z 405.1 [M+1]$^+$.

Example 75: Synthesis of 3-chloro-N-ethyl-5-(1-((3S,4S)-3-fluoro-1-(oxetan-3-yl)piperidin-4-yl)-1H-pyrazol-4-yl)-1H-pyrrolo[2,3-b]pyridin-4-amine (71)

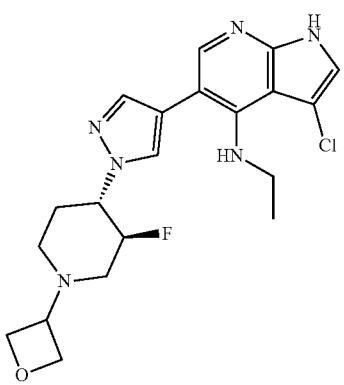
(71)

Compound 71 was synthesized via procedure 7 in Example 73 and obtained as a white solid (25.57 mg, 36% yield over 1 step).
$^1$H NMR (400 MHz, CDCl$_3$) δ 9.95 (brs, 1H), 7.96 (s, 1H), 7.69 (s, 1H), 7.61 (s, 1H), 7.07 (s, 1H), 5.26 (t, J=4.9 Hz, 1H), 5.04-4.84 (m, 1H), 4.74-4.61 (m, 4H), 4.19 (m, 1H), 3.67 (m, 1H), 3.26-3.19 (m, 1H), 3.06-2.96 (m, 2H), 2.92-2.85 (m, 1H), 2.46-2.34 (m, 1H), 2.25 (m, 1H), 2.17-2.05 (m, 2H), 1.10 (t, J=7.2 Hz, 3H).
LCMS: m/z 419.2 [M+1]$^+$.

Example 76: Synthesis of 3-chloro-5-(1-((3S,4S)-3-fluoro-1-(oxetan-3-yl)piperidin-4-yl)-1H-pyrazol-4-yl)-N-isopropyl-1H-pyrrolo[2,3-b]pyridin-4-amine (72)

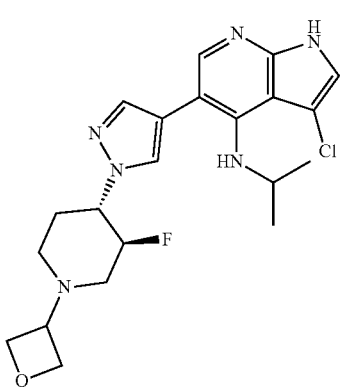
(72)

Compound 72 was synthesized via procedure 7 in Example 73 and obtained as an off-white solid (16.78 mg, 35% yield over 1 step).
$^1$H NMR (400 MHz, CDCl$_3$) δ 10.19 (brs, 1H), 7.99 (s, 1H), 7.73 (s, 1H), 7.67 (s, 1H), 7.09 (s, 1H), 5.08-4.84 (m, 2H), 4.75-4.61 (m, 4H), 4.26-4.15 (m, 1H), 3.72-3.50 (m, 2H), 3.27-3.19 (m, 1H), 2.92-2.86 (m, 1H), 2.47-2.34 (m, 1H), 2.26 (m, 1H), 2.18-2.05 (m, 2H), 1.04 (m, 6H).
LCMS: m/z 433.2 [M+1]$^+$.

Example 77: Synthesis of 3-chloro-N-cyclopropyl-5-(1-((3S,4S)-3-fluoro-1-(oxetan-3-yl)piperidin-4-yl)-1H-pyrazol-4-yl)-1H-pyrrolo[2,3-b]pyridin-4-amine (73)

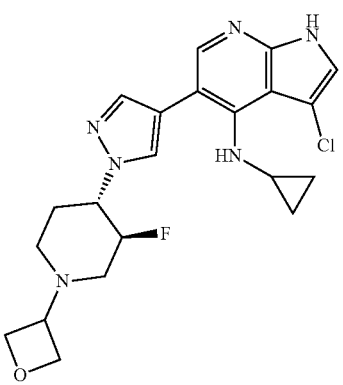
(73)

Compound 73 was synthesized via procedure 7 in Example 73 and obtained as a yellow solid (14.06 mg, 19% yield over 1 step).
$^1$H NMR (400 MHz, CDCl$_3$) δ 10.05 (brs, 1H), 7.94 (s, 1H), 7.66 (s, 1H), 7.56 (s, 1H), 7.03 (s, 1H), 5.85 (m, 1H), 5.04-4.83 (m, 1H), 4.73-4.61 (m, 4H), 4.24-4.12 (m, 1H), 3.67 (m, 1H), 3.26-3.17 (m, 1H), 2.92-2.83 (m, 1H), 2.45-2.33 (m, 2H), 2.28-2.19 (m, 1H), 2.17-2.00 (m, 2H), 0.43-0.35 (m, 4H).
LCMS: m/z 431.1 [M+1]$^+$.

Example 78: Synthesis of 3-chloro-5-(1-((3S,4S)-3-fluoro-1-(oxetan-3-yl)piperidin-4-yl)-1H-pyrazol-4-yl)-N-(2-methoxyethyl)-1H-pyrrolo[2,3-b]pyridin-4-amine (74)

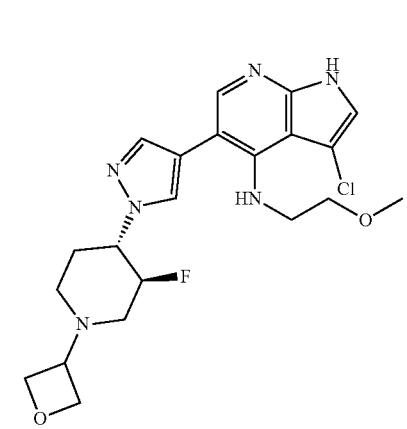
(74)

Compound 74 was synthesized via procedure 7 in Example 73 and obtained as a yellow solid (21.0 mg, 52% yield over 1 step).
$^1$H NMR (400 MHz, CDCl$_3$) δ 9.65 (brs, 1H), 7.98 (s, 1H), 7.70 (s, 1H), 7.63 (s, 1H), 7.08 (s, 1H), 5.77 (t, J=5.5 Hz, 1H), 5.06-4.83 (m, 1H), 4.74-4.68 (m, 2H), 4.64 (m, 2H), 4.26-4.10 (m, 1H), 3.67 (m, 1H), 3.45-3.38 (m, 2H), 3.33 (s, 3H), 3.26-3.08 (m, 3H), 2.93-2.82 (m, 1H), 2.48-2.32 (m, 1H), 2.25 (m, 1H), 2.17-2.03 (m, 2H).
LCMS: m/z 449.2 [M+1]+.

Example 79: Synthesis of 3-chloro-N-cyclopentyl-5-(1-((3S,4S)-3-fluoro-1-(oxetan-3-yl)piperidin-4-yl)-1H-pyrazol-4-yl)-1H-pyrrolo[2,3-b]pyridin-4-amine (75)

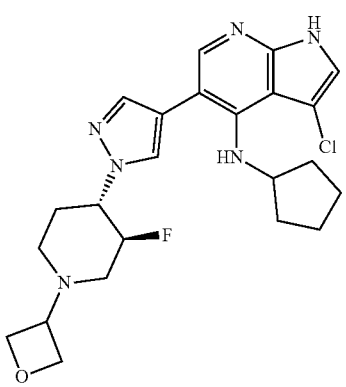

(75)

Compound 75 was synthesized via procedure 6 in Example 73 and obtained as a yellow solid (15.03 mg, 25% yield over 1 step).
Method A, 15.03 mg was obtained as a yellow solid, yield 25% over 1 step.
$^1$H NMR (400 MHz, CDCl$_3$) δ 7.94 (s, 1H), 7.70 (s, 1H), 7.63 (s, 1H), 7.06 (s, 1H), 5.41 (d, J=9.6 Hz, 1H), 5.04-4.84 (m, 1H), 4.74-4.62 (m, 4H), 4.20 (m, 1H), 3.81-3.60 (m, 2H), 3.27-3.19 (m, 1H), 2.93-2.84 (m, 1H), 2.48-2.33 (m, 1H), 2.25 (m, 1H), 2.17-2.04 (m, 2H), 1.70-1.57 (m, 4H), 1.51-1.37 (m, 4H).
LCMS: m/z 459.2 [M+1]+.

Example 80: Synthesis of 3-chloro-5-(1-((3S,4S)-3-fluoro-1-(oxetan-3-yl)piperidin-4-yl)-5-methyl-1H-pyrazol-4-yl)-N-methyl-1H-pyrrolo[2,3-b]pyridin-4-amine (76)

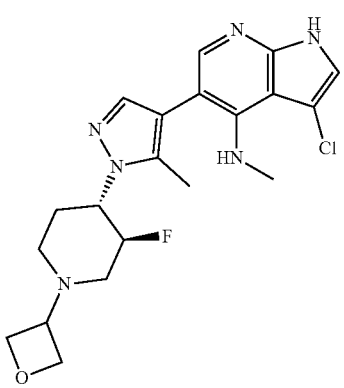

(76)

Compound 76 was synthesized via procedure 7 in Example 73 and obtained as an off-white solid (22.68 mg, 25% yield over 1 step).

$^1$H NMR (400 MHz, CDCl$_3$) δ 10.46 (brs, 1H), 7.85 (s, 1H), 7.57 (s, 1H), 7.05 (s, 1H), 5.57 (m, 1H), 5.14-4.91 (m, 1H), 4.75-4.62 (m, 4H), 4.16-4.05 (m, 1H), 3.69 (m, 1H), 3.27-3.19 (m, 1H), 2.94-2.86 (m, 1H), 2.60 (m, 4H), 2.21-2.01 (m, 6H).
LCMS: m/z 419.2 [M+1]+.

Example 81: Synthesis of 1-((3S,4S)-4-(4-(3-chloro-4-(methylamino)-1H-pyrrolo[2,3-b]pyridin-5-yl)-1H-pyrazol-1-yl)-3-fluoropiperidin-1-yl)ethan-1-one (77)

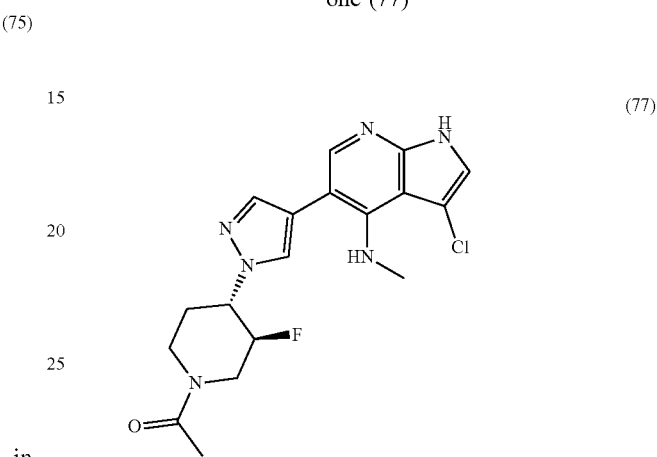

(77)

Compound 77 was synthesized via procedure 6 in Example 73 and obtained as a brown oil (26.48 mg, 43% yield over 1 step).
Method A, 11.23 mg was obtained as a yellow solid, yield 15% over 1 step.
$^1$H NMR (400 MHz, CDCl$_3$) δ 10.07 (brs, 1H), 7.95 (s, 1H), 7.69 (s, 1H), 7.60 (d, J=3.5 Hz, 1H), 7.07 (s, 1H), 5.31-4.58 (m, 3H), 4.42-3.95 (m, 2H), 3.44-3.17 (m, 1H), 3.07-2.74 (m, 3H), 2.46-2.23 (m, 2H), 2.19 (d, J=2.9 Hz, 3H), 1.11 (t, J=7.2 Hz, 3H).
LCMS: m/z 405.1 [M+1]+.

Example 82: Synthesis of 1-((3S,4S)-4-(4-(3-chloro-4-(ethylamino)-1H-pyrrolo[2,3-b]pyridin-5-yl)-1H-pyrazol-1-yl)-3-fluoropiperidin-1-yl)ethan-1-one (78)

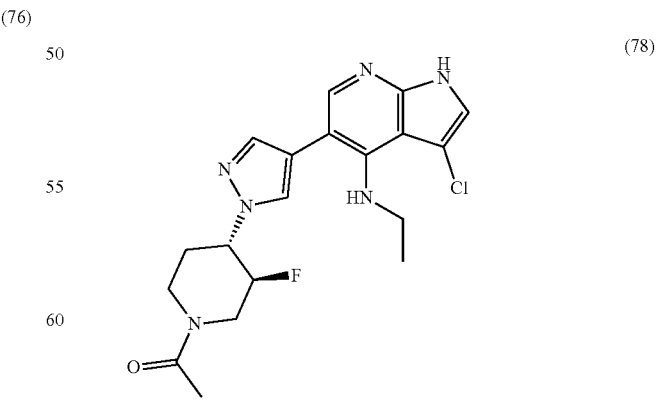

(78)

Compound 78 was synthesized via procedure 6 in Example 73 and obtained as a yellow solid (11.23 mg, 15% yield over 1 step).

¹H NMR (400 MHz, CDCl₃) δ 10.07 (brs, 1H), 7.95 (s, 1H), 7.69 (s, 1H), 7.60 (d, J=3.5 Hz, 1H), 7.07 (s, 1H), 5.31-4.58 (m, 3H), 4.42-3.95 (m, 2H), 3.44-3.17 (m, 1H), 3.07-2.74 (m, 3H), 2.46-2.23 (m, 2H), 2.19 (d, J=2.9 Hz, 3H), 1.11 (t, J=7.2 Hz, 3H).
LCMS: m/z 405.1 [M+1]⁺.

Example 83: Synthesis of 1-((3S,4S)-4-(4-(3-chloro-4-(isopropylamino)-1H-pyrrolo[2,3-b]pyridin-5-yl)-1H-pyrazol-1-yl)-3-fluoropiperidin-1-yl)ethan-1-one (79)

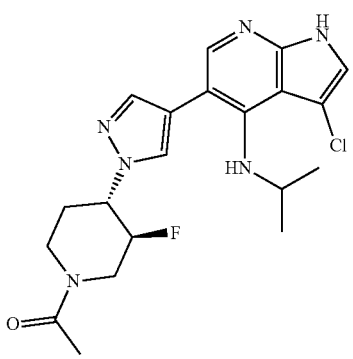
(79)

Compound 79 was synthesized via procedure 7 in Example 73 and obtained as a yellow solid (50.02 mg, 27% yield over 1 step).
¹H NMR (400 MHz, CDCl₃) δ 10.12 (brs, 1H), 7.97 (s, 1H), 7.73 (s, 1H), 7.66 (d, J=3.8 Hz, 1H), 7.09 (s, 1H), 5.10-4.59 (m, 3H), 4.43-3.93 (m, 2H), 3.53 (m, 1H), 3.40-3.22 (m, 1H), 2.98-2.76 (m, 1H), 2.43-2.24 (m, 2H), 2.19 (d, J=2.7 Hz, 3H), 1.08-1.02 (m, 6H).
LCMS: m/z 419.1 [M+1]⁺.

Example 84: Synthesis of 1-((3S,4S)-4-(4-(3-chloro-4-(cyclopropylamino)-1H-pyrrolo[2,3-b]pyridin-5-yl)-1H-pyrazol-1-yl)-3-fluoropiperidin-1-yl)ethan-1-one (80)

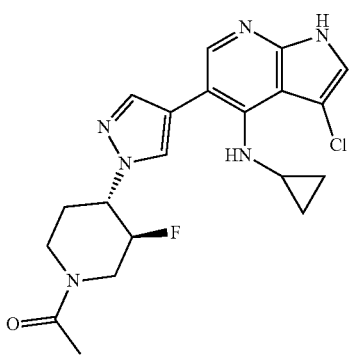
(80)

Compound 80 was synthesized via procedure 7 in Example 73 and obtained as a yellow solid (22.29 mg, 13% yield over 1 step).
¹H NMR (400 MHz, CDCl₃) δ 9.98 (brs, 1H), 7.93 (s, 1H), 7.66 (s, 1H), 7.55 (d, J=2.2 Hz, 1H), 7.03 (s, 1H), 5.86 (s, 1H), 5.12-4.61 (m, 2H), 4.42-3.94 (m, 2H), 3.40-3.19 (m, 1H), 2.95-2.74 (m, 1H), 2.41-2.22 (m, 3H), 2.18 (d, J=2.1 Hz, 3H), 0.45-0.33 (m, 4H).
LCMS: m/z 417.1 [M+1]⁺.

Example 85: Synthesis of 1-((3S,4S)-4-(4-(3-chloro-4-((2-methoxyethyl)amino)-1H-pyrrolo[2,3-b]pyridin-5-yl)-1H-pyrazol-1-yl)-3-fluoropiperidin-1-yl)ethan-1-one (81)

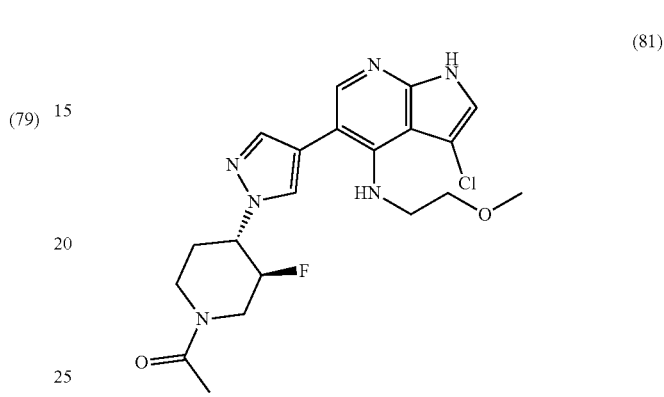
(81)

Compound 81 was synthesized via procedure 7 in Example 73 and obtained as a yellow solid (35.0 mg, 39% yield over 1 step).
¹H NMR (400 MHz, CDCl₃) δ 9.89 (brs, 1H), 7.98 (s, 1H), 7.72 (s, 1H), 7.64 (d, J=3.0 Hz, 1H), 7.09 (s, 1H), 5.79 (s, 1H), 5.19-4.58 (m, 2H), 4.47-3.93 (m, 2H), 3.45-3.12 (m, 8H), 2.98-2.75 (m, 1H), 2.46-2.24 (m, 2H), 2.20 (d, J=3.0 Hz, 3H).
LCMS: m/z 435.1 [M+1]⁺.

Example 86: Synthesis of 1-((3S,4S)-4-(4-(3-chloro-4-(cyclopentylamino)-1H-pyrrolo[2,3-b]pyridin-5-yl)-1H-pyrazol-1-yl)-3-fluoropiperidin-1-yl)ethan-1-one (82)

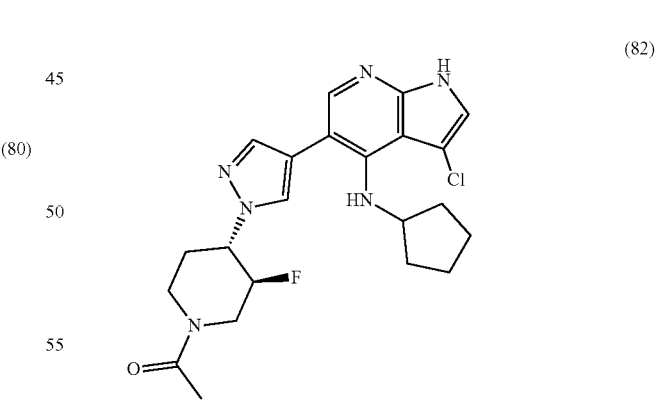
(82)

Compound 82 was synthesized via procedure 6 in Example 73 and obtained as a yellow solid (14.9 mg, 10% yield over 1 step).
¹H NMR (400 MHz, CDCl₃) 7.93 (s, 1H), 7.70 (s, 1H), 7.62 (d, J=3.1 Hz, 1H), 7.06 (s, 1H), 5.46-5.38 (m, 1H), 5.14-4.59 (m, 2H), 4.44-3.95 (m, 2H), 3.79-3.64 (m, 1H), 3.41-3.21 (m, 1H), 2.98-2.76 (m, 1H), 2.47-2.22 (m, 2H), 2.19 (m, 3H), 1.70-1.56 (m, 4H), 1.53-1.34 (m, 4H).
LCMS: m/z 445.2 [M+1]⁺.

Example 87: Synthesis of 1-((3S,4S)-4-(4-(3-chloro-4-(methylamino)-1H-pyrrolo[2,3-b]pyridin-5-yl)-5-methyl-1H-pyrazol-1-yl)-3-fluoropiperidin-1-yl)ethan-1-one (83)

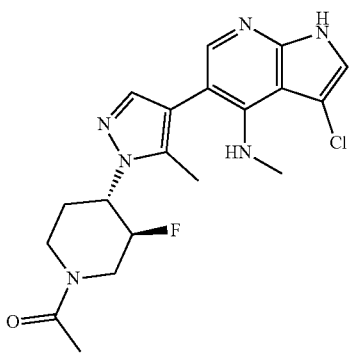

(83)

Compound 83 was synthesized via procedure 7 in Example 73 and obtained as a yellow solid (25.11 mg, 24% yield over 1 step).

$^1$HNMR (400 MHz, DMSO-$d_6$) δ 11.59 (s, 1H), 7.65 (s, 1H), 7.47 (s, 1H), 7.31 (s, 1H), 5.62-5.51 (m, 1H), 5.05-3.80 (m, 4H), 2.96-2.71 (m, 1H), 2.47 (s, 3H), 2.14-1.98 (m, 8H).

LCMS: m/z 405.1 [M+1]$^+$.

Example 88: Synthesis of 1-((3S,4S)-4-(4-(3-chloro-4-(ethylamino)-1H-pyrrolo[2,3-b]pyridin-5-yl)-5-methyl-1H-pyrazol-1-yl)-3-fluoropiperidin-1-yl)ethan-1-one (84)

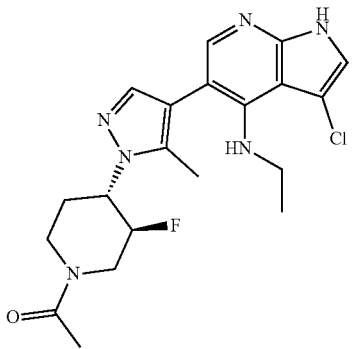

(84)

Compound 84 was synthesized via procedure 7 in Example 73 and obtained as a white solid (12.71 mg, 24% yield over 1 step).

$^1$HNMR (400 MHz, CDCl$_3$) δ 10.17 (brs, 1H), 7.84 (s, 1H), 7.55 (s, 1H), 7.06 (s, 1H), 5.38 (s, 1H), 5.14-4.66 (m, 2H), 4.37-3.97 (m, 2H), 3.39-3.20 (m, 1H), 2.94-2.74 (m, 3H), 2.59-2.30 (m, 1H), 2.24-2.16 (m, 7H), 1.06 (t, J=7.2 Hz, 3H).

LCMS: m/z 419.1 [M+1]$^+$.

Example 89: Synthesis of 1-((3S,4S)-4-(4-(3-chloro-4-(isopropylamino)-1H-pyrrolo[2,3-b]pyridin-5-yl)-5-methyl-1H-pyrazol-1-yl)-3-fluoropiperidin-1-yl)ethan-1-one (85)

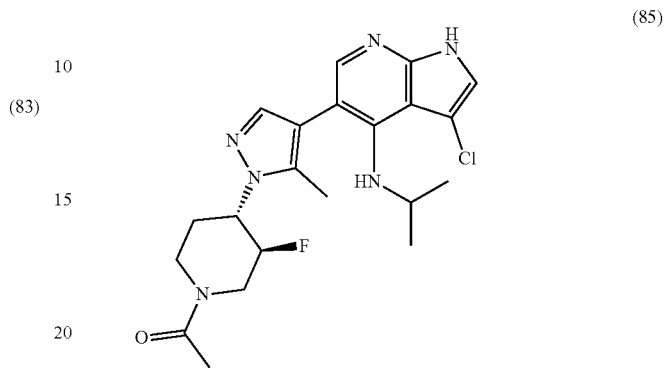

(85)

Compound 85 was synthesized via procedure 7 in Example 73 and obtained as an off-white solid (15.05 mg, 29% yield over 1 step).

$^1$HNMR (400 MHz, CDCl$_3$) δ 10.36 (brs, 1H), 7.86 (s, 1H), 7.57 (s, 1H), 7.08 (s, 1H), 5.26-5.17 (m, 1H), 5.14-4.66 (m, 2H), 4.37-3.96 (m, 2H), 3.38-3.22 (m, 2H), 2.92-2.74 (m, 1H), 2.59-2.31 (m, 1H), 2.20 (d, J=13.6 Hz, 7H), 1.03-0.94 (m, 6H).

LCMS: m/z 433.1 [M+1]$^+$.

Example 90: Synthesis of 1-((3R,4R)-4-(4-(3-chloro-4-(cyclopropylamino)-1H-pyrrolo[2,3-b]pyridin-5-yl)-5-methyl-1H-pyrazol-1-yl)-3-fluoropiperidin-1-yl)ethan-1-one (86)

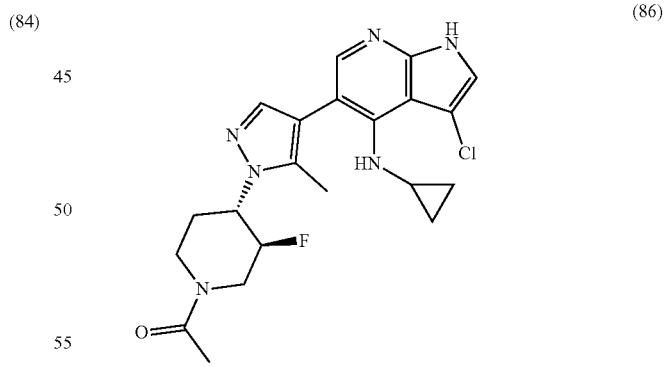

(86)

Compound 86 was synthesized via procedure 7 in Example 73 and obtained as an off-white solid (14.91 mg, 20% yield over 1 step).

$^1$HNMR (400 MHz, CDCl$_3$) δ 9.95 (brs, 1H), 7.84 (d, J=1.9 Hz, 1H), 7.56 (s, 1H), 7.03 (s, 1H), 5.87 (s, 1H), 5.13-4.67 (m, 2H), 4.35-3.97 (m, 2H), 3.37-3.21 (m, 1H), 2.90-2.72 (m, 1H), 2.57-2.29 (m, 1H), 2.26-2.16 (m, 8H), 0.44-0.24 (m, 4H).

LCMS: m/z 431.1 [M+1]$^+$.

Example 91: Synthesis of 1-((3S,4S)-4-(4-(3-chloro-4-((2-methoxyethyl)amino)-1H-pyrrolo[2,3-b]pyridin-5-yl)-5-methyl-1H-pyrazol-1-yl)-3-fluoropiperidin-1-yl)ethan-1-one (87)

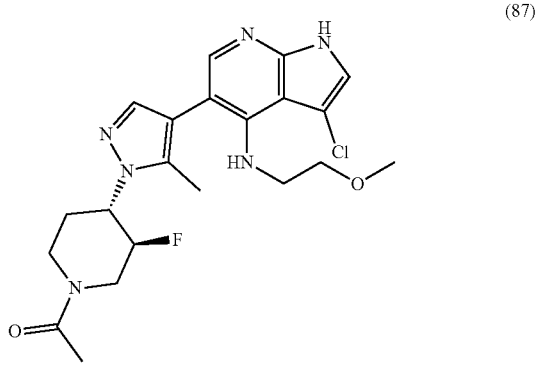 [SMILES: COCCNc1c(-c2cnn([C@H]3CCN(C(C)=O)C[C@@H]3F)c2C)cnc2[nH]cc(Cl)c12]

(87)

Compound 87 was synthesized via procedure 7 in Example 73 and obtained as an off-white solid (16.90 mg, 19% yield over 1 step).

$^1$HNMR (400 MHz, CDCl$_3$) δ 10.11 (brs, 1H), 7.85 (s, 1H), 7.55 (s, 1H), 7.07 (s, 1H), 5.93-5.86 (m, 1H), 5.15-4.66 (m, 2H), 4.37-3.96 (m, 2H), 3.37 (t, J=5.1 Hz, 2H), 3.34-3.22 (m, 4H), 2.99 (m, 2H), 2.92-2.74 (m, 1H), 2.59-2.29 (m, 1H), 2.25-2.16 (m, 7H).

LCMS: m/z 449.1 [M+1]$^+$.

Example 92: Synthesis of 1-((3S,4S)-4-(4-(3-chloro-4-(cyclopentylamino)-1H-pyrrolo[2,3-b]pyridin-5-yl)-5-methyl-1H-pyrazol-1-yl)-3-fluoropiperidin-1-yl)ethan-1-one (88)

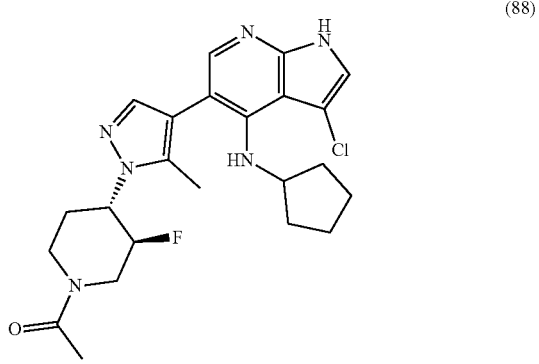 [SMILES: CC(=O)N1CC[C@H](n2ncc(-c3cnc4[nH]cc(Cl)c4c3NC3CCCC3)c2C)[C@@H](F)C1]

(88)

Compound 88 was synthesized via procedure 7 in Example 73 and obtained as an off-white solid (13.76 mg, 30% yield over 1 step).

$^1$HNMR (400 MHz, CDCl$_3$) δ 10.16 (brs, 1H), 7.84 (d, J=1.6 Hz, 1H), 7.57 (s, 1H), 7.06 (s, 1H), 5.50 (m, 1H), 5.14-4.66 (m, 2H), 4.37-3.98 (m, 2H), 3.55-3.45 (m, 1H), 3.38-3.22 (m, 1H), 2.92-2.74 (m, 1H), 2.59-2.30 (m, 1H), 2.25-2.15 (m, 7H), 1.63-1.31 (m, 8H).

LCMS: m/z 459.2 [M+1]$^+$.

Example 93: Synthesis of 1-((3S,4S)-4-(5-chloro-4-(3-chloro-4-(methylamino)-1H-pyrrolo[2,3-b]pyridin-5-yl)-1H-pyrazol-1-yl)-3-fluoropiperidin-1-yl)ethan-1-one (89)

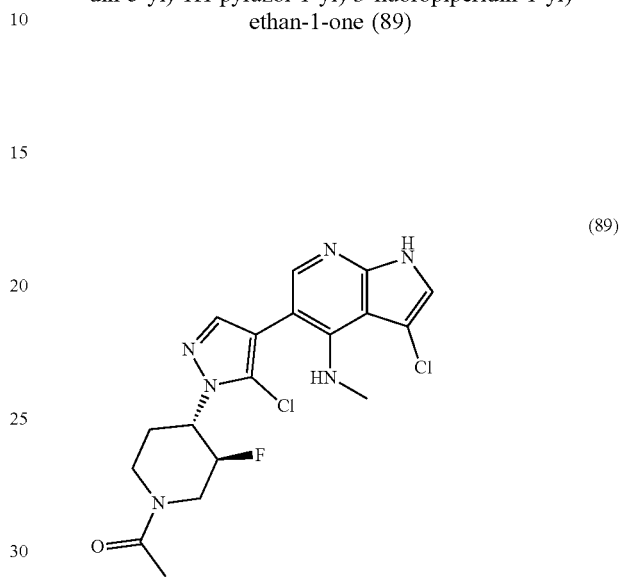

(89)

Compound 89 was synthesized via procedure 7 in Example 73 and obtained as an off-white solid (19.37 mg, 25% yield over 1 step).

$^1$H NMR (400 MHz, CDCl$_3$) δ 10.55 (brs, 1H), 7.85 (s, 1H), 7.67 (s, 1H), 7.05 (s, 1H), 5.71 (m, 1H), 5.13-4.55 (m, 3H), 4.33-3.96 (m, 1H), 3.44-3.22 (m, 1H), 2.98-2.80 (m, 1H), 2.64 (d, J=5.5 Hz, 3H), 2.19 (m, 5H).

LCMS: m/z 425.1 [M+1]$^+$.

Example 94: Synthesis of (4-(3-chloro-4-(methylamino)-1H-pyrrolo[2,3-b]pyridin-5-yl)phenyl)(morpholino)methanone (90)

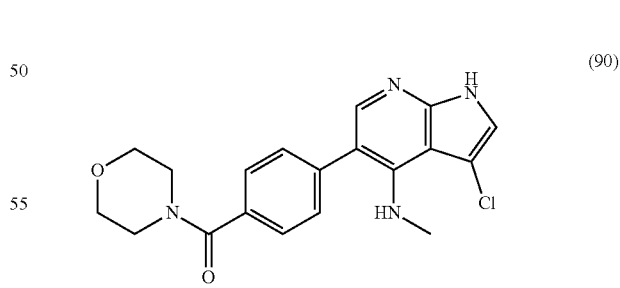

(90)

Compound 90 was synthesized via procedure 8 in Example 73 and obtained as a pink solid (32.0 mg, 14% yield over 2 steps).

$^1$HNMR (400 MHz, DMSO-d$_6$) δ 11.68 (brs, 1H), 7.78 (s, 1H), 7.46 (s, 4H), 7.37 (d, J=2.0 Hz, 1H), 5.69 (m, 1H), 3.73-3.44 (m, 8H), 2.48 (d, J=5.4 Hz, 3H).

LCMS: m/z 371.0 [M+1]$^+$.

Example 95: Synthesis of (4-(3-chloro-4-(ethylamino)-1H-pyrrolo[2,3-b]pyridin-5-yl)phenyl)(morpholino)methanone (91)

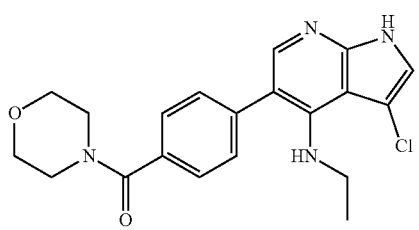
(91)

Compound 91 was synthesized via procedure 8 in Example 73 and obtained as a yellow solid (21.0 mg, 7% yield over 2 steps).

$^1$HNMR (400 MHz, CDCl$_3$) δ 9.89-9.51 (m, 1H), 7.84 (s, 1H), 7.48-7.37 (m, 4H), 7.00 (s, 1H), 5.34 (m, 1H), 3.86-3.47 (m, 8H), 2.76-2.64 (m, 2H), 0.98 (t, J=7.2 Hz, 3H).

LCMS: m/z 385.2 [M+1]$^+$.

Example 96: Synthesis of (4-(3-chloro-4-(isopropylamino)-1H-pyrrolo[2,3-b]pyridin-5-yl)phenyl)(morpholino)methanone (92)

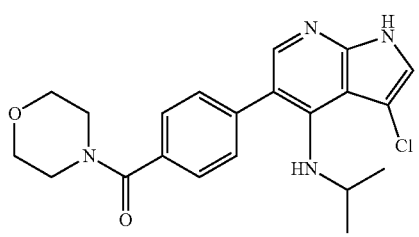
(92)

Compound 92 was synthesized via procedure 8 in Example 73 and obtained as a yellow solid (39.13 mg, 23% yield over 2 steps).

$^1$HNMR (400 MHz, CDCl$_3$) δ 9.92 (brs, 1H), 7.93 (d, J=2.1 Hz, 1H), 7.59-7.55 (m, 2H), 7.53-7.48 (m, 2H), 7.10 (s, 1H), 5.20 (m, 1H), 3.83-3.61 (m, 9H), 3.23-3.21 (m, 1H), 1.00-0.96 (m, 6H).

LCMS: m/z 399.1 [M+1]$^+$.

Example 97: Synthesis of (4-(3-chloro-4-(cyclopropylamino)-1H-pyrrolo[2,3-b]pyridin-5-yl)phenyl)(morpholino)methanone (93)

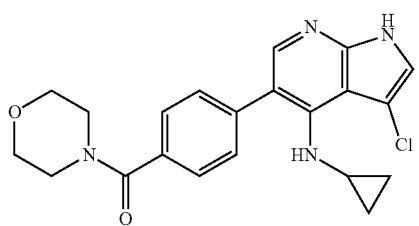
(93)

Compound 93 was synthesized via procedure 8 in Example 73 and obtained as a yellow solid (22.36 mg, 15% yield over 2 steps).

$^1$HNMR (400 MHz, CDCl$_3$) δ 9.98 (s, 1H), 8.00-7.87 (m, 1H), 7.56-7.51 (m, 2H), 7.48-7.43 (m, 2H), 7.10-7.01 (m, 1H), 5.91 (s, 1H), 3.74 (m, 8H), 2.15 (m, 1H), 0.39-0.21 (m, 4H).

LCMS: m/z 397.1 [M+1]$^+$.

Example 98: Synthesis of (4-(3-chloro-4-((2-methoxyethyl)amino)-1H-pyrrolo[2,3-b]pyridin-5-yl)phenyl)(morpholino)methanone (94)

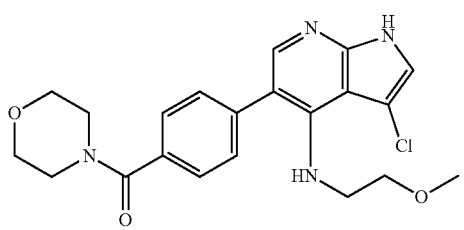
(94)

Compound 94 was synthesized via procedure 6 in Example 73 and obtained as a yellow solid (17.0 mg, 78% yield over 1 step).

$^1$HNMR (400 MHz, CDCl$_3$) δ 9.58 (brs, 1H), 7.93 (s, 1H), 7.57-7.43 (m, 4H), 7.08 (s, 1H), 5.97 (m, 1H), 3.96-3.51 (m, 8H), 3.36 (m, 2H), 3.32 (s, 3H), 2.91 (q, J=5.2 Hz, 2H).

LCMS: m/z 415.2 [M+1]$^+$.

Example 99: Synthesis of (4-(3-chloro-4-(cyclopentylamino)-1H-pyrrolo[2,3-b]pyridin-5-yl)phenyl)(morpholino)methanone (95)

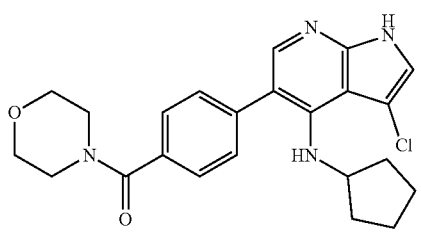
(95)

Compound 95 was synthesized via procedure 8 in Example 73 and obtained as a yellow solid (26.21 mg, 15% yield over 2 steps).

$^1$H NMR (400 MHz, CDCl$_3$) δ 9.82-9.68 (m, 1H), 7.91-7.89 (m, 1H), 7.57-7.53 (m, 2H), 7.51-7.47 (m, 2H), 7.09-7.07 (m, 1H), 5.52-5.43 (m, 1H), 3.97-3.55 (m, 8H), 3.47-3.36 (m, 1H), 1.56-1.33 (m, 8H).

LCMS: m/z 425.2 [M+1]$^+$.

Example 100: Synthesis of (4-(3-chloro-4-(methylamino)-1H-pyrrolo[2,3-b]pyridin-5-yl)phenyl)(4-morpholinopiperidin-1-yl)methanone (96)

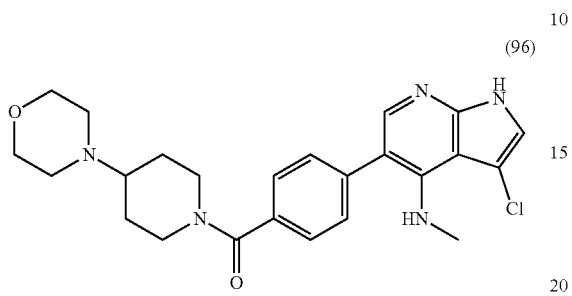
(96)

Compound 96 was synthesized via procedure 8 in Example 73 and obtained as a yellow solid (13.0 mg, 5% yield over 2 steps).

$^1$H NMR (400 MHz, CDCl$_3$) δ 10.65-10.16 (m, 1H), 7.93 (s, 1H), 7.55-7.43 (m, 4H), 7.07 (s, 1H), 5.64 (m, 1H), 4.91-4.61 (m, 1H), 4.07-3.83 (m, 1H), 3.78-3.72 (m, 4H), 3.19-2.79 (m, 2H), 2.68-2.53 (m, 7H), 2.48 (m, 1H), 2.07-1.84 (m, 2H), 1.64-1.45 (m, 2H).

LCMS: m/z 454.3 [M+1]$^+$.

Example 101: Synthesis of (4-(3-chloro-4-(ethylamino)-1H-pyrrolo[2,3-b]pyridin-5-yl)phenyl)(4-morpholinopiperidin-1-yl)methanone (97)

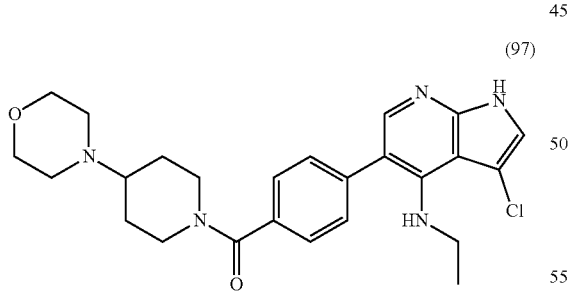
(97)

Compound 97 was synthesized via procedure 8 in Example 73 and obtained as an off-white solid (16.0 mg, 6% yield over 2 steps).

$^1$H NMR (400 MHz, CDCl$_3$) δ 9.89 (brs, 1H), 7.93 (s, 1H), 7.54-7.42 (m, 4H), 7.08 (s, 1H), 5.40 (m, 1H), 4.89-4.54 (m, 1H), 4.10-3.82 (m, 1H), 3.79-3.67 (m, 4H), 3.19-2.85 (m, 4H), 2.65-2.53 (m, 4H), 2.48 (m, 1H), 2.10-1.78 (m, 2H), 1.58-1.42 (m, 2H), 1.06 (m, 3H).

LCMS: m/z 468.2 [M+1]$^+$.

Example 102: Synthesis of (4-(3-chloro-4-(isopropylamino)-1H-pyrrolo[2,3-b]pyridin-5-yl)phenyl)(4-morpholinopiperidin-1-yl)methanone (98)

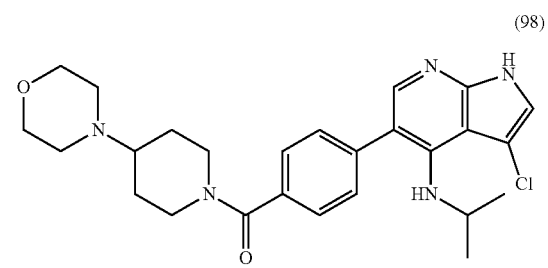 [SMILES: CC(C)Nc1c(-c2ccc(C(=O)N3CCC(N4CCOCC4)CC3)cc2)cnc2[nH]cc(Cl)c12]
(98)

Compound 98 was synthesized via procedure 8 in Example 73 and obtained as a white solid (24.48 mg, 9% yield over 2 steps).

$^1$H NMR (400 MHz, CDCl$_3$) δ 10.09 (brs, 1H), 7.93 (s, 1H), 7.58-7.53 (m, 2H), 7.51-7.46 (m, 2H), 7.10 (s, 1H), 5.19 (m, 1H), 4.92-4.61 (m, 1H), 4.08-3.78 (m, 1H), 3.78-3.71 (m, 4H), 3.33-2.81 (m, 3H), 2.61-2.44 (m, 5H), 2.08-1.82 (m, 2H), 1.60-1.48 (m, 2H), 0.97 (d, J=6.2 Hz, 6H).

LCMS: m/z 482.2 [M+1]$^+$.

Example 103: Synthesis of (4-(3-chloro-4-(cyclopropylamino)-1H-pyrrolo[2,3-b]pyridin-5-yl)phenyl)(4-morpholinopiperidin-1-yl)methanone (99)

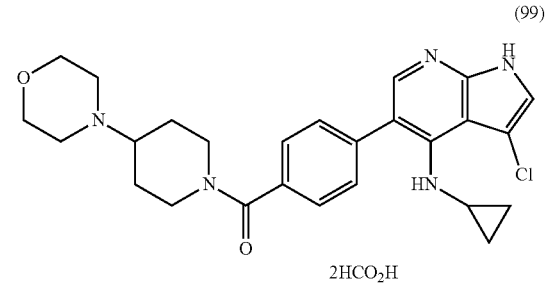 [SMILES: O=C(c1ccc(-c2cnc3[nH]cc(Cl)c3c2NC2CC2)cc1)N1CCC(N2CCOCC2)CC1]
(99)

2HCO$_2$H

Compound 99 was synthesized via procedure 8 in Example 73 and obtained as a yellow solid (11.0 mg, 7% yield over 2 steps). Compound 99 was isolated as a formic acid salt.

$^1$H NMR (400 MHz, DMSO-d$_6$) δ 11.85-11.63 (m, 1H), 8.17 (s, 2H), 7.81 (s, 1H), 7.50-7.45 (m, 2H), 7.43-7.34 (m, 3H), 5.79 (d, J=2.8 Hz, 1H), 4.63-4.29 (m, 1H), 3.83-3.50 (m, 8H), 3.10-2.78 (m, 4H), 2.14-2.06 (m, 1H), 1.92-1.68 (m, 2H), 1.46-1.28 (m, 2H), 0.30 (m, 2H), 0.21-0.12 (m, 2H).

LCMS: m/z 480.2 [M+1]$^+$.

Example 104: Synthesis of (4-(3-chloro-4-((2-methoxyethyl)amino)-1H-pyrrolo[2,3-b]pyridin-5-yl)phenyl)(4-morpholinopiperidin-1-yl)methanone (100)

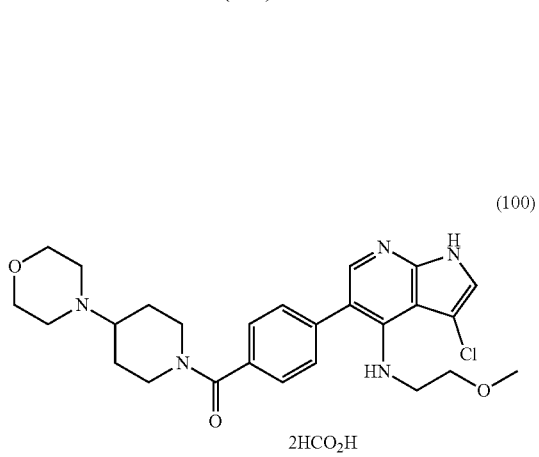

Compound 100 was synthesized via procedure 6 in Example 73 and obtained as a brown gum (24.0 mg, 9% yield over 1 step). Compound 100 was isolated as a formic acid salt.

$^1$H NMR (400 MHz, DMSO-d$_6$) δ11.75 (brs, 1H), 8.16 (s, 2H), 7.83 (s, 1H), 7.49-7.44 (m, 4H), 7.41 (s, 1H), 5.70-5.67 (m, 1H), 4.50-4.44 (m, 1H), 3.80-3.20 (m, 15H), 2.86-2.82 (m, 4H), 1.95-1.70 (m, 2H), 1.47-1.30 (m, 2H).

LCMS: m/z 498.2 [M+1]$^+$.

Example 105: Synthesis of (4-(3-chloro-4-(cyclopentylamino)-1H-pyrrolo[2,3-b]pyridin-5-yl)phenyl)(4-morpholinopiperidin-1-yl)methanone (101)

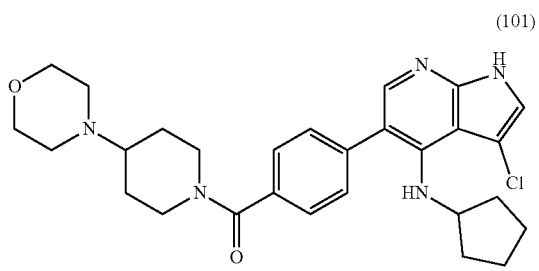 [SMILES: O=C(c1ccc(-c2cnc3[nH]cc(Cl)c3c2NC2CCCC2)cc1)N1CCC(N2CCOCC2)CC1]

Compound 101 was synthesized via procedure 8 in Example 73 and obtained as a white solid (8.59 mg, 4% yield over 2 steps).

$^1$H NMR (400 MHz, CDCl$_3$) δ 9.87-9.33 (m, 1H), 7.91 (s, 1H), 7.55-7.50 (m, 2H), 7.49-7.45 (m, 2H), 7.07 (s, 1H), 5.56-5.35 (m, 1H), 4.88-4.67 (m, 1H), 4.02-3.81 (m, 1H), 3.80-3.67 (m, 4H), 3.55-3.31 (m, 1H), 3.25-2.70 (m, 2H), 2.58 (br s, 4H), 2.52-2.43 (m, 1H), 2.09-1.83 (m, 2H), 1.56-1.21 (m, 10H).

LCMS: m/z 508.2 [M+1]$^+$.

Example 106: Synthesis of (4-(3-chloro-4-(ethylamino)-1H-pyrrolo[2,3-b]pyridin-5-yl)-3-methoxyphenyl)(morpholino)methanone (102)

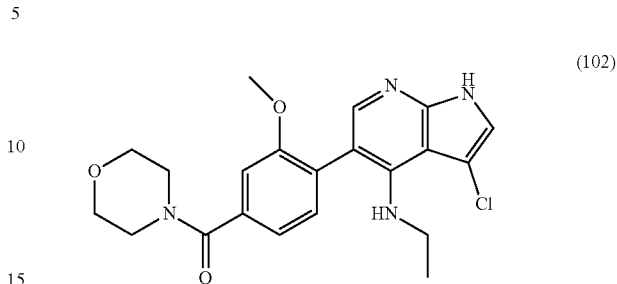

Compound 102 was synthesized via procedure 6 in Example 73 and obtained as a yellow solid (20.67 mg, 10% yield over 1 step).

$^1$H NMR (400 MHz, CDCl$_3$) δ 10.02 (brs, 1H), 7.81 (s, 1H), 7.33 (d, J=7.7 Hz, 1H), 7.12-6.95 (m, 3H), 5.45 (m, J=5.1 Hz, 1H), 3.84 (s, 11H), 2.81-2.72 (m, 2H), 1.05 (t, J=7.2 Hz, 3H).

LCMS: m/z 415.1 [M+1]$^+$.

Example 107: Synthesis of (4-(3-chloro-4-(isopropylamino)-1H-pyrrolo[2,3-b]pyridin-5-yl)-3-methoxyphenyl)(morpholino)methanone (103)

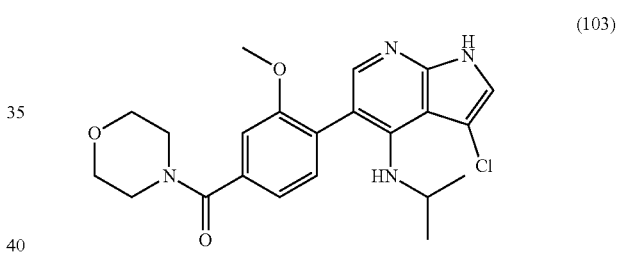

Compound 103 was synthesized via procedure 8 in Example 73 and obtained as an off-white solid (44.71 mg, 17% yield over 2 steps).

$^1$H NMR (400 MHz, CDCl$_3$) δ 9.97-9.87 (m, 1H), 7.85-7.79 (m, 1H), 7.38-7.34 (m, 1H), 7.12-7.00 (m, 3H), 5.31-5.25 (m, 1H), 3.83 (s, 11H), 3.26-3.13 (m, 1H), 1.06-0.85 (m, 6H).

LCMS: m/z 429.1 [M+1]$^+$.

Example 108: Synthesis of (4-(3-chloro-4-(cyclopropylamino)-1H-pyrrolo[2,3-b]pyridin-5-yl)-3-methoxyphenyl)(morpholino)methanone (104)

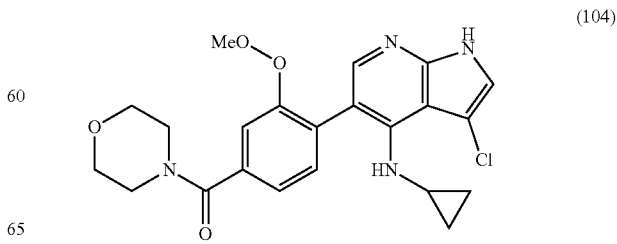

Compound 104 was synthesized via procedure 8 in Example 73 and obtained as a white solid (6.0 mg, 9% yield over 2 steps).

$^1$H NMR (400 MHz, CDCl$_3$) δ 9.82 (brs, 1H), 7.76 (s, 1H), 7.29 (d, J=7.4 Hz, 1H), 6.98-6.91 (m, 3H), 5.94 (d, J=1.6 Hz, 1H), 3.87-3.38 (m, 11H), 2.03 (br dd, J=3.5, 6.3 Hz, 1H), 0.42-0.31 (m, 1H), 0.28-0.15 (m, 2H), 0.06--0.08 (m, 1H).

LCMS: m/z 427.1 [M+1]$^+$.

Example 109: Synthesis of (4-(3-chloro-4-((2-methoxyethyl)amino)-1H-pyrrolo[2,3-b]pyridin-5-yl)-3-methoxyphenyl)(morpholino)methanone (105)

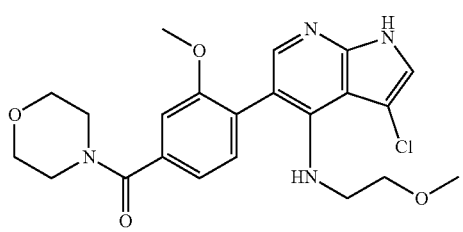

(105)

Compound 105 was synthesized via procedure 8 in Example 73 and obtained as a white solid (34.0 mg, 18% yield over 2 steps).

$^1$H NMR (400 MHz, DMSO-d$_6$) δ 11.65 (brs, 1H), 7.64 (s, 1H), 7.36 (d, J=2.0 Hz, 1H), 7.30 (d, J=7.6 Hz, 1H), 7.09 (d, J=1.1 Hz, 1H), 7.03 (m, 1H), 5.67 (t, J=5.4 Hz, 1H), 3.77 (s, 3H), 3.71-3.43 (m, 8H), 3.25 (t, J=5.3 Hz, 2H), 3.16 (s, 3H), 2.88-2.78 (m, 2H).

LCMS: m/z 445.0 [M+1]$^+$.

Example 110: Synthesis of (4-(3-chloro-4-(cyclopentylamino)-1H-pyrrolo[2,3-b]pyridin-5-yl)-3-methoxyphenyl)(morpholino)methanone (106)

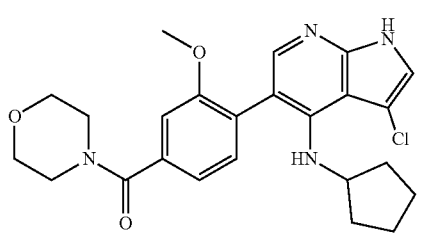

(106)

Compound 106 was synthesized via procedure 8 in Example 73 and obtained as a pink solid (12.46 mg, 4% yield over 2 steps).

$^1$H NMR (400 MHz, CDCl$_3$) δ 9.90-9.25 (m, 1H), 7.82-7.80 (m, 1H), 7.39-7.30 (m, 1H), 7.11-7.05 (m, 1H), 7.05-6.98 (m, 2H), 5.59-5.52 (m, 1H), 3.86-3.76 (m, 11H), 3.45-3.31 (m, 1H), 1.50-1.29 (m, 8H).

LCMS: m/z 455.1 [M+1]$^+$.

Example 111: Synthesis of (4-(3-chloro-4-(methylamino)-1H-pyrrolo[2,3-b]pyridin-5-yl)-3-methoxyphenyl)(4-morpholinopiperidin-1-yl)methanone (107)

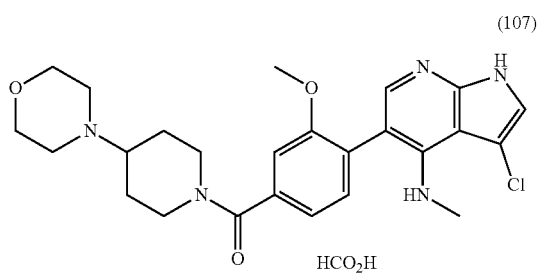 [SMILES: CNc1c(-c2ccc(C(=O)N3CCC(N4CCOCC4)CC3)cc2OC)cnc2[nH]cc(Cl)c12 ; "HCO2H"]

(107)

Compound 107 was synthesized via procedure 6 in Example 73 and obtained as a yellow solid (13.0 mg, 10% yield over 1 step). Compound 107 was isolated as a formic acid salt.

$^1$H NMR (400 MHz, CDCl$_3$) δ 8.41 (s, 1H), 7.59 (s, 1H), 7.29 (s, 2H), 7.08 (s, 1H), 7.04-6.97 (m, 2H), 4.87-4.63 (m, 1H), 3.98-3.85 (m, 1H), 3.82 (s, 3H), 3.78-3.72 (m, 4H), 3.19-2.98 (m, 3H), 2.66-2.58 (m, 7H), 2.57-2.48 (m, 1H), 2.11-1.84 (m, 2H), 1.67-1.42 (m, 2H).

LCMS: m/z 484.4 [M+1]$^+$.

Example 112: Synthesis of (4-(3-chloro-4-(ethylamino)-1H-pyrrolo[2,3-b]pyridin-5-yl)-3-methoxyphenyl)(4-morpholinopiperidin-1-yl)methanone (108)

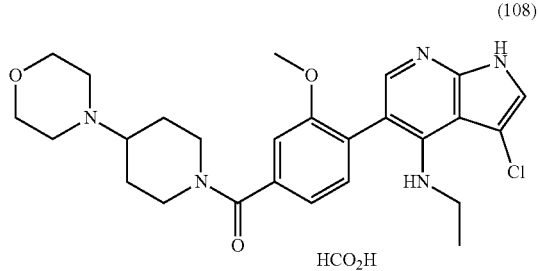 [SMILES: CCNc1c(-c2ccc(C(=O)N3CCC(N4CCOCC4)CC3)cc2OC)cnc2[nH]cc(Cl)c12 ; "HCO2H"]

(108)

Compound 108 was synthesized via procedure 8 in Example 73 and obtained as a yellow solid (20.0 mg, 6% yield over 2 steps). Compound 108 was isolated as a formic acid salt.

$^1$H NMR (400 MHz, CDCl$_3$) δ 8.48 (s, 1H), 7.62 (s, 1H), 7.30 (s, 2H), 7.10 (s, 1H), 7.05-7.00 (m, 2H), 4.93-4.59 (m, 1H), 4.02-3.69 (m, 9H), 3.22-2.76 (m, 5H), 2.68-2.57 (m, 4H), 2.12-1.84 (m, 2H), 1.70-1.38 (m, 2H), 1.10 (m, 3H).

LCMS: m/z 498.2 [M+1]+.

Example 113: Synthesis of (4-(3-chloro-4-(isopropylamino)-1H-pyrrolo[2,3-b]pyridin-5-yl)-3-methoxyphenyl)(4-morpholinopiperidin-1-yl)methanone (109)

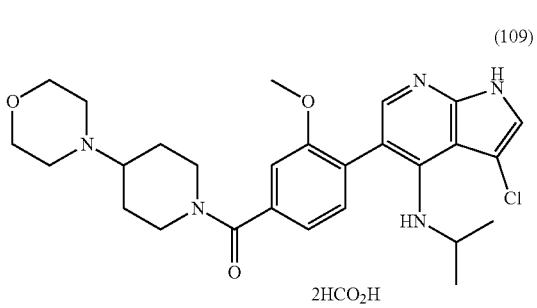 [SMILES: COc1cc(C(=O)N2CCC(N3CCOCC3)CC2)ccc1-c1cnc2[nH]cc(Cl)c2c1NC(C)C]

Compound 109 was synthesized via procedure 8 in Example 73 and obtained as a yellow solid (10.38 mg, 4% yield over 2 steps). Compound 109 was isolated as a formic acid salt.

$^1$H NMR (400 MHz, CDCl$_3$) δ 8.33 (s, 2H), 7.52 (s, 1H), 7.22 (d, J=7.6 Hz, 2H), 7.05-6.93 (m, 3H), 4.83-4.54 (m, 1H), 3.77-3.65 (m, 9H), 3.30-3.20 (m, 1H), 3.10-2.73 (m, 2H), 2.64-2.55 (m, 4H), 2.49 (m, 1H), 2.03-1.78 (m, 2H), 1.64-1.37 (m, 2H), 1.03-0.78 (m, 6H).

LCMS (Method 4): m/z 512.3 [M+1]+.

Example 114: Synthesis of (4-(3-chloro-4-(cyclopropylamino)-1H-pyrrolo[2,3-b]pyridin-5-yl)-3-methoxyphenyl)(4-morpholinopiperidin-1-yl)methanone (110)

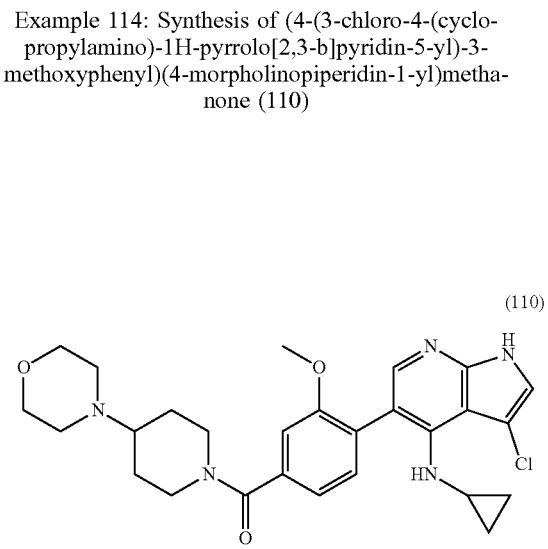

Compound 110 was synthesized via procedure 8 in Example 73 and obtained as a white solid (14.0 mg, 7% yield over 2 steps).

$^1$H NMR (400 MHz, CDCl$_3$) δ 10.04-9.82 (m, 1H), 7.77 (s, 1H), 7.27 (m, 1H), 7.04-6.87 (m, 3H), 5.92 (br s, 1H), 4.86-4.55 (m, 1H), 3.96-3.59 (m, 8H), 3.15-2.73 (m, 2H), 2.64-2.32 (m, 5H), 2.34-2.30 (m, 3H), 1.52-1.31 (m, 2H), 0.46-0.15 (m, 3H), 0.10-0.06 (m, 1H).

LCMS (Method 4): m/z 510.2 [M+1]$^+$.

Example 115: Synthesis of (4-(3-chloro-4-((2-methoxyethyl)amino)-1H-pyrrolo[2,3-b]pyridin-5-yl)-3-methoxyphenyl)(4-morpholinopiperidin-1-yl)methanone (111)

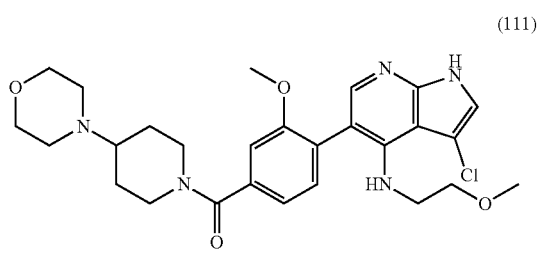 [SMILES: COCCNc1c(-c2ccc(C(=O)N3CCC(N4CCOCC4)CC3)cc2OC)cnc2[nH]cc(Cl)c12]

Compound 111 was synthesized via procedure 8 in Example 73 and obtained as a yellow solid (40.0 mg, 42% yield over 2 steps).

$^1$H NMR (400 MHz, CDCl$_3$) δ 9.52-9.32 (m, 1H), 7.82 (s, 1H), 7.32 (d, J=7.6 Hz, 1H), 7.08-6.97 (m, 3H), 6.03-5.95 (m, 1H), 4.92-4.56 (m, 1H), 4.11-3.67 (m, 8H), 3.40-3.25 (m, 5H), 3.16-2.98 (m, 1H), 2.97-2.84 (m, 3H), 2.59 (br s, 4H), 2.52-2.41 (m, 1H), 2.09-1.81 (m, 2H), 1.57-1.43 (m, 2H).

LCMS (Method 1): m/z 528.4 [M+1]$^+$.

Example 116: Synthesis of (4-(3-chloro-4-(cyclopentylamino)-1H-pyrrolo[2,3-b]pyridin-5-yl)-3-methoxyphenyl)(4-morpholinopiperidin-1-yl)methanone (112)

Compound 112 was synthesized via procedure 8 in Example 73 and obtained as a yellow solid (7.77 mg, 3% yield over 2 steps). Compound 112 was isolated as a formic acid salt.

$^1$H NMR (400 MHz, CDCl$_3$) δ 8.42-8.41 (m, 2H), 7.59 (s, 1H), 7.30 (d, J=8.1 Hz, 2H), 7.12-7.00 (m, 3H), 4.92-4.61 (m, 1H), 3.82 (s, 3H), 3.80-3.74 (m, 4H), 3.50 (br s, 1H), 3.11-2.80 (m, 4H), 2.70-2.61 (m, 4H), 2.60-2.50 (m, 1H), 2.10-1.89 (m, 2H), 1.72-1.31 (m, 10H).

LCMS (Method 5): m/z 538.3 [M+1]$^+$.

Example 117: LRRK2 Inhibition with Inventive Compounds

IC$_{50}$ experiments were performed for inventive compounds. The results are shown in Table 1. An exemplary kit to perform this assay includes the Adapta™ Screening Protocol and Assay Conditions by Invitrogen™ (Fisher Scientific™, Catalog No. PV5099).

All LRRK2 kinase inhibition assays were conducted by using Promega ADP-Glo™ Kinase assay systems (Catalog number; V4475). Inhibitors were tested with 12 concentrations over a 5-fold serial dilution series (50 µM, 10 µM, 2 µM, 400 nM, 80 nM, 16 nM, 3.2 nM, 640 µM, 128 µM, 25.6 µM, 5.12 µM and 1.024 µM) and PF06447475 as positive control. For the LRRK2 wild type (WT) enzyme assay, each inhibitor was mixed with 0.2 µg/µL of substrate (LRRKtide, SignalChem, Richmond, BC, Canada), 10 mol/L ATP (Invitrogen™, Carlsbad, CA), 24 ng of LRRK2 WT enzyme (Thermo Fisher Scientific, PR8604B) in 384-well plate. For LRRK G2019S, each compound was mixed with 0.2 µg/µL of substrate, 25 mol/L ATP, 16 ng of LRRK2 G2019S enzyme (SignalChem, L10-12GG). All samples were diluted with kinase reaction buffer (40 mmol/L TrisHCl, 10 mmol/L MgCl$_2$, and 0.1 µg/µL BSA (bovine serum albumin)). After 2 hours at 25° C., ADP-Glo™ (Promega, Madison, WI) reagent was added and the samples were incubated at rt for 40 min. Finally, Kinase Detection Reagent was added and the resulting mixtures were allowed to react at rt for 10 min. Luminescence signals were detected using Synergy™ Neo$_2$ microplate reader (Bio-Tek). Compound inhibition curve was fitted using Graphpad Prism 8.0 software.

TABLE 1

IC$_{50}$ of inventive compounds.

| Inventive Compound | IC$_{50}$ (nM) | |
|---|---|---|
| | LRRK2 wt | LRRK2 G2019S |
| 1 | 544 | 326 |
| 2 | 891 | 825 |
| 3 | 264 | 164 |
| 4 | 15 | 14 |
| 5 | 22 | 20 |
| 6 | 10 | 15 |
| 7 | 38 | 26 |
| 8 | 103 | 61 |
| 9 | 36.6 | 83.1 |
| 10 | 259.3 | 522.7 |
| 11 | 8.4 | 30.9 |
| 12 | 135.9 | 514.4 |
| 13 | 3596 | >10,000 |
| 14 | 95.2 | 305.1 |
| 15 | 139.9 | 396.8 |
| 16 | 6227 | >10,000 |

TABLE 2

Enzyme activity against LRRK2 WT and LRRK2 G2019S (IC$_{50}$).

| Inventive Compound | LRRK2 WT | LRRK2 G2019S |
|---|---|---|
| 31 | B | B |
| 38 | B | B |
| 48 | B | B |
| 54 | B | B |
| 70 | B | B |
| 77 | B | B |
| 78 | B | B |
| 81 | B | C |
| 90 | A | A |
| 91 | B | B |
| 93 | B | B |
| 96 | B | A |
| 97 | A | B |
| 99 | B | C |

A: <0.010 µM
B: 0.010~0.100 µM
C: >0.1 µM

The data in Table 1 and Table 2 show that the inventive compounds potently inhibited wild-type LRRK2 and LRRK2(G2019S) mutant in an enzyme assay.

Example 118: Kinase Profiling

The kinase selectivity of inventive compounds 77, 96 and 101 was evaluated by KinomeScan®. KinomeScan® analysis was performed against a near comprehensive panel of 468 kinases. The results are shown in Table 3. The control percentage (% control) for inventive compounds at 1 µM in DMSO was determined by Equation 1:

% control=(inventive compound−positive control)/(negative control−positive control)×100%,   Equation 1 wherein the positive control is a compound with a % control value of 0% relative light units (RLU), and the negative control (i.e., DMSO) has % control value of 100% RLU. The enzyme selectivity in the present invention is defined as follows: inventive compounds are considered active for an enzyme when the observed % control is less than 35% (<35%).

TABLE 3

Kinase profiling assay with inventive compounds 77, 96 and 101.

| Kinases | Compound 96 | Compound 77 | Compound 101 |
|---|---|---|---|
| AAK1 | 23 | 36 | 67 |
| ABL1(E255K)-phosphorylated | 92 | 73 | 100 |
| ABL1(F317I)-nonphosphorylated | 100 | 100 | 100 |
| ABL1(F317I)-phoshorylated | 100 | 81 | 10 |
| ABL1(F317L)-nonphosphorylated | 100 | 95 | 10 |
| ABL1(F317L)-phosphorylated | 81 | 91 | 43 |
| ABL1(H396P)-nonphosphorylated | 76 | 36 | 100 |
| ABL1(H396P)-phosphorylated | 100 | 81 | 100 |
| ABL1(M351T)-phosphorylated | 71 | 75 | 93 |
| ABL1(Q252H)-nonphosphorylated | 64 | 50 | 92 |
| ABL1(Q252H)-phosphorylated | 100 | 95 | 100 |
| ABL1(T315I)-nonphosphorylated | 100 | 100 | 85 |
| ABL1(T315I)-phosphorylated | 52 | 31 | 95 |
| ABL1(Y253F)-phosphorylated | 98 | 79 | 100 |
| ABL1-nonphosphorylated | 63 | 54 | 98 |
| ABL1-phosphorylated | 88 | 62 | 97 |
| ABL2 | 100 | 92 | 99 |
| ACVR1 | 81 | 100 | 100 |
| ACVR1B | 74 | 83 | 98 |
| ACVR2A | 97 | 99 | 95 |
| ACVR2B | 91 | 77 | 100 |
| ACVRL1 | 100 | 100 | 100 |
| ADCK3 | 100 | 100 | 68 |
| ADCK4 | 100 | 100 | 100 |
| AKT1 | 100 | 100 | 96 |
| AKT2 | 100 | 100 | 84 |
| AKT3 | 100 | 95 | 99 |
| ALK | 46 | 40 | 75 |
| ALK(C1156Y) | 37 | 47 | 66 |
| ALK(L1196M) | 51 | 91 | 94 |
| AMPK-alpha1 | 75 | 100 | 78 |
| AMPK-alpha2 | 66 | 99 | 55 |
| ANKK1 | 51 | 73 | 100 |
| ARK5 | 64 | 86 | 67 |

TABLE 3-continued

Kinase profiling assay with inventive compounds 77, 96 and 101.

| Kinases | Compound 96 | Compound 77 | Compound 101 |
|---|---|---|---|
| ASK1 | 5.9 | 4.3 | 94 |
| ASK2 | 42 | 30 | 100 |
| AURKA | 36 | 35 | 82 |
| AURKB | 53 | 24 | 100 |
| AURKC | 49 | 26 | 71 |
| AXL | 33 | 8.5 | 40 |
| BIKE | 0.85 | 0.4 | 6.8 |
| BLK | 100 | 100 | 100 |
| BMPR1A | 66 | 93 | 87 |
| BMPR1B | 54 | 47 | 95 |
| BMPR2 | 53 | 40 | 98 |
| BMX | 93 | 88 | 34 |
| BRAF | 90 | 91 | 84 |
| BRAF(V600E) | 87 | 98 | 99 |
| BRK | 78 | 95 | 86 |
| BRSK1 | 100 | 100 | 100 |
| BRSK2 | 95 | 100 | 94 |
| BTK | 78 | 68 | 100 |
| BUB1 | 86 | 80 | 100 |
| CAMK1 | 87 | 84 | 98 |
| CAMK1B | 87 | 74 | 69 |
| CAMK1D | 69 | 85 | 100 |
| CAMK1G | 98 | 100 | 93 |
| CAMK2A | 96 | 100 | 92 |
| CAMK2B | 100 | 100 | 99 |
| CAMK2D | 100 | 100 | 93 |
| CAMK2G | 95 | 90 | 96 |
| CAMK4 | 100 | 100 | 87 |
| CAMKK1 | 78 | 74 | 87 |
| CAMKK2 | 82 | 79 | 88 |
| CASK | 94 | 95 | 100 |
| CDC2L1 | 96 | 99 | 94 |
| CDC2L2 | 100 | 91 | 92 |
| CDC2L5 | 100 | 100 | 2.1 |
| CDK11 | 68 | 96 | 35 |
| CDK2 | 100 | 100 | 100 |
| CDK3 | 89 | 95 | 97 |
| CDK4 | 98 | 85 | 100 |
| CDK4-cyclinD1 | 73 | 74 | 100 |
| CDK4-cyclinD3 | 100 | 98 | 99 |
| CDK5 | 97 | 91 | 94 |
| CDK7 | 90 | 94 | 93 |
| CDK8 | 82 | 100 | 59 |
| CDK9 | 87 | 83 | 96 |
| CDKL1 | 78 | 76 | 100 |
| CDKL2 | 97 | 95 | 100 |
| CDKL3 | 100 | 94 | 100 |
| CDKL5 | 92 | 94 | 70 |
| CHEK1 | 84 | 89 | 83 |
| CHEK2 | 22 | 56 | 92 |
| CIT | 11 | 6.8 | 21 |
| CLK1 | 33 | 84 | 59 |
| CLK2 | 11 | 57 | 65 |
| CLK3 | 98 | 88 | 97 |
| CLK4 | 11 | 72 | 42 |
| CSF1R | 73 | 74 | 28 |
| CSF1R-autoinhibited | 49 | 30 | 3.2 |
| CSK | 44 | 22 | 100 |
| CSNK1A1 | 100 | 96 | 89 |
| CSNK1A1L | 48 | 79 | 100 |
| CSNK1D | 90 | 84 | 92 |
| CSNK1E | 17 | 68 | 81 |
| CSNK1G1 | 19 | 81 | 92 |
| CSNK1G2 | 93 | 81 | 73 |
| CSNK1G3 | 16 | 24 | 93 |
| CSNK2A1 | 72 | 75 | 100 |
| CSNK2A2 | 92 | 90 | 100 |
| CTK | 100 | 97 | 95 |
| DAPK1 | 74 | 73 | 80 |
| DAPK2 | 82 | 72 | 100 |
| DAPK3 | 96 | 79 | 88 |
| DCAMKL1 | 77 | 79 | 90 |
| DCAMKL2 | 78 | 89 | 99 |
| DCAMKL3 | 99 | 95 | 84 |
| DDR1 | 100 | 100 | 61 |
| DDR2 | 79 | 86 | 100 |
| DLK | 24 | 14 | 65 |
| DMPK | 36 | 36 | 52 |
| DMPK2 | 91 | 80 | 100 |
| DRAK1 | 56 | 81 | 100 |
| DRAK2 | 19 | 47 | 92 |
| DYRK1A | 69 | 58 | 4 |
| DYRK1B | 100 | 100 | 89 |
| DYRK2 | 12 | 49 | 100 |
| EGFR | 100 | 95 | 97 |
| EGFR(E746-A750del) | 93 | 100 | 97 |
| EGFR(G719C) | 100 | 91 | 91 |
| EGFR(G719S) | 100 | 100 | 100 |
| EGFR(L747-E749del, A750P) | 100 | 100 | 88 |
| EGFR(L747-S752del, P753S) | 77 | 92 | 100 |
| EGFR(L747-T751del, Sins) | 76 | 88 | 100 |
| EGFR(L858R) | 100 | 100 | 96 |
| EGFR(L858R, T790M) | 98 | 99 | 100 |
| EGFR(L861Q) | 90 | 96 | 89 |
| EGFR(S752-I759del) | 98 | 100 | 100 |
| EGFR(T790M) | 83 | 93 | 100 |
| EIF2AK1 | 100 | 100 | 100 |
| EPHA1 | 81 | 83 | 76 |
| EPHA2 | 100 | 96 | 30 |
| EPHA3 | 100 | 90 | 82 |
| EPHA4 | 100 | 96 | 88 |
| EPHA5 | 100 | 96 | 98 |
| EPHA6 | 98 | 93 | 43 |
| EPHA7 | 96 | 78 | 96 |
| EPHA8 | 96 | 94 | 93 |
| EPHB1 | 100 | 93 | 95 |
| EPHB2 | 97 | 98 | 97 |
| EPHB3 | 100 | 100 | 79 |
| EPHB4 | 100 | 100 | 62 |
| EPHB6 | 99 | 55 | 100 |
| ERBB2 | 80 | 63 | 92 |
| ERBB3 | 86 | 88 | 55 |
| ERBB4 | 100 | 100 | 97 |
| ERK1 | 100 | 100 | 98 |
| ERK2 | 95 | 91 | 93 |
| ERK3 | 85 | 87 | 100 |
| ERK4 | 94 | 90 | 93 |
| ERK5 | 81 | 100 | 100 |
| ERK8 | 100 | 92 | 91 |
| ERN1 | 73 | 56 | 86 |
| FAK | 65 | 90 | 71 |
| FER | 100 | 100 | 100 |
| FES | 95 | 95 | 72 |
| FGFR1 | 85 | 87 | 77 |
| FGFR2 | 94 | 72 | 54 |
| FGFR3 | 82 | 64 | 67 |
| FGFR3(G697C) | 55 | 51 | 74 |
| FGFR4 | 59 | 61 | 85 |
| FGR | 95 | 80 | 94 |
| FLT1 | 33 | 21 | 51 |
| FLT3 | 6.7 | 3.3 | 4.9 |
| FLT3(D835H) | 9.9 | 7.9 | 41 |
| FLT3(D835V) | 2.9 | 0.5 | 6.4 |
| FLT3(D835Y) | 11 | 9.7 | 33 |
| FLT3(ITD) | 8.1 | 6.2 | 41 |
| FLT3(ITD, D835V) | 3.6 | 2.5 | 55 |
| FLT3(ITD, F691L) | 0 | 0 | 49 |
| FLT3(K663Q) | 15 | 15 | 28 |
| FLT3(N841I) | 14 | 1 | 2.6 |
| FLT3(R834Q) | 52 | 45 | 75 |
| FLT3-autoinhibited | 93 | 53 | 62 |
| FLT4 | 66 | 47 | 100 |
| FRK | 84 | 100 | 100 |
| FYN | 96 | 94 | 87 |
| GAK | 99 | 100 | 99 |
| GCN2(Kin.Dom.2, S808G) | 54 | 34 | 100 |
| GRK1 | 63 | 60 | 84 |
| GRK2 | 94 | 93 | 100 |
| GRK3 | 92 | 93 | 94 |
| GRK4 | 28 | 21 | 14 |

TABLE 3-continued

Kinase profiling assay with inventive compounds 77, 96 and 101.

| Kinases | Compound 96 | Compound 77 | Compound 101 |
|---|---|---|---|
| GRK7 | 100 | 100 | 94 |
| GSK3A | 65 | 98 | 42 |
| GSK3B | 63 | 69 | 100 |
| HASPIN | 1.3 | 9.8 | 22 |
| HCK | 100 | 100 | 96 |
| HIPK1 | 68 | 70 | 92 |
| HIPK2 | 74 | 81 | 100 |
| HIPK3 | 79 | 85 | 100 |
| HIPK4 | 64 | 84 | 79 |
| HPK1 | 84 | 6.7 | 53 |
| HUNK | 100 | 100 | 100 |
| ICK | 35 | 35 | 100 |
| IGF1R | 100 | 91 | 86 |
| IKK-alpha | 14 | 17 | 49 |
| IKK-beta | 32 | 28 | 93 |
| IKK-epsilon | 68 | 64 | 99 |
| INSR | 71 | 53 | 68 |
| INSRR | 96 | 92 | 84 |
| IRAK1 | 41 | 33 | 100 |
| IRAK3 | 76 | 40 | 37 |
| IRAK4 | 62 | 26 | 100 |
| ITK | 93 | 71 | 90 |
| JAK1(JH1domain-catalytic) | 100 | 98 | 90 |
| JAK1(JH2domain-pseudokinase) | 94 | 57 | 47 |
| JAK2(JH1domain-catalytic) | 29 | 7.9 | 100 |
| JAK3(JH1domain-catalytic) | 7.8 | 8.2 | 62 |
| JNK1 | 0.05 | 1.1 | 7.1 |
| JNK2 | 0.85 | 17 | 8.8 |
| JNK3 | 0.35 | 1.9 | 7.6 |
| KIT | 11 | 4.8 | 58 |
| KIT(A829P) | 53 | 46 | 100 |
| KIT(D816H) | 75 | 51 | 92 |
| KIT(D816V) | 86 | 46 | 95 |
| KIT(L576P) | 19 | 10 | 46 |
| KIT(V559D) | 4.5 | 2.8 | 50 |
| KIT(V559D, T670I) | 27 | 9.7 | 71 |
| KIT(V559D, V654A) | 94 | 53 | 100 |
| KIT-autoinhibited | 64 | 23 | 100 |
| LATS1 | 100 | 91 | 100 |
| LATS2 | 78 | 86 | 82 |
| LCK | 100 | 96 | 100 |
| LIMK1 | 100 | 100 | 76 |
| LIMK2 | 100 | 97 | 99 |
| LKB1 | 91 | 88 | 78 |
| LOK | 88 | 99 | 81 |
| LRRK2 | 2.6 | 15 | 33 |
| LRRK2(G2019S) | 3.2 | 11 | 22 |
| LTK | 62 | 75 | 72 |
| LYN | 100 | 99 | 100 |
| LZK | 89 | 61 | 76 |
| MAK | 97 | 100 | 87 |
| MAP3K1 | 73 | 56 | 100 |
| MAP3K15 | 1.8 | 1.4 | 100 |
| MAP3K2 | 29 | 25 | 35 |
| MAP3K3 | 51 | 44 | 47 |
| MAP3K4 | 68 | 91 | 71 |
| MAP4K2 | 1.1 | 20 | 20 |
| MAP4K3 | 83 | 94 | 74 |
| MAP4K4 | 19 | 58 | 78 |
| MAP4K5 | 39 | 77 | 88 |
| MAPKAPK2 | 100 | 100 | 51 |
| MAPKAPK5 | 100 | 100 | 100 |
| MARK1 | 72 | 71 | 80 |
| MARK2 | 60 | 86 | 68 |
| MARK3 | 84 | 82 | 89 |
| MARK4 | 38 | 36 | 82 |
| MAST1 | 24 | 50 | 70 |
| MEK1 | 12 | 29 | 94 |
| MEK2 | 19 | 31 | 87 |
| MEK3 | 4.2 | 36 | 33 |
| MEK4 | 7.3 | 45 | 28 |
| MEK5 | 7.3 | 3.2 | 100 |
| MEK6 | 16 | 60 | 95 |
| MELK | 16 | 20 | 30 |
| MERTK | 42 | 45 | 41 |
| MET | 84 | 63 | 16 |
| MET(M1250T) | 78 | 49 | 23 |
| MET(Y1235D) | 83 | 56 | 30 |
| MINK | 6 | 17 | 62 |
| MKK7 | 79 | 67 | 100 |
| MKNK1 | 100 | 97 | 100 |
| MKNK2 | 22 | 56 | 94 |
| MLCK | 5 | 13 | 100 |
| MLK1 | 96 | 91 | 96 |
| MLK2 | 39 | 62 | 69 |
| MLK3 | 99 | 93 | 100 |
| MRCKA | 100 | 100 | 100 |
| MRCKB | 93 | 86 | 82 |
| MST1 | 81 | 93 | 82 |
| MST1R | 88 | 100 | 77 |
| MST2 | 99 | 100 | 74 |
| MST3 | 74 | 72 | 86 |
| MST4 | 99 | 67 | 100 |
| MTOR | 78 | 60 | 95 |
| MUSK | 100 | 100 | 67 |
| MYLK | 85 | 72 | 83 |
| MYLK2 | 51 | 79 | 94 |
| MYLK4 | 100 | 90 | 95 |
| MYO3A | 64 | 69 | 100 |
| MYO3B | 73 | 96 | 93 |
| NDR1 | 69 | 74 | 84 |
| NDR2 | 19 | 21 | 63 |
| NEK1 | 100 | 96 | 100 |
| NEK10 | 100 | 100 | 100 |
| NEK11 | 96 | 97 | 100 |
| NEK2 | 100 | 100 | 100 |
| NEK3 | 82 | 68 | 95 |
| NEK4 | 65 | 82 | 100 |
| NEK5 | 99 | 79 | 99 |
| NEK6 | 88 | 92 | 100 |
| NEK7 | 100 | 100 | 95 |
| NEK9 | 100 | 100 | 98 |
| NIK | 13 | 55 | 88 |
| NIM1 | 50 | 69 | 99 |
| NLK | 100 | 95 | 88 |
| OSR1 | 66 | 75 | 100 |
| p38-alpha | 92 | 100 | 100 |
| p38-beta | 58 | 95 | 92 |
| p38-delta | 99 | 96 | 94 |
| p38-gamma | 92 | 97 | 79 |
| PAK1 | 99 | 99 | 100 |
| PAK2 | 96 | 100 | 80 |
| PAK3 | 74 | 97 | 86 |
| PAK4 | 31 | 65 | 100 |
| PAK6 | 100 | 99 | 99 |
| PAK7 | 41 | 100 | 95 |
| PCTK1 | 86 | 85 | 100 |
| PCTK2 | 97 | 100 | 96 |
| PCTK3 | 100 | 100 | 96 |
| PDGFRA | 45 | 11 | 92 |
| PDGFRB | 21 | 20 | 83 |
| PDPK1 | 68 | 94 | 94 |
| PFCDPK1(P. falciparum) | 94 | 86 | 95 |
| PFPK5(P. falciparum) | 100 | 100 | 100 |
| PFTAIRE2 | 100 | 100 | 91 |
| PFTK1 | 100 | 100 | 100 |
| PHKG1 | 86 | 100 | 87 |
| PHKG2 | 19 | 52 | 100 |
| PIK3C2B | 96 | 100 | 96 |
| PIK3C2G | 94 | 100 | 92 |
| PIK3CA | 100 | 100 | 99 |
| PIK3CA(C420R) | 75 | 75 | 100 |
| PIK3CA(E542K) | 100 | 100 | 98 |
| PIK3CA(E545A) | 62 | 80 | 98 |
| PIK3CA(E545K) | 31 | 18 | 79 |
| PIK3CA(H1047L) | 92 | 97 | 100 |
| PIK3CA(H1047Y) | 84 | 70 | 100 |
| PIK3CA(I800L) | 64 | 566 | 80 |
| PIK3CA(M1043I) | 81 | 66 | 100 |
| PIK3CA(Q546K) | 100 | 100 | 93 |

TABLE 3-continued

Kinase profiling assay with inventive compounds 77, 96 and 101.

| Kinases | Compound 96 | Compound 77 | Compound 101 |
|---|---|---|---|
| PIK3CB | 100 | 100 | 100 |
| PIK3CD | 84 | 85 | 100 |
| PIK3CG | 100 | 99 | 95 |
| PIK4CB | 58 | 59 | 100 |
| PIKFYVE | 66 | 53 | 98 |
| PIM1 | 100 | 95 | 95 |
| PIM2 | 100 | 100 | 94 |
| PIM3 | 100 | 99 | 96 |
| PIP5K1A | 16 | 7.7 | 12 |
| PIP5K1C | 49 | 37 | 57 |
| PIP5K2B | 4.9 | 3.4 | 12 |
| PIP5K2C | 63 | 93 | 77 |
| PKAC-alpha | 100 | 100 | 100 |
| PKAC-beta | 100 | 100 | 90 |
| PKMYT1 | 100 | 98 | 97 |
| PKN1 | 95 | 100 | 100 |
| PKN2 | 87 | 51 | 75 |
| PKNB(M. tuberculosis) | 61 | 30 | 89 |
| PLK1 | 64 | 65 | 98 |
| PLK2 | 100 | 85 | 100 |
| PLK3 | 99 | 78 | 84 |
| PLK4 | 27 | 27 | 78 |
| PRKCD | 94 | 100 | 88 |
| PRKCE | 66 | 51 | 70 |
| PRKCH | 92 | 83 | 73 |
| PRKCI | 69 | 67 | 100 |
| PRKCQ | 76 | 91 | 45 |
| PRKD1 | 19 | 58 | 48 |
| PRKD2 | 13 | 90 | 59 |
| PRKD3 | 13 | 56 | 35 |
| PRKG1 | 100 | 100 | 89 |
| PRKG2 | 100 | 100 | 100 |
| PRKR | 70 | 68 | 82 |
| PRKX | 100 | 100 | 82 |
| PRP4 | 47 | 14 | 38 |
| PYK2 | 92 | 89 | 78 |
| QSK | 76 | 76 | 97 |
| RAF1 | 100 | 91 | 91 |
| RET | 80 | 27 | 85 |
| RET(M918T) | 72 | 33 | 95 |
| RET(V804L) | 59 | 45 | 97 |
| RET(V804M) | 61 | 52 | 99 |
| RIOK1 | 0.15 | 0 | 11 |
| RIOK2 | 26 | 73 | 28 |
| RIOK3 | 36 | 24 | 50 |
| RIPK1 | 44 | 19 | 47 |
| RIPK2 | 99 | 100 | 100 |
| RIPK4 | 7.8 | 1.3 | 100 |
| RIPK5 | 8.6 | 31 | 50 |
| ROCK1 | 4.7 | 20 | 63 |
| ROCK2 | 1.4 | 8.9 | 81 |
| ROS1 | 89 | 74 | 73 |
| RPS6KA4(Kin.Dom.1-N-terminal) | 100 | 97 | 84 |
| RPS6KA4(Kin.Dom.2-C-terminal) | 65 | 90 | 99 |
| RPS6KA5(Kin.Dom.1-N-terminal) | 100 | 100 | 90 |
| RPS6KA5(Kin.Dom.2-C-terminal) | 100 | 100 | 96 |
| RSK1(Kin.Dom.1-N-terminal) | 100 | 93 | 80 |
| RSK1(Kin.Dom.2-C-terminal) | 100 | 99 | 88 |
| RSK2(Kin.Dom.1-N-terminal) | 54 | 54 | 65 |
| RSK2(Kin.Dom.2-C-terminal) | 97 | 98 | 83 |
| RSK3(Kin.Dom.1-N-terminal) | 78 | 80 | 66 |
| RSK3(Kin.Dom.2-C-terminal) | 78 | 100 | 77 |
| RSK4(Kin.Dom.1-N-terminal) | 77 | 32 | 100 |
| RSK4(Kin.Dom.2-C-terminal) | 91 | 98 | 88 |
| S6K1 | 87 | 50 | 100 |
| SBK1 | 63 | 44 | 67 |
| SGK | 7.3 | 17 | 86 |
| SgK110 | 100 | 100 | 100 |
| SGK2 | 30 | 43 | 65 |
| SGK3 | 48 | 37 | 96 |
| SIK | 87 | 94 | 100 |
| SIK2 | 85 | 100 | 84 |
| SLK | 68 | 86 | 78 |
| SNARK | 64 | 96 | 33 |
| SNRK | 100 | 100 | 100 |
| SRC | 100 | 99 | 100 |
| SRMS | 100 | 90 | 72 |
| SRPK1 | 17 | 10 | 27 |
| SRPK2 | 16 | 12 | 60 |
| SRPK3 | 17 | 16 | 9.9 |
| STK16 | 2 | 2.9 | 13 |
| STK33 | 100 | 100 | 100 |
| STK35 | 50 | 63 | 99 |
| STK36 | 99 | 100 | 96 |
| STK39 | 9.7 | 16 | 80 |
| SYK | 100 | 100 | 100 |
| TAK1 | 6.9 | 21 | 6.1 |
| TAOK1 | 96 | 100 | 99 |
| TAOK2 | 69 | 69 | 81 |
| TAOK3 | 91 | 95 | 88 |
| TBK1 | 91 | 57 | 90 |
| TEC | 100 | 100 | 93 |
| TESK1 | 74 | 89 | 99 |
| TGFBR1 | 56 | 60 | 100 |
| TGFBR2 | 100 | 100 | 100 |
| TIE1 | 93 | 97 | 92 |
| TIE2 | 81 | 80 | 97 |
| TLK1 | 95 | 95 | 90 |
| TLK2 | 100 | 99 | 100 |
| TNIK | 14 | 29 | 89 |
| TNK1 | 83 | 80 | 50 |
| TNK2 | 94 | 100 | 98 |
| TNNI3K | 74 | 65 | 100 |
| TRKA | 11 | 0.65 | 49 |
| TRKB | 48 | 23 | 100 |
| TRKC | 82 | 51 | 100 |
| TRPM6 | 82 | 89 | 100 |
| TSSK1B | 100 | 99 | 41 |
| TSSK3 | 45 | 65 | 98 |
| TTK | 3.6 | 34 | 54 |
| TXK | 81 | 81 | 84 |
| TYK2(JH1domain-catalytic) | 29 | 15 | 100 |
| TYK2(JH2domain-pseudokinase) | 89 | 84 | 100 |
| TYRO3 | 100 | 100 | 56 |
| ULK1 | 3.8 | 3.1 | 73 |
| ULK2 | 8.7 | 15 | 98 |
| ULK3 | 10 | 5.5 | 92 |
| VEGFR2 | 4.2 | 2.8 | 33 |
| VPS34 | 51 | 35 | 100 |
| VRK2 | 79 | 66 | 100 |
| WEE1 | 88 | 97 | 100 |
| WEE2 | 100 | 95 | 94 |
| WNK1 | 80 | 67 | 90 |
| WNK2 | 100 | 92 | 100 |
| WNK3 | 73 | 86 | 92 |
| WNK4 | 84 | 77 | 100 |
| YANK1 | 100 | 100 | 100 |
| YANK2 | 100 | 100 | 100 |
| YANK3 | 99 | 97 | 57 |
| YES | 100 | 100 | 100 |
| YSK1 | 97 | 84 | 100 |
| YSK4 | 2.2 | 2.6 | 63 |
| ZAK | 75 | 70 | 86 |
| ZAP70 | 100 | 100 | 55 |

All patent publications and non-patent publications are indicative of the level of skill of those skilled in the art to which this invention pertains. All these publications are herein incorporated by reference to the same extent as if each individual publication were specifically and individually indicated as being incorporated by reference.

Although the invention herein has been described with reference to particular embodiments, it is to be understood that these embodiments are merely illustrative of the principles and applications of the present invention. It is therefore to be understood that numerous modifications may be made to the illustrative embodiments and that other arrange-

What is claimed is:
1. A compound having a structure represented by formula (I):
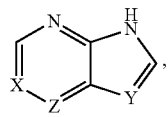
wherein:
X and Y each independently represents CR$_1$ or CR$_2$, wherein R$_1$ represents
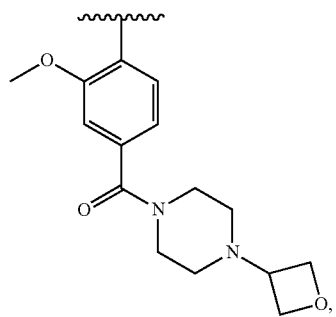
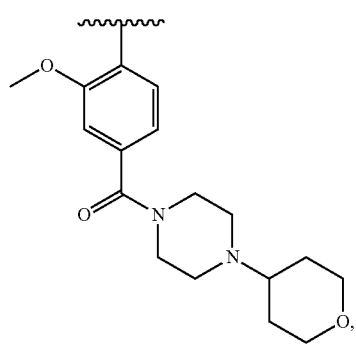
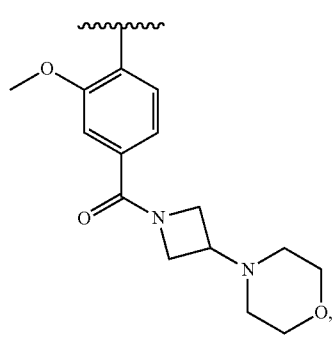
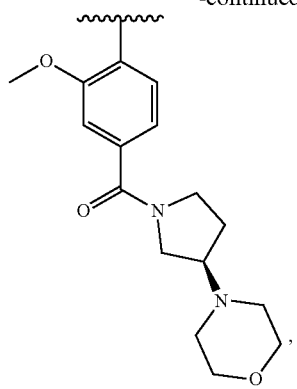
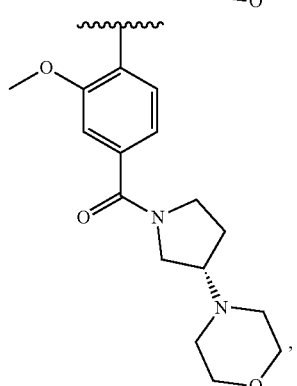
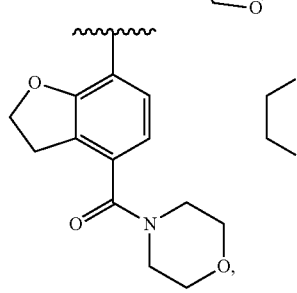
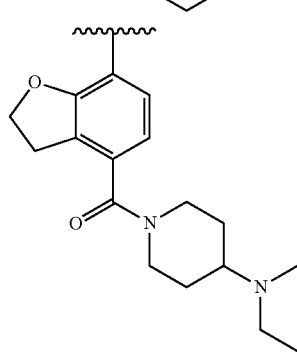
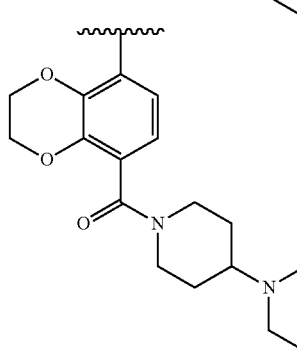

-continued
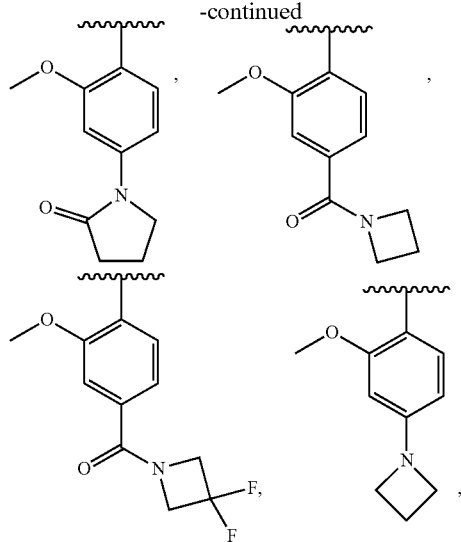
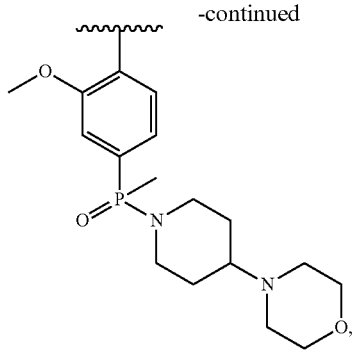
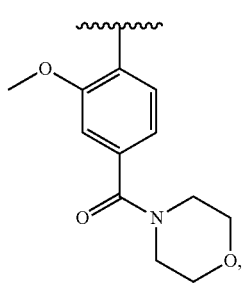
-continued
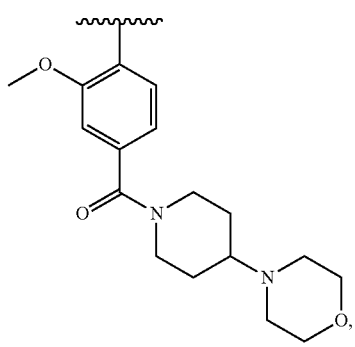
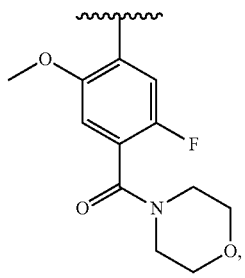
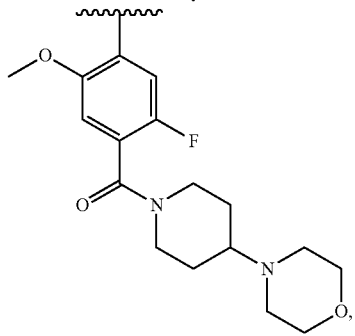

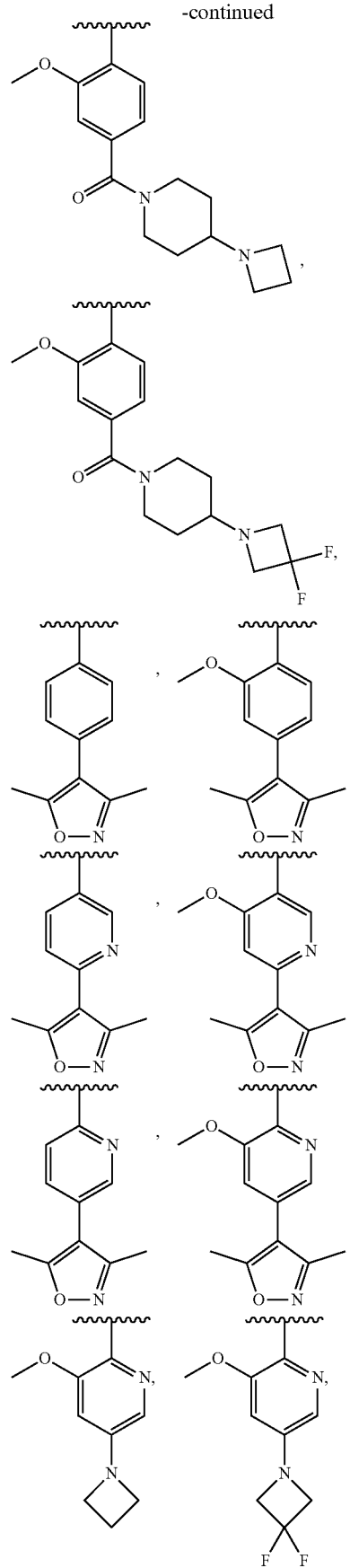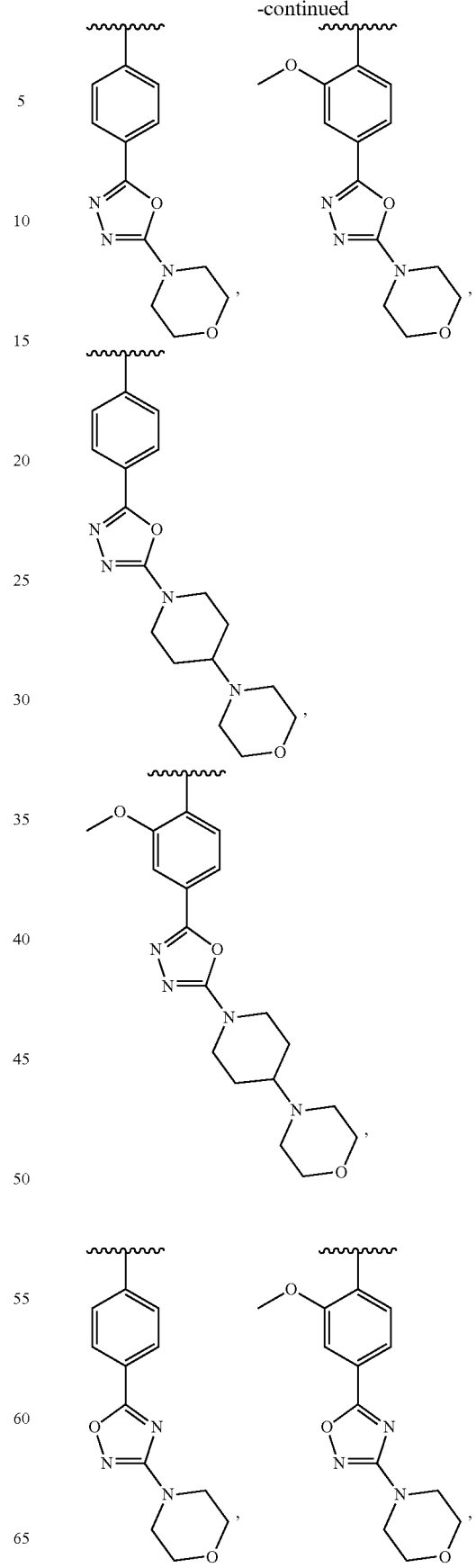

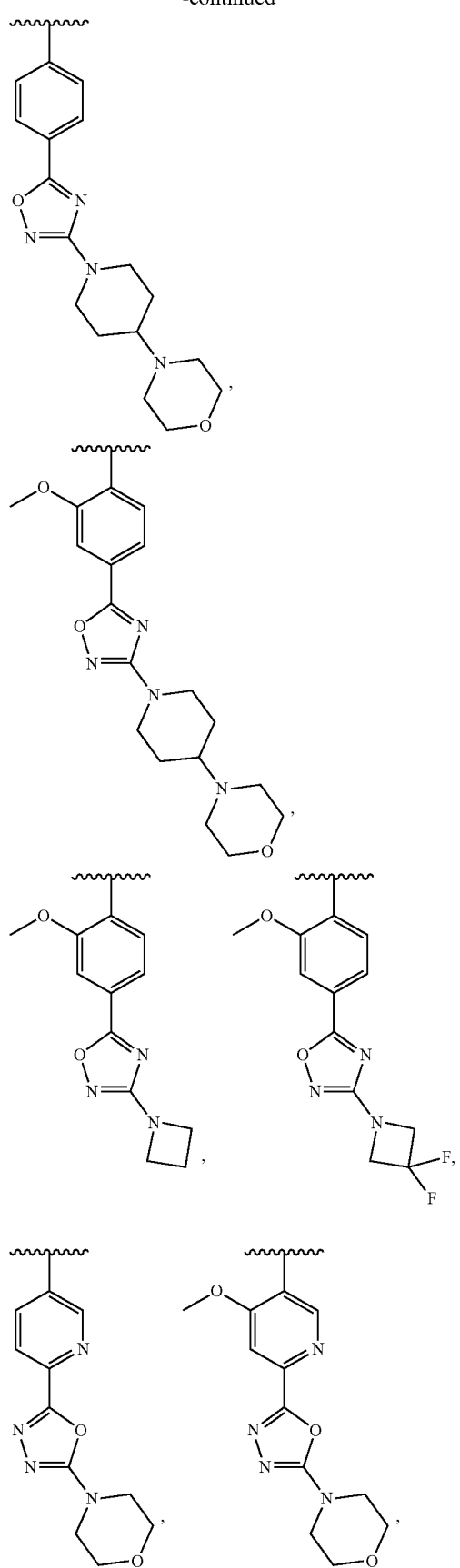
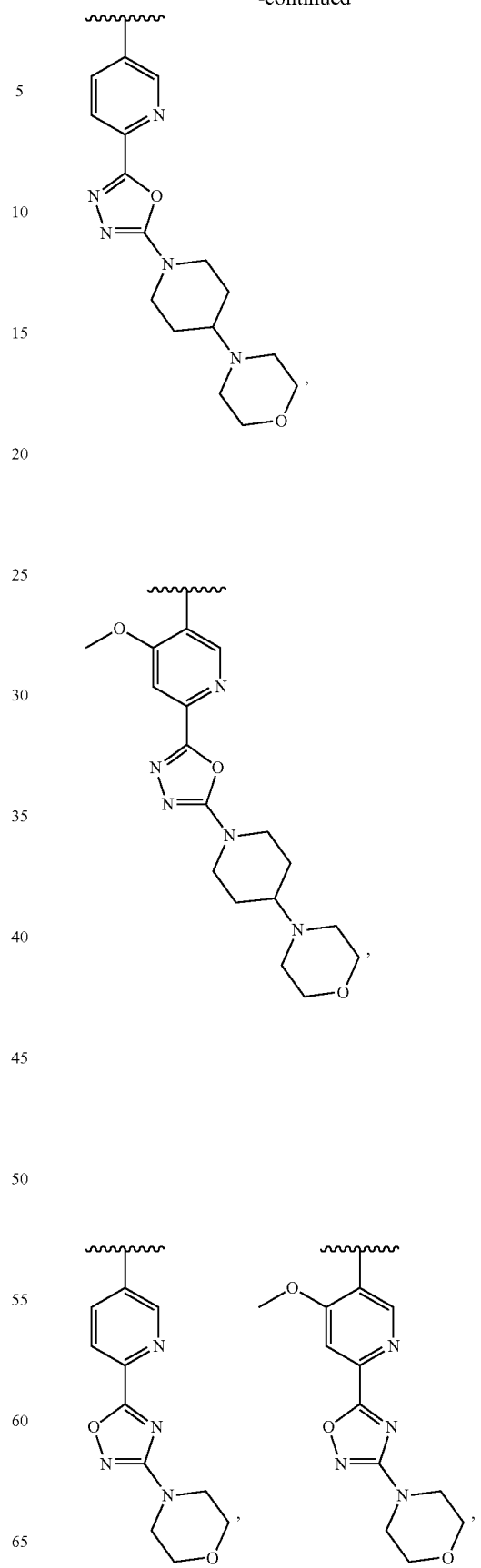

173
-continued
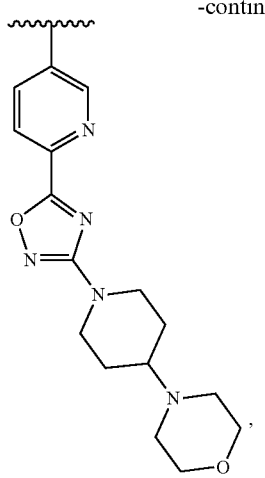
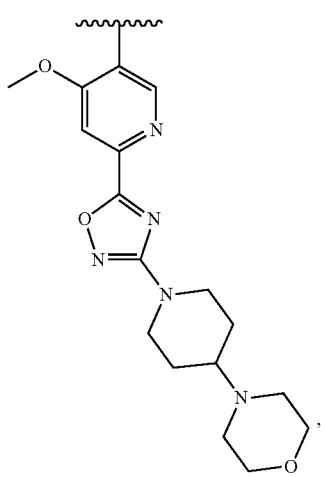
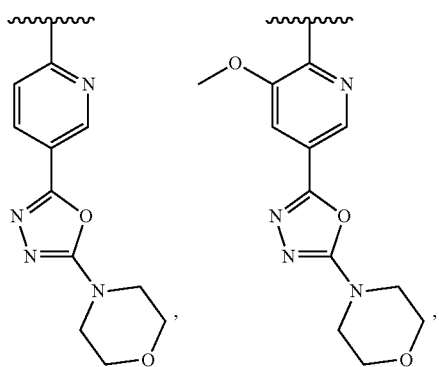
174
-continued
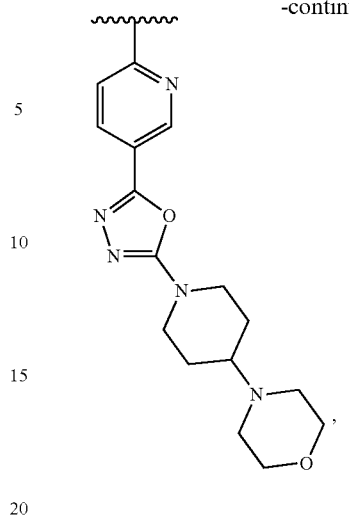

175
-continued
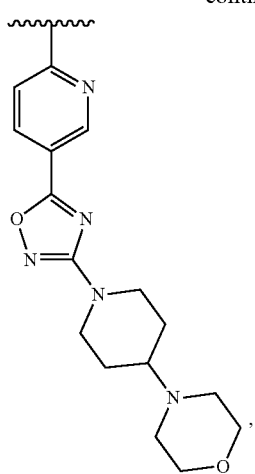
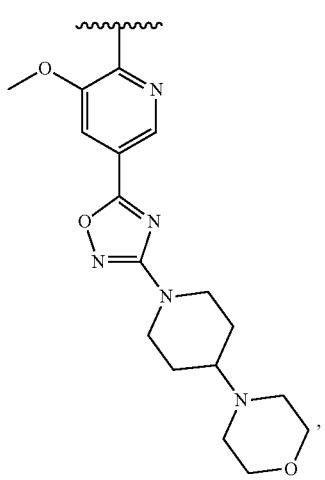
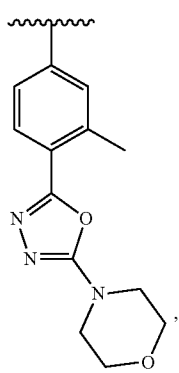
176
-continued
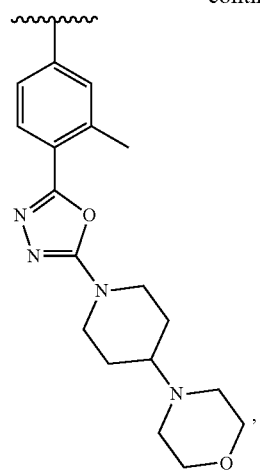
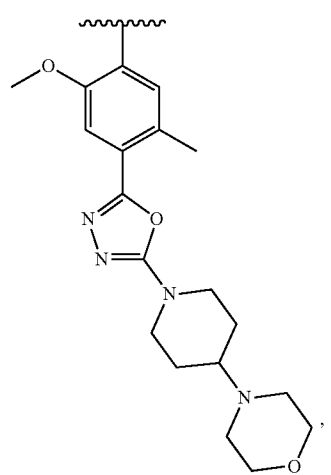
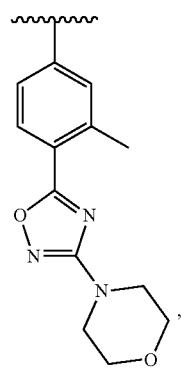 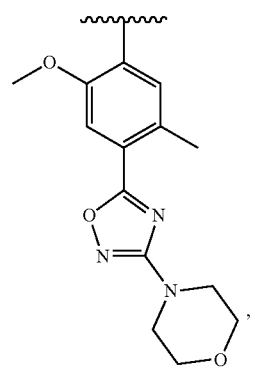

177
-continued
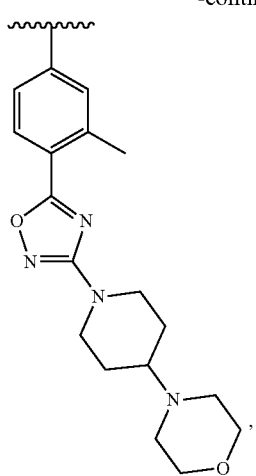
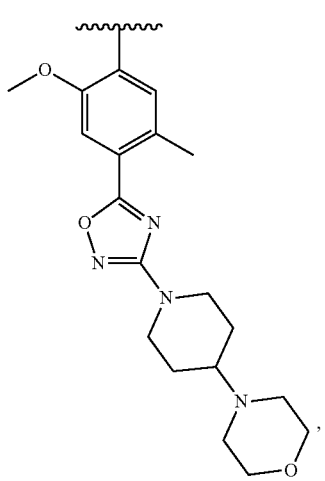
178
-continued
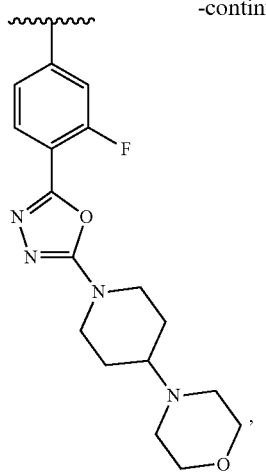
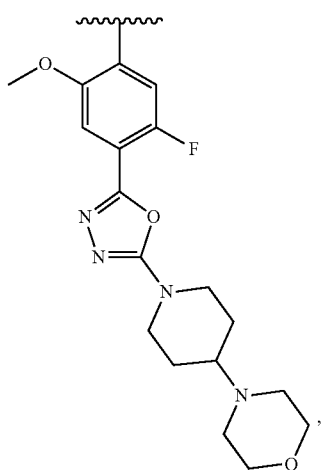
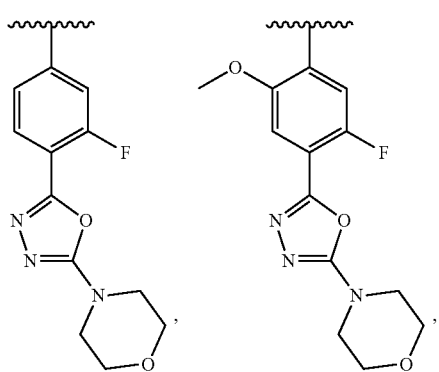

-continued
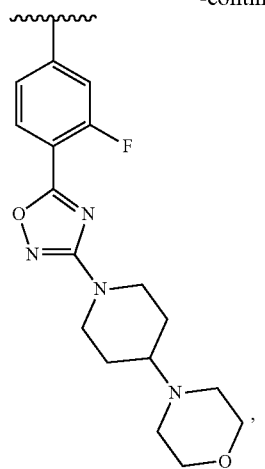
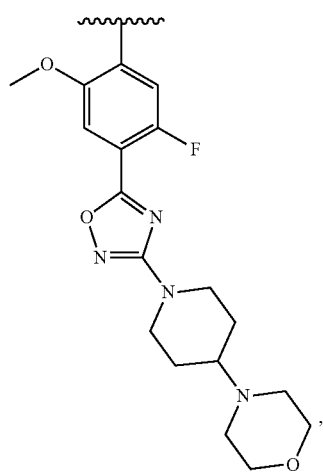
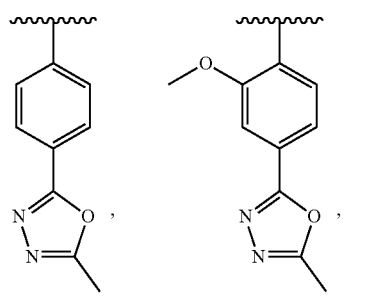
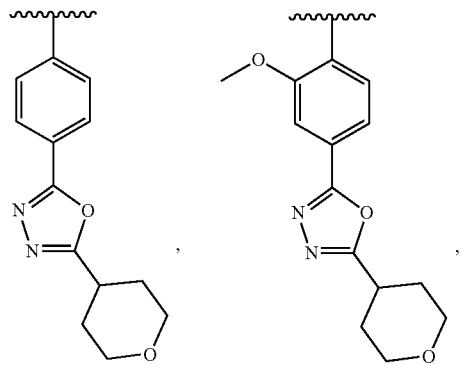
-continued
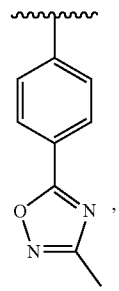, 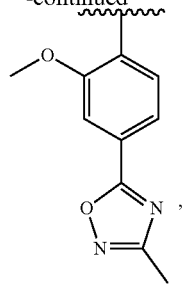,
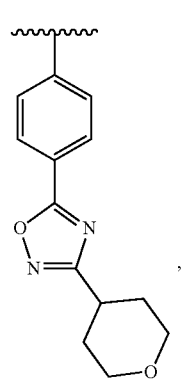, 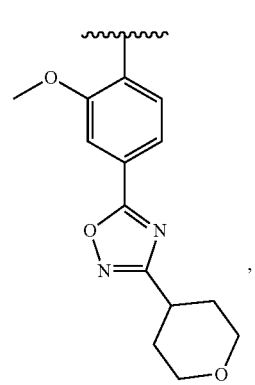,
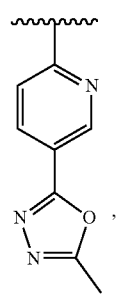, 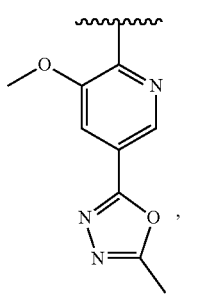,
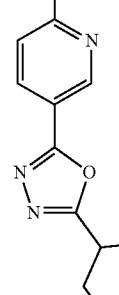, 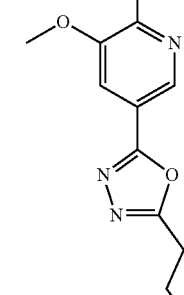,
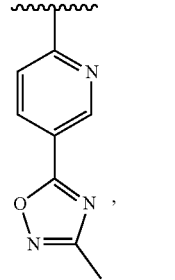, 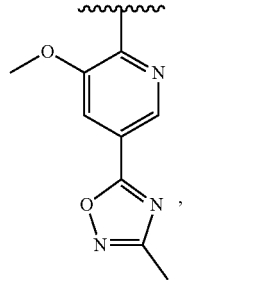,

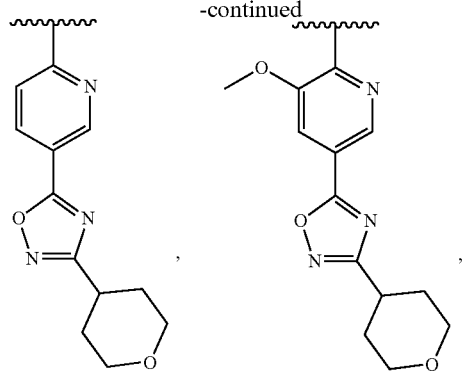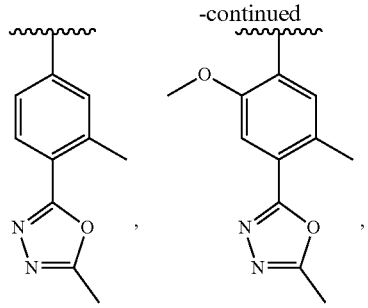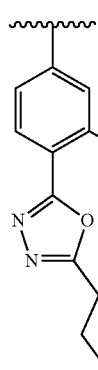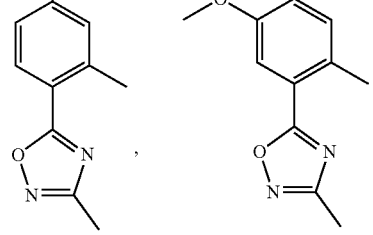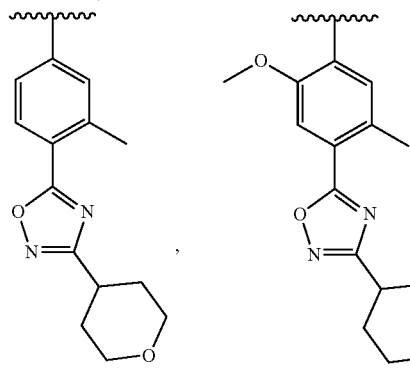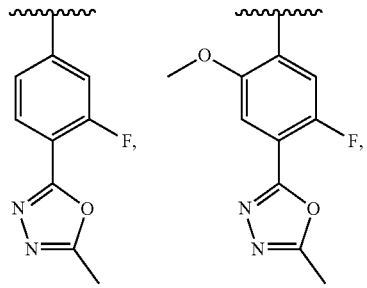

-continued
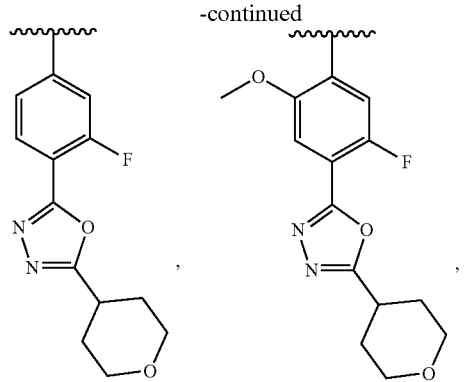
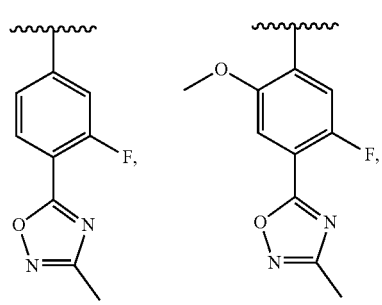
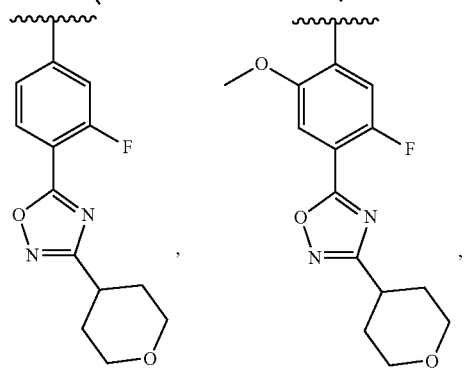
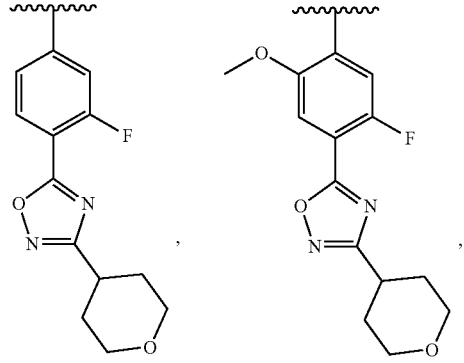
-continued
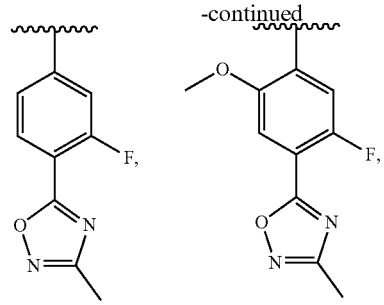
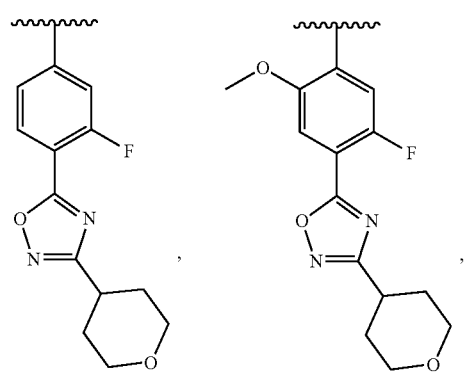
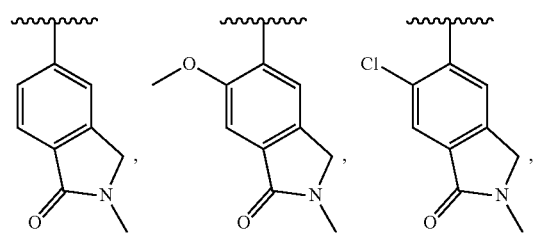
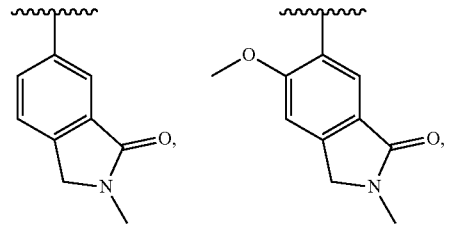
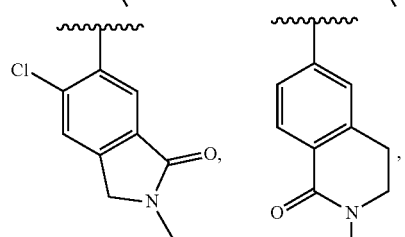
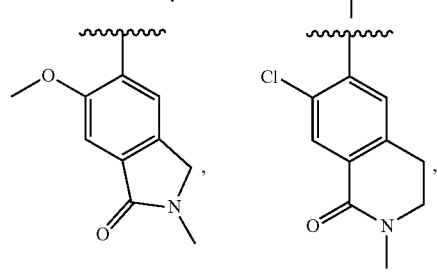

185
-continued
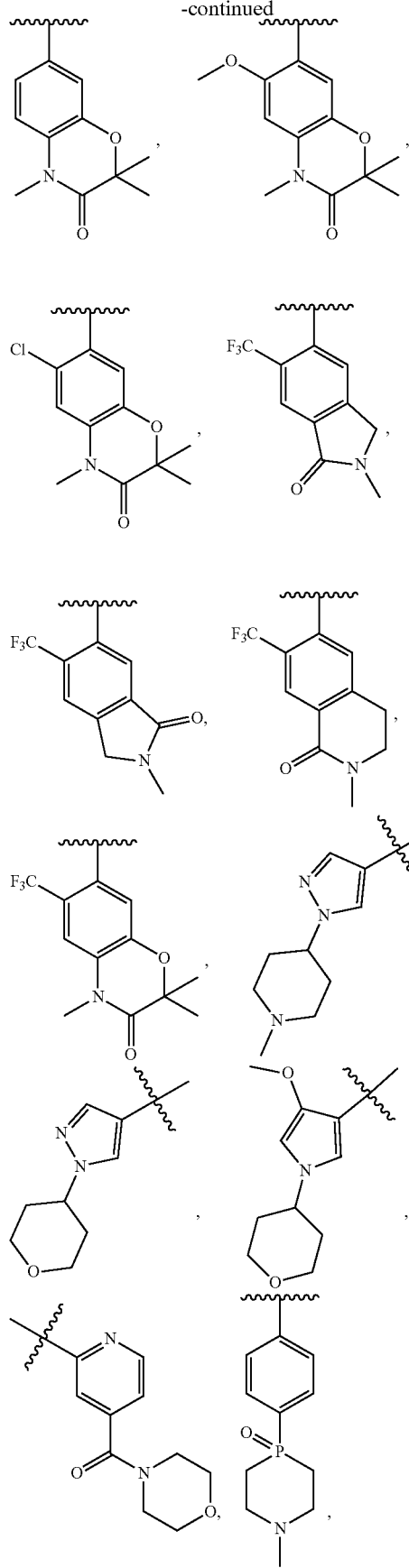
186
-continued
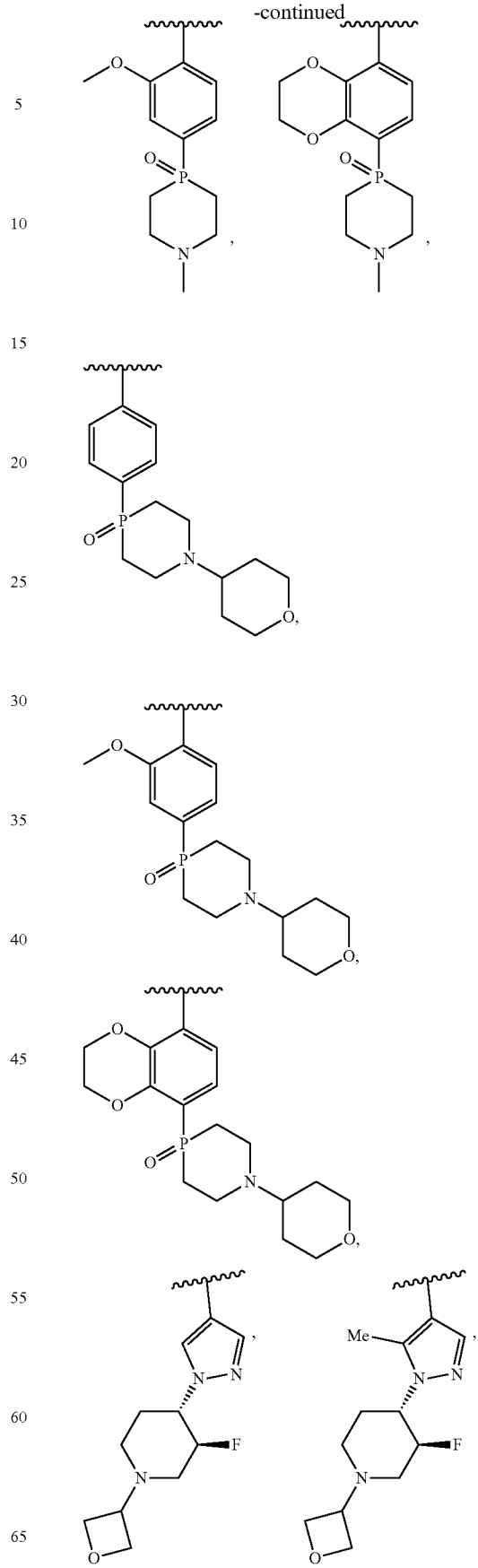

-continued

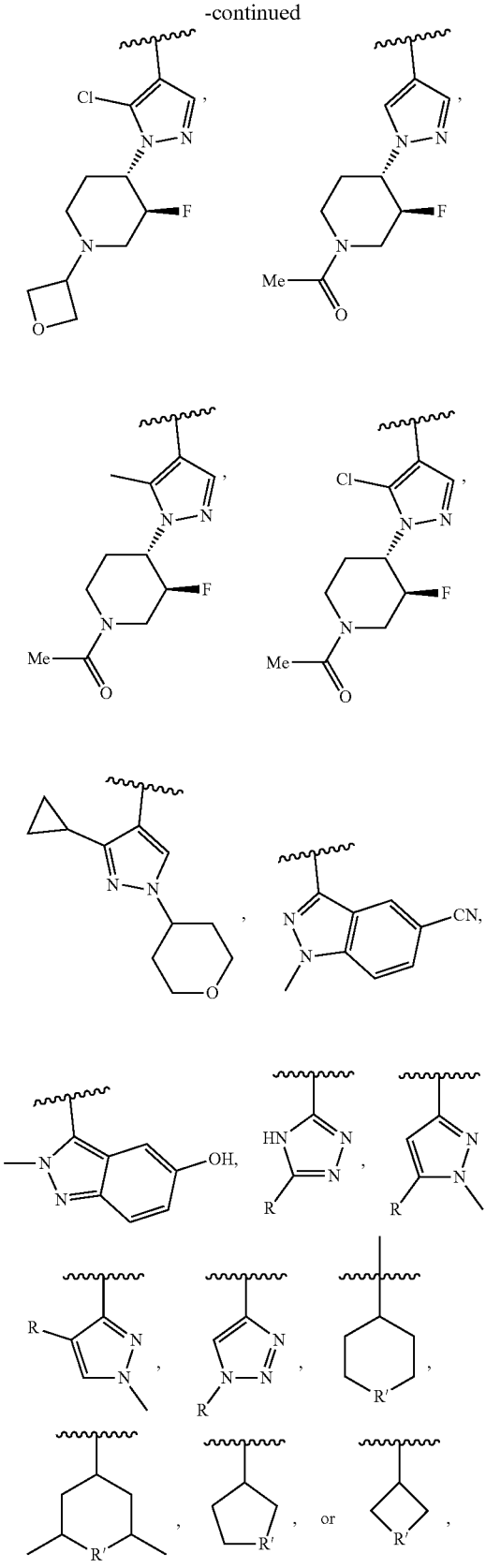

wherein R represents methyl, ethyl, isopropyl, cyclopropyl, or CF₃, and R' represents O, NH or NMe, $R_2$ represents H, halogen, or $CF_3$,
and Z represents $CR_3$, wherein $R_3$ represents

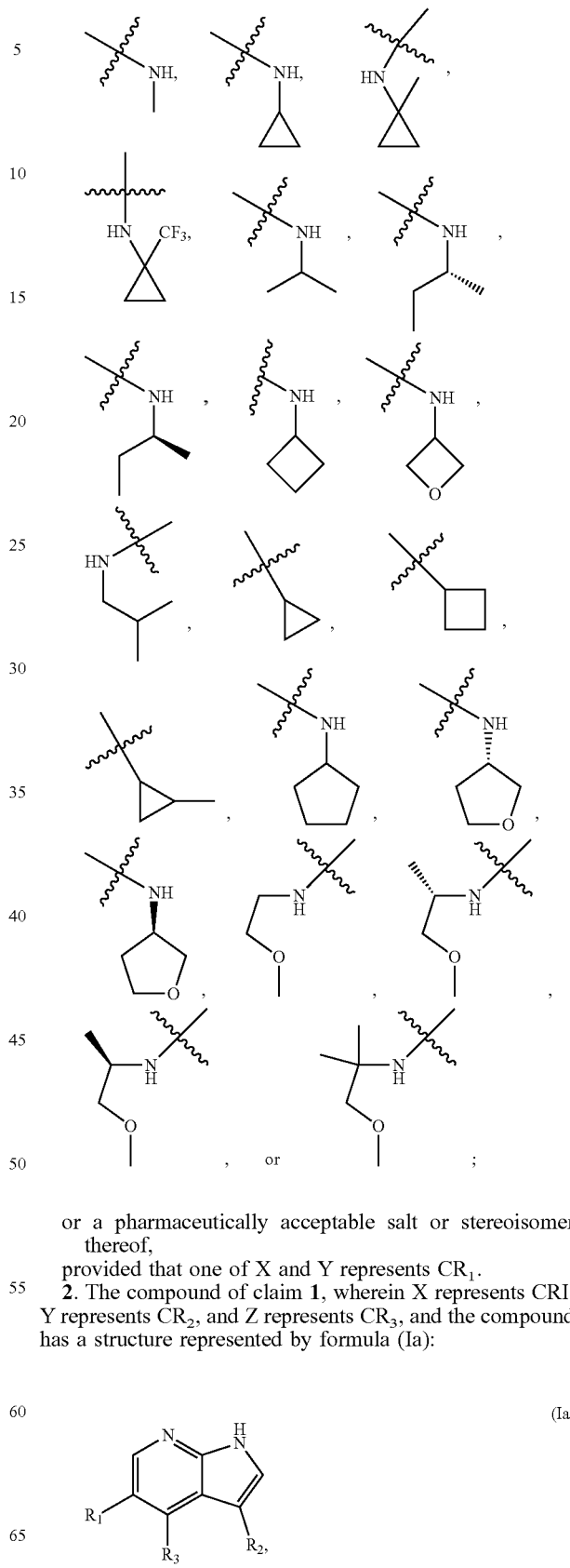

or a pharmaceutically acceptable salt or stereoisomer thereof,
provided that one of X and Y represents $CR_1$.

2. The compound of claim 1, wherein X represents CRI, Y represents $CR_2$, and Z represents $CR_3$, and the compound has a structure represented by formula (Ia):

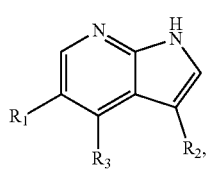

(Ia)

or a pharmaceutically acceptable salt or stereoisomer thereof.
3. The compound of claim 2, which is selected from the group consisting of:
(1)
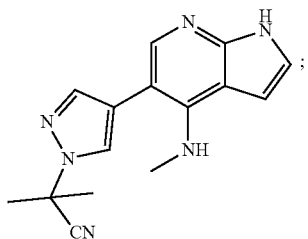
(2)
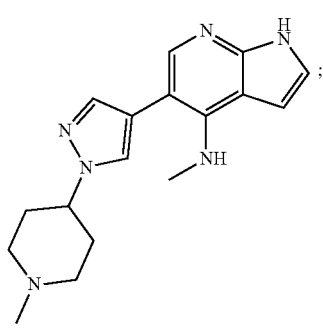
(3)
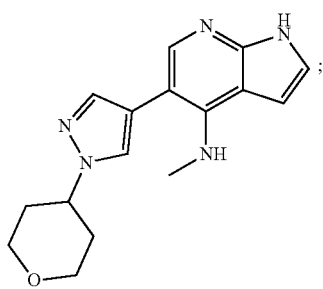
(4)
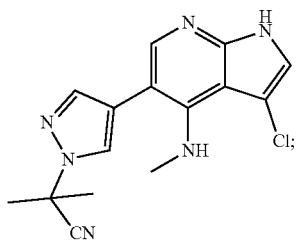
(5)
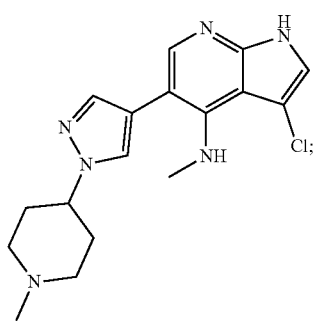
(6)
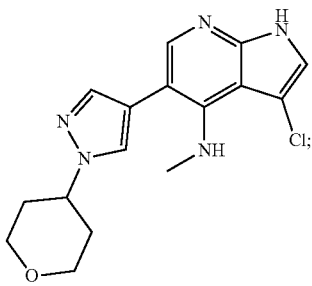
(9)
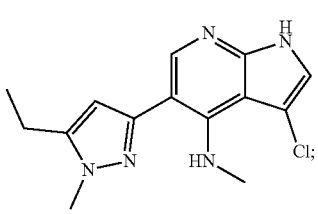
(10)
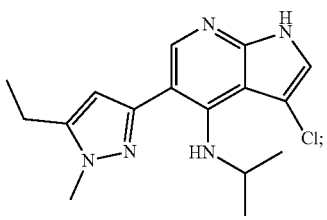
(11)
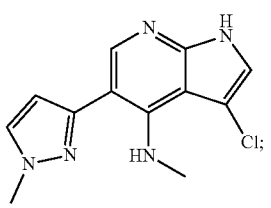
(12)
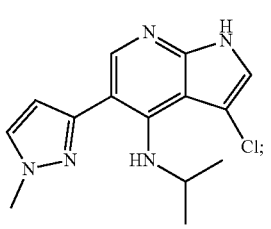
(13)
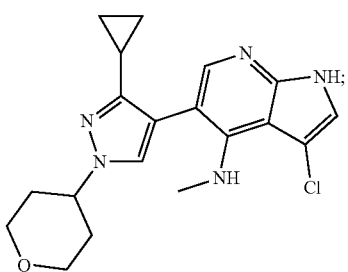

(14) 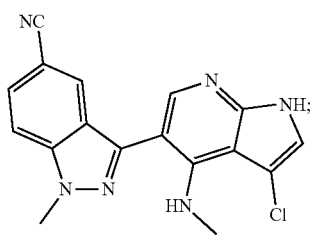
(15) 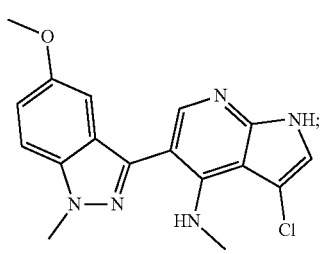
(16) 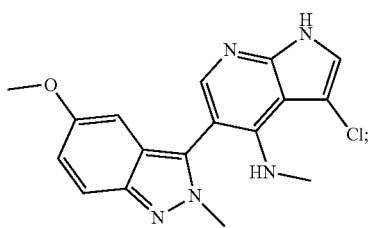
(17) 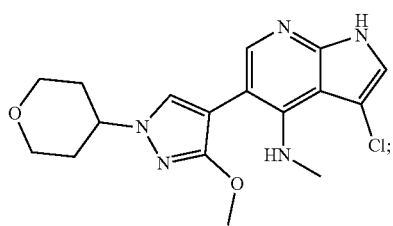
(18) 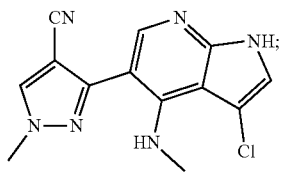
(19) 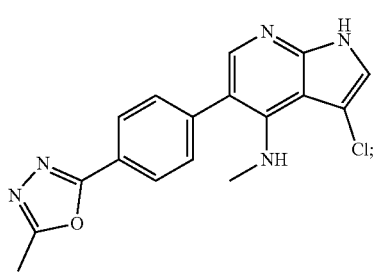
(20) 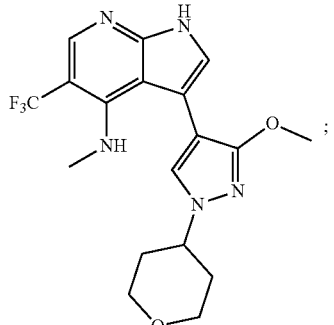
(21) 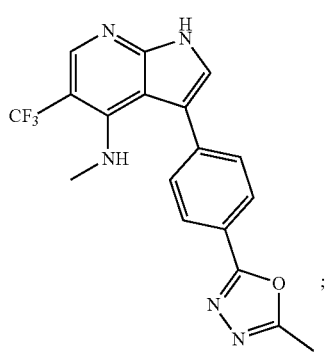
(22) 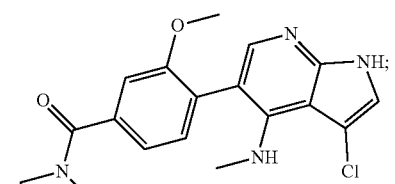
(23) 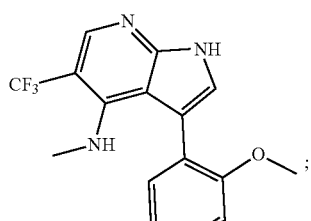
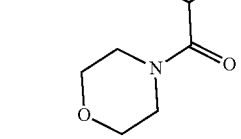
(24) 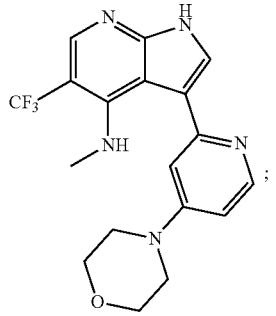

(25)
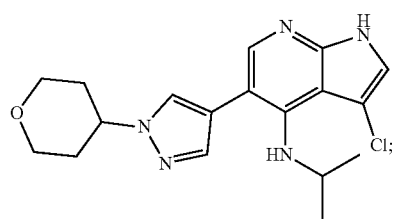
(26)
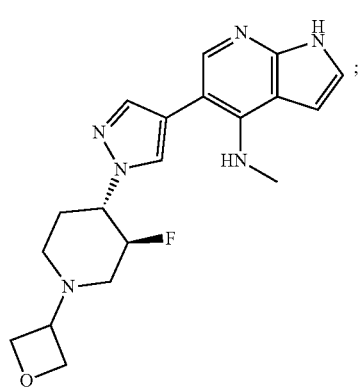
(27)
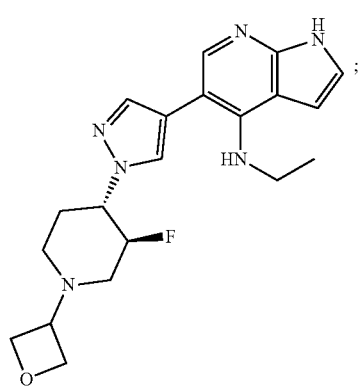
(28)
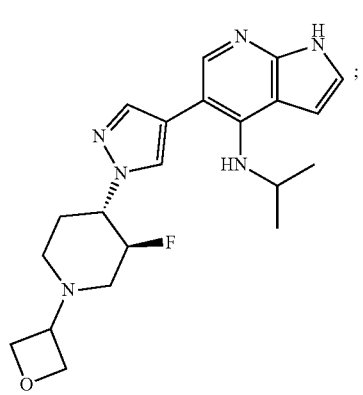
(29)
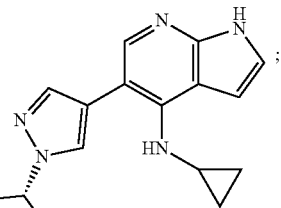
(30)
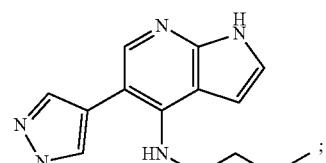
(31)
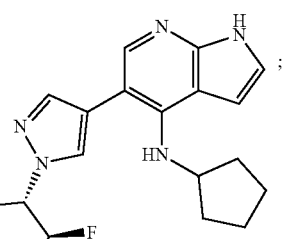
(32)
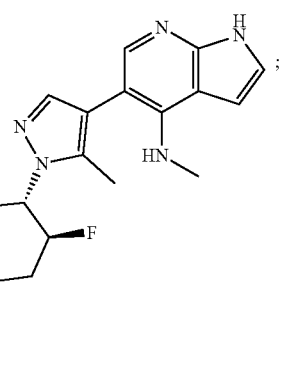

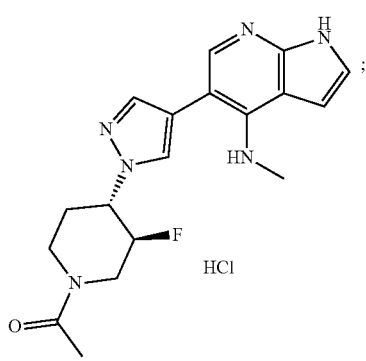
(33)
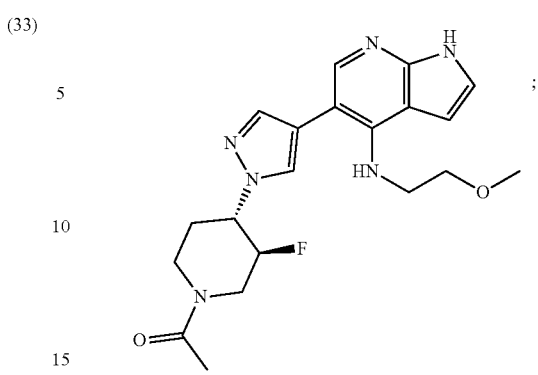
(37)
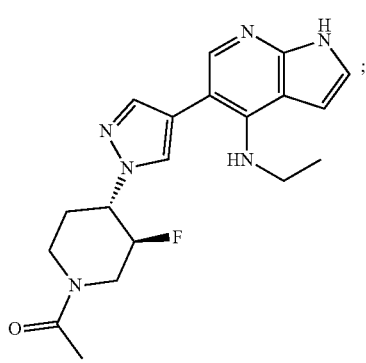
(34)
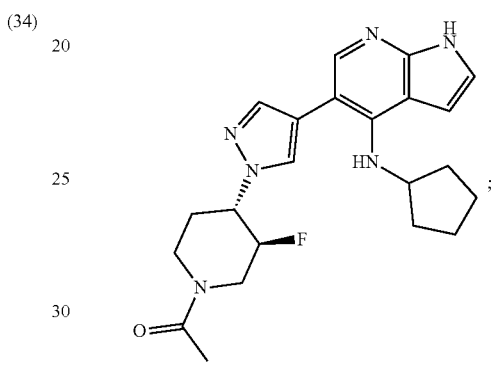
(38)
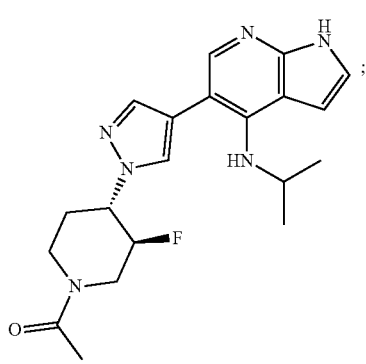
(35)
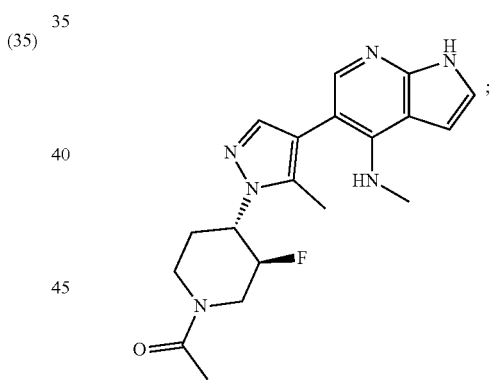
(39)
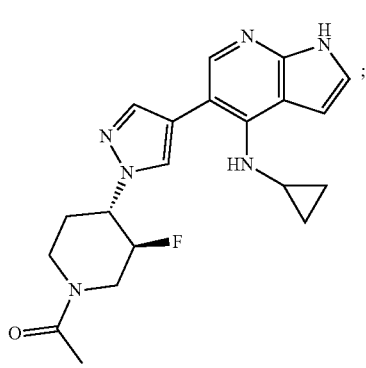
(36)
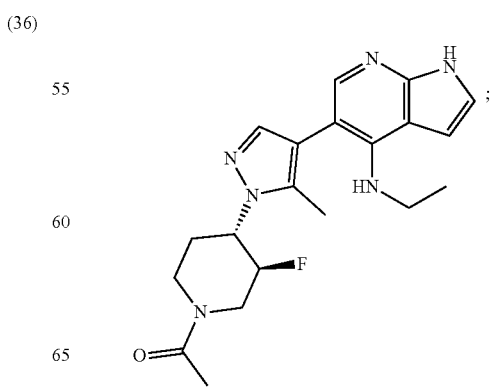
(40)

(41) 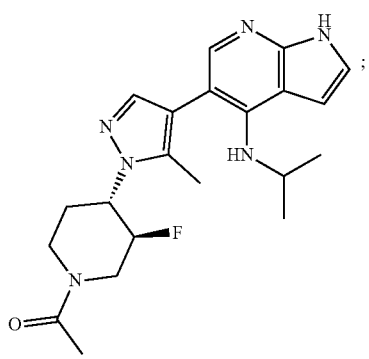
(42) 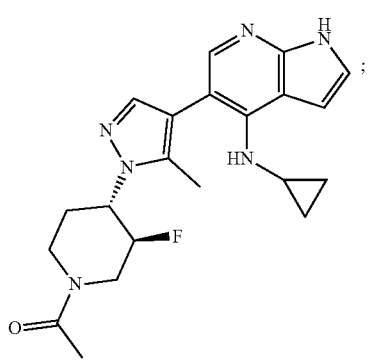
(43) 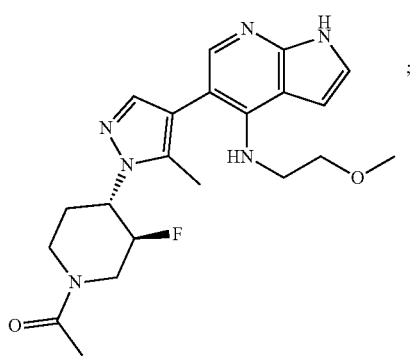
(44) 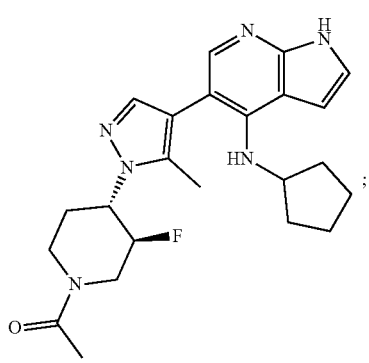
(45) 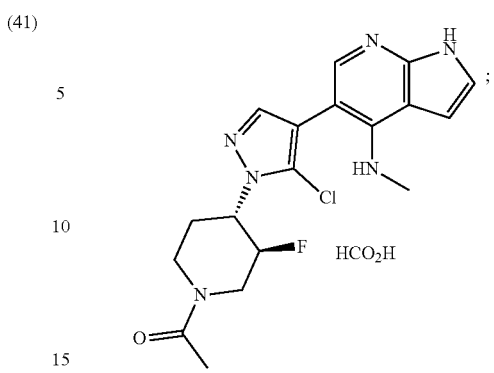
(46) 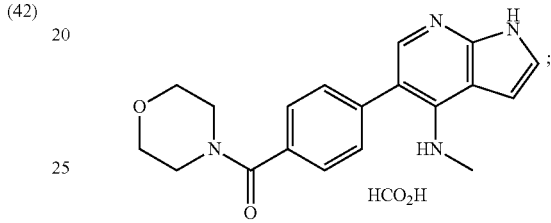
(47) 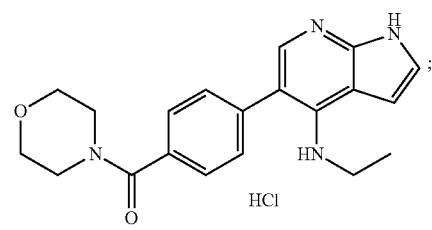
(48) 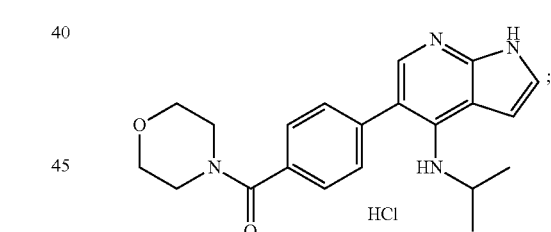
(49) 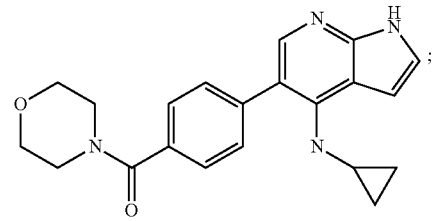
(50) 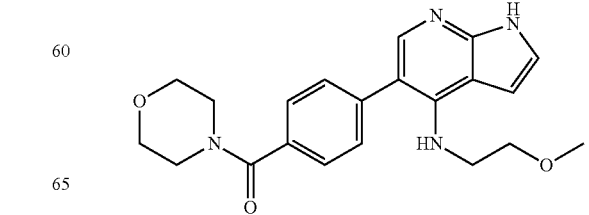

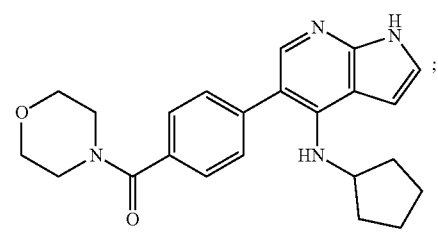
(51)
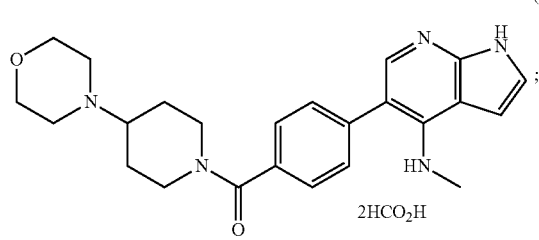
(52)
2HCO₂H
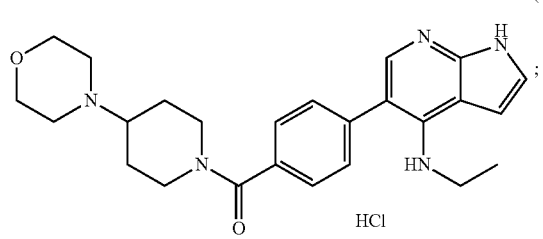
(53)
HCl
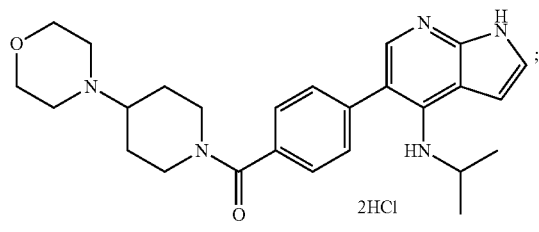
(54)
2HCl
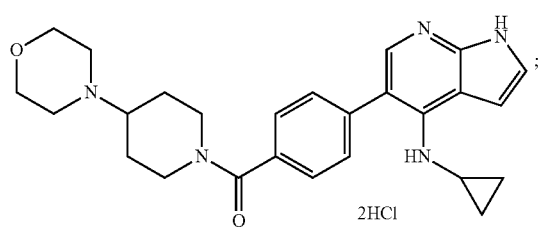
(55)
2HCl
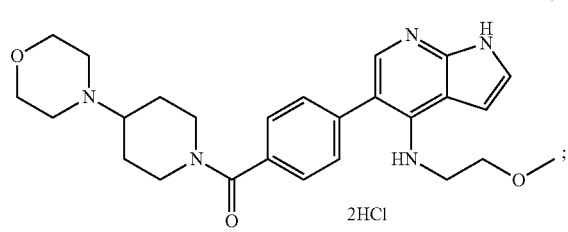
(56)
2HCl
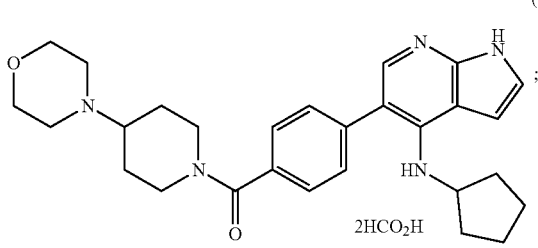
(57)
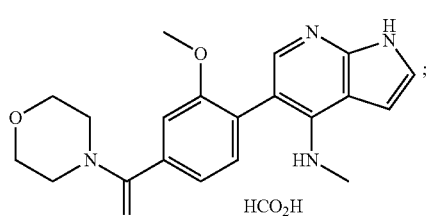
(58)
2HCO₂H
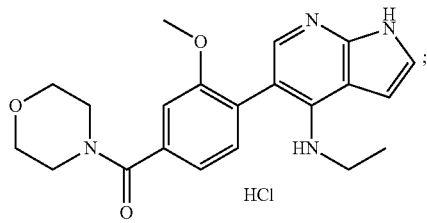
(59)
HCO₂H
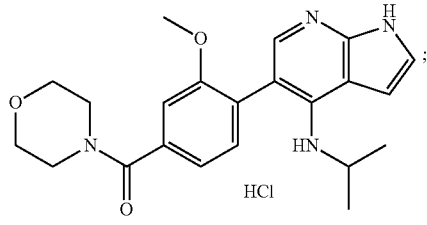
(60)
HCl
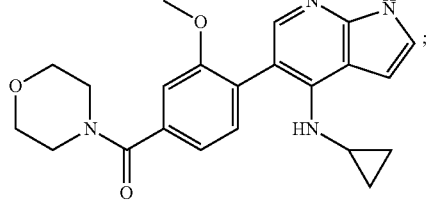
(61)
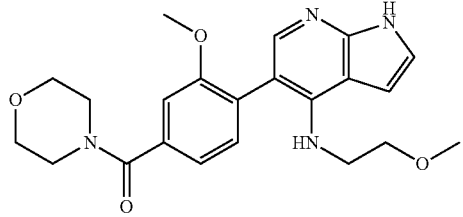
(62)
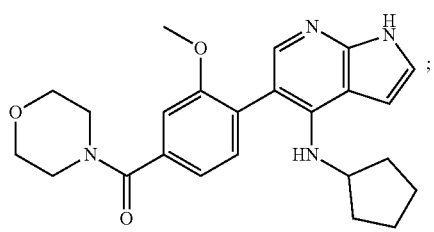
(63)

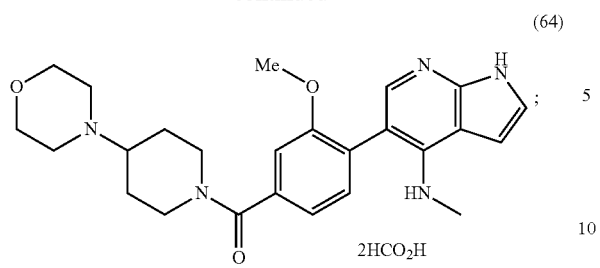
(64)
2HCO₂H
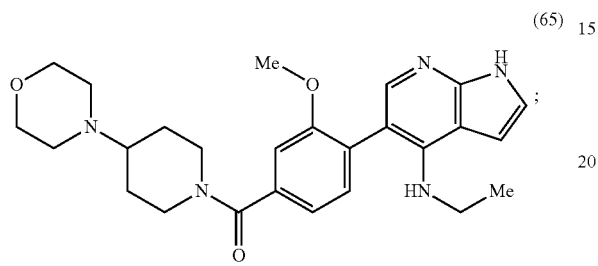
(65)
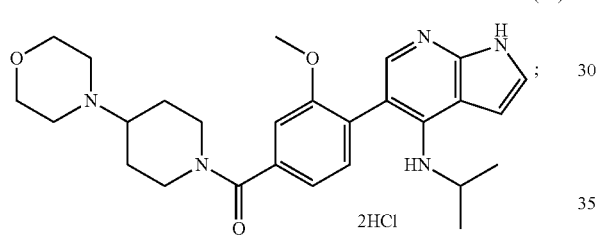
(66)
2HCl
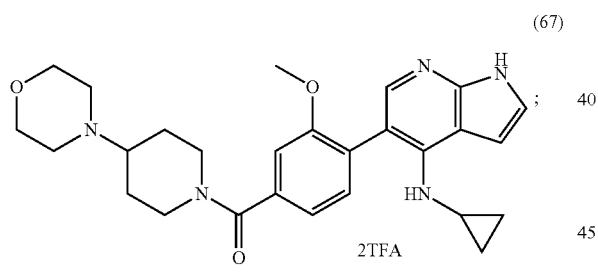
(67)
2TFA
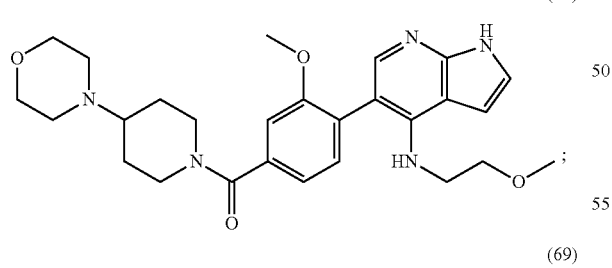
(68)
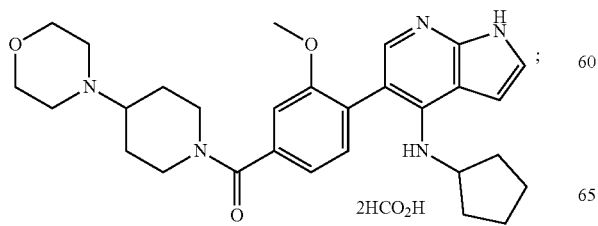
(69)
2HCO₂H
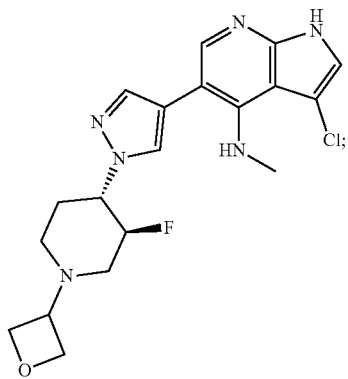
(70)
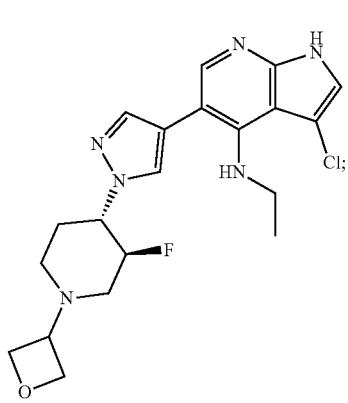
(71)
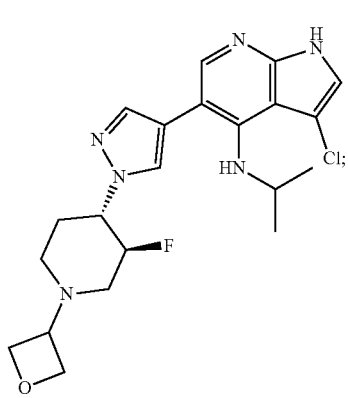
(72)
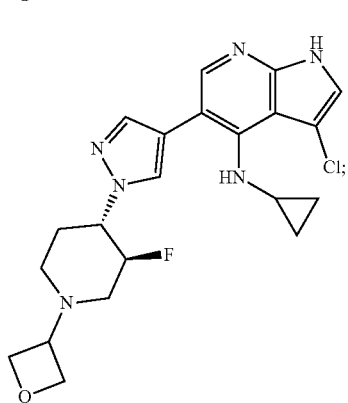
(73)

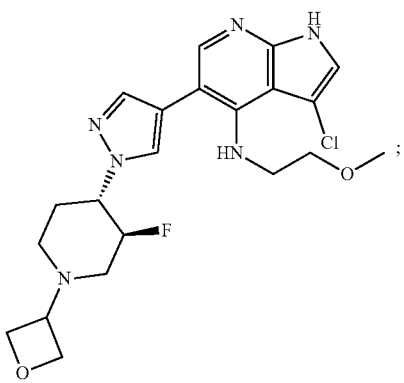
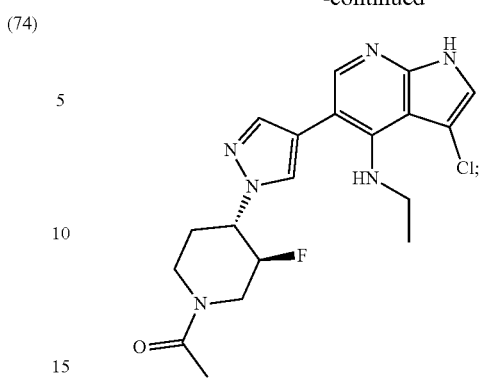

-continued
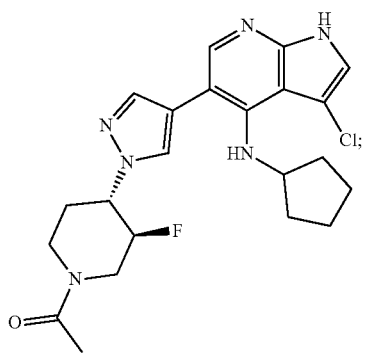
(82)
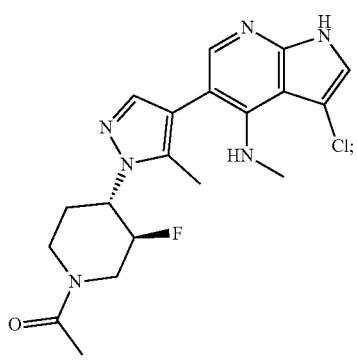
(83)
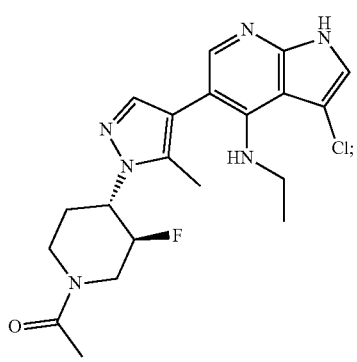
(84)
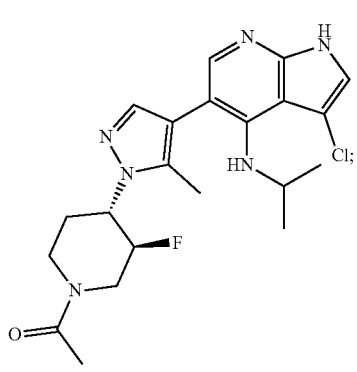
(85)
-continued
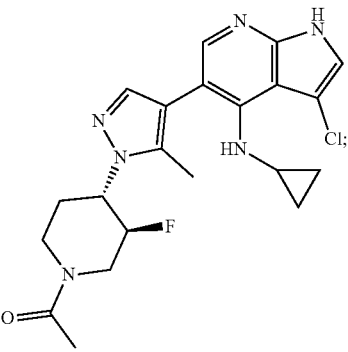
(86)
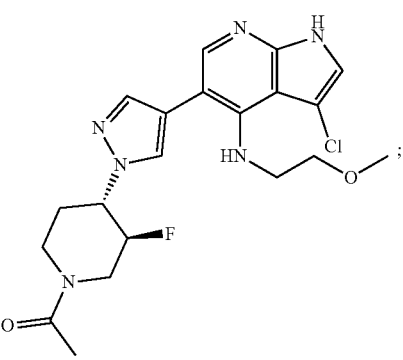
(87)
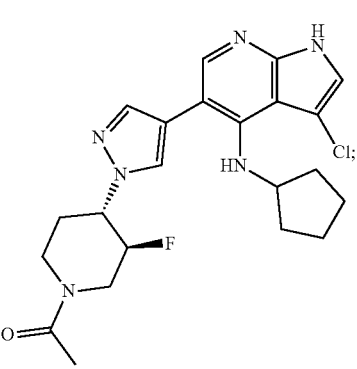
(88)
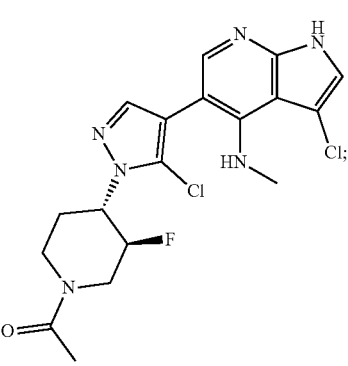
(89)
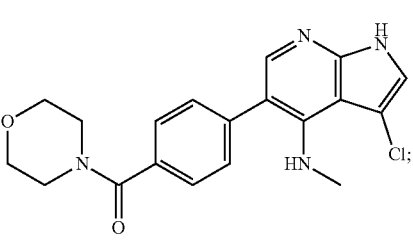
(90)

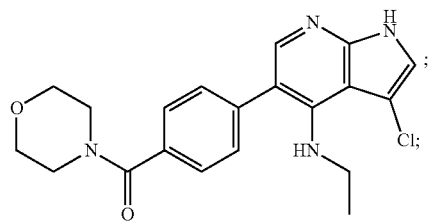
(91)
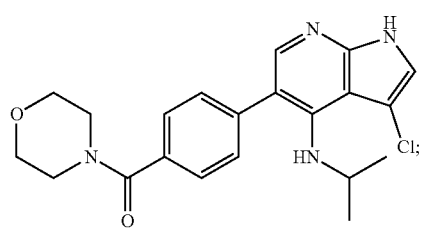
(92)
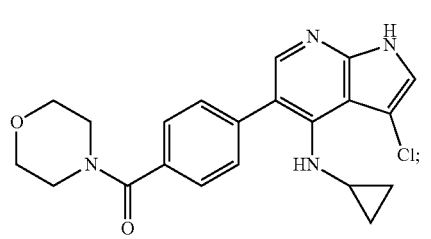
(93)
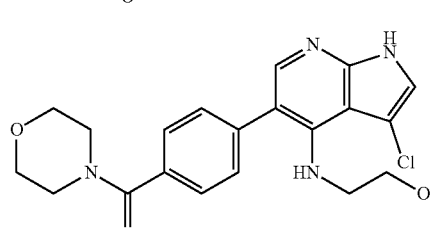
(94)
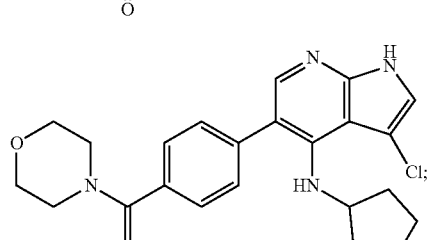
(95)
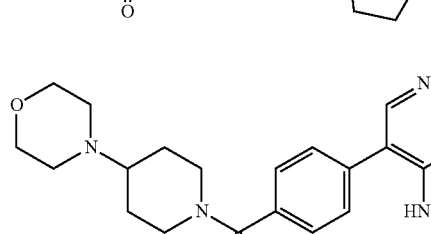
(96)
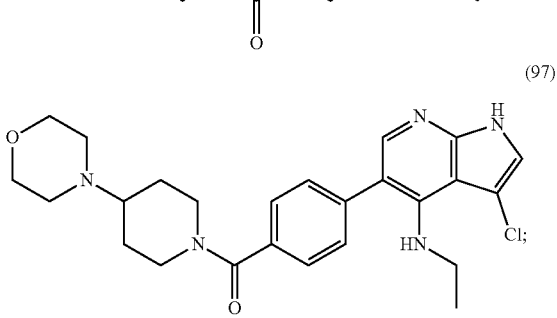
(97)
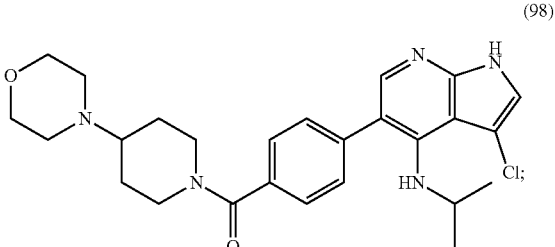
(98)
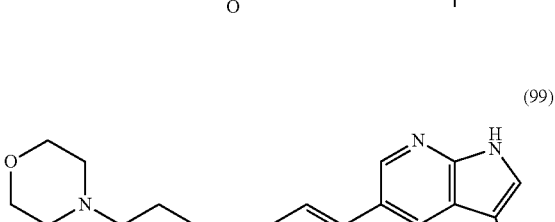
(99)
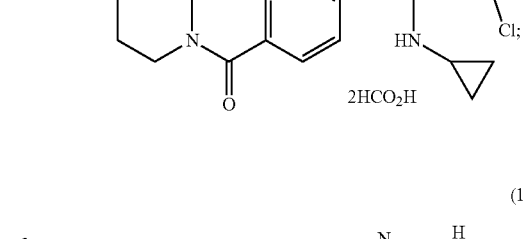
(100)
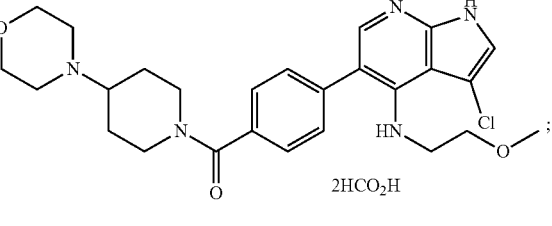
(101)
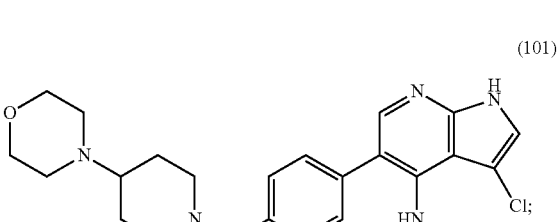
(102)
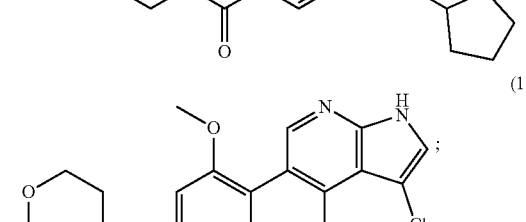
(103)

-continued
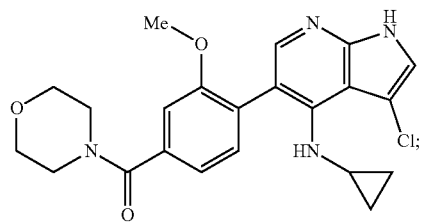 (104)
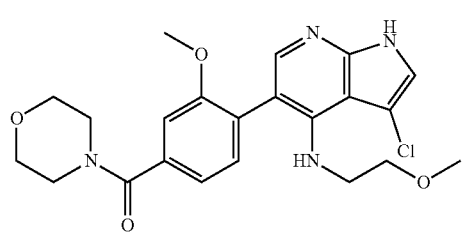 (105)
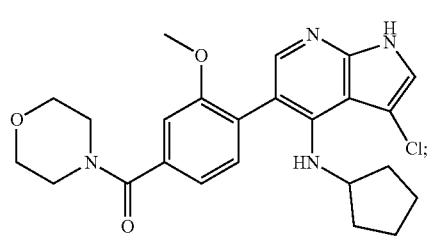 (106)
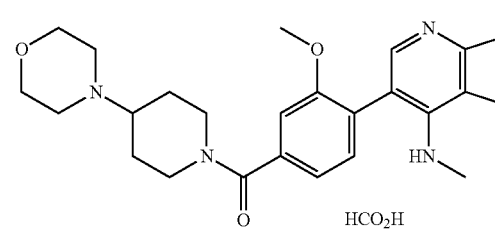 (107)
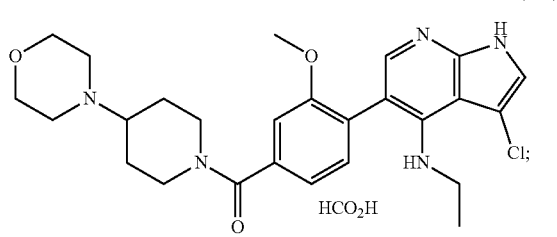 (108)
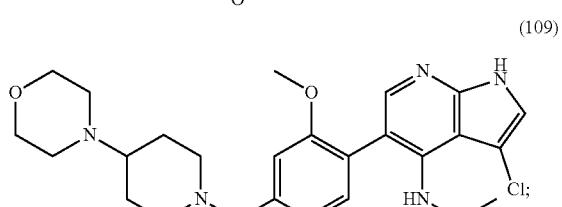 (109)
-continued
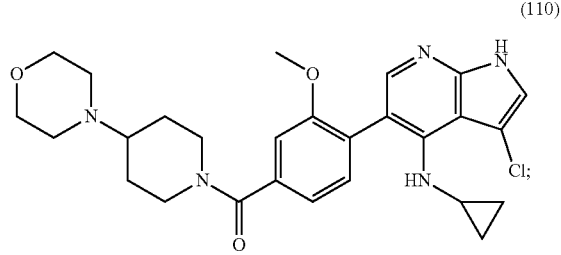 (110)
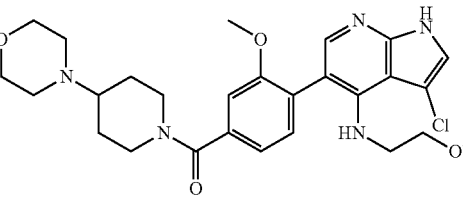 (111)
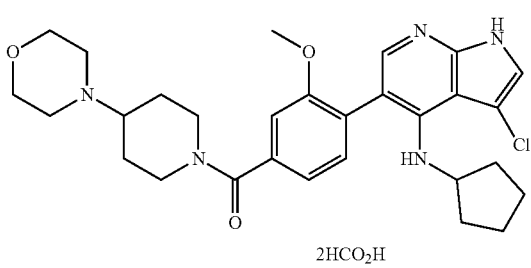 (112)
2HCO₂H
or a pharmaceutically acceptable salt or stereoisomer thereof.
4. The compound of claim 1, wherein X represents CR₂, Y represents CR₁, and Z represents CR₃, and the compound has a structure represented by formula (Ib):
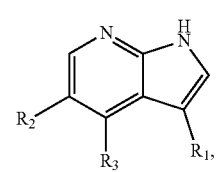 (Ib)
or a pharmaceutically acceptable salt or stereoisomer thereof.
5. The compound of claim 4, which is:
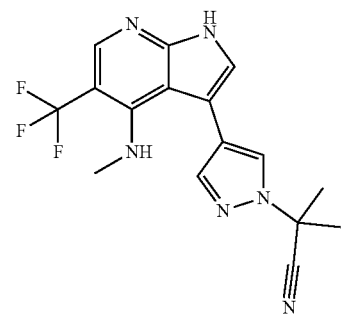 (7)
or -continued

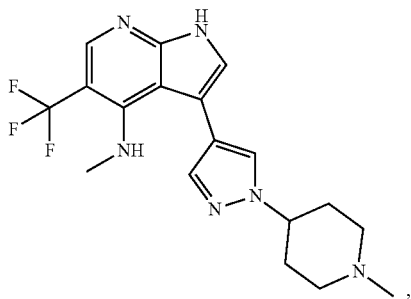 (8)

or a pharmaceutically acceptable salt or stereoisomer thereof.

6. The compound of claim 1, which is:

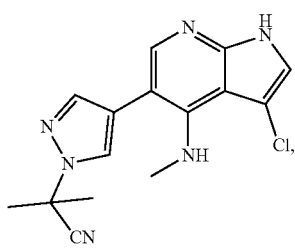 (4)

or a pharmaceutically acceptable salt or stereoisomer thereof.

7. The compound of claim 1, which is:

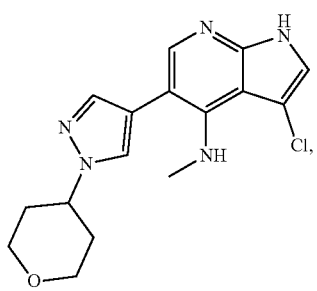 (6)

or a pharmaceutically acceptable salt or stereoisomer thereof.

8. The compound of claim 1, which is:

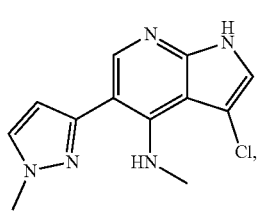 (11)

or a pharmaceutically acceptable salt or stereoisomer thereof.

9. The compound of claim 1, which is:

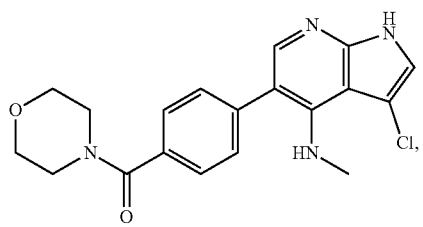 (90)

or a pharmaceutically acceptable salt or stereoisomer thereof.

10. The compound of claim 1, which is:

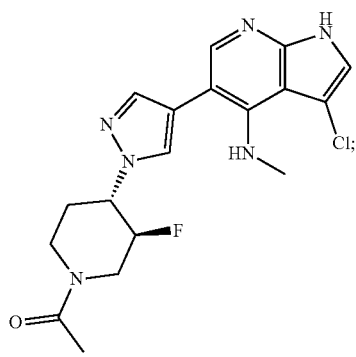 (77)

;

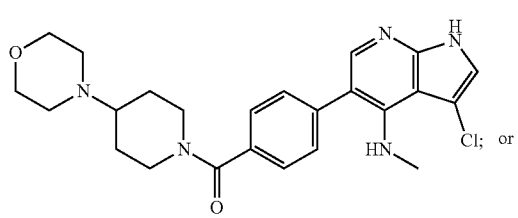 (96)

or

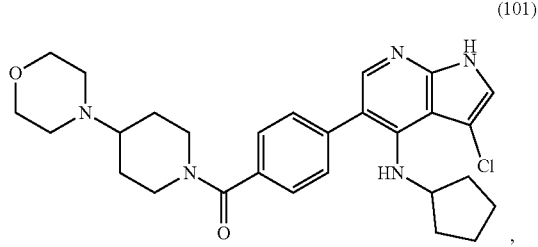 (101)

or a pharmaceutically acceptable salt or stereoisomer thereof.

11. A pharmaceutical composition comprising a therapeutically effective amount of the compound of claim 1, or a pharmaceutically acceptable salt or stereoisomer thereof, and a pharmaceutically acceptable carrier.

12. The composition of claim 11, which is in the form of a tablet or capsule.

13. The composition of claim 11, wherein the pharmaceutically acceptable carrier is a liquid.

14. A method of treating a disease or disorder involving aberrant LRRK2 activity, comprising administering a therapeutically effective amount of the compound of claim 1, or a pharmaceutically acceptable salt or stereoisomer thereof, to a subject in need thereof.

15. The method of claim 14, wherein the disease is a neurodegenerative disease.

16. The method of claim 15, wherein the neurodegenerative disease is Parkinson's disease.

17. The method of claim 14, wherein the disease is brain cancer.

18. The method of claim 17, wherein the brain cancer is a glioma.

19. The method of claim 17, wherein the brain cancer is a glioblastoma.

20. A method of treating a disease or disorder associated with aberrant activity of at least one kinase selected from adaptor-associated protein kinase 1 (AAK1), receptor tyrosine kinase (ABL1(T315I)-phosphorylated), apoptosis signal-regulating kinase 1 (ASK1), ASK2, aurora kinase A (AURKA), AURKB, AURKC, AXL receptor tyrosine kinase (AXL), BMP-2-inducible protein kinase (BIKE), BMX (BMX non-receptor tyrosine kinase), cell division cycle 2-like protein kinase 5 (CDC2L5), cyclin-dependent kinase 11 (CDK11), checkpoint kinase 2 (CHEK2), citron rho-interacting serine/threonine kinase (CIT), CDC-like kinase 1 (CLK1), CLK2, CLK4, colony stimulating factor 1 receptor (CSF1R), CSF1R-autoinhibited, C-terminal Src kinase (CSK), casein kinase I isoform epsilon (CSNKIE), casein kinase I isoform gamma 1 (CSNK1G1), CSNK1G3, dual leucine zipper kinase (DLK), death-associated protein kinase-related 2 (DRAK2), dual-specificity tyrosine phosphorylation-regulated kinase 1A (DYRKIA), DYRK2, ephrin type-A receptor 2 (EPHA2), fms-related tyrosine kinase 1 (FLT1), FLT3, FLT3(D835H), FLT3(D835V), FLT3(D835Y), FLT3(ITD), FLT3(ITD,D835V), FLT3(ITD,F691L), FLT3(K663Q), FLT3(N841I), G protein-coupled receptor kinase 4 (GRK4), serine/threonine-protein kinase haspin (HASPIN), homeodomain-interacting protein kinase 1 (HPK1), intestinal cell kinase (ICK), I kappa B kinase alpha (IKK-alpha), IKK-beta, interleukin 1 receptor associated kinase 1 (IRAK1), IRAK4, Janus kinase 2 (JAK2)(JH1domain-catalytic), JAK3(JH1domain-catalytic), c-Jun N-terminal kinase 1 (JNK1), JNK2, JNK3, tyrosine-protein kinase kit (KIT), KIT(L576P), KIT(V559D), KIT(V559D, T670I), KIT-autoinhibited, LRRK2, LRRK2(G2019S), mitogen-activated protein kinase kinase 2 (MAP3K2), MAP3K15, mitogen-activated protein kinase kinase kinase 2 (MAP4K2), MAP4K4, microtubule associated serine/threonine kinase 1 (MAST1), mitogen-acitvated protein kinase kinase 1 (MEK1), MEK2, MEK3, MEK4, MEK5, MEK6, maternal embryonic leucine zipper kinase (MELK), met proto-oncogene (MET), MET(M1250T), MET(Y1235D), Misshapen-like kinase 1 (MINK), mitogen-activated protein kinase-interacting serine/threonine kinase-2 (MKNK2), myosin light chain kinase (MLCK), nuclear Dbf2-related kinase 2 (NDR2), F-kappa-B-inducing kinase (NIK), p21-activated kinase 4 (PAK4), platelet-derived growth factor receptor alpha (PDGFRA), PDGFR beta (PDGFRB), phosphorylase b kinase gamma catalytic chain, skeletal muscle isoform 2 (PHKG2), phosphatidylinositol-4,5-bisphosphate 3-kinase catalytic subunit alpha (PIK3CA)(E545K), phosphatidylinositol 4-Phosphate-5 kinase 1A (PIP5K1A), PIP5K2B, polo-like kinase 4 (PLK4), serine/threonine-protein kinase D1 (PRKD1), PRKD2, PRKD3, ret proto-oncogene (RET), (RET) (M918T), RIO kinase 1 (RIOK1), RIOK2, RIOK3, receptor-interacting serine/threonine-protein kinase 1 (RIPK1), RIPK4, dual serine/threonine and tyrosine protein kinase (RIPK5), rho-associated protein kinase 1 (ROCK1), ROCK2, ribosomal S6 Kinase 4 (RSK4)(Kin.Dom.1-N-terminal), serum and glucocorticoid-regulated kinase (SGK), SGK2, serine-arginine protein kinase 1 (SRPK1), SRPK2, SRPK3, serine/threonine kinase 16 (STK16), STK39, TGF-beta activated kinase 1 (TAK1), TRAF2 and NCK-interacting kinase (TNIK), tropomyosin receptor kinase A (TRKA), TRKB, monopolar spindle 1 (Mps1) kinase (TTK), tyrosine kinase 2 (TYK2)(JH1domain-catalytic), unc-51 like autophagy activating kinase 1 (ULK1), ULK2, ULK3, vascular endothelial growth factor receptor 2 (VEGFR2), and YSK4a, comprising administering a therapeutically effective amount of the compound of claim 1, or a pharmaceutically acceptable salt or stereoisomer thereof, to a subject in need thereof.

* * * * *

UNITED STATES PATENT AND TRADEMARK OFFICE
CERTIFICATE OF CORRECTION

PATENT NO. : 12,275,731 B2
APPLICATION NO. : 17/283441
DATED : April 15, 2025
INVENTOR(S) : Nathanael S. Gray et al.

It is certified that error appears in the above-identified patent and that said Letters Patent is hereby corrected as shown below:

In the Claims

Column 185, Lines 45-55 Claim 1:
Delete the following structure:

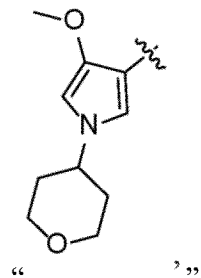

" ,"

Replace with the following structure:

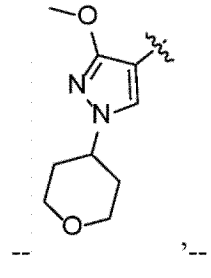

-- ,--

Signed and Sealed this
Thirteenth Day of May, 2025

Coke Morgan Stewart
*Acting Director of the United States Patent and Trademark Office*

Column 206, Lines 17-29 Claim 3:
Delete the following structure:
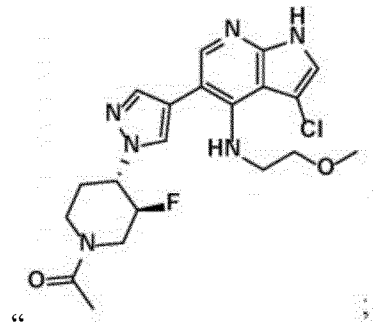
(87)
" ; "
Replace with the following structure:
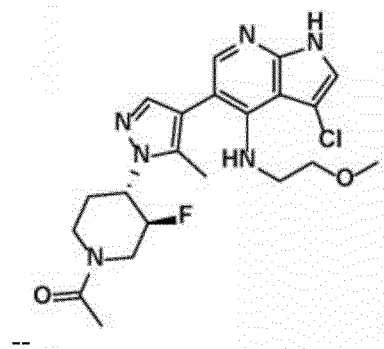
(87)
-- ; --
Column 206, Lines 30-43 Claim 3:
Delete the following structure:
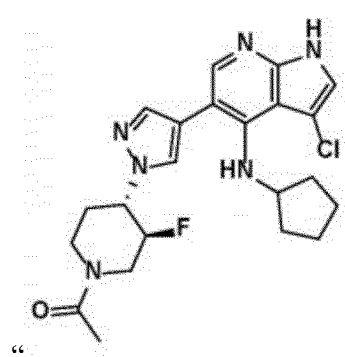
(88)
" ; "

Replace with the following structure:
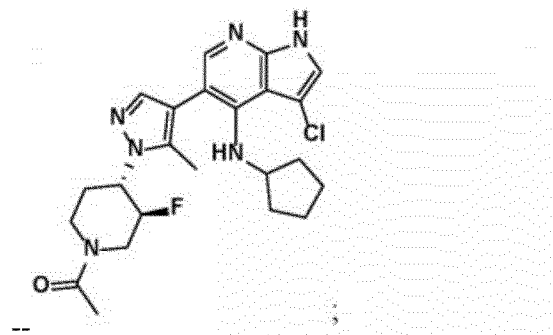
(88)